US012527325B2

(12) United States Patent
Schaetzer et al.

(10) Patent No.: US 12,527,325 B2
(45) Date of Patent: Jan. 20, 2026

(54) PESTICIDALLY ACTIVE DIAZINE-AMIDE COMPOUNDS

(71) Applicant: SYNGENTA CROP PROTECTION AG, Basel (CH)

(72) Inventors: Jürgen Harry Schaetzer, Stein (CH); Andrew Edmunds, Stein (CH); Julien Daniel Henri Gagnepain, Stein (CH); Roger Graham Hall, Stein (CH); André Jeanguenat, Stein (CH); Amandine Kolleth Krieger, Stein (CH); Camille Le Chapelain, Stein (CH); Shrikant Palwe, Goa (IN); Mangala Phadte, Goa (IN); Thomas Pitterna, Stein (CH); Sebastian Rendler, Stein (CH); Christopher Charles Scarborough, Stein (CH)

(73) Assignee: SYNGENTA CROP PROTECTION AG, Basel (CH)

( * ) Notice: Subject to any disclaimer, the term of this patent is extended or adjusted under 35 U.S.C. 154(b) by 1144 days.

(21) Appl. No.: 17/594,118

(22) PCT Filed: Apr. 2, 2020

(86) PCT No.: PCT/EP2020/059338
§ 371 (c)(1),
(2) Date: Oct. 4, 2021

(87) PCT Pub. No.: WO2020/201398
PCT Pub. Date: Oct. 8, 2020

(65) Prior Publication Data

US 2022/0159958 A1 May 26, 2022

(30) Foreign Application Priority Data

Apr. 5, 2019 (EP) .................................... 19167690
Sep. 9, 2019 (EP) .................................... 19196235
Jan. 14, 2020 (EP) .................................... 20151656

(51) Int. Cl.

| | |
|---|---|
| ***A01N 43/60*** | (2006.01) |
| ***A01P 5/00*** | (2006.01) |
| ***A01P 7/02*** | (2006.01) |
| ***A01P 7/04*** | (2006.01) |
| ***A01P 9/00*** | (2006.01) |
| ***A61K 31/497*** | (2006.01) |
| ***A61K 31/506*** | (2006.01) |
| ***C07D 401/04*** | (2006.01) |
| ***C07D 401/14*** | (2006.01) |

(52) U.S. Cl.
CPC ................ *A01N 43/60* (2013.01); *A01P 5/00* (2021.08); *A01P 7/02* (2021.08); *A01P 7/04* (2021.08); *A01P 9/00* (2021.08); *A61K 31/497* (2013.01); *A61K 31/506* (2013.01); *C07D 401/04* (2013.01); *C07D 401/14* (2013.01)

(58) Field of Classification Search
None
See application file for complete search history.

(56) References Cited

U.S. PATENT DOCUMENTS 3,501,472 A * 3/1970 Horne .................. C07D 241/18 340/463
2021/0395228 A1 12/2021 Schaetzer et al.

FOREIGN PATENT DOCUMENTS

| | | | | |
|---|---|---|---|---|
| CN | 112839933 A | 5/2021 | | |
| WO | 2013092943 A1 | 6/2013 | | |
| WO | 2016091776 A1 | 6/2016 | | |
| WO | WO-2017192385 A1 * | 11/2017 | | A61K 31/454 |
| WO | 2020/070049 A1 | 4/2020 | | |

OTHER PUBLICATIONS

Extended European Search Report for EP19196235.6, mailed Oct. 31, 2019.
Written Opinion of the International Searching Authority and International Search Report for PCT/EP2020/059338, mailed May 6, 2020.

* cited by examiner

*Primary Examiner* — Bethany P Barham
*Assistant Examiner* — Judith Marie Kamm
(74) *Attorney, Agent, or Firm* — BakerHostetler; Toni-Junell Herbert

(57) ABSTRACT

Compounds of formula I (Formula I),

I

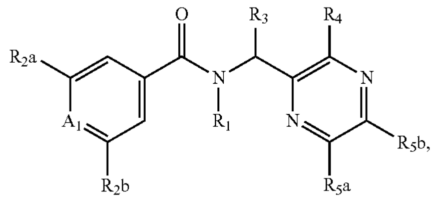

where the substituents $R_1$ through $R_5$ are defined herein, and agrochemically acceptable salts, stereoisomers, enantiomers, tautomers and N-oxides of the compounds of Formula (I). In addition, methods and uses of compounds of Formula I as, for example, insecticides. Compositions having compounds of Formula (I) and their uses in controlling insects, particularly in crops of useful plants. Methods and intermediates related to the synthesis of compounds of Formula (I).

20 Claims, No Drawings

PESTICIDALLY ACTIVE DIAZINE-AMIDE COMPOUNDS

CROSS-REFERENCE TO RELATED APPLICATIONS

This application is a 371 National Stage application of International Application No. PCT/EP2020/059338 filed Apr. 2, 2020, which claims priority to EP 19167690.7 filed Apr. 5, 2019, EP 19196235.6 filed Sep. 9, 2019, and EP 20151656.4 filed Jan. 14, 2020, the entire contents of these applications are hereby incorporated by reference.

The present invention relates to pesticidally active, in particular insecticidally active diazine-amide compounds, to processes for their preparation, to compositions comprising those compounds, and to their use for controlling animal pests, including arthropods and in particular insects or representatives of the order Acarina.

WO2017192385 describes certain heteroaryl-1,2,4-triazole and heteroaryl-tetrazole compounds for use for controlling ectoparasites in animals (such as a mammal and a non-mammal animal).

There have now been found novel pesticidally active-diazine amide compounds.

The present invention accordingly relates, in a first aspect, to a compound of the formula I

I

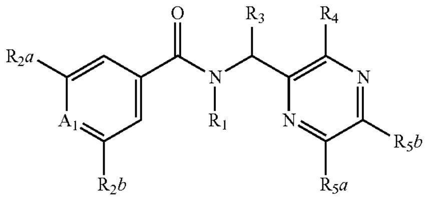

wherein $R_1$ is H, $C_1$-$C_6$alkyl, $C_1$-$C_6$cyanoalkyl, aminocarbonyl$C_1$-$C_6$alkyl, hydroxycarbonyl$C_1$-$C_6$alkyl, $C_1$-$C_6$nitroalkyl, trimethylsilane$C_1$-$C_6$alkyl, $C_1$-$C_6$haloalkyl, $C_2$-$C_6$alkenyl, $C_2$-$C_6$haloalkeny, $C_2$-$C_6$alkynyl, $C_2$-$C_6$haloalkynyl, $C_3$-$C_4$cycloalkyl$C_1$-$C_2$alkyl-, $C_3$-$C_4$cycloalkyl$C_1$-$C_2$alkyl- wherein the $C_3$-$C_4$cycloalkyl group is substituted with 1 or 2 halogen atoms, oxetan-3-yl-$CH_2$—, benzyl or benzyl substituted with halogen or $C_1$-$C_6$haloalkyl;

$A_1$ is N or C—$R_{2C}$;

$R_{2c}$ is H, halogen, $C_1$-$C_3$alkyl, $C_1$-$C_3$haloalkyl, $C_1$-$C_3$alkoxy, or $C_1$-$C_3$haloalkoxy;

$R_{2a}$ is $C_3$-$C_6$cycloalkyl, $C_3$-$C_6$cycloalkoxy, $C_3$-$C_6$cycloalkyl substituted with one to three substituents independently selected from $C_1$-$C_3$alkyl, $C_1$-$C_3$haloalkyl, $C_1$-$C_3$alkoxy, cyano, and halogen, $C_3$-$C_6$cycloalkoxy substituted with one to three substituents independently selected from $C_1$-$C_3$alkyl, $C_1$-$C_3$haloalkyl, cyano, and halogen, $C_3$-$C_6$cycloalkyl$C_1$-$C_4$alkyl, $C_3$-$C_6$cycloalkyl$C_1$-$C_4$alkoxy, $C_3$-$C_6$cycloalkyl$C_1$-$C_4$alkyl substituted with one to five substituents independently selected from $C_1$-$C_3$alkyl, $C_1$-$C_3$haloalkyl, $C_1$-$C_3$alkoxy, cyano, and halogen, $C_3$-$C_6$cycloalkyl$C_1$-$C_4$alkoxy substituted with one to five substituents independently selected from $C_1$-$C_3$alkyl, $C_1$-$C_3$haloalkyl, cyano, and halogen, $C_1$-$C_5$cyanoalkyl, $C_1$-$C_4$alkylsulfonyl, $C_1$-$C_4$haloalkylsulfonyl, $C_1$-$C_4$alkylsulfinyl, or $C_1$-$C_4$haloalkylsulfinyl;

$R_{2b}$ is H, halogen, $C_1$-$C_3$alkyl, $C_1$-$C_3$haloalkyl, $C_1$-$C_3$haloalkylthio, $C_1$-$C_3$alkoxy, $C_1$-$C_3$haloalkoxy, SFs, or CN;

$R_3$ is $C_1$-$C_3$alkyl or $C_1$-$C_3$haloalkyl;

$R_4$ is pyridine, pyrimidine, pyrazine, pyridazine, or pyridine, pyrimidine, pyrazine and pyridazine, each of which is substituted with one substituent selected from $C_1$-$C_3$alkyl, $C_1$-$C_3$haloalkyl, $C_1$-$C_3$alkoxy, $C_3$-$C_4$cycloalkyl, halogen and hydroxy;

$R_{5a}$ and $R_{5b}$ are, independently of each other, selected from hydrogen, halogen, CN, $C_1$-$C_3$alkyl, $C_1$-$C_3$haloalkyl, $C_3$-$C_4$cycloalkyl, $C_1$-$C_3$alkoxy, and $C_1$-$C_3$haloalkoxy; or agrochemically acceptable salts, stereoisomers, enantiomers, tautomers and N-oxides of the compounds of formula I.

Compounds of formula I which have at least one basic centre can form, for example, acid addition salts, for example with strong inorganic acids such as mineral acids, for example perchloric acid, sulfuric acid, nitric acid, nitrous acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

In each case, the compounds of formula I according to the invention are in free form, in oxidized form as a N-oxide or in salt form, e.g. an agronomically usable salt form.

N-oxides are oxidized forms of tertiary amines or oxidized forms of nitrogen containing heteroaromatic compounds. They are described for instance in the book "Heterocyclic N-oxides" by A. Albini and S. Pietra, CRC Press, Boca Raton 1991.

The compounds of formula I according to the invention also include hydrates which may be formed during the salt formation.

The term "$C_1$-$C_n$alkyl" as used herein refers to a saturated straight-chain or branched hydrocarbon radical attached via any of the carbon atoms having 1 to n carbon atoms, for example, any one of the radicals methyl, ethyl, n-propyl, 1-methylbutyl, 2-methylbutyl, 3-methylbutyl, 2, 2-dimethylpropyl, 1-ethylpropyl, n-hexyl, n-pentyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl.

The term "$C_1$-$C_n$haloalkyl" as used herein refers to a straight-chain or branched saturated alkyl radical attached via any of the carbon atoms having 1 to n carbon atoms (as mentioned above), where some or all of the hydrogen atoms in these radicals may be replaced by fluorine, chlorine, bromine and/or iodine, i.e., for example, any one of chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl. According a term "$C_1$-$C_2$fluoroalkyl" would refer to a $C_1$-$C_2$alkyl radical which carries 1, 2, 3, 4, or 5 fluorine atoms, for example, any one of difluoromethyl, trifluoromethyl, 1-fluoroethyl, 2-fluoroethyl, 2,2-difluoroethyl, 2,2,2-trifluoroethyl, 1,1,2,2-tetrafluoroethyl or pentafluoroethyl.

The term "$C_1$-$C_n$alkoxy" as used herein refers to a straight-chain or branched saturated alkyl radical having 1 to n carbon atoms (as mentioned above) which is attached via an oxygen atom, i.e., for example, any one of the radicals methoxy, ethoxy, n-propoxy, 1-methylethoxy, n-butoxy, 1-methylpropoxy, 2-methylpropoxy or 1,1-dimethylethoxy. The term "halo$C_1$-$C_n$alkoxy" as used herein refers to a $C_1$-$C_n$alkoxy radical where one or more hydrogen atoms on the alkyl radical is replaced by the same or different halogen atom(s)—examples include trifluoromethoxy, 2-fluoroetlioxy, 3-fluoropropoxy, 3,3,3-trifluoropropoxy, 4-chlorobutoxy.

The term "$C_1$-$C_n$cyanoalkyl" as used herein refers to a straight chain or branched saturated $C_1$-$C_n$alkyl radical having 1 to n carbon atoms (as mentioned above), where one of the hydrogen atoms in these radicals is be replaced by a cyano group: for example, cyanomethyl, 2-cyanoethyl, 2-cyanopropyl, 3-cyanopropyl, 1-(cyanomethyl)-2-ethyl, 1-(methyl)-2-cyanoethyl, 4-cyanobutyl, and the like.

The term "$C_3$-$C_n$cycloalkyl" as used herein refers to 3-n membered cycloalkyl groups such as cyclopropane, cyclobutane, cyclopentane and cyclohexane.

The term "$C_3$-$C_n$cycloalkyl$C_1$-$C_n$alkyl" as used herein refers to 3 to n membered cycloalkyl group with an alkyl radical, which alkyl radical is connected to the rest of the molecule. In the instance, the $C_3$-$C_n$cycloalkyl$C_1$-$C_2$alkyl-group is substituted, the substituent(s) can be on the cycloalkyl group or alkyl radical.

The term "aminocarbonyl$C_1$-$C_n$alkyl" as used herein refers to an alkyl radical where one of the hydrogen atoms in the radical is replaced by CONH2 group.

The term "hydroxycarbonyl$C_1$-$C_n$alkyl" as used herein refers to an alkyl radical where one of the hydrogen atoms in the radical is replaced by COOH group.

The term "$C_1$-$C_n$nitroalkyl" as used herein refers to an alkyl radical where one of the hydrogen atoms in the radical is replaced by NO2 group.

The term "$C_1$-$C_n$alkylsulfanyl" or "$C_1$-$C_n$haloalkylthio" as used herein refers to a $C_1$-$C_n$alkyl moiety linked through a sulfur atom. Similarly, the term "$C_1$-$C_n$haloalkylsulfanyl" as used herein refers to a $C_1$-$C_n$haloalkyl moiety linked through a sulfur atom.

The term "$C_1$-$C_n$alkylsulfinyl" as used herein refers to a $C_1$-$C_n$alkyl moiety linked through the sulfur atom of the S(=O) group. Similarly, the term "$C_1$-$C_n$haloalkylsulfinyl" as used herein refers to a $C_1$-$C_n$haloalkyl moiety linked through the sulfur atom of the S(=O) group.

The term "$C_1$-$C_n$alkylsulfonyl" as used herein refers to a $C_1$-$C_n$alkyl moiety linked through the sulfur atom of the $S(=O)_2$ group. Similarly, the term "$C_1$-$C_n$haloalkylsulfonyl" as used herein refers to a $C_1$-$C_n$haloalkyl moiety linked through the sulfur atom of the $S(=O)_2$ group The term "trimethylsilane$C_1$-$C_n$alkyl" as used herein refers to an alkyl radical where one of the hydrogen atoms in the radical is replaced by a $—Si(CH_3)_3$ group.

The term "$C_2$-$C_n$alkenyl" as used herein refers to a straight or branched alkenyl chain having from two to n carbon atoms and one or two double bonds, for example, ethenyl, prop-I-enyl, but-2-enyl.

The term "$C_2$-$C_n$haloalkenyl" as used herein refers to a $C_2$-$C_n$alkenyl moiety substituted with one or more halogen atoms which may be the same or different.

The term "$C_2$-$C_n$alkynyl" as used herein refers to a straight or branched alkynyl chain having from two to n carbon atoms and one triple bond, for example, ethynyl, prop-2-ynyl, but-3-ynyl, The term "$C_2$-$C_n$haloalkynyl" as used herein refers to a $C_2$-$C_n$alkynyl moiety substituted with one or more halogen atoms which may be the same or different.

Halogen is generally fluorine, chlorine, bromine or iodine. This also applies, correspondingly, to halogen in combination with other meanings, such as haloalkyl The pyridine, pyrimidine, pyrazine and pyridazine groups (unsubstituted or substituted) for $R_2$ and $R_4$ are each connected via a carbon atom on the respective ring to the rest of the compound.

As used herein, the term "controlling" refers to reducing the number of pests, eliminating pests and/or preventing further pest damage such that damage to a plant or to a plant derived product is reduced.

The staggered line as used herein, for example, in K-1, and O-1, represent the point of connection/attachment to the rest of the compound.

As used herein, the term "pest" refers to insects, acarines, nematodes and molluscs that are found in agriculture, horticulture, forestry, the storage of products of vegetable origin (such as fruit, grain and timber); and those pests associated with the damage of man-made structures. The term pest encompasses all stages in the life cycle of the pest.

As used herein, the term "effective amount" refers to the amount of the compound, or a salt thereof, which, upon single or multiple applications provides the desired effect.

An effective amount is readily determined by the skilled person in the art, by the use of known techniques and by observing results obtained under analogous circumstances. In determining the effective amount a number of factors are considered including, but not limited to: the type of plant or derived product to be applied; the pest to be controlled & its lifecycle; the particular compound applied; the type of application; and other relevant circumstances.

As one of ordinary skill in the art will appreciate, compounds of formula I contain a stereogenic centre which is indicated with an asterisk in the structure below:

I*

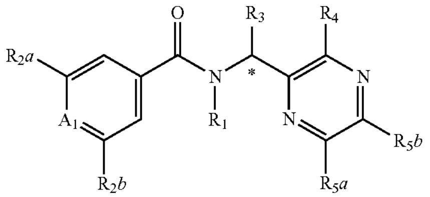

where $R_1$, $R_{2a}$, $R_{2b}$, $R_3$, $R_4$, $R_{5a}$, $R_{5b}$, and $A_1$ are as defined in the first aspect.

The present invention contemplates both racemates and individual enantiomers. Compounds having preferred stereochemistry are set out below.

I'a

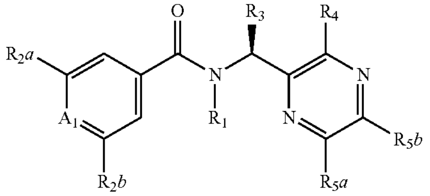

Particularly preferred compounds of the present invention are compounds of formula I'a:

where $R_1$, $R_{2a}$, $R_{2b}$, $R_3$, $R_4$, $R_{5a}$, $R_{5b}$, and $A_1$ are as defined in the first aspect, and stereoisomers, enantiomers, tautomers and N-oxides of the compounds of formula (I'a), and agrochemically acceptable salts thereof.

The term "optionally substituted" as used herein means that the group referenced is either unsubstituted or is substituted by a designated substituent, for example, "$C_3$-$C_4$cycloalkyl is optionally substituted with 1 or 2 halogen atoms" means $C_3$-$C_4$cycloalkyl, $C_3$-$C_4$cycloalkyl substituted with 1 halogen atom and $C_3$-$C_4$cycloalkyl substituted with 2 halogen atoms.

Embodiments according to the invention are provided as set out below.

In an embodiment of each aspect of the invention, $A_1$ is

A. N; or

B. C—$R_{2c}$, where $R_{2c}$ is hydrogen or halogen (such as Cl, F, Br and I); preferably hydrogen.

In an embodiment of each aspect of the invention, $R_{2a}$ is

A. $C_3$-$C_6$cycloalkyl, $C_3$-$C_6$cycloalkoxy, $C_3$-$C_6$cycloalkyl substituted with one to three substituents independently selected from $C_1$-$C_3$alkyl, $C_1$-$C_3$haloalkyl, $C_1$-$C_3$alkoxy, cyano, and halogen, $C_3$-$C_6$cycloalkyl$C_1$-$C_4$alkyl substituted with one to five substituents independently selected from halogen and $C_1$-$C_3$haloalkyl, $C_1$-$C_5$cyanoalkyl, $C_3$-$C_6$cycloalkoxy, $C_1$-$C_4$haloalkylsulfonyl or $C_1$-$C_4$haloalkylsulfinyl; or B. $C_3$-$C_4$cycloalkyl, $C_3$-$C_4$cycloalkoxy, $C_3$-$C_4$cycloalkyl substituted with one to three substituents independently selected from $C_1$-$C_2$alkyl, $C_1$-$C_2$haloalkyl, $C_1$-$C_2$alkoxy, cyano, and halogen, $C_3$-$C_4$cycloalkyl$C_1$-$C_2$alkyl substituted with one to five substituents independently selected from halogen and $C_1$-$C_3$haloalkyl, $C_1$-$C_3$cyanoalkyl, $C_3$-$C_4$cycloalkoxy, $C_1$-$C_3$haloalkylsulfonyl or $C_1$-$C_3$haloalkylsulfinyl; or C. cyclopropyl, cyclopropyl substituted with one to three substituents independently selected from methyl, trifluormethyl, methoxy, cyano, fluoro and chloro, cyclopropylmethyl substituted with one to five fluoro substituents, $C_1$-$C_3$cyanoalkyl, cyclopropoxy, trifluoromethylsulfonyl or trifluoromethyl sulfinyl; or D. cyclopropyl, cyclopropyl substituted with one to three substituents independently selected from methyl, trifluoromethyl, methoxy, cyano, fluoro and chloro, cyclopropylmethyl substituted with one or two fluoro substituents on the methyl part, $C_1$-$C_3$cyanoalkyl, trifluoromethylsulfonyl or trifluoromethyl sulfinyl; or E. cyclopropyl, cyclopropyl substituted with one to three substituents independently selected from trifluoromethyl, methoxy, cyano, fluoro and chloro, cyclopropylmethyl substituted with one or two fluoro substituents on the methyl part, $C_1$-$C_3$cyanoalkyl, trifluoromethylsulfonyl.

In an embodiment of each aspect of the invention, $R_{2b}$ is

A. halogen, $C_1$-$C_3$haloalkyl, $C_1$-$C_3$haloalkylthio, $C_1$-$C_3$alkoxy, $C_1$-$C_3$haloalkoxy, or CN; or B. halogen, $C_1$-$C_3$haloalkyl, or $C_1$-$C_3$haloalkoxy; or C. chlorine, fluorine, difluoromethyl, trifluoromethyl, difluoromethoxy or trifluoromethoxy; or D. difluoromethyl or trifluoromethyl.

In an embodiment of each aspect of the invention, $R_1$ is

A. hydrogen, methyl, ethyl, n-propyl, isobutyl, cyclopropylmethyl or HCH≡$CCH_2$—; or B. hydrogen, methyl, or cyclopropylmethyl; or C. hydrogen; or D. methyl; or E. cyclopropylmethyl.

In an embodiment of each aspect of the invention, $R_3$ is

A. $C_1$-$C_3$alkyl or $C_1$-$C_3$haloalkyl; or

B. methyl.

In an embodiment of each aspect of the invention, $R_4$ is

A. 2-pyridine, 2-pyrimidine, 2-pyridine substituted with one substituent selected from cyclopropyl or halogen, or 2-pyrimidine substituted with one substituent selected from cyclopropyl or halogen; or B. selected from O-1 to O-8

O-1

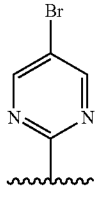

O-2

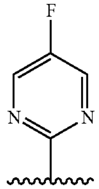

O-3

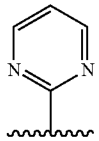

-continued

O-4

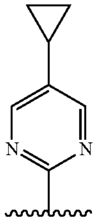

O-5

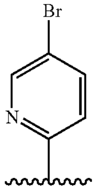

O-6

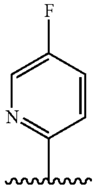

O-7

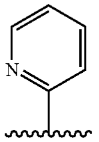

O-8

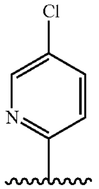

C. selected from O-1, O-3, O-4, O-5, O-6 and O-8; or

D. O-3, O-4, O-5, O-6 or O-8; or.

E. O-3, O-4, O-5 or O-8; or

F. O-5 or O-8.

In an embodiment of each aspect of the invention, $R_{5a}$ and $R_{5b}$, independent of each other, are A. hydrogen, halogen, $C_1$-$C_3$alkyl, or $C_1$-$C_3$alkoxy; or B. selected from hydrogen, bromo, chloro, methyl, and methoxy; or C. hydrogen.

The present invention, accordingly, makes available a compound of formula I having the substituents $R_1$, $R_{2a}$, $R_{2b}$, $R_3$, $R_4$, $R_{5a}$, $R_{5b}$, and $A_1$ as defined above in all combinations/each permutation. Accordingly, made available, for example, is a compound of formula I with $A_1$ being of the first aspect (i.e. $A_1$ is N or C—$R_{2c}$, where $R_{2c}$ is H, halogen, $C_1$-$C_3$alkyl, $C_1$-$C_3$haloalkyl, $C_1$-$C_3$alkoxy, or $C_1$-$C_3$haloalkoxy); $R_1$ being embodiment B (i.e. hydrogen, methyl, cyclopropylmethyl); $R_{2a}$ being an embodiment C (i.e. cyclopropyl, cyclopropyl substituted with one to three substituents independently selected from methyl, trifluormethyl, methoxy, cyano, fluoro and chloro, cyclopropylmethyl substituted with one to five fluoro substituents, $C_1$-$C_3$cyanoalkyl, cyclopropoxy, trifluoromethylsulfonyl or trifluoromethyl sulfinyl); $R_{2b}$ being embodiment B (i.e. halogen, $C_1$-$C_3$haloalkyl, or $C_1$-$C_3$haloalkoxy); $R_3$ being embodiment B (i.e. methyl); $R_4$ being embodiment B (i.e. selected from O-1 to O-8); and $R_{5a}$ being embodiment A (i.e selected from hydrogen, halogen, $C_1$-$C_3$alkyl, or $C_1$-$C_3$alkoxy); and $R_{5b}$ being embodiment C (i.e hydrogen).

In an embodiment, the compound of formula I can be represented as

I-A

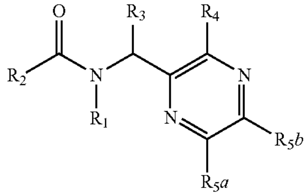

or

I'-A

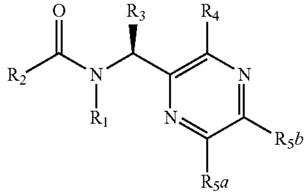

wherein $R_1$, $R_3$, $R_4$, $R_{5a}$, and $R_{5b}$ are as defined in the first aspect, $R_2$ is the cyclic group containing $A_1$ and the substituents $R_{2a}$ and $R_{2b}$ as defined in the first aspect.

In an embodiment of each aspect of the invention, the $R_2$ (the cyclic group containing $A_1$ and the substituents $R_{2a}$ and $R_{2b}$) is A. selected from K-1 to K-15

K-1

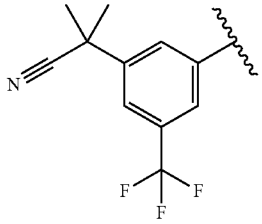

K-2

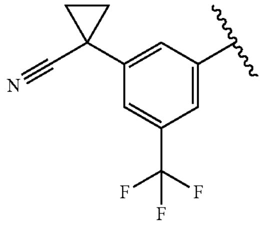

K-3

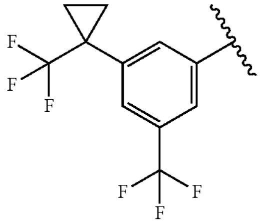

-continued
K-4
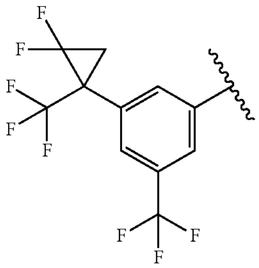
K-5
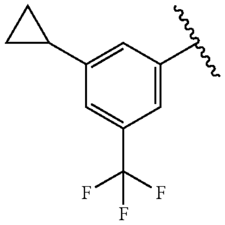
K-6
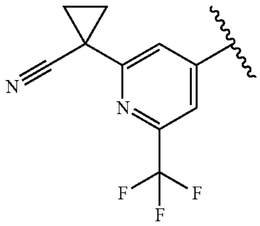
K-7
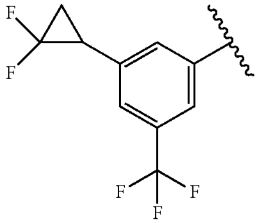
K-8
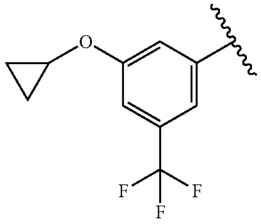
K-9
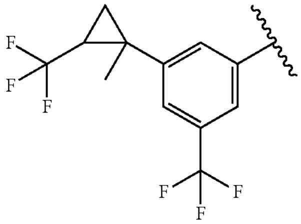
-continued
K-10
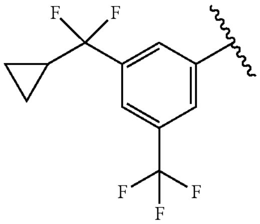
K-11
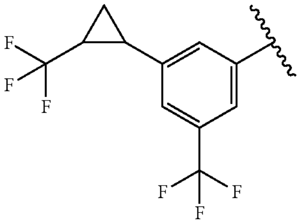
K-12
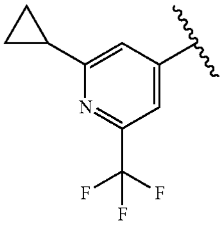
K-13
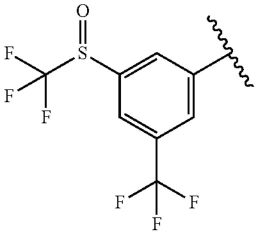
K-14
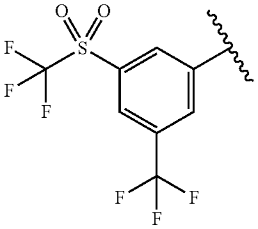
K-15
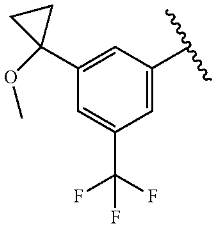

-continued

K-16

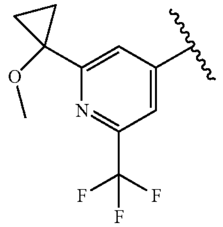

B. selected from K-1, K-2, K-3, K-5, K-6, K-10, K-11, K-12, K-14, K-15 and K-16; or
C. selected from K-1, K-2, K-6, K-10, K-12, K-14, K-15 and K-16; or
D. selected from K-1, K-2, K-5, K-10, K-11, K-14, K-15 and K-16: or
E. selected from K-1, K-2, K-5, K-6, K-10, K-14, K-15 and K-16; or
F. selected from K-1, K-2, K-6, K-10, K-14, K-15 and K-16; or
G. selected from K-5, K-10, K-14 and K-15; or
H. selected from K-2, K-6, K-14 and K-15; or
I. selected from K-2, K-6 and K-10.

In an embodiment of each aspect of the invention, the compound of formula I has as $R_1$ hydrogen, methyl, ethyl, n-propyl, isobutyl, cyclopropylmethyl or HCH≡CCH2-; as $R_2$ one of K-1 to K-16; as $R_3$ methyl; as $R_4$ one of O-1 to O-8; and as $R_{5a}$ and $R_{5b}$, independently selected from hydrogen, halogen, methyl.

In an embodiment of each aspect of the invention, the compound of formula I has as $R_1$ hydrogen, methyl, or cyclopropylmethyl; as $R_2$ one of K-1 to K-16; as $R_3$ methyl; as $R_4$ one of O-1 to O-8; and as $R_{5a}$ and $R_{5b}$, independently selected from hydrogen, halogen, methyl.

In an embodiment of each aspect of the invention, the compound of formula I has as $R_1$ hydrogen; as $R_2$ one of K-1 to K-16; as $R_3$ methyl; as $R_4$ one of O-1 to O-8; and as $R_{5a}$ and $R_{5b}$, independently selected from hydrogen, halogen, methyl.

In an embodiment of each aspect of the invention, the compound of formula I has as $R_1$ hydrogen, methyl, or cyclopropylmethyl; as $R_2$ one of K-1, K-2, K-3, K-5, K-6, K-10, K-11, K-12, K-14, K-15 and K-16; as $R_3$ methyl; as $R_4$ one of O-1 to O-8 and as $R_{5a}$ and $R_{5b}$, independently selected from hydrogen, halogen, methyl.

In an embodiment of each aspect of the invention, the compound of formula I has as $R_1$ hydrogen, methyl, or cyclopropylmethyl; as $R_2$ one of K-1, K-2, K-5, K-6, K-10, K-11, K-14, K-15 and K-16; as $R_3$ methyl; as $R_4$ one of O-1 to O-8; and as $R_{5a}$ and $R_{5b}$, independently selected from hydrogen, halogen, methyl.

In an embodiment of each aspect of the invention, the compound of formula I has as $R_1$ hydrogen, methyl, or cyclopropylmethyl; as $R_2$ one of K-1, K-2, K-5, K-6, K-10, K-11, K-14, K-15 and K-16 as $R_3$ methyl; as $R_4$ one of O-1, O-3, O-4, O-5, O-6 or O-8; and as $R_{5a}$ and $R_{5b}$, independently selected from hydrogen, halogen, methyl.

In an embodiment of each aspect of the invention, the compound of formula I has as $R_1$ hydrogen, methyl, or cyclopropylmethyl; as $R_2$ one of K-1, K-2, K-5, K-6, K-10, K-11 K-14, K-15 and K-16; as $R_3$ methyl; as $R_4$ one of O-1, O-3, O-4, O-5, O-6 or O-8; and as $R_{5a}$ and $R_{5b}$, each hydrogen.

In an embodiment of each aspect of the invention, the compound of formula I has as $R_1$ hydrogen, methyl, or cyclopropylmethyl; as $R_2$ one of K-2, K-6 and K-10; as $R_3$ methyl; as $R_4$ one of O-3, O-4, O-5 or O-8; and as $R_{5a}$ and $R_{5b}$, each hydrogen.

In a second aspect, the present invention makes available a composition comprising a compound of formula I as defined in the first aspect, one or more auxiliaries and diluent, and optionally one more other active ingredient.

In a third aspect, the present invention makes available a method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound as defined in the first aspect or a composition as defined in the second aspect.

In a fourth aspect, the present invention makes available a method for the protection of plant propagation material from the attack by insects, acarines, nematodes or molluscs, which comprises treating the propagation material or the site, where the propagation material is planted, with an effective amount of a compound of formula I as defined in the first aspect or a composition as defined in the second aspect.

In a fifth aspect, the present invention makes available a plant propagation material, such as a seed, comprising, or treated with or adhered thereto, a compound of formula I as defined in the first aspect or a composition as defined in the second aspect.

The present invention in a further aspect provides a method of controlling parasites in or on an animal in need thereof comprising administering an effective amount of a compound of the first aspect. The present invention further provides a method of controlling ectoparasites on an animal in need thereof comprising administering an effective amount of a compound of formula I as defined om the first aspect. The present invention further provides a method for preventing and/or treating diseases transmitted by ectoparasites comprising administering an effective amount of a compound of formula I as defined in the first aspect, to an animal in need thereof.

Compounds of formula I can be prepared by those skilled in the art following known methods. More specifically compounds of formulae I, and I'a, and intermediates therefor can be prepared as described below in the schemes and examples. Certain stereogenic centers have been left unspecified for the clarity and are not intended to limit the teaching of the schemes in any way.

The process according to the invention for preparing compounds of formula I is carried out by methods known to those skilled in the art.

Compounds of Formula I

I

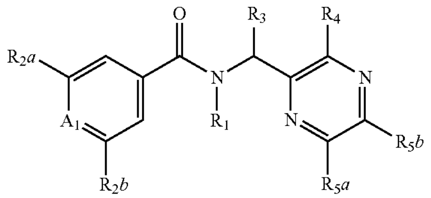

can be prepared by reaction of an amine of formula II

II

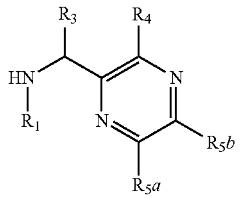

wherein $R_1$, $R_3$, $R_4$, $R_{5a}$, and $R_{5b}$ are as defined in formula I, with a carboxylic acid derivative of formula III

III

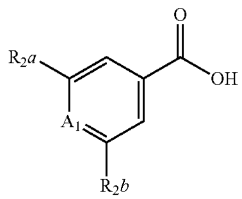

wherein $R_{2a}$, $R_{2b}$, and $A_1$ are as defined in formula I. The chemistry is described in more detail in Scheme 1.

Scheme 1

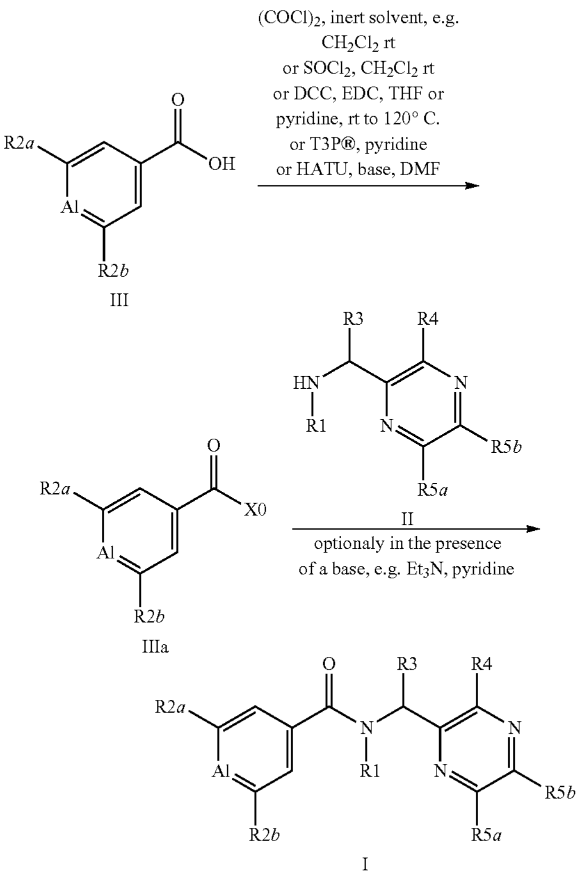

-continued

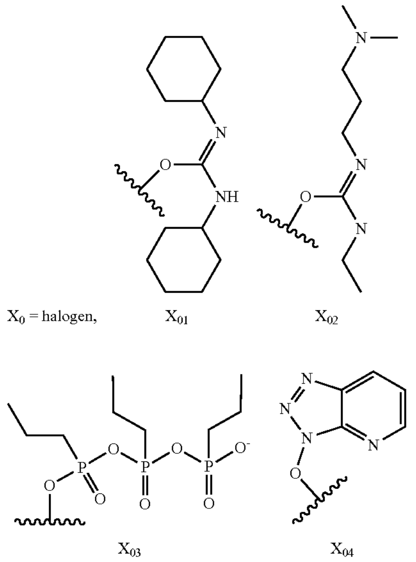

In Scheme 1 compounds of formula III, wherein $R_{2a}$, $R_{2b}$ and $A_1$ are as defined in formula I, are activated to compounds of formula IIIa by methods known to those skilled in the art and described for example in Tetrahedron, 61 (46), 10827-10852, 2005. For example, compounds where $X_0$ is halogen are formed by treatment of compounds of formula III with for example, oxalyl chloride or thionyl chloride in the presence of catalytic quantities of DMF in inert solvents such as methylene dichloride or THE at temperatures between 20° C. to 100° C., preferably 25° C. Treatment of IIIa with compounds of formula II, wherein $R_1$, $R_3$, $R_4$, $R_{5a}$, and $R_{5b}$ are as defined in formula I, optionally in the presence of a base, e.g. triethylamine or pyridine leads to compounds of formula I. Alternatively, compounds of formula I can be prepared by treatment of compounds of formula III with dicyclohexyl carbodiimide (DCC) or 1-ethyl-3-(3-dimethylaminopropyl)carbodiimide (EDC) to give the activated species IIIa, wherein $X_0$ is $X_{01}$ or $X_{02}$, in an inert solvent, e.g. pyridine, or THE optionally in the presence of a base, e.g. triethylamine, at temperatures between 50-180° C. In addition, an acid of the formula III can also be activated by reaction with a coupling reagent such as propanephosphonic acid anhydride (T3P®) or O-(7-Aza-1-benzotriazolyl)-N,N,N,N'-tetramethyluronium-hexafluorophosphat (HATU) to provide compounds of formula IIIa, wherein $X_0$ is $X_{03}$ or $X_{04}$ as described for example in Synthesis 2013, 45, 1569 and Journal Prakt. Chemie 1998, 340, 581. Subsequent reaction with an amine of the formula II provides compounds of formula I.

Intermediates of formula II, wherein $R_1$, $R_3$, $R_4$, $R_{5a}$ and $R_5$ are as defined in formula I, can be prepared according to Scheme 2:

Scheme 2

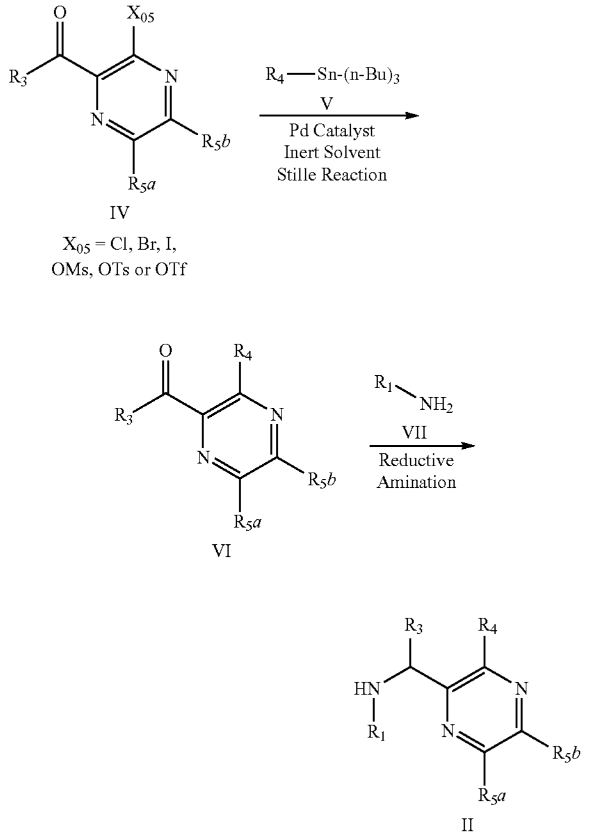

IV $X_{05}$ = Cl, Br, I, OMs, OTs or OTf

VI

II

In Scheme 2, a Stille reaction of compounds of formula IV, wherein $X_{05}$ is a leaving group such as chlorine, bromine, iodine, arysulfonate, alkylsulfonate or trifluoromethanesulfonate and $R_3$, $R_{5a}$ and $R_{5b}$ are as defined in formula I, are reacted with tin compounds of formula V (wherein $R_4$ is as defined in formula I), in the presence of a palladium catalyst, for example tetrakis(triphenylphosphine)palladium (0), or (1,1'bis(diphenylphosphino)-ferrocene)dichloropalladium-dichloromethane (1:1 complex), in an inert solvent such as DMF, acetonitrile, or dioxane, optionally in the presence of an additive, such as potassium or cesium fluoride, or lithium chloride, and optionally in the presence of a further catalyst, for example copper(I) iodide to give compounds of formula VI (wherein $R_3$, $R_4$, $R_{5a}$ and $R_{5b}$ are as defined in formula I). Such Stille coupling reactions are well known to those skilled in the art, and have been described in for example J. Org. Chem., 2005, 70, 8601, J. Org. Chem., 2009, 74, 5599, Angew. Chem. Int. Ed., 2004, 43, 1132, Heterocycles 2010, 80, 1215 and J. Am. Chem. Soc. 2004, 126, 16433. Compounds of formula VI can be treated with compounds of formula VII (wherein $R_1$ is as defined in formula I), e.g. in the presence of $NaBH(OAc)_3$ or $NaBH_3CN$, preferable with $NaBH_3CN$ as reductive reagent, in a suitable solvent, preferable in acetic acid at room temperature analog to WO2002/088073, page 35 to form compounds of formula II (wherein $R_1$, $R_3$, $R_4$, $R_{5a}$ and $R_{5b}$ are as defined in formula I). Another reagent system for the reductive amination uses a combination of $Ti(i\text{-}OPr)_4$ and $NaBH_4$ in the presence of an amine of formula VII to provide compounds of formula II (see Synthesis 2003 (14), 2206).

Compounds of formula VI, wherein $R_3$, $R_4$, $R_{5a}$, and $R_{5b}$ are as defined in formula I, can also be prepared by a Suzuki reaction (Scheme 3), which involves for example, reacting compounds of formula IV (wherein $R_3$, $R_{5a}$, and $R_{5b}$ are as defined in formula I and $X_{05}$ is a leaving group like, for example, chlorine, bromine, iodine, arysulfonate, alkylsulfonate or trifluoromethanesulfonate) with compounds of formula VIII, wherein W can be a boron-derived functional group, as for example $B(OH)_2$ or a pinacol boronic ester. The reaction can be catalyzed by a palladium based catalyst, for example tetrakis(triphenylphosphine)-palladium or (1,1'bis(diphenylphosphino)-ferrocene)dichloropalladium-dichloromethane (1:1 complex), in presence of a base, like sodium carbonate or cesium fluoride, in a solvent or a solvent mixture, like, for example a mixture of 1,2-dimethoxyethane and water, dioxane and water, or DMF and water preferably under inert atmosphere. The reaction temperature can preferentially range from room temperature to the boiling point of the reaction mixture. Such Suzuki reactions are well known to those skilled in the art and have been reported, for example in J. Organomet. Chem. 576, 1999, 147-168, Science of Synthesis 2010, 45b, 547, Eur. J. Org. Chem. 2012, (31), 6248 and Synthesis 2017, 49, 4372.

Scheme 3

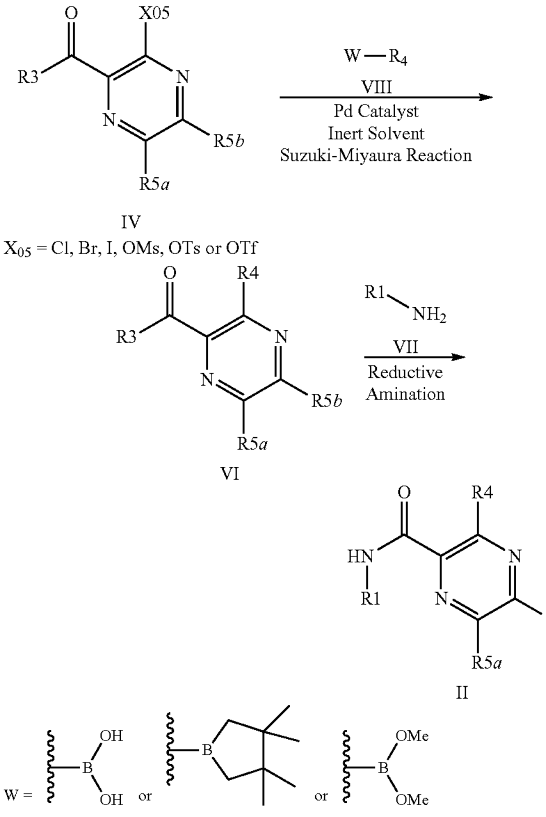

IV $X_{05}$ = Cl, Br, I, OMs, OTs or OTf

VI

II

W = or or

Reductive amination as already described in Scheme 2 leads then in the same manner to compounds of formula II. Compounds of formula IV are generally commercially available.

Yet another process for the preparation of compounds of formula II, wherein $R_1$, $R_3$, $R_4$, $R_{5a}$, and $R_{5b}$ are as defined in formula I, is outlined in Scheme 4.

Scheme 4

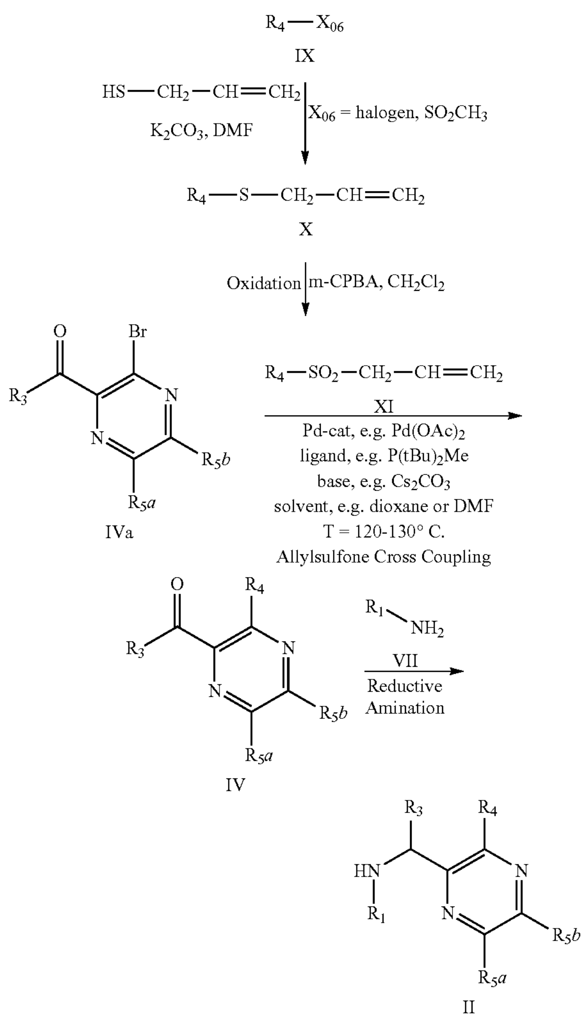

For example, compounds of formula VI, wherein $R_3$, $R_4$, $R_{5a}$, and $R_{5b}$ is as defined in formula I, may be prepared by allyl sulfone coupling reaction of compounds of formula IVa (wherein $R_3$, $R_{5a}$, and $R_{5b}$ are as defined in formula I) with compounds of formula XI, wherein $R_4$ is defined in formula I, in suitable solvents, preferable dioxane or DMF, in the presence of a Pd-catalyst, preferable palladium acetate, a ligand, e.g. ditert-butyl(methyl)phosphane, and a base, e.g. $Cs_2CO_3$ usually upon heating at temperatures between 120 to 130° C. Such processes have been described, for example, in J. Am. Chem. Soc. 2018, 140, 15916.

The required intermediates of formula XI can be obtained from compounds of formula IX (wherein $R_4$ is as defined in formula I and $X_{06}$ is a halogen or methyl sulfone) through nucleophilic substitution with prop-2-ene-1-thiol and subsequent oxidation with m-CPBA. Such transformation are well known and reported, for instance, in J. Am. Chem. Soc. 2018, 140, 15916.

In an alternative process (Scheme 5), ketones of formula VI (wherein $R_3$, $R_4$, $R_{5a}$, and $R_{5b}$ are as defined in formula I) can be reduced to alcohols of formula XII by reduction, for example with $NaBH_4$ in the usual manner (see e.g. WO2012/082997, page 141), preferably in MeOH as solvent. Subsequent activation of the alcohols of formula XII with compounds of formula XIII, wherein Y is $CH_3$, $CF_3$ or p-$CH_3$—$C_6H_4$, in an inert solvent, preferable in methylene dichloride and in the presence of a base, e.g. triethyl amine affords compounds of formula XIV, wherein $X_{07}$ is OMs, OTs or OTf. Alcohols of formula XII may be also be activated to alkyl halides XIV (wherein $X_{07}$ is Cl or Br) by treatment with phosphorous compounds, e.g. $P(X_0)_3$, wherein $X_0$ is chlorine or bromine by methods known to those skilled in the art. Such general functional group transformations are described for example in Organische Chemie. 4. Auflage, Wiley-VCH Verlag, Weinheim 2005, p. 393 ff and Chem Commun. 2014, 50, 5756. Finally, nucleophilic substitution reaction of compound of formula XIV with amines of formula VII furnishes compounds of formula II, wherein $R_1$, $R_3$, $R_4$, $R_{5a}$, and $R_{5b}$ are as defined in formula I.

Scheme 5

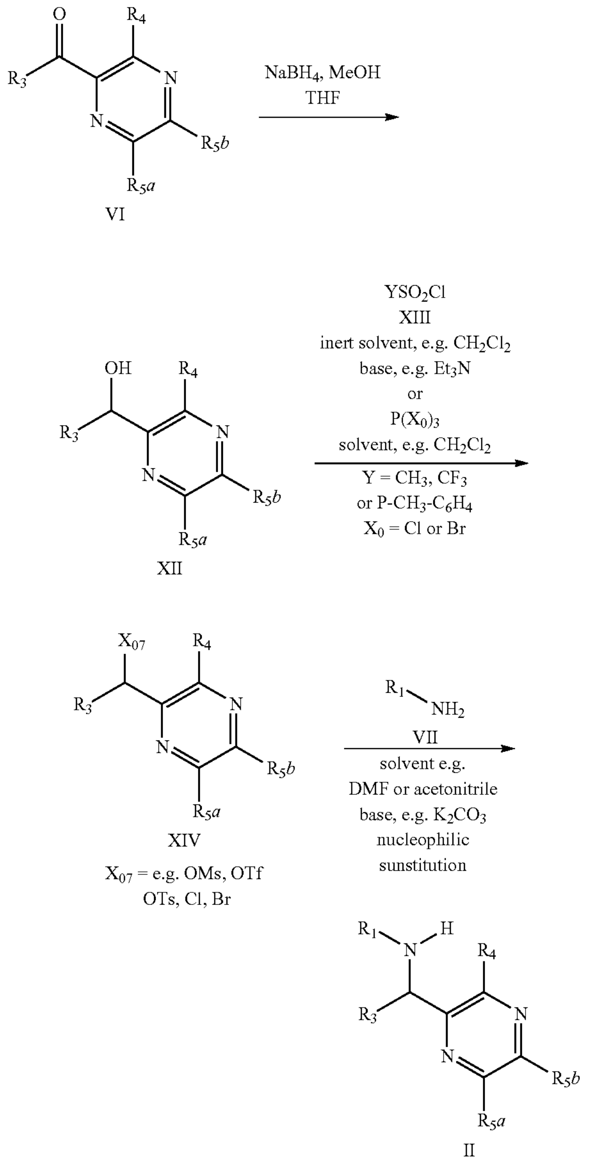

Ketone compounds of formula VI (wherein $R_3$, $R_4$, $R_{5a}$ and $R_{5b}$ are as defined in formula I) are either commercially available or can be prepared as shown in Scheme 6:

Scheme 6

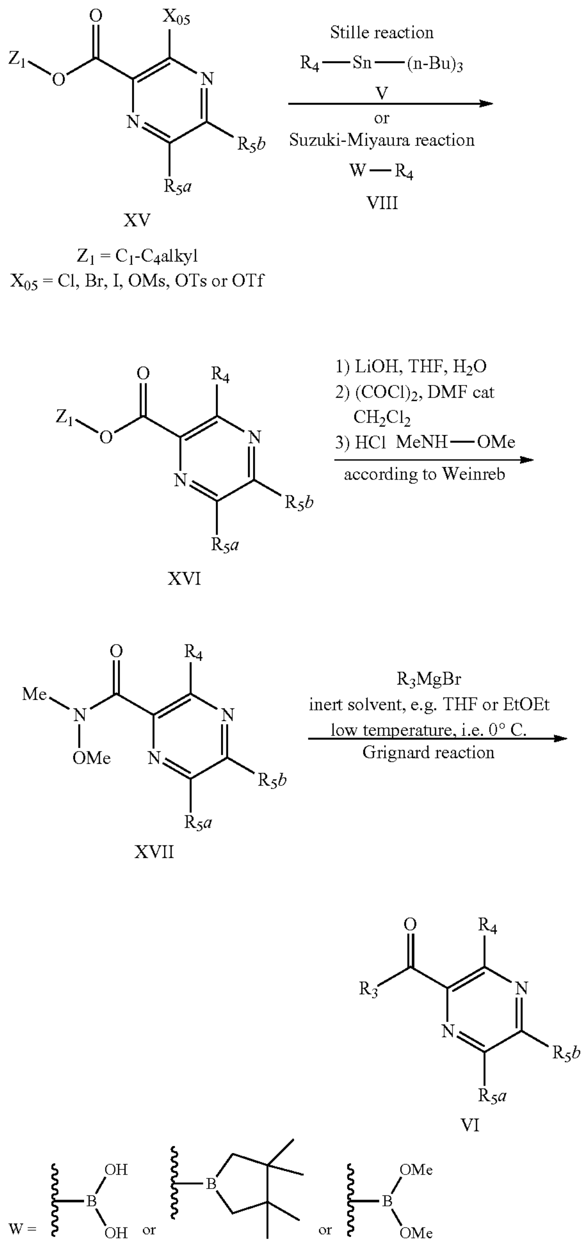

XV $Z_1 = C_1$-$C_4$alkyl $X_{05}$ = Cl, Br, I, OMs, OTs or OTf

XVI

XVII

VI

W = or or

As shown in Scheme 6, compounds of formula XV (wherein $R_{5a}$, and $R_{5b}$ are as defined in formula I, $Z_1$ is $C_1$-$C_4$alkyl, and $X_{05}$ is a leaving group as defined in formula IV) can be converted to compounds of formula XVI (wherein $R_4$, $R_{5a}$, $R_{5b}$ and $Z_1$ are as defined in formula XV) by reaction with compounds of formula V (Stille reaction) or compounds of formula VIII (Suzuki-Miyaura reaction) in the presence of a palladium catalyst as described in detail in Schemes 2 and 3. Compounds of formula XVI are then converted to carboxylic acids by methods known in the art (see e.g. WO2011/143365, page 138). Activation (see Scheme 1) of the carboxylic acids and treatment with N-methoxy-N-methylamine (according to Weinreb et al. Tet. Lett. 1981, 39, 3815) leads to Weinreb amides of formula XVII (wherein $R_4$, $R_{5a}$, and $R_{5b}$ are as defined in formula I). Treatment of compounds of formula XVII with a Grignard reagent $R_3MgBr$, e.g. MeMgBr at lower temperatures, preferable at 0 to 25° C., gives alkyl ketones of formula VI (wherein $R_3$, $R_4$, $R_{5a}$, and $R_{5b}$ are as defined in formula I).

Yet another methodology to prepare compounds of general formula of IIa is outlined in Scheme 7.

Scheme 7

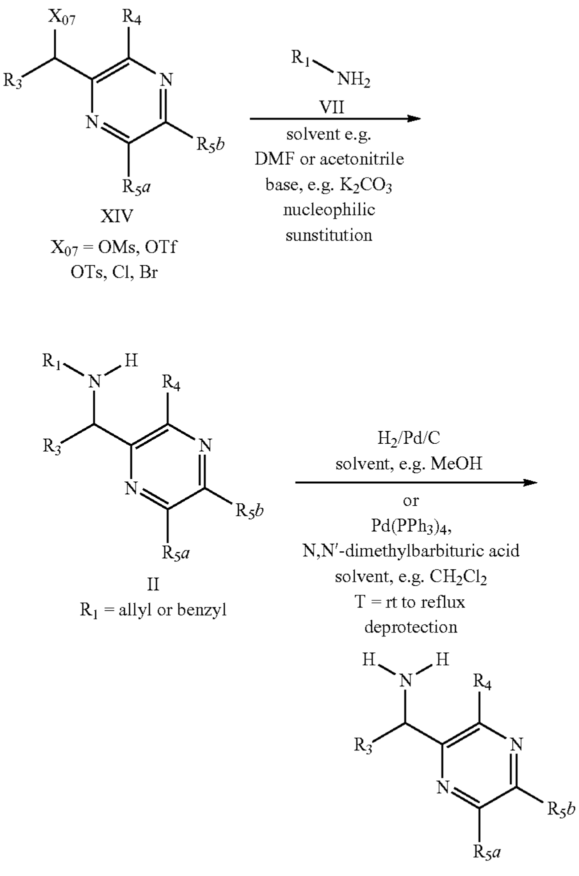

XIV $X_{07}$ = OMs, OTf
OTs, Cl, Br

II $R_1$ = allyl or benzyl

IIa

Thus, nucleophilic substitution reaction of compound of formula XIV with amines of formula VII furnishes compounds of formula II (wherein $R_1$, $R_3$, $R_4$, $R_{5a}$, and $R_{5b}$ are defined as in formula I) as already described in detail in Scheme 5. Compounds of formula II suited with a protecting group, e.g. $R_1$ is benzyl, can be hydrogenated with hydrogen in the presence of palladium (on charcoal) in a solvent, e.g. MeOH or EtOH, to give compounds of formula IIa, wherein $R_3$, $R_4$, $R_{5a}$, and $R_{5b}$ is defined as in formula I (see e.g. Synlett, 2010, (18), page 2708). Compounds of formula II, wherein $R_1$ is allyl, and $R_3$, $R_4$, $R_{5a}$, and $R_{5b}$ is as defined in formula I can also be converted to compounds of formula IIa by reaction with N'N'dimethylbarbituric acid in the presence of a Pd-catalyst, preferable tetrakis(triphenylphosphine)palladium(0), in a suitable solvent, for example $CH_2Cl_2$ to provide compounds of formula IIa according to J. Org. Chem. 1993, 58, 6109.

Carboxylic acids of formula XXI, wherein $R_{2b}$ and $A_1$ is as defined in formula I, are useful intermediates for the preparation of final compounds (see Scheme 1) and may be prepared by the process shown in Scheme 8.

Scheme 8

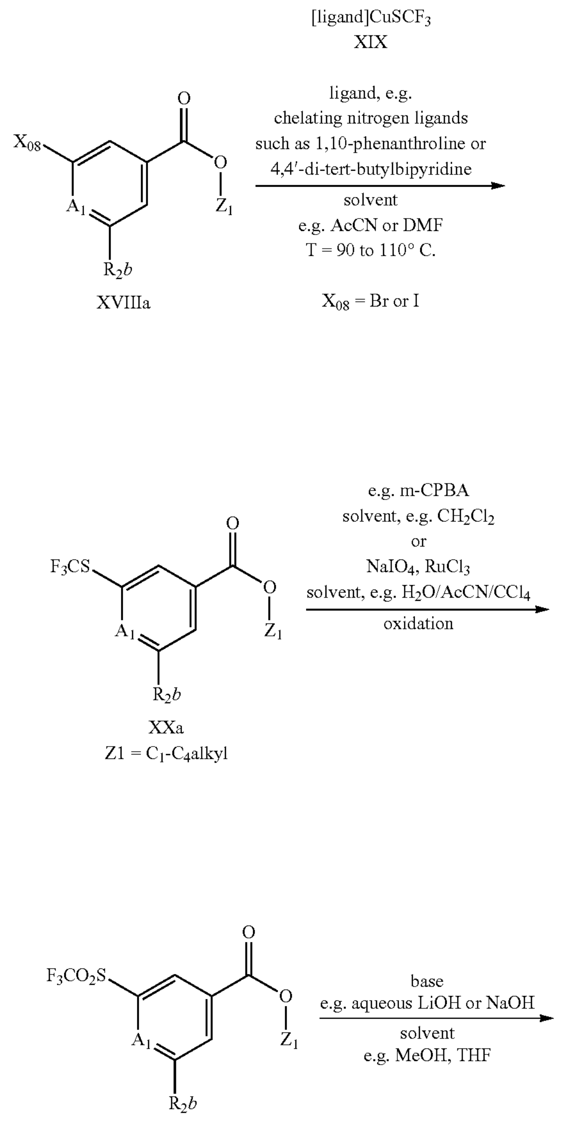

XVIIIa

XXa
Z1 = $C_1$-$C_4$alkyl

XXI

-continued

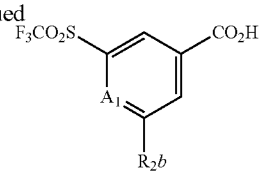

IIIa

Accordingly, compounds of formula IIIa, wherein $R_{2b}$ and $A_1$ are as defined in formula I, can be prepared by reaction of compounds of formula XXI (wherein $R_{2b}$ and $A_1$ are as defined in formula I and $Z_1$ is $C_1$-$C_4$alkyl) with a suitable base such as sodium or lithium hydroxide, in a suitable solvent like MeOH, THF, and $H_2O$ or a mixture of them, usually upon heating at temperatures between room temperature and reflux. Compounds of formula XXI are prepared through oxidation of compounds of formula XXa, e.g. with m-CPBA or $NaIO_4/RuCl_3$, in a solvent, preferable $CH_2Cl_2$, or $CHCl_3$ or a mixture of $H_2O$, AcCN and $CCl_4$. Such transformations are known to those skilled in the art and described for example in J. Med. Chem. 2008, 51, 6902 or WO2004/9086, pages 24-25.

Finally, compounds of formula XXa, wherein $R_{2b}$ and $A_1$ are as defined in formula I and $Z_1$ is $C_1$-$C_4$alkyl, may be prepared by reaction of compounds of formula XVIIIa with a suitable trifluoromethylthiolation copper reagent of formula XIX (wherein $R_{2b}$ and $A_1$ are as defined in formula I and $X_{08}$ is Br or Cl), ligands being e.g. 1,10-phenanthroline or 4,4'-di-tert-butylbipyridine, in suitable solvents, for example, acetonitrile or DMF, usually upon heating at temperatures between 20 to 150° C., preferably between 40° C. to the boiling point of the reaction mixture. Such processes have been described previously, for example, in Angew. Chem. Int. Ed. 2013, 52, 1548-1552, Angew. Chem. Int. Ed. 2011, 50, 3793, Org. Lett. 2014, 16, 1744, J. Org. Chem. 2017, 82, 11915.

Further intermediates of formula XX, wherein $R_{2a}$, $R_{2b}$, and $A_1$ are as defined in formula I and $Z_1$ is $C_1$-$C_4$alkyl, are generally known or can be easily prepared by those skilled in the art. A typical example of such a synthesis of compounds of formula XX is shown in Scheme 9.

Scheme 9

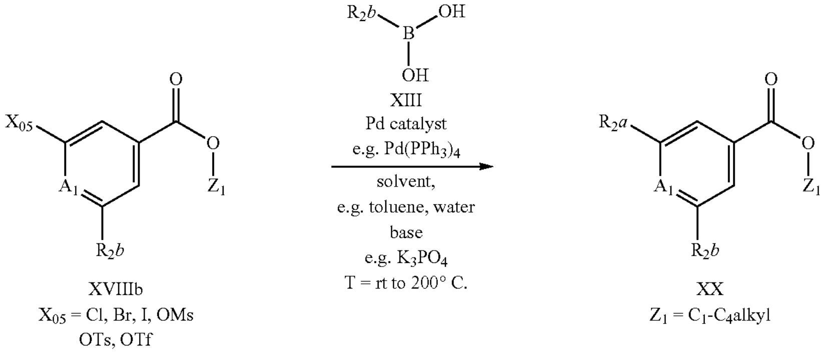

XVIIIb
$X_{05}$ = Cl, Br, I, OMs
OTs, OTf

XX
$Z_1$ = $C_1$-$C_4$alkyl

-continued

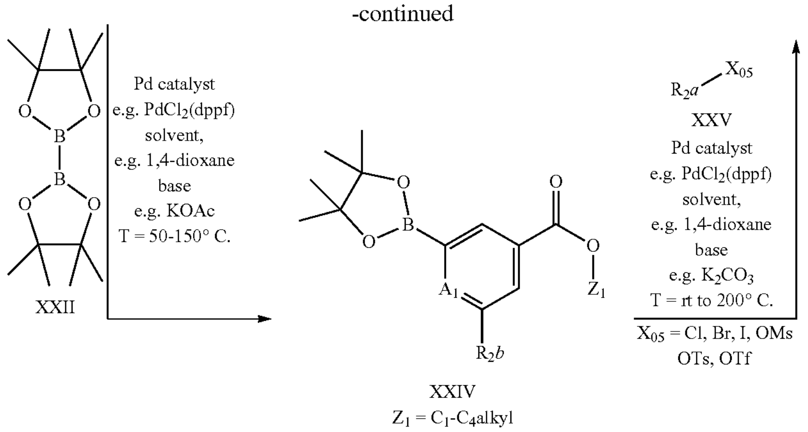

$R_{2a}$ is not $C_1$-$C_4$alkylsulfonyl, $C_1$-$C_4$-haloalkylsulfonyl, $C_1$-$C_4$-alkylsulfinyl, $C_1$-$C_4$-haloalkylsulfinyl For example, compounds of formula XX may be prepared by reaction of compounds of formula XVIIIb, wherein $R_{2b}$ and $A_1$ are as defined for formula I and $X_{05}$ is chlorine, bromine, iodine, OMs, OTs or OTf, with compounds of formula XXIII, wherein $R_{2a}$ is as defined in formula I, in the presence of a palladium catalyst, for example, $Pd(PPh_3)_4$, in suitable solvents, for example, toluene/water, 1,4-dioxane/water, in the presence of a suitable base, such as sodium, potassium or caesium carbonate or tripotassium phosphate usually upon heating at temperatures between room temperature and 200° C., preferably between 20° C. to the boiling point of the reaction mixture, optionally under microwave heating conditions. Such processes have been described previously, for example, in Tetrahedron Letters 2002, 43, 6987-6990.

Compounds of formula XX may also be prepared by reaction of compounds of formula XXIV, wherein $R_{2b}$ and $A_1$ and $Z_1$ are as defined in formula XX, and compounds of formula XXV, wherein $R_{2a}$ is as defined in formula I, and $X_{05}$ is a leaving group, for example, bromine or iodine, in the presence of a palladium catalyst, for example, $PdCl_2$(dppf), in suitable solvents that may include, for example, toluene/water, 1,4-dioxane/water, in the presence of a suitable base, such as sodium, potassium or caesium carbonate or tripotassium phosphate usually upon heating at temperatures between room temperature and 200° C., preferably between 20° C. to the boiling point of the reaction mixture, optionally under microwave heating conditions. Such processes have been described previously, for example, in WO12139775, page 73.

Compounds of formula XXIV, wherein $R_{2b}$ and $A_1$ and $Z_1$ are as defined in formula I, may be prepared by reaction of compounds of formula XVIIIb, wherein $R_{2b}$ and $A_1$ and $Z_1$ are as defined in formula XXIV, and $X_{05}$ is Cl, Br, I, OMs, OTs or OTf, with compound of formula XXII, e.g. bis (pinacolato)diboron (B2pin2), in the presence of a palladium catalyst, for example, $PdCl_2$(dppf), in suitable solvents that may include, for example, toluene/water, 1,4-dioxane/water, in the presence of a suitable base, such as sodium, potassium or caesium carbonate or potassium acetate, usually upon heating at temperatures between room temperature and 200° C., preferably between 20° C. to the boiling point of the reaction mixture, optionally under microwave heating conditions. Such processes have been described previously, for example, in Bioorg. Med. Chem. Lett. 2015, 25, 1730, and WO12139775, page 67.

Carboxylic acids of formula IIIb may be prepared from compound of formula XXVIII as outlined in Scheme 8, by treatment with, for example aqueous LiOH, NaOH or KOH, in suitable solvents that may include, for example, THF/MeOH mixture, usually upon heating at temperatures between room temperature and 100° C., preferably between 20° C. to the boiling point of the reaction mixture (see Scheme 10).

Compounds of formula XXVIII, wherein, $R_{2b}$ and $A_1$ are defined in formula I and $R_{2a}$ is H, $C_1$-$C_3$alkyl, $C_1$-$C_3$haloalkyl, cyano or halogen and $Z_1$ is $C_1$-$C_4$alkyl, may be prepared by treatment of compounds of formula XXVII, which are either commercially available or can be prepared by methods known to those skilled in the art (see e.g. Angew. Chem. Int. Ed. 2004, 43, 1132 and Pure Appl. Chem. 1985, 57, 1771) with compound of formula XXVI, e.g. (trifluoroethyl)-diphenyl-sulfonium triflate ($Ph_2S^+CH_2CF_3$—OTf in the presence of an Fe-catalyst and a base, preferable CsF at temperatures between 0 to 50°, preferable 20° C. in DMA as solvent (analog to Org. Lett. 2016, 18, 2471). Compounds of formula XXIX are obtained as mixture of stereoisomers with the trans isomer being the major isomer.

Yet another methodology (see Scheme 10) to prepare compounds of formula XXVIII uses trifluoroethylamine hydrochloride/$NaNO_2$/NaOAc in the presence of an Fe-catalyst; this reaction is conducted at room temperature in $H_2O$; or in a mixture of $CH_2Cl_2$ and $H_2O$, see e.g. Angew. Chem. Int. Ed. 2010, 49, 938 and Chem. Commun. 2018, 54, 5110.

Scheme 10

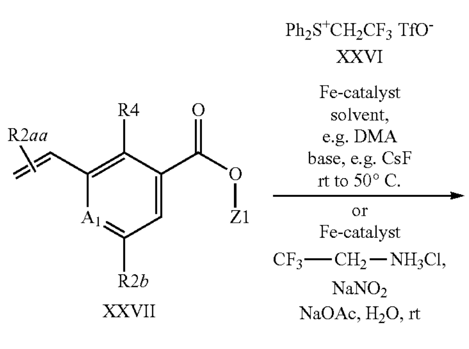

-continued

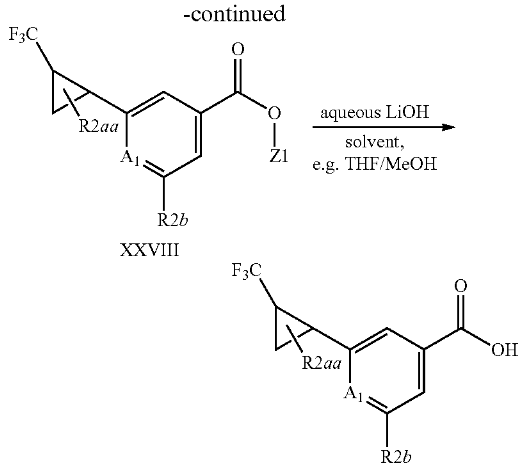

XXVIII

IIIb $R_2aa$ = H, $C_1$-$C_3$alkyl, $C_1$-$C_3$haloalkyl, cyano, halogen

Carboxylic acids of formula IIIc, wherein $R_{2b}$ and $A_1$ are as defined in formula I, and $R_{2aa}$ is H, $C_1$-$C_3$alkyl, $C_1$-$C_3$haloalkyl, cyano or halogen, may be prepared in quite a similar manner as already shown in Scheme 10.

Scheme 11

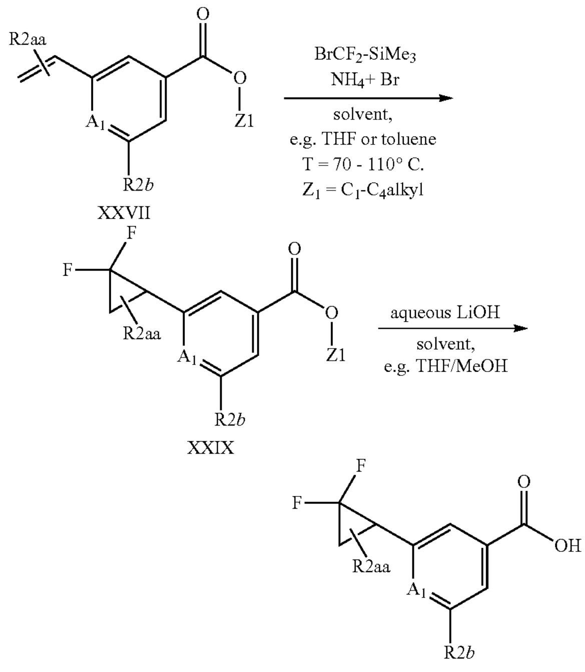

XXVII

XXIX

IIIc $R_1aa$ = H, $C_1$-$C_3$alkyl, $C_1$-$C_3$haloalkyl, cyano, halogen

Thus, compounds of formula XXIX, wherein $R_{2b}$ and $A_1$ are as defined in formula I, and $R_{2aa}$ is H, $C_1$-$C_3$alkyl, $C_1$-$C_3$haloalkyl, cyano or halogen and $Z_1$ is $C_1$-$C_4$alkyl, are prepared by reaction of compounds of formula XXVII (synthesized analog to ACS Med. Chem. Lett. 2013, 4, 514 or Tetrahedron Lett. 2001, 42, 4083) with (bromodifluoromethyl)-trimethylsilane in the presence of $NH_4^+Br$ in a suitable solvent, preferable in THF or toluene at temperatures between 70 to 110° C. Subsequent saponification of the ester intermediates XXIX provide compounds of formula IIIc (Scheme 11).

Scheme 12

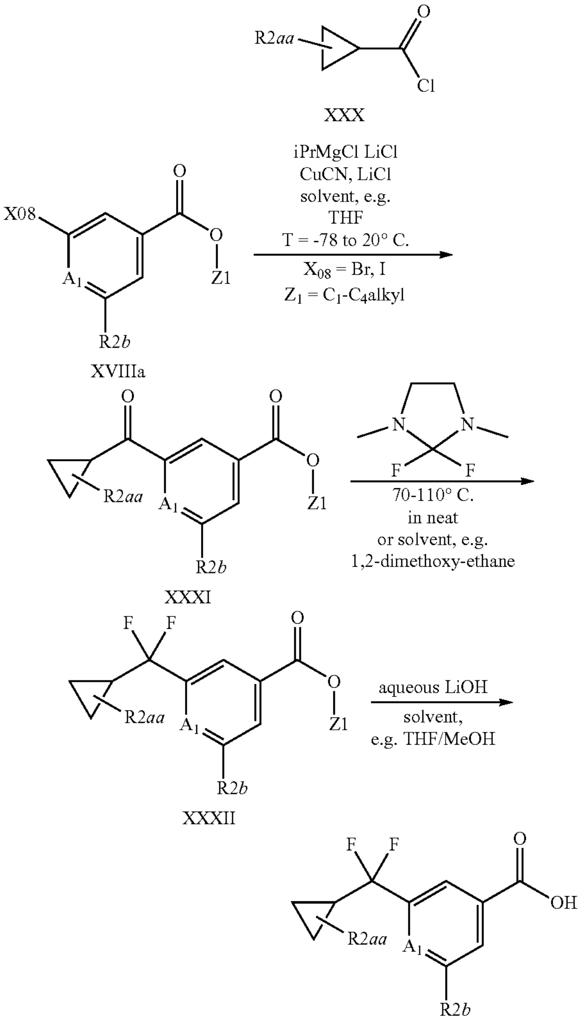

XXX

XVIIIa

XXXI

XXXII

IIId

R2aa = H, $C_1$-$C_3$alkyl, $C_1$-$C_3$haloalkyl, cyano, halogen

Carboxylic acids of formula IIId, wherein $R_{2b}$ and $A_1$ are as defined in formula I and $R_{2aa}$ is H, $C_1$-$C_3$alkyl, $C_1$-$C_3$haloalkyl, cyano or halogen, can be prepared according to reaction Scheme 12. Thus, compounds of formula XVIIIa, wherein $R_{2b}$ and $A_1$ are as defined in formula I, $Z_1$ is $C_1$-$C_4$alkyl and $X_{08}$ is bromine or iodine, are treated with iPrMgCl/LiCl-complex; subsequent reaction with CuCN and quenching with cyclopropane carbonyl chlorides of formula XXX (wherein $R_{2a}$ is H, $C_1$-$C_3$alkyl, $C_1$-$C_3$haloalkyl, cyano or halogen) provides compounds of formula XXXI (analog to WO2006/067445, page 148). Following fluorination with 2,2-difluoro-1,3-dimethylimidazoline either in a solvent, e.g. in 1,2-dimethoxy-ethane or in neat (see Chem. Commun. 2002, (15), 1618) affords compound of formula XXXII. Subsequent hydrolysis using e.g. LiOH as already described gives carboxylic acids of formula IIId.

Scheme 13

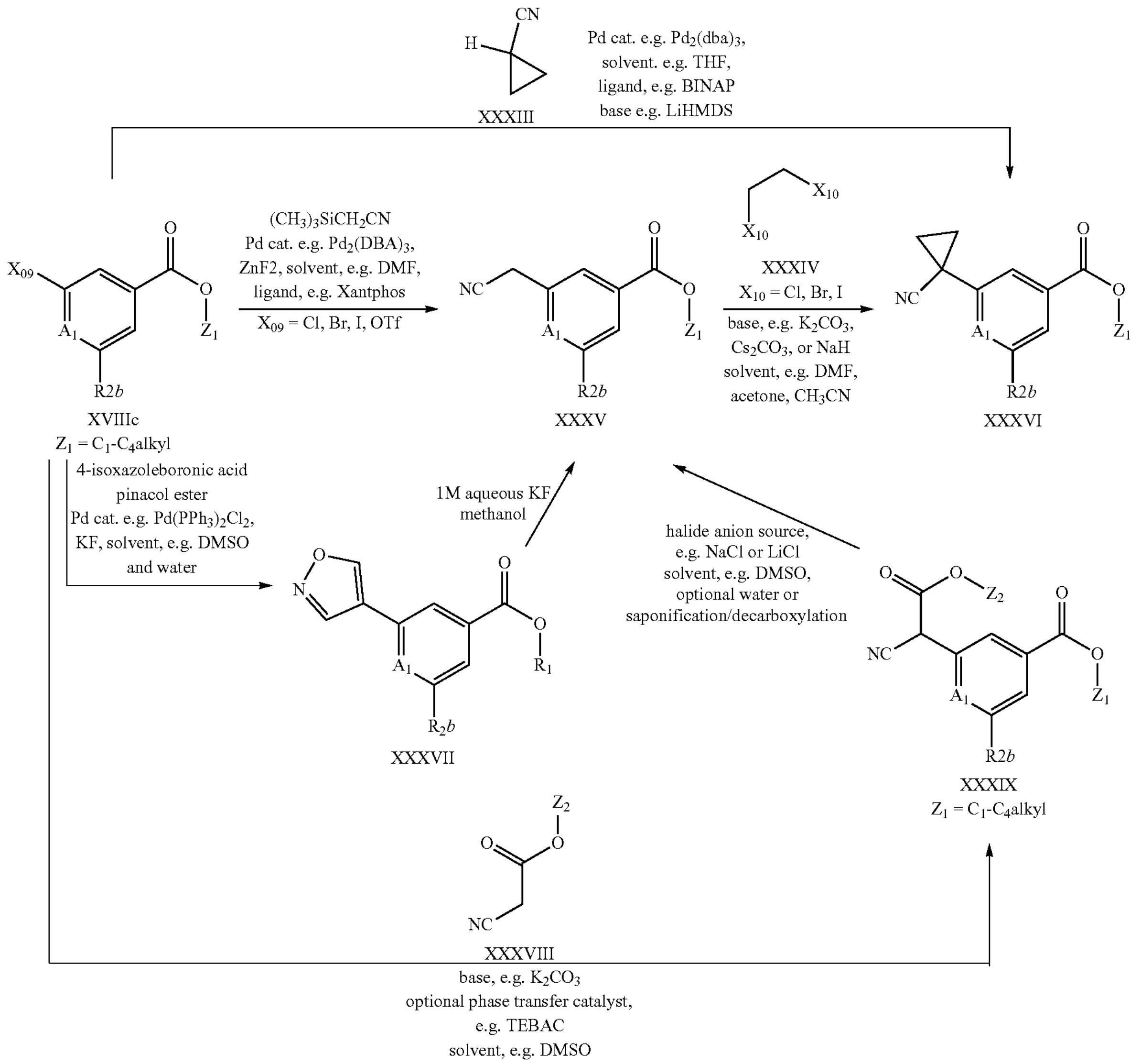

Treatment of compounds of formula XVIIIc, wherein $R_{2b}$ and $A_1$ are as defined in formula I, $X_{05}$ is a leaving group, for example a halogen or a sulfonate, preferably chlorine, bromine, iodine or trifluoromethanesulfonate, and $Z_1$ is $C_1$-$C_4$alkyl, with trimethylsilyl-acetonitrile TMSCN, in the presence of zinc(II)fluoride ($ZnF_2$), and a palladium(0) catalyst such as tris(dibenzylideneacetone)di-palladium(0)-chloroform adduct ($Pd_2(dba)_3$ $CHCl_3$), with a ligand, for example Xantphos, in an inert solvent, such as N,N-dimethylformamide (DMF) at temperatures between 100-180° C., optionally under microwave heating, leads to compounds of formula XXXV, wherein $R_{2b}$, $Z_1$ and $A_1$ are as defined in formula XVIIIc. Such chemistry has been described in the literature, e.g. in Org. Lett. 16(24), 6314-6317, 2014. Alternatively, reaction of compounds of formula XVIIIc, with 4-isoxazoleboronic acid or 4-isoxazoleboronic acid pinacol ester, in the presence of potassium fluoride (KF), and a palladium catalyst such as bis(triphenylphosphine)palladium(II) dichloride ($Pd(PPh_3)_2Cl_2$), in an inert solvent, such as dimethylsulfoxide DMSO, optionally in mixture with water, at temperatures between 40-150° C., optionally under microwave heating, leads to compounds of formula XXXVII, wherein $R_{2b}$, $A_1$ are as defined in formula I and $Z_1$ is $C_1$-$C_4$alkyl. Reaction of compounds of formula XXXVII with aqueous potassium fluoride (KF concentration between 0.5 and 3M, preferably 1M), in an inert solvent, such as dimethylsulfoxide DMSO or methanol, at temperatures between 20-150° C., optionally under microwave heating, leads to compounds of formula XXXV, wherein $R_{2b}$, $Z_1$ and $A_1$ are as defined in formula XVIIIc. Such chemistry has been described in the literature, e.g. in J. Am. Chem. Soc. 2011, 133, 6948-6951.

Compounds of formula XXXV, wherein $R_{2b}$ and $A_1$ are as defined in formula I and $Z_1$ is $C_1$-$C_4$alkyl, can be further treated with compounds of formula XXXIV, in which $X_{10}$ is a leaving group, such as a halogen (preferably chlorine, bromine or iodine), in the presence of a base such as sodium hydride, sodium carbonate, potassium carbonate $K_2CO_3$, or cesium carbonate $Cs_2CO_3$, in an inert solvent such as N,N-dimethylformamide (DMF), acetone, or acetonitrile, at temperatures between 0-120° C., to give compounds of formula XXXVI, wherein $R_{2b}$, and $A_1$ are as defined in formula I above and $Z_1$ is $C_1$-$C_4$alkyl. Alternatively, compounds of formula XXXVI can be prepared directly from compounds of formula XVIIIc by treatment with compounds of formula XXXVIII, in presence of a catalyst such as $Pd_2(dba)_3$, with a ligand, such as BINAP, a strong base such as lithium hexamethyldisilazane (LiHMDS), in an inert solvent such as tetrahydrofuran (THF), at temperatures between 30-80° C. Such chemistry has been described in, for example, J. Am. Chem. Soc. 127(45), 15824-15832, 2005.

Yet another method to prepare compounds of formula XXXV from compounds of formula XVIIIc is shown in Scheme 13. Reaction of compounds of formula XVIIIc, wherein $R_{2b}$, and $A_1$ are as defined in formula I, $Z_1$ is $C_1$-$C_4$alkyl and $X_{09}$ is a leaving group, for example a halogen or a sulfonate, preferably chlorine, bromine, iodine or trifluoromethanesulfonate, with reagents of the formula XXXVIII, wherein $Z_2$ is $C_1$-$C_4$alkyl, in the presence of a base, such as sodium carbonate, potassium carbonate or cesium carbonate, or sodium hydride, sodium methoxide or ethoxide, potassium tert-butoxide, optionally under palladium (for example involving $Pd(PPh_3)_2Cl_2$) or copper (for example involving CuI) catalysis, in an appropriate solvent such as for example toluene, dioxane, tetrahydrofuran, acetonitrile, N,N-dimethylformamide, N,N-dimethylacetamide, N-methyl-2-pyrrolidone (NMP) or dimethylsulfoxide (DMSO), optionally in presence of a phase transfer catalyst PTC, such as for example tetrabutyl ammonium bromide or triethyl benzyl ammonium chloride TEBAC, at temperatures between room temperature and 180° C., gives compounds of formula XXXIX, wherein $R_{2b}$, and $A_1$ are as defined in formula land $Z_1$ and $Z_2$ are each $C_1$-$C_4$alkyl. Compounds of formula XXXIX can be decarboxylated using conditions such as heating in moist DMSO optionally in the presence of lithium or sodium chloride at temperatures between 50° C. and 180° C. to afford compounds of formula XXXV. Similar chemistry has been described in, for example, Synthesis 2010, No. 19, 3332-3338.

Compounds of formula I'a

I'a

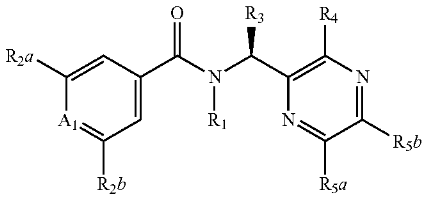

can be prepared by reaction of an amine of formula IIb

IIb

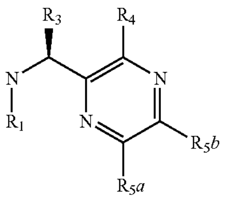

wherein $R_1$, $R_3$, $A_2$, $R_4$, $R_{5a}$, and $R_{5b}$ are as described in formula I, with a carboxylic acid derivative of formula III wherein $A_1$, $R_{2a}$ and $R_{2b}$ are described as above under formula I.

III

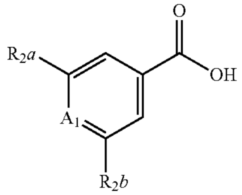

The chemistry is described in in more detail in Scheme 14.

Scheme 14

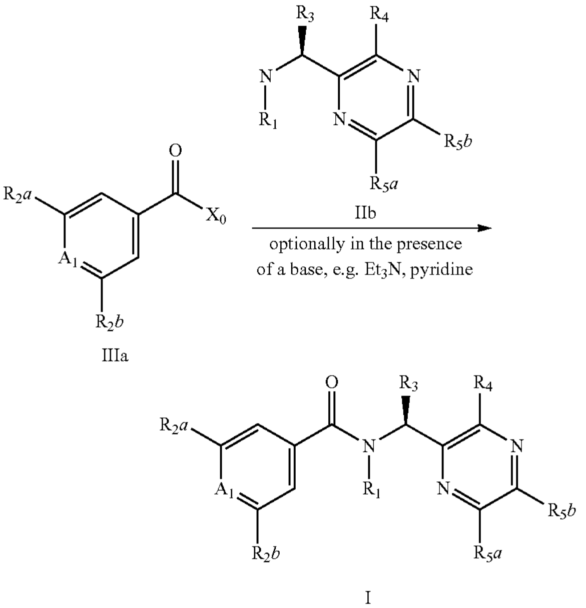

IIb

IIIa

I

Compounds of formula IIIa, wherein $A_1$, $R_{2a}$, $R_{2b}$ and $X_0$ are described in Scheme 1, can be treated with compounds of formula IIb, wherein $R_1$, $R_3$, $R_4$, $R_{5a}$, and $R_{5b}$ are described in formula I, under the conditions described in detail in Scheme 1. The formation of compounds of formula IIIa from compounds of formula III is described in Scheme 1.

The formation of compounds of formula IIb is outlined in Scheme 15. Compounds of formula IIb can be prepared by treatment of compounds of formula IIc, wherein $R_3$, $R_4$, $R_{5a}$, and $R_{5b}$ are as described in formula I, with compounds of formula XL (wherein $R_1$ is as defined in formula I), e.g. in the presence of $NaBH(OAc)_3$ or $NaBH_3CN$, in a suitable solvent, preferably in acetic acid at room temperature analog to WO2002/088073, page 35. Alternatively, another reagent system for the reductive amination uses a combination of $Ti(i\text{-}OiPr)_4$ and $NaBH_4$ (see Synthesis 2003 (14), 2206).

Amines of formula IIc may be obtained by biocatalyzed deracemization of amines of formula IIa. This may be done for instance using a lipase, e.g. *Candida Antarctica* lipase B or *Pseudomonas fluorescens* lipase, eventually in immobilized form (e.g. Novozym® 435) in presence of an acyl donor, e.g. ethyl methoxyacetate or vinyl acetate, in a suitable solvent such as acetonitrile or methyl tert-butyl ether at temperatures between 20° C. to 100° C. Such processes are described for instance in *J. Org. Chem.* 2007, 72, 6918-6923 or *Adv. Synth. Catal.* 2007, 349, 1481-1488. The expected stereochemical outcome of such enzymatic deracemization are known of those skilled in the art and are documented in the literature, for instance in *J. Org. Chem.* 1991, 56, 2656-2665 or *J. Am. Chem. Soc.* 2015, 137, 3996-4009.

Scheme 15

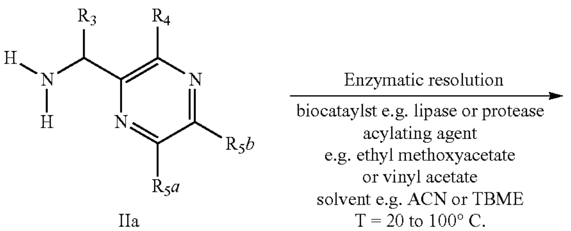

IIa

-continued

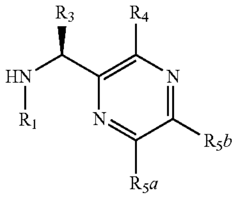

IIb

In an alternative process, compounds of formula IIc can be obtained from XIIa, wherein $R_3$, $R_4$, $R_{5a}$, and $R_{5b}$ are as described in formula I, following the synthesis described in Scheme 16.

Scheme 16

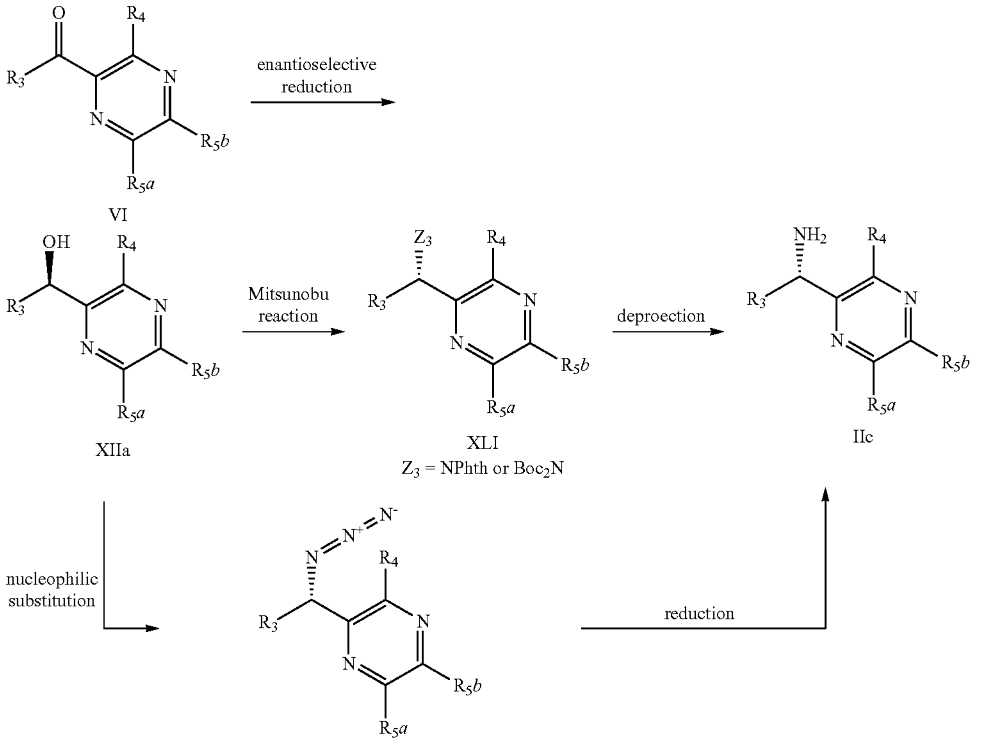

VI

XIIa

XLI $Z_3$ = NPhth or $Boc_2N$

IIc

XLII

-continued

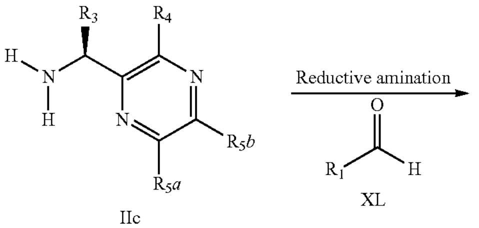

IIc

XL

Amines of formula IIc may be obtained from intermediates of formula XLI, wherein $R_3$, $R_4$, $R_{5a}$, and $R_{5b}$ are as described in formula I and $Z_3$ is NPhth or $NBoc_2$. Such intermediates can be obtained from alcohols of formula XIIa by a Mitsunobu reaction, which involves treating alcohols of formula XIIa by diisopropyl azodicarboxylate in the presence of a phosphine such as triphenylphosphine or tributylphosphine and of an amine such as phthalimide or bis(tert-butoxycarbonyl)amine. Mitsunobu reactions are known by those skilled in the art to proceed with inversion of the stereocenter, as described for instance in Chem. Rev.

2009, 109, 2551-2651. Amines of formula XLI can then be transformed into amines of formula IIc by treatment with hydrazine if $Z_3$=NPhth or with TFA if $Z_3$=$NBoc_2$.

Alternatively, amines of formula IIc may be obtained by reduction of azides of formula XLII, wherein $R_3$, $R_4$, $R_{5a}$, and $R_{5b}$ are as described in formula I, by treatment with triphenylphosphine and water (Staudinger reaction) or by hydrogenation for example using a palladium catalyst in the presence of hydrogen. Azides of formula XLII may be obtained by treatment of alcohols of formula XIIa, wherein $R_3$, $R_4$, $R_{5a}$, and $R_{5b}$ are as described in formula I, with an azidation reagent such as diphenyl phosphoryl azide in a solvent such as toluene or THE in presence of a base such as DBU. Such processes are known by those skilled in the art to proceed with inversion of the stereocenter and are described in the literature for instance in *Adv. Synth. Catal.* 2018, 360, 2157-2165.

Alcohols of formula XIIa may be obtained by enantioselective reduction of ketones of formula VI, wherein $R_3$, $R_4$, $R_{5a}$, and $R_{5b}$ are as described in formula I. Such reductions can be done using a catalyst, for instance a ruthenium or a rhodium catalyst with a chiral ligand such as RuCl[(R,R)-TsDPEN](mesitylene) or $RuBF_4$[(R,R)-TsDPEN](p-cymene) in the presence of a hydrogen donor system such as for example $HCOOH/Et_3N$ or $HCO_2NH_4$. Such processes are described in the literature for instance in J. Org. Chem. 2017, 82, 5607.

Alternatively, compounds of formula IIc may also be prepared as outlined in Scheme 17.

Amines of formula IIc can be prepared by deprotection of amines of formula XLIX, wherein $R_3$, $R_4$, $R_{5a}$, and $R_{5b}$ are as described in formula I, for instance using an acid such as trifluoroacetic acid or hydrochloric acid. Amines of formula XLIX can be obtained from amines of formula XLVIII, wherein $R_3$, $R_4$ are described in formula I and $Z_{5a}$ and $Z_{5b}$ are, independently of each other, selected from $R_{5a}$, $R_{5b}$, halogen, $NH_2$ or OH. Such functional group interconversions are known to those skilled in the art and examples of such transformations have been described in the literature, for instance in *Eur. J. Org. Chem.* 2005, 19, 4141-4153 or in *J. Org. Chem.* 2008, 73, 7481-7485. Amines of formula XLVIII can be obtained by condensation of diamines of formula XLVII, wherein Z5a and Z5b are, independently of each other, selected from R5a, R5b, halogen, NH2 or OH, on diketones of formula XLVI, wherein $R_3$ and $R_4$ are as described in formula I. This condensation can take place in the presence of a suitable solvent such as ethanol or isopropanol in presence of an oxidant such as air or DDQ. Diketones of formula XLVI may be formed by oxidation of hydroxyketones of formula XLIV wherein $R_3$ and $R_4$ are as described in formula I. This oxidation can involve for instance $SO_3$-pyridine in presence of DMSO and a base, for instance triethylamine or alternatively sodium hypochlorite in presence of a catalyst such as $TEMPO/Bu_4NHSO_4$. Examples of such oxidations can be found in the literature, for instance in *Synlett,* 2014, 25, 596 or *J. Am. Chem. Soc.* 1990, 112, 5290-5313. Hydroxyketones of formula XLIV may be synthesized by cross-benzoin condensation between Scheme 17

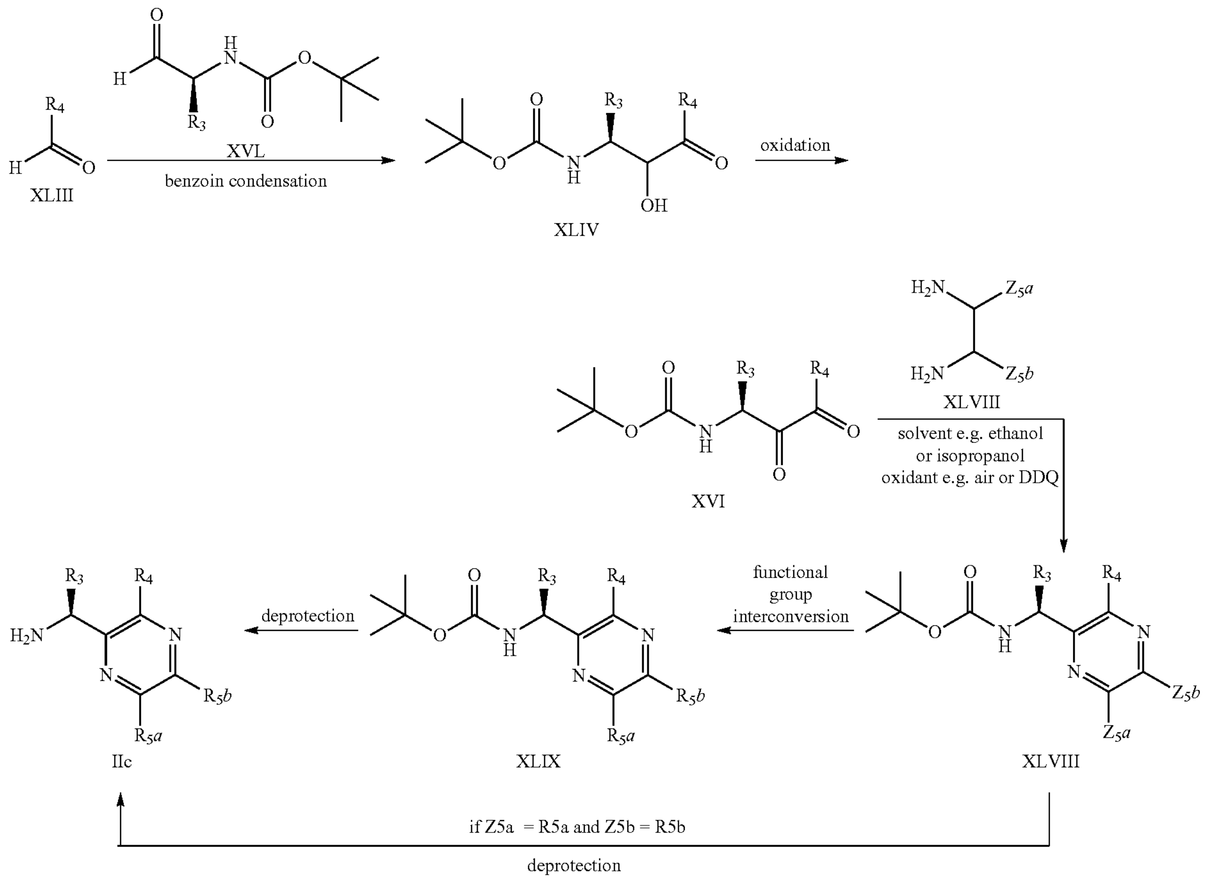

aldehydes of formula XLIII, wherein $R_4$ is described in formula I, and aldehydes of formula XLV, wherein $R_3$ is described in formula I. Aldehydes of formula XLV are commercially available in chiral form, like for instance Boc-L-alaninal (CAS 79069-50-4) or tert-butyl N-[(1S)-1-(cyclopropylmethyl)-2-oxo-ethyl]carbamate (CAS 881902-36-9). Cross-benzoin condensations are done in the usual way by employing an organocatalyst such as a triazolium salt or a thiazolium salt in the presence of a base such as potassium tert-butoxide or isopropyldiethylamine in a suitable solvent such as dichloromethane or tetrahydrofuran at a temperature between −20° C. and the boiling point of the solvent. Examples of catalysts for such transformations have been described in the literature for instance in *J. Am. Chem. Soc.* 2014, 136, 7539-7542 or in Org. Lett. 2016, 18, 4518-4521.

Alternatively, compounds of formula I'a can be prepared from chiral compounds of formula L, wherein $A_1$, $R_1$, $R_{2a}$, $R_{2b}$, $R_3$, $R_{5a}$, and $R_{5b}$ are defined in formula I, and $X_{05}$ is a leaving group like, for example, chlorine, bromine or iodine, as shown in Scheme 18.

Compounds of formula I'a can be prepared by reaction of compounds of formula L with compounds of formula V (Stille reaction) or compounds of formula VIII (Suzuki-Miyaura reaction) in the presence of a palladium catalyst as described in detail in Schemes 2 and 3.

Compounds of formula L can be prepared by coupling of amines of formula LIa (wherein $R_1$, $R_3$, $R_{5a}$, and $R_{5b}$ are defined in formula I, and $X_{05}$ is a leaving group like, for example, chlorine, bromine, iodine) and compounds of formula IIIa, wherein $A_1$, $R_{2a}$, $R_{2b}$ and $X_0$ are described in Scheme 1, under the conditions described in detail in Scheme 1. Under the same conditions, if $R_1$=H, compounds of formula L may be obtained directly from compounds of formula LI, wherein R1, R3, R5a, and R5b are defined in formula I, and X05 is a leaving group like, for example, chlorine, bromine, iodine.

Compounds of formula LIa can be prepared by treatment of compounds of formula LI, with compounds of formula XL (wherein $R_1$ is as defined in formula I), e.g. in the presence of $NaBH(OAc)_3$ or $NaBH_3CN$, in a suitable solvent, preferably in acetic acid at room temperature analog to Scheme 18

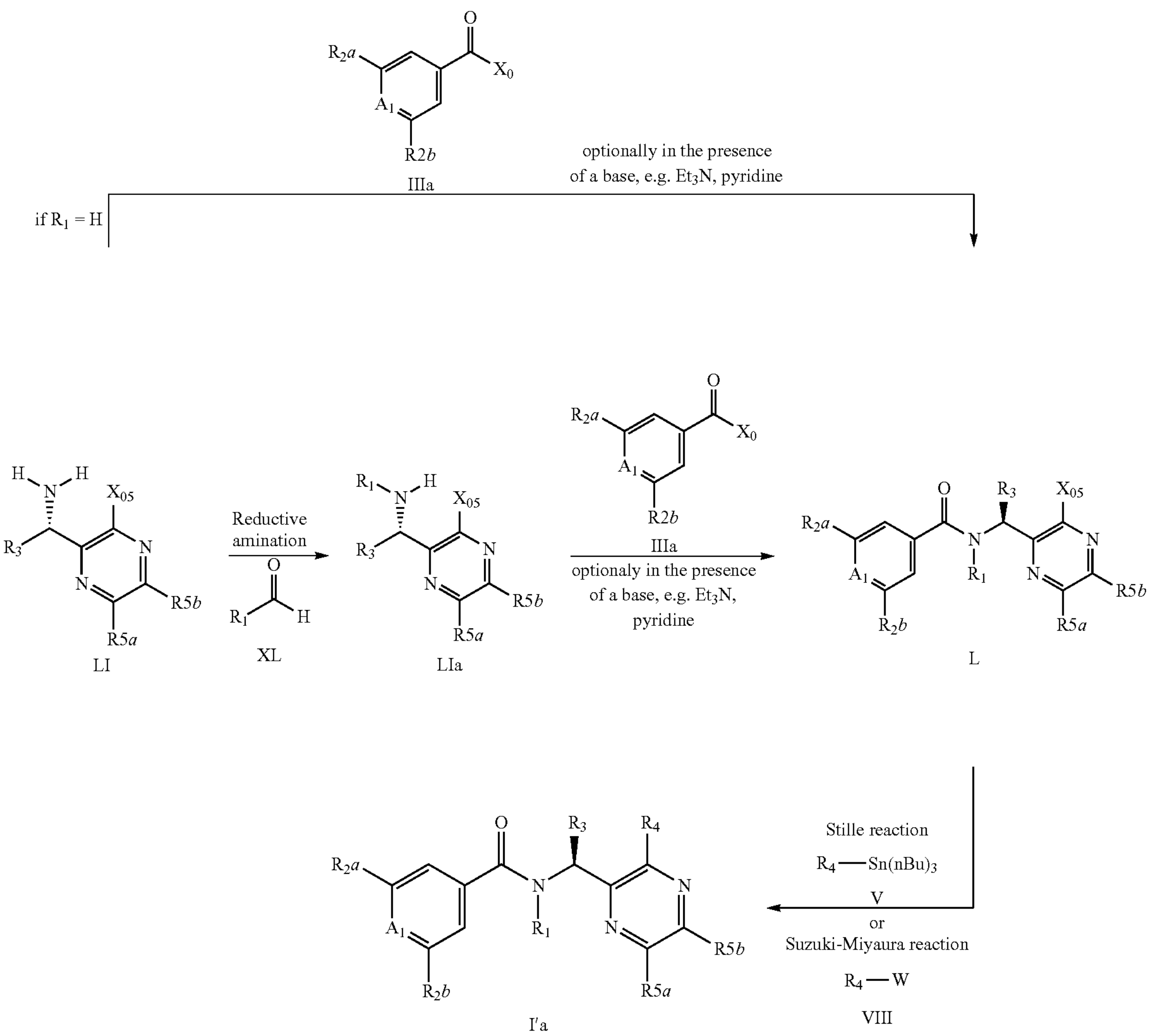

$X_{05}$= Cl, Br, I, OMs, OTs, OTf

WO2002/088073, page 35. Alternatively, another reagent system for the reductive amination uses a combination of $Ti(OiPr)_4$ and $NaBH_4$ (see *Synthesis* 2003 (14), 2206).

Amines of formula LI can be prepared by deracemization procedure method, which involves for example, a selective acylation of one enantiomer. Such an example is described more in details in Scheme 19.

Scheme 19

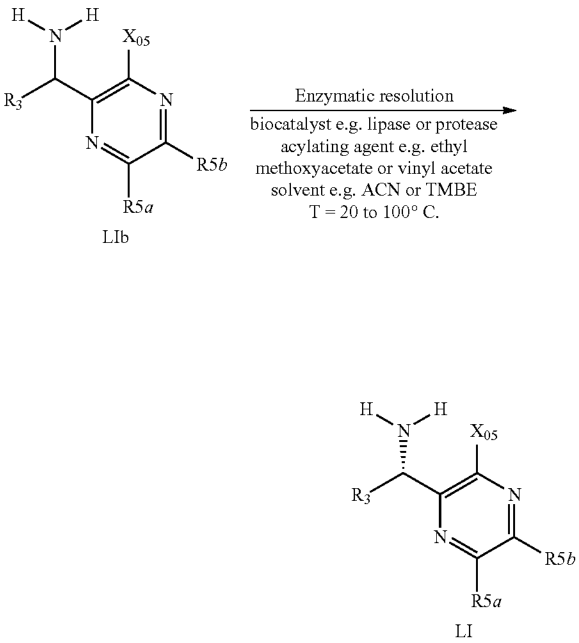

LIb

LI $X_{05}$ = Cl, Br, I, OMs, ITs or OTf

Amines of formula LI may be obtained by biocatalyzed deracemization of amines of formula LIb, wherein $R_3$, $R_{5a}$, and $R_{5b}$ are described in Scheme 1 and $X_{05}$ is a leaving group such as bromine, chlorine, iodine, mesylate, tosylate or triflate. This may be done for instance using a lipase, e.g. *Candida Antarctica* lipase B or *Pseudomonas fluorescens* lipase, eventually in immobilized form (e.g. Novozym® 435) in presence of an acyl donor, e.g. ethyl methoxyacetate or vinyl acetate, in a suitable solvent such as acetonitrile or methyl tert-butyl ether at temperatures between 20° C. to 100° C. Such processes are described for instance in *J. Org. Chem.* 2007, 72, 6918-6923 or *Adv. Synth. Catal.* 2007, 349, 1481-1488. The expected stereochemical outcome of such enzymatic deracemization are known of those skilled in the art and are documented in the literature, for instance in *J. Org. Chem.* 1991, 56, 2656-2665 or *J. Am. Chem. Soc.* 2015, 137, 3996-4009.

Alternatively, resolution of amines of formula LIb may be achieved using a chiral auxiliary, as described in Scheme 20.

Scheme 20

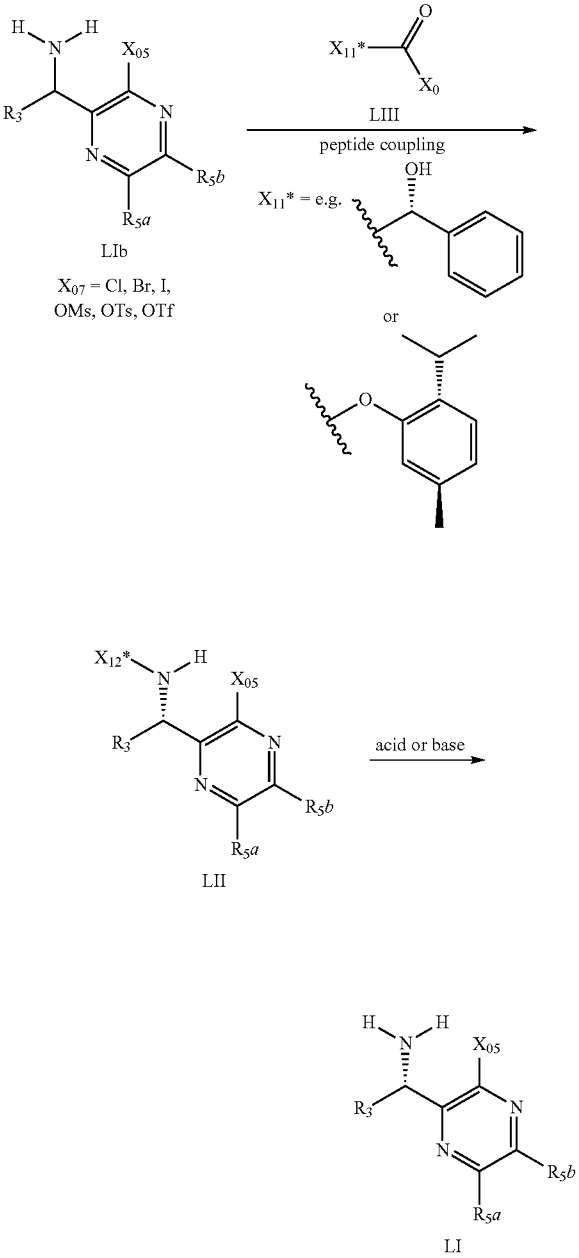

LIb $X_{07}$ = Cl, Br, I, OMs, OTs, OTf

LII

LI

Amines of formula LI can be prepared from intermediates of formula LII, wherein $R_3$, $R_{5a}$, and $R_{5b}$ are described in Scheme 1, $X_{05}$ is a leaving group such as bromine, chlorine, iodine, mesylate, tosylate or triflate and $X_{11}$* is a chiral auxiliary, by treatment with acids such as HCl or bases such as NaOH. Amines of formula LII can be formed by coupling of a chiral compound of formula LIII, wherein $X_0$ is described in Scheme 1 and $X_{11}$* is a chiral moiety of known chirality, with amines of formula LIb following the conditions detailed in Scheme 1. Chiral auxiliaries of formula LIII are for instance derived from mandelic acid or (1R)-menthylchloroformate. Examples of such deracemization are reported in the literature for instance in *J. Org. Chem.* 2007, 72, 485-493.

Alternatively, amines of formula LI can be formed as described in Scheme 21.

Scheme 21

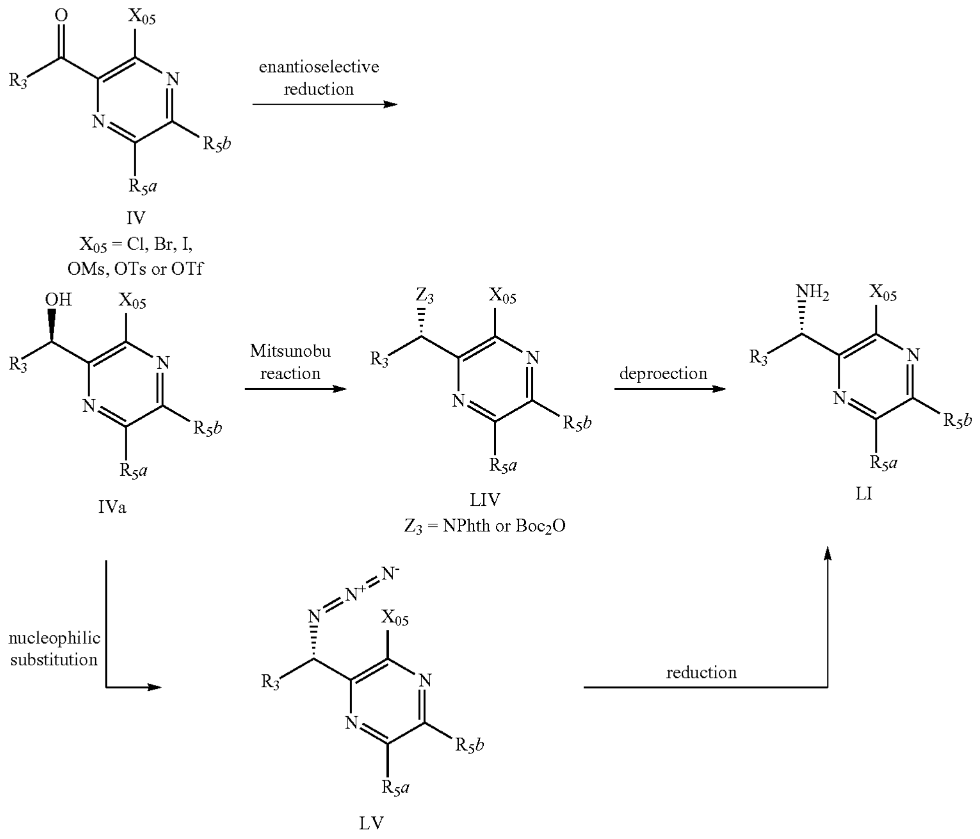

IV
$X_{05}$ = Cl, Br, I,
OMs, OTs or OTf
IVa
LIV
$Z_3$ = NPhth or $Boc_2O$
LI
LV Amines of formula LI may be obtained from intermediates of formula LIV, wherein $R_3$, $R_{5a}$, and $R_{5b}$ are as described in formula I, $X_{05}$ is a leaving group as described in Scheme 3 and $Z_3$ is NPhth or $NBoc_2$. Such intermediates can be obtained from alcohols of formula IVa, wherein $R_3$, $R_{5a}$, and $R_{5b}$ are as described in formula I and $X_{05}$ is a leaving group as described in Scheme 3, by a Mitsunobu reaction, which involves treating alcohols of formula IVa by diisopropyl azodicarboxylate in the presence of a phosphine such as triphenylphosphine or tributylphosphine and of an amine such as phthalimide or bis(tert-butoxycarbonyl) amine. Mitsunobu reactions are known by those skilled in the art to proceed with inversion of the stereocenter, as described for instance in *Chem. Rev.* 2009, 109, 2551-2651. Amines of formula LIV can then be transformed into amines of formula LI by treatment with hydrazine if $Z_3$=NPhth or with TFA if $Z_3$=$NBoc_2$.

Alternatively, amines of formula LI may be obtained by reduction of azides of formula LV, wherein $R_3$, $R_{5a}$, and $R_{5b}$ are as described in formula I and $X_{05}$ is a leaving group as described in Scheme 3, by treatment with triphenylphosphine and water (Staudinger reaction) or by hydrogenation for example using a palladium catalyst in the presence of hydrogen. Azides of formula LV may be obtained by treatment of alcohols of formula IVa with an azidation reagent such as diphenyl phosphoryl azide in a solvent such as toluene or THE in presence of a base such as DBU. Such processes are known by those skilled in the art to proceed with inversion of the stereocenter and are described in the literature for instance in Adv. Synth. Catal. 2018, 360, 2157-2165.

Alcohols of formula IVa may be obtained by enantioselective reduction of ketones of formula IV, wherein $R_3$, $R_{5a}$, and $R_{5b}$ are as described in formula I and $X_{05}$ is a leaving group as described in Scheme 3. Such reductions can be done using catalysts, for instance a ruthenium or a rhodium catalyst with a chiral ligand such as RuCl[(R,R)-TsDPEN](mesitylene) or $RuBF_4$[(R,R)-TsDPEN](p-cymene) in the presence of a hydrogen donor system such as for example $HCOOH/Et_3N$ or $HCO_2NH_4$. Such processes are described in the literature for instance in *J. Org. Chem.* 2017, 82, 5607.

Depending on the procedure or the reaction conditions, the reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo [5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reactions are advantageously carried out in a temperature range from approximately −80° C. to approximately +140° C., preferably from approximately −30° C. to approximately +100° C., in many cases in the range between ambient temperature and approximately +80° C.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties can be obtained in free form or in the form of salts.

The compounds of formula I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from *J. Med. Chem.*, 32 (12), 2561-73, 1989 or WO 2000/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds of formula I according to the following Tables A-1 to A-21 can be prepared according to the methods described above. The examples which follow are intended to illustrate the invention and show preferred compounds of formula I, in the form of a compound of formula Iaa.

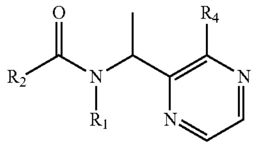

Iaa

TABLE A-1
| |
|---|
| provides 16 compounds A-1.001 to A-1.016 of formula Iaa wherein $R_1$ is H, $R_4$ is (5-bromopyrimidin-2-yl) and $R_2$ is as defined in table Z. For example, A-1.002 is |
| 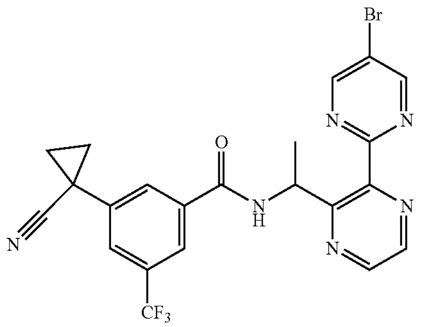 [SMILES: CC(NC(=O)c1cc(C(F)(F)F)cc(C2(C#N)CC2)c1)c1nccnc1-c1ncc(Br)cn1] I |
TABLE Z
| Substituent definitions of $R_2$: | |
|---|---|
| Index | $R_2$ |
| 1 | 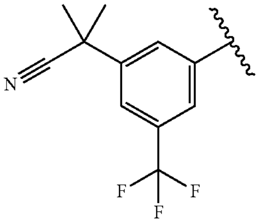 [SMILES: *c1cc(C(F)(F)F)cc(C(C)(C)C#N)c1] |
| 2 | 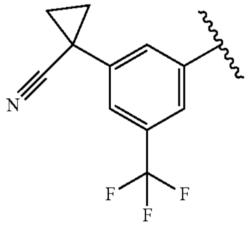 [SMILES: *c1cc(C(F)(F)F)cc(C2(C#N)CC2)c1] |
| 3 | 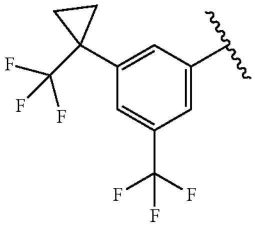 [SMILES: *c1cc(C(F)(F)F)cc(C2(C(F)(F)F)CC2)c1] |
| 4 | 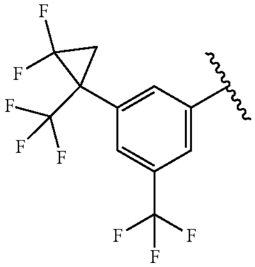 [SMILES: *c1cc(C(F)(F)F)cc(C2(C(F)(F)F)CC2(F)F)c1] |
TABLE Z-continued
| Substituent definitions of $R_2$: | |
|---|---|
| Index | $R_2$ |
| 5 | 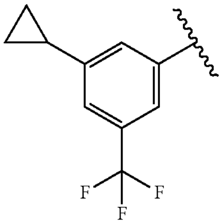 [SMILES: *c1cc(C2CC2)cc(C(F)(F)F)c1] |
| 6 | 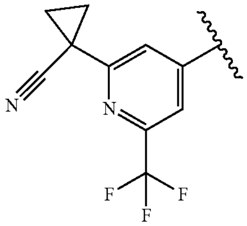 [SMILES: *c1cc(C(F)(F)F)nc(C2(C#N)CC2)c1] |
| 7 | 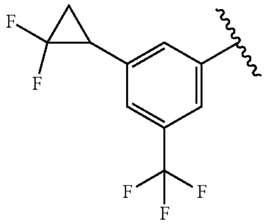 [SMILES: *c1cc(C2CC2(F)F)cc(C(F)(F)F)c1] |
| 8 | 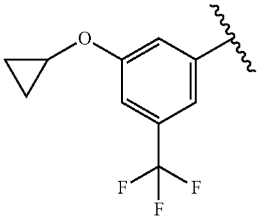 [SMILES: *c1cc(OC2CC2)cc(C(F)(F)F)c1] |
| 9 | 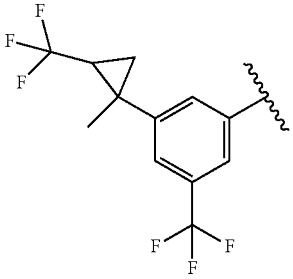 [SMILES: *c1cc(C(F)(F)F)cc(C2(C)CC2C(F)(F)F)c1] |
| 10 | 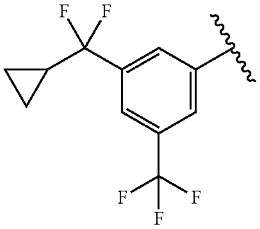 [SMILES: *c1cc(C(F)(F)F)cc(C(F)(F)C2CC2)c1] |

TABLE Z-continued

| Substituent definitions of $R_2$: | |
|---|---|
| Index | $R_2$ |
| 11 | 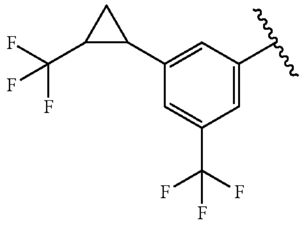 [SMILES: *c1cc(C2CC2C(F)(F)F)cc(C(F)(F)F)c1] |
| 12 | 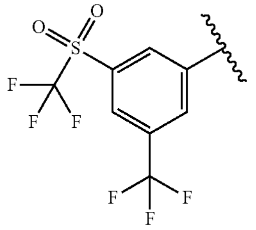 [SMILES: *c1cc(C(F)(F)F)cc(S(=O)(=O)C(F)(F)F)c1] |
| 13 | 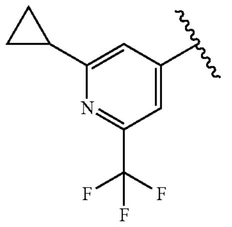 [SMILES: *c1cc(C2CC2)nc(C(F)(F)F)c1] |
| 14 | 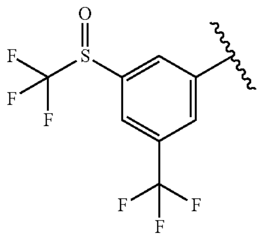 [SMILES: *c1cc(S(=O)C(F)(F)F)cc(C(F)(F)F)c1] |
| 15 | 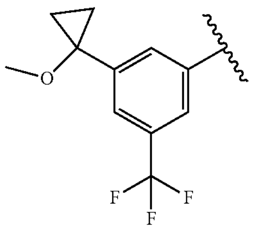 [SMILES: *c1cc(C(F)(F)F)cc(C2(OC)CC2)c1] |
| 16 | 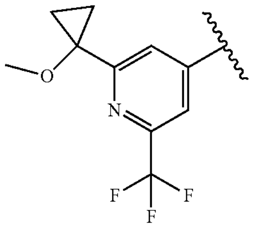 [SMILES: *c1cc(C(F)(F)F)nc(C2(OC)CC2)c1] |

Table A-2 provides 16 compounds A-2.001 to A-2.016 of formula Iaa wherein $R_1$ is H, $R_4$ is (5-fluoropyrimidin-2-yl) and $R_2$ is as defined in table Z.

Table A-3 provides 16 compounds A-3.001 to A-3.016 of formula Iaa wherein $R_1$ is H, $R_4$ is pyrimidin-2-yl and $R_2$ is as defined in table Z.

Table A-4 provides 16 compounds A-4.001 to A-4.016 of formula Iaa wherein $R_1$ is H, $R_4$ is (5-cyclopropylpyrimidin-2-yl) and $R_2$ is as defined in table Z.

Table A-5 provides 16 compounds A-5.001 to A-5.016 of formula Iaa wherein $R_1$ is H, $R_4$ is (5-bromo-2-pyridyl) and $R_2$ is as defined in table Z.

Table A-6 provides 16 compounds A-6.001 to A-6.016 of formula Iaa wherein $R_1$ is H, $R_4$ is (5-fluoro-2-pyridyl) and $R_2$ is as defined in table Z.

Table A-7 provides 16 compounds A-7.001 to A-7.016 of formula Iaa wherein $R_1$ is H, $R_4$ is 2-pyridyl and $R_2$ is as defined in table Z.

Table A-8 provides 16 compounds A-8.001 to A-8.016 of formula Iaa wherein $R_1$ is $CH_3$, $R_4$ is (5-bromopyrimidin-2-yl) and $R_2$ is as defined in table Z.

Table A-9 provides 16 compounds A-9.001 to A-9.016 of formula Iaa wherein $R_1$ is $CH_3$, $R_4$ is (5-fluoropyrimidin-2-yl) and $R_2$ is as defined in table Z.

Table A-10 provides 16 compounds A-10.001 to A-10.016 of formula Iaa wherein $R_1$ is $CH_3$, $R_4$ is pyrimidin-2-yl and $R_2$ is as defined in table Z.

Table A-11 provides 16 compounds A-11.001 to A-11.016 of formula Iaa wherein $R_1$ is $CH_3$, $R_4$ is (5-cyclopropylpyrimidin-2-yl) and $R_2$ is as defined in table Z.

Table A-12 provides 16 compounds A-12.001 to A-12.016 of formula Iaa wherein $R_1$ is $CH_3$, $R_4$ is (5-bromo-2-pyridyl) and $R_2$ is as defined in table Z.

Table A-13 provides 16 compounds A-13.001 to A-13.016 of formula Iaa wherein $R_1$ is $CH_3$, $R_4$ is (5-fluoro-2-pyridyl) and $R_2$ is as defined in table Z.

Table A-14 provides 16 compounds A-14.001 to A-14.016 of formula Iaa wherein $R_1$ is $CH_3$, $R_4$ is 2-pyridyl and $R_2$ is as defined in table Z.

Table A-15 provides 16 compounds A-15.001 to A-15.016 of formula Iaa wherein $R_1$ is $CH_2Cyp$, $R_4$ is (5-bromopyrimidin-2-yl) and $R_2$ is as defined in table Z.

Table A-16 provides 16 compounds A-16.001 to A-16.016 of formula Iaa wherein $R_1$ is $CH_2Cyp$, $R_4$ is (5-fluoropyrimidin-2-yl) and $R_2$ is as defined in table Z.

Table A-17 provides 16 compounds A-17.001 to A-17.016 of formula Iaa wherein $R_1$ is $CH_2Cyp$, $R_4$ is pyrimidin-2-yl and $R_2$ is as defined in table Z.

Table A-18 provides 16 compounds A-18.001 to A-18.016 of formula Iaa wherein $R_1$ is $CH_2Cyp$, $R_4$ is (5-cyclopropylpyrimidin-2-yl) and $R_2$ is as defined in table Z.

Table A-19 provides 16 compounds A-19.001 to A-19.016 of formula Iaa wherein $R_1$ is $CH_2Cyp$, $R_4$ is (5-bromo-2-pyridyl) and $R_2$ is as defined in table Z.

Table A-20 provides 16 compounds A-20.001 to A-20.016 of formula Iaa wherein $R_1$ is $CH_2Cyp$, $R_4$ is (5-fluoro-2-pyridyl) and $R_2$ is as defined in table Z.

Table A-21 provides 16 compounds A-21.001 to A-21.016 of formula Iaa wherein $R_1$ is $CH_2Cyp$, $R_4$ is 2-pyridyl and $R_2$ is as defined in table Z.

The compounds of formula I according to the following Tables B-1 to B-21 can be prepared according to the methods described above. The examples which follow are intended to illustrate the invention and show preferred compounds of formula I, in the form of a compound of formula Iab.

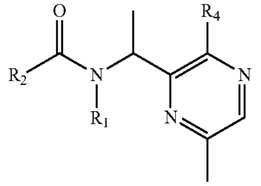

Iab

Table B-1 provides 16 compounds B-1.001 to B-1.016 of formula Iab wherein $R_1$ is H, $R_4$ is (5-bromopyrimidin-2-yl) and $R_2$ is as defined in table Z.

Table B-2 provides 16 compounds B-2.001 to B-2.016 of formula Iab wherein $R_1$ is H, $R_4$ is (5-fluoropyrimidin-2-yl) and $R_2$ is as defined in table Z.

Table B-3 provides 16 compounds B-3.001 to B-3.016 of formula Iab wherein $R_1$ is H, $R_4$ is pyrimidin-2-yl and $R_2$ is as defined in table Z.

Table B-4 provides 16 compounds B-4.001 to B-4.016 of formula Iab wherein $R_1$ is H, $R_4$ is (5-cyclopropylpyrimidin-2-yl) and $R_2$ is as defined in table Z.

Table B-5 provides 16 compounds B-5.001 to B-5.016 of formula Iab wherein $R_1$ is H, $R_4$ is (5-bromo-2-pyridyl) and $R_2$ is as defined in table Z.

Table B-6 provides 16 compounds B-6.001 to B-6.016 of formula Iab wherein $R_1$ is H, $R_4$ is (5-fluoro-2-pyridyl) and $R_2$ is as defined in table Z.

Table B-7 provides 16 compounds B-7.001 to B-7.016 of formula Iab wherein $R_1$ is H, $R_4$ is 2-pyridyl and $R_2$ is as defined in table Z.

Table B-8 provides 16 compounds B-8.001 to B-8.016 of formula Iab wherein $R_1$ is $CH_3$, $R_4$ is (5-bromopyrimidin-2-yl) and $R_2$ is as defined in table Z.

Table B-9 provides 16 compounds B-9.001 to B-9.016 of formula Iab wherein $R_1$ is $CH_3$, $R_4$ is (5-fluoropyrimidin-2-yl) and $R_2$ is as defined in table Z.

Table B-10 provides 16 compounds B-10.001 to B-10.016 of formula Iab wherein $R_1$ is $CH_3$, $R_4$ is pyrimidin-2-yl and $R_2$ is as defined in table Z.

Table B-11 provides 16 compounds B-11.001 to B-11.016 of formula Iab wherein $R_1$ is $CH_3$, $R_4$ is (5-cyclopropylpyrimidin-2-yl) and $R_2$ is as defined in table Z.

Table B-12 provides 16 compounds B-12.001 to B-12.016 of formula Iab wherein $R_1$ is $CH_3$, $R_4$ is (5-bromo-2-pyridyl) and $R_2$ is as defined in table Z.

Table B-13 provides 16 compounds B-13.001 to B-13.016 of formula Iab wherein $R_1$ is $CH_3$, $R_4$ is (5-fluoro-2-pyridyl) and $R_2$ is as defined in table Z.

Table B-14 provides 16 compounds B-14.001 to B-14.016 of formula Iab wherein $R_1$ is $CH_3$, $R_4$ is 2-pyridyl and $R_2$ is as defined in table Z.

Table B-15 provides 16 compounds B-15.001 to B-15.016 of formula Iab wherein $R_1$ is $CH_2Cyp$, $R_4$ is (5-bromopyrimidin-2-yl) and $R_2$ is as defined in table Z.

Table B-16 provides 16 compounds B-16.001 to B-16.016 of formula Iab wherein $R_1$ is $CH_2Cyp$, $R_4$ is (5-fluoropyrimidin-2-yl) and $R_2$ is as defined in table Z.

Table B-17 provides 16 compounds B-17.001 to B-17.016 of formula Iab wherein $R_1$ is $CH_2Cyp$, $R_4$ is pyrimidin-2-yl and $R_2$ is as defined in table Z.

Table B-18 provides 16 compounds B-18.001 to B-18.016 of formula Iab wherein $R_1$ is $CH_2Cyp$, $R_4$ is (5-cyclopropylpyrimidin-2-yl) and $R_2$ is as defined in table Z.

Table B-19 provides 16 compounds B-19.001 to B-19.016 of formula Iab wherein $R_1$ is $CH_2Cyp$, $R_4$ is (5-bromo-2-pyridyl) and $R_2$ is as defined in table Z.

Table B-20 provides 16 compounds B-20.001 to B-20.016 of formula Iab wherein $R_1$ is $CH_2Cyp$, $R_4$ is (5-fluoro-2-pyridyl) and $R_2$ is as defined in table Z.

Table B-21 provides 16 compounds B-21.001 to B-21.016 of formula Iab wherein $R_1$ is $CH_2Cyp$, $R_4$ is 2-pyridyl and $R_2$ is as defined in table Z.

The compounds of formula I according to the following Tables C-1 to C-21 can be prepared according to the methods described above. The examples which follow are intended to illustrate the invention and show preferred compounds of formula I, in the form of a compound of formula lac.

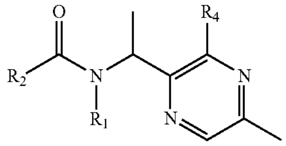

Iac

Table C-1 provides 16 compounds C-1.001 to C-1.016 of formula lac wherein $R_1$ is H, $R_4$ is (5-bromopyrimidin-2-yl) and $R_2$ is as defined in table Z.

Table C-2 provides 16 compounds C-2.001 to C-2.016 of formula lac wherein $R_1$ is H, $R_4$ is (5-fluoropyrimidin-2-yl) and $R_2$ is as defined in table Z.

Table C-3 provides 16 compounds C-3.001 to C-3.016 of formula lac wherein $R_1$ is H, $R_4$ is pyrimidin-2-yl and $R_2$ is as defined in table Z.

Table C-4 provides 16 compounds C-4.001 to C-4.016 of formula lac wherein $R_1$ is H, $R_4$ is (5-cyclopropylpyrimidin-2-yl) and $R_2$ is as defined in table Z.

Table C-5 provides 16 compounds C-5.001 to C-5.016 of formula lac wherein $R_1$ is H, $R_4$ is (5-bromo-2-pyridyl) and $R_2$ is as defined in table Z.

Table C-6 provides 16 compounds C-6.001 to C-6.016 of formula lac wherein $R_1$ is H, $R_4$ is (5-fluoro-2-pyridyl) and $R_2$ is as defined in table Z.

Table C-7 provides 16 compounds C-7.001 to C-7.016 of formula lac wherein $R_1$ is H, $R_4$ is 2-pyridyl and $R_2$ is as defined in table Z.

Table C-8 provides 16 compounds C-8.001 to C-8.016 of formula lac wherein $R_1$ is $CH_3$, $R_4$ is (5-bromopyrimidin-2-yl) and $R_2$ is as defined in table Z.

Table C-9 provides 16 compounds C-9.001 to C-9.016 of formula lac wherein $R_1$ is $CH_3$, $R_4$ is (5-fluoropyrimidin-2-yl) and $R_2$ is as defined in table Z.

Table C-10 provides 16 compounds C-10.001 to C-10.016 of formula lac wherein $R_1$ is $CH_3$, $R_4$ is pyrimidin-2-yl and $R_2$ is as defined in table Z.

Table C-11 provides 16 compounds C-11.001 to C-11.016 of formula lac wherein $R_1$ is $CH_3$, $R_4$ is (5-cyclopropylpyrimidin-2-yl) and $R_2$ is as defined in table Z.

Table C-12 provides 16 compounds C-12.001 to C-12.016 of formula lac wherein $R_1$ is $CH_3$, $R_4$ is (5-bromo-2-pyridyl) and $R_2$ is as defined in table Z.

Table C-13 provides 16 compounds C-13.001 to C-13.016 of formula lac wherein $R_1$ is $CH_3$, $R_4$ is (5-fluoro-2-pyridyl) and $R_2$ is as defined in table Z.

Table C-14 provides 16 compounds C-14.001 to C-14.016 of formula lac wherein $R_1$ is $CH_3$, $R_4$ is 2-pyridyl and $R_2$ is as defined in table Z.

Table C-15 provides 16 compounds C-15.001 to C-15.016 of formula lac wherein $R_1$ is $CH_2Cyp$, $R_4$ is (5-bromopyrimidin-2-yl) and $R_2$ is as defined in table Z.

Table C-16 provides 16 compounds C-16.001 to C-16.016 of formula Iac wherein $R_1$ is $CH_2Cyp$, $R_4$ is (5-fluoropyrimidin-2-yl) and $R_2$ is as defined in table Z.

Table C-17 provides 16 compounds C-17.001 to C-17.016 of formula Iac wherein $R_1$ is $CH_2Cyp$, $R_4$ is pyrimidin-2-yl and $R_2$ is as defined in table Z.

Table C-18 provides 16 compounds C-18.001 to C-18.016 of formula Iac wherein $R_1$ is $CH_2Cyp$, $R_4$ is (5-cyclopropylpyrimidin-2-yl) and $R_2$ is as defined in table Z.

Table C-19 provides 16 compounds C-19.001 to C-19.016 of formula Iac wherein $R_1$ is $CH_2Cyp$, $R_4$ is (5-bromo-2-pyridyl) and $R_2$ is as defined in table Z.

Table C-20 provides 16 compounds C-20.001 to C-20.016 of formula Iac wherein $R_1$ is $CH_2Cyp$, $R_4$ is (5-fluoro-2-pyridyl) and $R_2$ is as defined in table Z.

Table C-21 provides 16 compounds C-21.001 to C-21.016 of formula Iac wherein $R_1$ is $CH_2Cyp$, $R_4$ is 2-pyridyl and $R_2$ is as defined in table Z.

The compounds of formula I according to the following Tables D-1 to D-21 can be prepared according to the methods described above. The examples which follow are intended to illustrate the invention and show preferred compounds of formula I, in the form of a compound of formula Iad.

Iad

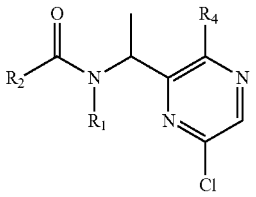

Table D-1 provides 16 compounds D-1.001 to D-1.016 of formula Iad wherein $R_1$ is H, $R_4$ is (5-bromopyrimidin-2-yl) and $R_2$ is as defined in table Z.

Table D-2 provides 16 compounds D-2.001 to D-2.016 of formula Iad wherein $R_1$ is H, $R_4$ is (5-fluoropyrimidin-2-yl) and $R_2$ is as defined in table Z.

Table D-3 provides 16 compounds D-3.001 to D-3.016 of formula Iad wherein $R_1$ is H, $R_4$ is pyrimidin-2-yl and $R_2$ is as defined in table Z.

Table D-4 provides 16 compounds D-4.001 to D-4.016 of formula Iad wherein $R_1$ is H, $R_4$ is (5-cyclopropylpyrimidin-2-yl) and $R_2$ is as defined in table Z.

Table D-5 provides 16 compounds D-5.001 to D-5.016 of formula Iad wherein $R_1$ is H, $R_4$ is (5-bromo-2-pyridyl) and $R_2$ is as defined in table Z.

Table D-6 provides 16 compounds D-6.001 to D-6.016 of formula Iad wherein $R_1$ is H, $R_4$ is (5-fluoro-2-pyridyl) and $R_2$ is as defined in table Z.

Table D-7 provides 16 compounds D-7.001 to D-7.016 of formula Iad wherein $R_1$ is H, $R_4$ is 2-pyridyl and $R_2$ is as defined in table Z.

Table D-8 provides 16 compounds D-8.001 to D-8.016 of formula Iad wherein $R_1$ is $CH_3$, $R_4$ is (5-bromopyrimidin-2-yl) and $R_2$ is as defined in table Z.

Table D-9 provides 16 compounds D-9.001 to D-9.016 of formula Iad wherein $R_1$ is $CH_3$, $R_4$ is (5-fluoropyrimidin-2-yl) and $R_2$ is as defined in table Z.

Table D-10 provides 16 compounds D-10.001 to D-10.016 of formula Iad wherein $R_1$ is $CH_3$, $R_4$ is pyrimidin-2-yl and $R_2$ is as defined in table Z.

Table D-11 provides 16 compounds D-11.001 to D-11.016 of formula Iad wherein $R_1$ is $CH_3$, $R_4$ is (5-cyclopropylpyrimidin-2-yl) and $R_2$ is as defined in table Z.

Table D-12 provides 16 compounds D-12.001 to D-12.016 of formula Iad wherein $R_1$ is $CH_3$, $R_4$ is (5-bromo-2-pyridyl) and $R_2$ is as defined in table Z.

Table D-13 provides 16 compounds D-13.001 to D-13.016 of formula Iad wherein $R_1$ is $CH_3$, $R_4$ is (5-fluoro-2-pyridyl) and $R_2$ is as defined in table Z.

Table D-14 provides 16 compounds D-14.001 to D-14.016 of formula Iad wherein $R_1$ is $CH_3$, $R_4$ is 2-pyridyl and $R_2$ is as defined in table Z.

Table D-15 provides 16 compounds D-15.001 to D-15.016 of formula Iad wherein $R_1$ is $CH_2Cyp$, $R_4$ is (5-bromopyrimidin-2-yl) and $R_2$ is as defined in table Z.

Table D-16 provides 16 compounds D-16.001 to D-16.016 of formula Iad wherein $R_1$ is $CH_2Cyp$, $R_4$ is (5-fluoropyrimidin-2-yl) and $R_2$ is as defined in table Z.

Table D-17 provides 16 compounds D-17.001 to D-17.016 of formula Iad wherein $R_1$ is $CH_2Cyp$, $R_4$ is pyrimidin-2-yl and $R_2$ is as defined in table Z.

Table D-18 provides 16 compounds D-18.001 to D-18.016 of formula Iad wherein $R_1$ is $CH_2Cyp$, $R_4$ is (5-cyclopropylpyrimidin-2-yl) and $R_2$ is as defined in table Z.

Table D-19 provides 16 compounds D-19.001 to D-19.016 of formula Iad wherein $R_1$ is $CH_2Cyp$, $R_4$ is (5-bromo-2-pyridyl) and $R_2$ is as defined in table Z.

Table D-20 provides 16 compounds D-20.001 to D-20.016 of formula Iad wherein $R_1$ is $CH_2Cyp$, $R_4$ is (5-fluoro-2-pyridyl) and $R_2$ is as defined in table Z.

Table D-21 provides 16 compounds D-21.001 to D-21.016 of formula Iad wherein $R_1$ is $CH_2Cyp$, $R_4$ is 2-pyridyl and $R_2$ is as defined in table Z.

The compounds of formula I according to the following Tables E-1 to E-21 can be prepared according to the methods described above. The examples which follow are intended to illustrate the invention and show preferred compounds of formula I, in the form of a compound of formula Iae.

Iae

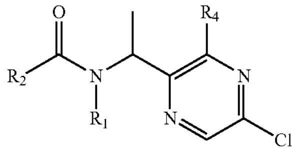

Table E-1 provides 16 compounds E-1.001 to E-1.016 of formula Iae wherein $R_1$ is H, $R_4$ is (5-bromopyrimidin-2-yl) and $R_2$ is as defined in table Z.

Table E-2 provides 16 compounds E-2.001 to E-2.016 of formula Iae wherein $R_1$ is H, $R_4$ is (5-fluoropyrimidin-2-yl) and $R_2$ is as defined in table Z.

Table E-3 provides 16 compounds E-3.001 to E-3.016 of formula Iae wherein $R_1$ is H, $R_4$ is pyrimidin-2-yl and $R_2$ is as defined in table Z Table E-4 provides 16 compounds E-4.001 to E-4.016 of formula Iae wherein $R_1$ is H, $R_4$ is (5-cyclopropylpyrimidin-2-yl) and $R_2$ is as defined in table Z.

Table E-5 provides 16 compounds E-5.001 to E-5.016 of formula Iae wherein $R_1$ is H, $R_4$ is (5-bromo-2-pyridyl) and $R_2$ is as defined in table Z.

Table E-6 provides 16 compounds E-6.001 to E-6.016 of formula Iae wherein $R_1$ is H, $R_4$ is (5-fluoro-2-pyridyl) and $R_2$ is as defined in table Z.

Table E-7 provides 16 compounds E-7.001 to E-7.016 of formula Iae wherein $R_1$ is H, $R_4$ is 2-pyridyl and $R_2$ is as defined in table Z.

Table E-8 provides 16 compounds E-8.001 to E-8.016 of formula Iae wherein $R_1$ is $CH_3$, $R_4$ is (5-bromopyrimidin-2-yl) and $R_2$ is as defined in table Z.

Table E-9 provides 16 compounds E-9.001 to E-9.016 of formula Iae wherein $R_1$ is $CH_3$, $R_4$ is (5-fluoropyrimidin-2-yl) and $R_2$ is as defined in table Z.

Table E-10 provides 16 compounds E-10.001 to E-10.016 of formula Iae wherein $R_1$ is $CH_3$, $R_4$ is pyrimidin-2-yl and $R_2$ is as defined in table Z.

Table E-11 provides 16 compounds E-11.001 to E-11.016 of formula Iae wherein $R_1$ is $CH_3$, $R_4$ is (5-cyclopropylpyrimidin-2-yl) and $R_2$ is as defined in table Z.

Table E-12 provides 16 compounds E-12.001 to E-12.016 of formula Iae wherein $R_1$ is $CH_3$, $R_4$ is (5-bromo-2-pyridyl) and $R_2$ is as defined in table Z.

Table E-13 provides 16 compounds E-13.001 to E-13.016 of formula Iae wherein $R_1$ is $CH_3$, $R_4$ is (5-fluoro-2-pyridyl) and $R_2$ is as defined in table Z.

Table E-14 provides 16 compounds E-14.001 to E-14.016 of formula Iae wherein $R_1$ is $CH_3$, $R_4$ is 2-pyridyl and $R_2$ is as defined in table Z.

Table E-15 provides 16 compounds E-15.001 to E-15.016 of formula Iae wherein $R_1$ is $CH_2Cyp$, $R_4$ is (5-bromopyrimidin-2-yl) and $R_2$ is as defined in table Z.

Table E-16 provides 16 compounds E-16.001 to E-16.016 of formula Iae wherein $R_1$ is $CH_2Cyp$, $R_4$ is (5-fluoropyrimidin-2-yl) and $R_2$ is as defined in table Z.

Table E-17 provides 16 compounds E-17.001 to E-17.016 of formula Iae wherein $R_1$ is $CH_2Cyp$, $R_4$ is pyrimidin-2-yl and $R_2$ is as defined in table Z.

Table E-18 provides 16 compounds E-18.001 to E-18.016 of formula Iae wherein $R_1$ is $CH_2Cyp$, $R_4$ is (5-cyclopropylpyrimidin-2-yl) and $R_2$ is as defined in table Z.

Table E-19 provides 16 compounds E-19.001 to E-19.016 of formula Iae wherein $R_1$ is $CH_2Cyp$, $R_4$ is (5-bromo-2-pyridyl) and $R_2$ is as defined in table Z.

Table E-20 provides 16 compounds E-20.001 to E-20.016 of formula Iae wherein $R_1$ is $CH_2Cyp$, $R_4$ is (5-fluoro-2-pyridyl) and $R_2$ is as defined in table Z.

Table E-21 provides 16 compounds E-21.001 to E-21.016 of formula Iae wherein $R_1$ is $CH_2Cyp$, $R_4$ is 2-pyridyl and $R_2$ is as defined in table Z.

Also made available are certain intermediate compounds of the amine of formulae IIaa to IIae, some of which are novel. The stereogenic centre is indicated with an asterisk in the structures below; and accordingly the invention makes available both racemates and individual enantiomers.

IIaa

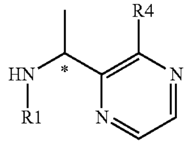

IIab

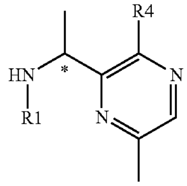

-continued

IIac

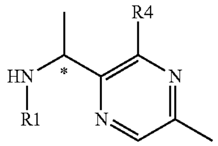

IIad

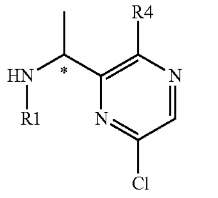

IIae

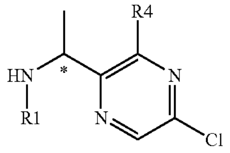

Specific examples of compounds of formula IIaa to IIae are where $R_1$ and $R_4$ are as defined for a compound in Tables A-1 to A-21.

Also made available are compounds of formulae III, IIIa, VI, XII, XLI, XLII, XLIV, XLVI, XLVIII, XLIX, LI, LIa, L, LIV, IV, IVa, LV, XX, XXa, XVIIIa, XVIIIb, XVIIIc, XXI, XXVII, XXVIII, XXIX, XXXI, XXXII, XXXV, XXXVI, XXXVII; and XXXIX wherein, as applicable, the substituents $R_1$, $R_2$ (corresponding to the ring having $R_{2a}$, $R_{2b}$ and $A_1$), $R_3$, $R_{5a}$, $R_{5b}$ and $R_4$, are as defined in any one of compounds in Tables A-1 to A-21, B-1 to B-21, C-1 to C-21, D-1 to D-21 and E-1 to E-21. An especially preferred enantiomer of the compounds of formulae III, IIIa, VI, XII, XLI, XLII, XLIV, XLVI, XLVIII, XLIX, LI, LIa, L, LIV, IV, IVa, LV, XX, XXa, XVIIIa, XVIIIb, XVIIIc, XXI, XXVII, XXVIII, XXIX, XXXI, XXXII, XXXV, XXXVI, XXXVII; and XXXIX, as applicable, is the enantiomer having the same spatial arrangement at the stereogenic centre as depicted in formula I'a or I'-A.

The present invention also makes available

- a compound of formula II, wherein $R_1$, $R_3$, $R_4$, $R_{5a}$, and $R_{5b}$ are as defined for formula I; accordingly preferred embodiments of $R_1$, $R_3$, $R_4$, $R_{5a}$, and $R_{5b}$ for a compound of formula I are likewise preferred embodiments of $R_1$, $R_3$, $R_4$, $R_{5a}$, and $R_{5b}$ for a compound of formula II;
- a compound of formulae IIaa, IIab, IIac, IIad and IIae, wherein $R_1$ is as defined formula I. and $R_4$ is as defined formula I; accordingly preferred embodiments of $R_1$ and $R_4$ for a compound of formula I are likewise preferred embodiments of $R_1$ and $R_4$ for a any one of a compound of formulae IIaa, IIab, IIac, IIad and IIae;
- a compound of formula III, wherein $A_1$, $R_{2a}$ and $R_{2b}$ are as defined for formula I; accordingly preferred embodiments of $A_1$, $R_{2a}$ and $R_{2b}$ for a compound of formula I are likewise preferred embodiments of $A_1$, $R_{2a}$ and $R_{2b}$ for a compound of formula III;
- a compound of formula IIIa, wherein $A_1$, $R_{2a}$ and $R_{2b}$ are as defined for formula I and $X_0$ is halogen (such as chlorine of bromine) or $X_{01}$ to $X_{04}$ (as defined in Scheme 1); accordingly preferred embodiments of $A_1$, $R_{2a}$ and $R_{2b}$ for a compound of formula I are likewise preferred embodiments of $A_1$, $R_{2a}$ and $R_{2b}$ for a compound of formula IIIa;

- a compound of formula VI, wherein $R_3$, $R_4$, $R_{5a}$, and $R_{5b}$ are as defined for formula I; accordingly preferred embodiments of $R_3$, $R_4$, $R_{5a}$, and $R_{5b}$ for a compound of formula I are likewise preferred embodiments of $R_3$, $R_4$, $R_{5a}$, and $R_{5b}$ for a compound of formula VI;
- a compound of formula XII, wherein $R_3$, $R_4$, $R_{5a}$, and $R_{5b}$ are as defined for formula I; accordingly preferred embodiments of $R_3$, $R_4$, $R_{5a}$, and $R_{5b}$ for a compound of formula I are likewise preferred embodiments of $R_3$, $R_4$, $R_{5a}$, and $R_{5b}$ for a compound of formula XII;
- a compound of formula XLI, wherein $R_3$, $R_{4a}$, $R_{5a}$, and $R_{5b}$ are as defined for formula I and $Z_3$ is NPhth or $NBoc_2$; accordingly preferred embodiments of $R_3$, $R_4$, $R_{5a}$, and $R_{5b}$ for a compound of formula I are likewise preferred embodiments of $R_3$, $R_4$, $R_{5a}$, and $R_{5b}$ for a compound of formula XLI;
- a compound of formula XLIII, wherein $R_3$, $R_4$, $R_{5a}$, and $R_{5b}$ are as defined for formula I; accordingly preferred embodiments of $R_3$, $R_4$, $R_{5a}$, and $R_{5b}$ for a compound of formula I are likewise preferred embodiments of $R_3$, $R_{4a}$ $R_{5a}$, and $R_{5b}$ for a compound of formula XLIII;
- a compound of formula XLIV, wherein $R_3$ and $R_4$ are as defined for formula I; accordingly preferred embodiments of $R_3$ and $R_4$ for a compound of formula I are likewise preferred embodiments of $R_3$ and $R_4$ for a compound of formula XLIV;
- a compound of formula XLVI, wherein $R_3$ and $R_4$ are as defined for formula I; accordingly preferred embodiments of $R_3$ and $R_4$ for a compound of formula I are likewise preferred embodiments of $R_3$ and $R_4$ for a compound of formula XLVI;
- a compound of formula XLVIII, wherein $R_3$ and $R_4$ are as defined for formula I and $Z_{5a}$ and $Z_{5b}$ are independent of each other selected from $R_{5a}$, $R_{5b}$, halogen, $NH_2$ and OH; accordingly preferred embodiments of $R_3$ and $R_{4a}$ for a compound of formula I are likewise preferred embodiments of $R_3$ and $R_4$ for a compound of formula XLVIII;
- a compound of formula XLIX, wherein $R_3$, $R_4$, $R_{5a}$, and $R_{5b}$ are as defined for formula I; accordingly preferred embodiments of $R_3$, $R_4$, $R_{5a}$, and $R_{5b}$ for a compound of formula I are likewise preferred embodiments of $R_3$, $R_4$, $R_{5a}$, and $R_{5b}$ for a compound of formula XLIX;
- a compound of formula LI, wherein $R_3$, $R_{5a}$, and $R_{5b}$ are as defined for formula I, and $X_{05}$ is a leaving group such as bromine, chlorine, iodine, mesylate, tosylate or triflate; accordingly preferred embodiments of $R_3$, $R_{5a}$, and $R_{5b}$ for a compound of formula I are likewise preferred embodiments $R_3$, $R_{5a}$, and $R_{5b}$ for a compound of formula LI
- a compound of formula LIa, wherein $R_1$, $R_3$, $R_{5a}$, and $R_{5b}$ are as defined for formula I, and $X_{05}$ is a leaving group such as bromine, chlorine, iodine, mesylate, tosylate or triflate; accordingly preferred embodiments of $R_1$, $R_3$, $R_{5a}$, and $R_{5b}$ for a compound of formula I are likewise preferred embodiments $R_1$, $R_3$, $R_{5a}$, and $R_{5b}$ for a compound of formula LIa;
- a compound of formula L, wherein $A_1$, $R_{2a}$, $R_{2b}$, $R_1$, $R_3$, $R_{5a}$ and $R_{5b}$ are as defined for formula I, and $X_{05}$ is a leaving group such as bromine, chlorine, iodine, mesylate, tosylate or triflate; accordingly preferred embodiments of $A_1$, $R_{2a}$, $R_{2b}$, $R_1$, $R_3$, $R_{5a}$ and $R_{5b}$ for a compound of formula I are likewise preferred embodiments $A_1$, $R_{2a}$ $R_{2b}$, $R_1$, $R_3$, $R_{5a}$ and $R_{5b}$ for a compound of formula L;
- a compound of formula LIV, wherein $R_3$, $R_{5a}$ and $R_{5b}$ are as defined for formula I, $Z_3$ is NPhth or $NBoc_2$ and $X_{05}$ is a leaving group, for example, chlorine, bromine, iodine, arysulfonate, alkylsulfonate or trifluoromethanesulfonate; accordingly preferred embodiments of $R_3$, $R_{5a}$ and $R_{5b}$ for a compound of formula I are likewise preferred embodiments $R_3$, $R_{5a}$ and $R_{5b}$ for a compound of formula LIV;
- a compound of formula IV or IVa, wherein $R_3$, $R_{5a}$ and $R_{5b}$ are as defined for formula I, and $X_{05}$ is a leaving group, for example, chlorine, bromine, iodine; accordingly preferred embodiments of $R_3$, $R_{5a}$ and $R_{5b}$ for a compound of formula I are likewise preferred embodiments $R_3$, $R_{5a}$ and $R_{5b}$ for a compound of formula IV or IVa respectively;
- a compound of formula LV, wherein $R_3$, $R_{5a}$ and $R_{5b}$ are as defined for formula I, and $X_{05}$ is a leaving group, for example, chlorine, bromine, iodine, arysulfonate, alkylsulfonate or trifluoromethanesulfonate; accordingly preferred embodiments of $R_3$, $R_{5a}$ and $R_{5b}$ for a compound of formula I are likewise preferred embodiments $R_3$, $R_{5a}$ and $R_{5b}$ for a compound of formula LV;
- a compound of formula XX, wherein $R_{2a}$, $R_{2b}$ and $A_1$ are as defined for formula I, and $Z_1$ is a $C_1$-$C_4$ alkyl group, for example, methyl, ethyl isopropyl, propyl, tert-butyl, sec butyl or n-butyl; accordingly preferred embodiments of $R_{2a}$, $R_{2b}$ and $A_1$ for a compound of formula I are likewise preferred embodiments $R_{2a}$, $R_{2b}$ and $A_1$ for a compound of formula XX;
- a compound of formula XXa, wherein $R_{2b}$ and $A_1$ are as defined for formula I, and $Z_1$ is a $C_1$-$C_4$alkyl group, for example, methyl, ethyl isopropyl, propyl, tert-butyl, sec butyl or n-butyl; accordingly preferred embodiments of $R_{2b}$ and $A_1$ for a compound of formula I are likewise preferred embodiments $R_{2b}$ and $A_1$ for a compound of formula XXa;
- a compound of formula XXVIIIa, wherein $A_1$ and $R_{2b}$ are as defined for formula I, $Z_1$ is a $C_1$-$C_4$ alkyl group, for example, methyl, ethyl isopropyl, propyl, tert-butyl, sec butyl or n-butyl, and $X_{08}$ is chlorine or bromine; accordingly preferred embodiments of $A_1$ and $R_{2b}$ for a compound of formula I are likewise preferred embodiments $A_1$ and $R_{2b}$ for a compound of formula XXVIIIa;
- a compound of formula XXVIIIb, wherein $A_1$ and $R_{2b}$ are as defined for formula I, $Z_1$ is a $C_1$-$C_4$ alkyl group, for example, methyl, ethyl isopropyl, propyl, tert-butyl, sec butyl or n-butyl, and $X_{05}$ is a leaving group, for example, chlorine, bromine, iodine, arysulfonate, alkylsulfonate or trifluoromethanesulfonate; accordingly preferred embodiments of $A_1$ and $R_{2b}$ for a compound of formula I are likewise preferred embodiments $A_1$ and $R_{2b}$ for a compound of formula XXVIIIb;
- a compound of formula XXVIIIc, wherein $A_1$ and $R_{2b}$ are as defined for formula I, and $Z_1$ and $X_{05}$ are independently selected from a $C_1$-$C_4$ alkyl group, for example, methyl, ethyl isopropyl, propyl, tert-butyl, sec butyl or n-butyl, is chlorine or bromine; accordingly preferred embodiments of $A_1$ and $R_{2b}$ for a compound of formula I are likewise preferred embodiments $A_1$ and $R_{2b}$ for a compound of formula XXVIIIc;
- a compound of formula XXI, wherein $A_1$ and $R_{2b}$ are as defined for formula I and $Z_1$ is a $C_1$-$C_4$ alkyl group, for example, methyl, ethyl isopropyl, propyl, tert-butyl, sec butyl or n-butyl; accordingly preferred embodiments of $A_1$ and $R_{2b}$ for a compound of formula I are likewise preferred embodiments $A_1$ and $R_{2b}$ for a compound of formula XXI;
- a compound of formula XXVII, wherein $R_{2b}$ and $A_1$ are as defined for formula I, $R_{2aa}$ is H, $C_1$-$C_3$alkyl, $C_1$-$C_3$haloalkyl, cyano or halogen, and $Z_1$ is a $C_1$-$C_4$ alkyl group, for example, methyl, ethyl isopropyl, propyl, tert-butyl, sec butyl or n-butyl; accordingly preferred embodiments of $R_{2b}$ and $A_1$ for a compound of formula I are likewise preferred embodiments $R_{2b}$ and $A_1$ for a compound of formula XXVII;

a compound of formula XXVIII, wherein $R_{2b}$ and $A_1$ are as defined for formula I, $R_{2aa}$ is H, $C_1$-$C_3$alkyl, $C_1$-$C_3$haloalkyl, cyano or halogen, and $Z_1$ is a $C_1$-$C_4$ alkyl group, for example, methyl, ethyl isopropyl, propyl, tert-butyl, sec butyl or n-butyl; accordingly preferred embodiments of $R_{2b}$ and $A_1$ for a compound of formula I are likewise preferred embodiments $R_{2b}$ and $A_1$ for a compound of formula XXVIII;

a compound of formula XXIX, $R_{2b}$ and $A_1$ are as defined for formula I, $R_{2aa}$ is H, $C_1$-$C_3$alkyl, $C_1$-$C_3$haloalkyl, cyano or halogen, and $Z_1$ is a $C_1$-$C_4$ alkyl group, for example, methyl, ethyl isopropyl, propyl, tert-butyl, sec butyl or n-butyl; accordingly preferred embodiments of $R_{2b}$ and $A_1$ for a compound of formula I are likewise preferred embodiments $R_{2b}$ and $A_1$ for a compound of formula XXIX;

a compound of formula XXXI, $R_{2b}$ and $A_1$ are as defined for formula I, $R_{2aa}$ is H, $C_1$-$C_3$alkyl, $C_1$-$C_3$haloalkyl, cyano or halogen, and $Z_1$ is a $C_1$-$C_4$ alkyl group, for example, methyl, ethyl isopropyl, propyl, tert-butyl, sec butyl or n-butyl; accordingly preferred embodiments of $R_{2b}$ and $A_1$ for a compound of formula I are likewise preferred embodiments $R_{2b}$ and $A_1$ for a compound of formula XXXI;

a compound of formula XXXII, $R_{2b}$ and $A_1$ are as defined for formula I, $R_{2aa}$ is H, $C_1$-$C_3$alkyl, $C_1$-$C_3$haloalkyl, cyano or halogen, and $Z_1$ is a $C_1$-$C_4$ alkyl group, for example, methyl, ethyl isopropyl, propyl, tert-butyl, sec butyl or n-butyl; accordingly preferred embodiments of $R_{2b}$ and $A_1$ for a compound of formula I are likewise preferred embodiments $R_{2b}$ and $A_1$ for a compound of formula XXXII;

a compound of formula XXXV, wherein $R_{2b}$ and $A_1$ are as defined for formula I, and $Z_1$ is a $C_1$-$C_4$alkyl group, for example, methyl, ethyl isopropyl, propyl, tert-butyl, sec butyl or n-butyl; accordingly preferred embodiments of $R_{2b}$ and $A_1$ for a compound of formula I are likewise preferred embodiments $R_{2b}$ and $A_1$ for a compound of formula XXXV;

a compound of formula XXXVI, $R_{2b}$ and $A_1$ are as defined for formula I, and $Z_1$ is a $C_1$-$C_4$ alkyl group, for example, methyl, ethyl isopropyl, propyl, tert-butyl, sec butyl or n-butyl; accordingly preferred embodiments of $R_{2b}$ and $A_1$ for a compound of formula I are likewise preferred embodiments $R_{2b}$ and $A_1$ for a compound of formula XXXVI;

a compound of formula XXXVII, $R_{2b}$ and $A_1$ are as defined for formula I, and $Z_1$ is a $C_1$-$C_4$ alkyl group, for example, methyl, ethyl isopropyl, propyl, tert-butyl, sec butyl or n-butyl; accordingly preferred embodiments of $R_{2b}$ and $A_1$ for a compound of formula I are likewise preferred embodiments $R_{2b}$ and $A_1$ for a compound of formula XXXVII; and a compound of formula XXXIX, wherein $R_{2b}$ and $A_1$ are as defined for formula I, and $Z_1$ and $Z_2$ are independently selected from a $C_1$-$C_4$ alkyl group, for example, methyl, ethyl isopropyl, propyl, tert-butyl, sec butyl or n-butyl; accordingly preferred embodiments of $R_{2b}$ and $A_1$ for a compound of formula I are likewise preferred embodiments $R_{2b}$ and $A_1$ for a compound of formula XXXIX.

The compounds of formula I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i. e. in destruction of the pests, which takes place either immediately or only after some time has elapsed, for example during ecdysiast, or indirectly, for example in a reduced oviposition and/or hatching rate.

Examples of the above mentioned animal pests are:

from the order Acarina, for example,

*Acalitus* spp, *Aculus* spp, *Acaricalus* spp, *Aceria* spp, *Acarus siro, Amblyomma* spp., *Argas* spp., *Boophilus* spp., *Brevipalpus* spp., *Bryobia* spp, *Calipitrimerus* spp., *Chorioptes* spp., *Dermanyssus gallinae, Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus, Panonychus* spp., *Phyllocoptruta oleivora, Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.;

from the order Coleoptera, for example,

*Agriotes* spp., *Amphimallon majale, Anomala orientalis, Anthonomus* spp., *Aphodius* spp, *Astylus atromaculatus, Ataenius* spp, *Atomaria linearis, Chaetocnema tibialis, Cerotoma* spp, *Conoderus* spp, *Cosmopolites* spp., *Cotinis nitida, Curculio* spp., *Cyclocephala* spp, *Dermestes* spp., *Diabrotica* spp., *Diloboderus abderus, Epilachna* spp., *Eremnus* spp., *Heteronychus arator, Hypothenemus hampei, Lagria vilosa, Leptinotarsa decemlineata, Lissorhoptrus* spp., *Liogenys* spp, *Maecolaspis* spp, *Maladera castanea, Megascelis* spp, *Melighetes aeneus, Melolontha* spp., *Myochrous armatus, Orycaephilus* spp., *Otiorhynchus* spp., *Phyllophaga* spp, *Phlyctinus* spp., *Popillia* spp., *Psylliodes* spp., *Rhyssomatus aubtilis, Rhizopertha* spp., *Scarabeidae, Sitophilus* spp., *Sitotroga* spp., *Somaticus* spp, *Sphenophorus* spp, *Sternechus subsignatus, Tenebrio* spp., *Tribolium* spp. and *Trogoderma* spp.;

from the order Diptera, for example,

*Aedes* spp., *Anopheles* spp, *Antherigona soccata, Bactrocea oleae, Bibio hortulanus, Bradysia* spp, *Calliphora erythrocephala, Ceratitis* spp., *Chrysomyia* spp., *Culex* spp., *Cuterebra* spp., *Dacus* spp., *Delia* spp, *Drosophila melanogaster, Fannia* spp., *Gastrophilus* spp., *Geomyza tripunctata, Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis* spp, *Rivelia quadrifasciata, Scatella* spp, *Sciara* spp., *Stomoxys* spp., *Tabanus* spp., *Tannia* spp. and *Tipula* spp.;

from the order Hemiptera, for example,

*Acanthocoris scabrator, Acrosternum* spp, *Adelphocoris lineolatus, Aleurodes* spp., *Amblypelta nitida, Bathycoelia thalassina, Blissus* spp, *Cimex* spp., *Clavigralla*

*tomentosicollis, Creontiades* spp, *Distantiella theobroma, Dichelops furcatus, Dysdercus* spp., *Edessa* spp, *Euchistus* spp., *Eurydema pulchrum, Eurygaster* spp., *Halyomorpha halys, Horcias nobilellus, Leptocorisa* spp., *Lygus* spp, *Margarodes* spp, *Murgantia histrionic, Neomegalotomus* spp, *Nesidiocoris tenuis, Nezara* spp., *Nysius simulans, Oebalus insularis, Piesma* spp., *Piezodorus* spp, *Rhodnius* spp., *Sahlbergella singularis, Scaptocoris castanea, Scotinophara* spp., *Thyanta* spp, *Triatoma* spp., *Vatiga illudens; Acyrthosium pisum, Adalges* spp, *Agalliana ensigera, Agonoscena targionii, Aleurodicus* spp, *Aleurocanthus* spp, *Aleurolobus barodensis, Aleurothrixus floccosus, Aleyrodes brassicae, Amarasca biguttula, Amritodus atkinsoni, Aonidiella* spp., *Aphididae, Aphis* spp., *Aspidiotus* spp., *Aulacorthum solani, Bactericera cockerelli, Bemisia* spp, *Brachycaudus* spp, *Brevicoryne brassicae, Cacopsylla* spp, *Cavariella aegopodii* Scop., *Ceroplaster* spp., *Chrysomphalus aonidium, Chrysomphalus dictyospermi, Cicadella* spp, *Cofana spectra, Cryptomyzus* spp, *Cicadulina* spp, *Coccus hesperidum, Dalbulus maidis, Dialeurodes* spp, *Diaphorina citri, Diuraphis noxia, Dysaphis* spp, *Empoasca* spp., *Eriosoma larigerum, Erythroneura* spp., *Gascardia* spp., *Glycaspis brimblecombei, Hyadaphis pseudobrassicae, Hyalopterus* spp, *Hyperomyzus pallidus, Idioscopus clypealis, Jacobiasca lybica, Laodelphax* spp., *Lecanium corni, Lepidosaphes* spp., *Lopaphis erysimi, Lyogenys maidis, Macrosiphum* spp., *Mahanarva* spp, *Metcalfa pruinosa, Metopolophium dirhodum, Myndus crudus, Myzus* spp., *Neotoxoptera* sp, *Nephotettix* spp., *Nilaparvata* spp., *Nippolachnus piri* Mats, *Odonaspis ruthae, Oregma lanigera* Zehnter, *Parabemisia myricae, Paratrioza cockerelli, Parlatoria* spp., *Pemphigus* spp., *Peregrinus maidis, Perkinsiella* spp, *Phorodon humuli, Phylloxera* spp, *Planococcus* spp., *Pseudaulacaspis* spp., *Pseudococcus* spp., *Pseudatomoscelis seriatus, Psylla* spp., *Pulvinaria aethiopica, Quadraspidiotus* spp., *Quesada gigas, Recilia dorsalis, Rhopalosiphum* spp., *Saissetia* spp., *Scaphoideus* spp., *Schizaphis* spp., *Sitobion* spp., *Sogatella furcifera, Spissistilus festinus, Tarophagus Proserpina, Toxoptera* spp, *Trialeurodes* spp, *Tridiscus sporoboli, Trionymus* spp, *Trioza erytreae, Unaspis citri, Zygina flammigera, Zyginidia scutellaris;* from the order Hymenoptera, for example,

*Acromyrmex, Arge* spp, *Atta* spp., *Cephus* spp., *Diprion* spp., *Diprionidae, Gilpinia polytoma, Hoplocampa* spp., *Lasius* spp., *Monomorium pharaonis, Neodiprion* spp., *Pogonomyrmex* spp, *Slenopsis invicta, Solenopsis* spp. and *Vespa* spp.;

from the order Isoptera, for example,

*Coptotermes* spp, *Corniternes cumulans, Incisitermes* spp, *Macrotermes* spp, *Mastotermes* spp, *Microtermes* spp, *Reticulitermes* spp.; *Solenopsis geminate* from the order Lepidoptera, for example,

*Acleris* spp., *Adoxophyes* spp., *Aegeria* spp., *Agrotis* spp., *Alabama argillaceae, Amylois* spp., *Anticarsia gemmatalis, Archips* spp., *Argyresthia* spp, *Argyrotaenia* spp., *Autographa* spp., *Bucculatrix thurberiella, Busseola fusca, Cadra cautella, Carposina nipponensis, Chilo* spp., *Choristoneura* spp., *Chrysoteuchia topiaria, Clysia ambiguella, Cnaphalocrocis* spp., *Cnephasia* spp., *Cochylis* spp., *Coleophora* spp., *Colias lesbia, Cosmophila flava, Crambus* spp, *Crocidolomia binotalis, Cryptophlebia leucotreta, Cydalima perspectalis, Cydia* spp., *Diaphania perspectalis, Diatraea* spp., *Diparopsis castanea, Earias* spp., *Elasmopalpus lignosellus, Eldana saccharina, Ephestia* spp., *Epinotia* spp, *Estigmene acrea, Etiella zinckinella, Eucosma* spp., *Eupoecilia ambiguella, Euproctis* spp., *Euxoa* spp., *Feltia jaculiferia, Grapholita* spp., *Hedya nubiferana, Heliothis* spp., *Hellula undalis, Herpetogramma* spp, *Hyphantria cunea, Keiferia lycopersicella, Lasmopalpus lignosellus, Leucoptera scitella, Lithocollethis* spp., *Lobesia botrana, Loxostege bifidalis, Lymantria* spp., *Lyonetia* spp., *Malacosoma* spp., *Mamestra brassicae, Manduca sexta, Mythimna* spp, *Noctua* spp, *Operophtera* spp., *Orniodes indica, Ostrinia nubilalis, Pammene* spp., *Pandemis* spp., *Panolis flammea, Papaipema nebris, Pectinophora gossypiela, Perileucoptera coffeella, Pseudaletia unipuncta, Phthorimaea operculella, Pieris rapae, Pieris* spp., *Plutella xylostella, Prays* spp., *Pseudoplusia* spp, *Rachiplusia nu, Richia albicosta, Scirpophaga* spp., *Sesamia* spp., *Sparganothis* spp., *Spodoptera* spp., *Sylepta derogate, Synanthedon* spp., *Thaumetopoea* spp., *Tortrix* spp., *Trichoplusia ni, Tuta absoluta*, and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae, Locusta* spp., *Neocurtilla hexadactyla, Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis;* from the order Thysanoptera, for example,

*Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp;

from the order Thysanura, for example, *Lepisma saccharina.*

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla, Meloidogyne incognita, Meloidogyne javanica, Meloidogyne arenaria* and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus* destructor, *Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other

*Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, Paratrichodorus species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

The compounds of the invention may also have activity against the molluscs. Examples of which include, for example, Ampullariidae; *Arion* (*A. ater, A. circumscriptus, A. hortensis, A. rufus*); Bradybaenidae (*Bradybaena fruticum*); *Cepaea* (*C. hortensis, C. Nemoralis*); ochlodina; *Deroceras* (*D. agrestis, D. empiricorum, D. laeve, D. reticulatum*); *Discus* (*D. rotundatus*); *Euomphalia; Galba* (*G. trunculata*); *Helicelia* (*H. itala, H. obvia*); Helicidae *Helicigona arbustorum*); *Helicodiscus; Helix* (*H. aperta*); *Limax* (*L. cinereoniger, L. flavus, L. marginatus, L. maximus, L. tenellus*); *Lymnaea; Milax* (*M. gagates, M. marginatus, M. sowerbyi*); *Opeas; Pomacea* (*P. canaticulata*); *Vallonia* and *Zanitoides.*

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp orjute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family and latex plants.

The compositions and/or methods of the present invention may be also used on any ornamental and/or vegetable crops, including flowers, shrubs, broad-leaved trees and evergreens.

For example the invention may be used on any of the following ornamental species: *Ageratum* spp., *Alonsoa* spp., *Anemone* spp., *Anisodontea capsenisis, Anthemis* spp., *Antirrhinum* spp., *Aster* spp., *Begonia* spp. (e.g. *B. elatior, B. semperflorens, B. tubereux*), *Bougainvillea* spp., *Brachycome* spp., *Brassica* spp. (ornamental), *Calceolaria* spp., *Capsicum annuum, Catharanthus roseus, Canna* spp., *Centaurea* spp., *Chrysanthemum* spp., *Cineraria* spp. (*C. maritime*), *Coreopsis* spp., *Crassula coccinea, Cuphea ignea, Dahlia* spp., *Delphinium* spp., *Dicentra spectabilis, Dorotheantus* spp., *Eustoma grandiflorum, Forsythia* spp., *Fuchsia* spp., *Geranium gnaphalium, Gerbera* spp., *Gomphrena globosa, Heliotropium* spp., *Helianthus* spp., *Hibiscus* spp., *Hortensia* spp., *Hydrangea* spp., *Hypoestes phyllostachya, Impatiens* spp. (*I. Walleriana*), *Iresines* spp., *Kalanchoe* spp., *Lantana camara, Lavatera trimestris, Leonotis leonurus, Lilium* spp., *Mesembryanthemum* spp., *Mimulus* spp., *Monarda* spp., *Nemesia* spp., *Tagetes* spp., *Dianthus* spp. (carnation), *Canna* spp., *Oxalis* spp., *Bellis* spp., *Pelargonium* spp. (*P. peltatum, P. Zonale*), *Viola* spp. (pansy), *Petunia* spp., *Phlox* spp., *Plecthranthus* spp., *Poinsettia* spp., *Parthenocissus* spp. (*P. quinquefolia, P. tricuspidata*), *Primula* spp., *Ranunculus* spp., *Rhododendron* spp., *Rosa* spp. (rose), *Rudbeckia* spp., *Saintpaulia* spp., *Salvia* spp., *Scaevola aemola, Schizanthus wisetonensis, Sedum* spp., *Solanum* spp., *Surfinia* spp., *Tagetes* spp., *Nicotinia* spp., *Verbena* spp., *Zinnia* spp. and other bedding plants.

For example the invention may be used on any of the following vegetable species: *Allium* spp. (*A. sativum, A. cepa, A. oschaninii, A. Porrum, A. ascalonicum, A. fistulosum*), *Anthriscus cerefolium, Apium graveolus, Asparagus officinalis, Beta vulgarus, Brassica* spp. (*B. Oleracea, B. Pekinensis, B. rapa*), *Capsicum annuum, Cicer arietinum, Cichorium endivia, Cichorum* spp. (*C. intybus, C. endivia*), *Citrillus lanatus, Cucumis* spp. (*C. sativus, C. melo*), *Cucurbita* spp. (*C. pepo, C. maxima*), *Cyanara* spp. (*C. scolymus, C. cardunculus*), *Daucus carota, Foeniculum vulgare, Hypericum* spp., *Lactuca sativa, Lycopersicon* spp. (*L. esculentum, L. lycopersicum*), *Mentha* spp., *Ocimum basilicum, Petroselinum crispum, Phaseolus* spp. (*P. vulgaris, P. coccineus*), *Pisum sativum, Raphanus sativus, Rheum rhaponticum, Rosemarinus* spp., *Salvia* spp., *Scorzonera hispanica, Solanum melongena, Spinacea oleracea, Valerianella* spp. (*V. locusta, V. eriocarpa*) and *Vicia faba.*

Preferred ornamental species include African violet, *Begonia, Dahlia, Gerbera, Hydrangea, Verbena, Rosa, Kalanchoe, Poinsettia, Aster, Centaurea, Coreopsis, Delphinium, Monarda, Phlox, Rudbeckia, Sedum, Petunia, Viola, Impatiens, Geranium, Chrysanthemum, Ranunculus, Fuchsia, Salvia, Hortensia*, rosemary, sage, St. Johnswort, mint, sweet pepper, tomato and cucumber.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatoes) and *Chilo supressalis* (preferably in rice).

The compounds of formula I are particularly suitable for control of 1. a pest of the order Hemiptera, for example, one or more of the species *Bemisia tabaci, Aphis craccivora, Myzus persicae, Rhopalosiphum Padi, Nilaparvata lugens*, and *Euschistus heros* (preferably in vegetables, soybeans, and sugarcane);
2. a pest of the order Lepidoptera, for example, one or more of the species *Spodoptera littoralis, Spodoptera frugiperda, Plutella xylostella, Cnaphalocrocis medinalis, Cydia pomonella, Chrysodeixis includes, Chilo suppressalis, Elasmopalpus lignosellus, Pseudoplusia includens*, and *Tuta absoluta* (preferably in vegetables and corn);
3. a pest of the order Thysanoptera, such as the family Thripidae, for example, one or more of *Thrips tabaci* and *Frankliniella occidentalis* (preferably in vegetables); and 4. soil pests (such as of the order Coleoptera), for example, the species *Diabrotica* balteata, *Agriotes* spp. and *Leptinotarsa decemlineata* (preferably in vegetables and corn).

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus.*

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cryl-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1 Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603×MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. kurstaki which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Crops may also be modified for enhanced resistance to fungal (for example *Fusarium*, Anthracnose, or *Phytophthora*), bacterial (for example *Pseudomonas*) or viral (for example potato leafroll virus, tomato spotted wilt virus, cucumber mosaic virus) pathogens.

Crops also include those that have enhanced resistance to nematodes, such as the soybean cyst nematode.

Crops that are tolerance to abiotic stress include those that have enhanced tolerance to drought, high salt, high temperature, chill, frost, or light radiation, for example through expression of NF-YB or other proteins known in the art.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defense (so-called "plant disease resistance genes", as described in WO 03/000906).

Further areas of use of the compositions according to the invention are the protection of stored goods and store rooms and the protection of raw materials, such as wood, textiles, floor coverings or buildings, and also in the hygiene sector, especially the protection of humans, domestic animals and productive livestock against pests of the mentioned type.

The present invention provides a compound of the first aspect for use in therapy. The present invention provides a compound of the first aspect, for use in controlling parasites in or on an animal. The present invention further provides a compound of the first aspect, for use in controlling ectoparasites on an animal. The present invention further provides a compound of the first aspect, for use in preventing and/or treating diseases transmitted by ectoparasites.

The present invention provides the use of a compound of the first aspect, for the manufacture of a medicament for controlling parasites in or on an animal. The present invention further provides the use of a compound of the first aspect, for the manufacture of a medicament for controlling ectoparasites on an animal. The present invention further provides the use of a compound of the first aspect, for the manufacture of a medicament for preventing and/or treating diseases transmitted by ectoparasites.

The present invention provides the use of a compound of the first aspect, in controlling parasites in or on an animal. The present invention further provides the use of a compound of the first aspect, in controlling ectoparasites on an animal.

The term "controlling" when used in context of parasites in or on an animal refers to reducing the number of pests or parasites, eliminating pests or parasites and/or preventing further pest or parasite infestation.

The term "treating" when used in context of parasites in or on an animal refers to restraining, slowing, stopping or reversing the progression or severity of an existing symptom or disease.

The term "preventing" when used in context of parasites in or on an animal refers to the avoidance of a symptom or disease developing in the animal.

The term "animal" when used in context of parasites in or on an animal may refer to a mammal and a non-mammal, such as a bird or fish. In the case of a mammal, it may be a human or non-human mammal. Non-human mammals include, but are not limited to, livestock animals and companion animals. Livestock animals include, but are not limited to, cattle, camelids, pigs, sheep, goats and horses. Companion animals include, but are not limited to, dogs, cats and rabbits.

A "parasite" is a pest which lives in or on the host animal and benefits by deriving nutrients at the host animal's expense. An "endoparasite" is a parasite which lives in the host animal. An "ectoparasite" is a parasite which lives on the host animal. Ectoparasites include, but are not limited to, acari, insects and crustaceans (e.g. sea lice). The Acari (or Acarina) sub-class comprises ticks and mites. Ticks include, but are not limited to, members of the following genera: *Rhipicaphalus*, for example, *Rhipicaphalus* (*Boophilus*) *microplus* and *Rhipicephalus sanguineus; Amblyomma; Dermacentor; Haemaphysalis; Hyalomma; Ixodes; Rhipicentor; Margaropus; Argas; Otobius*; and *Ornithodoros*. Mites include, but are not limited to, members of the following genera: *Chorioptes*, for example *Chorioptes bovis; Psoroptes*, for example *Psoroptes ovis; Cheyletiella; Dermanyssus*; for example *Dermanyssus gallinae; Ortnithonyssus; Demodex*, for example *Demodex canis; Sarcoptes*, for example *Sarcoptes scabiei*; and *Psorergates*. Insects include, but are not limited to, members of the orders: *Siphonaptera, Diptera, Phthiraptera, Lepidoptera, Coleoptera* and *Homoptera*. Members of the Siphonaptera order include, but are not limited to, *Ctenocephalides felis* and *Ctenocephalides canis*. Members of the Diptera order include, but are not limited to, *Musca* spp.; bot fly, for example *Gasterophilus intestinalis* and *Oestrus ovis*; biting flies; horse flies, for example *Haematopota* spp. and *Tabunus* spp.; *Haematobia*, for example *Haematobia irritans; Stomoxys; Lucilia*; midges; and mosquitoes. Members of the Phthiraptera class include, but are not limited to, blood sucking lice and chewing lice, for example *Bovicola Ovis* and *Bovicola Bovis*.

The term "effective amount" when used in context of parasites in or on an animal refers to the amount or dose of the compound of the invention, or a salt thereof, which, upon single or multiple dose administration to the animal, provides the desired effect in or on the animal. The effective amount can be readily determined by the attending diagnostician, as one skilled in the art, by the use of known techniques and by observing results obtained under analogous circumstances. In determining the effective amount a number of factors are considered by the attending diagnostician, including, but not limited to: the species of mammal; its size, age, and general health; the parasite to be controlled and the degree of infestation; the specific disease or disorder involved; the degree of or involvement or the severity of the disease or disorder; the response of the individual; the particular compound administered; the mode of administration; the bioavailability characteristics of the preparation administered; the dose regimen selected; the use of concomitant medication; and other relevant circumstances.

The compounds of the invention may be administered to the animal by any route which has the desired effect including, but not limited to topically, orally, parenterally and subcutaneously. Topical administration is preferred. Formulations suitable for topical administration include, for example, solutions, emulsions and suspensions and may take the form of a pour-on, spot-on, spray-on, spray race or dip. In the alternative, the compounds of the invention may be administered by means of an ear tag or collar.

Salt forms of the compounds of the invention include both pharmaceutically acceptable salts and veterinary acceptable salts, which can be different to agrochemically acceptable salts. Pharmaceutically and veterinary acceptable salts and common methodology for preparing them are well known in the art. See, for example, Gould, P. L., “Salt selection for basic drugs”, International Journal of Pharmaceutics, 33: 201-217 (1986); Bastin, R. J., et al. “Salt Selection and Optimization Procedures for Pharmaceutical New Chemical Entities”, Organic Process Research and Development, 4: 427-435 (2000); and Berge, S. M., et al., “Pharmaceutical Salts”, Journal of Pharmaceutical Sciences, 66: 1-19, (1977). One skilled in the art of synthesis will appreciate that the compounds of the invention are readily converted to and may be isolated as a salt, such as a hydrochloride salt, using techniques and conditions well known to one of ordinary skill in the art. In addition, one skilled in the art of synthesis will appreciate that the compounds of the invention are readily converted to and may be isolated as the corresponding free base from the corresponding salt.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO2006/128870, EP 1724392, WO 2005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables A and B:

TABLE A

Examples of exotic woodborers of economic importance.

| Family | Species | Host or Crop Infested |
|---|---|---|
| Buprestidae | *Agrilus planipennis* | Ash |
| Cerambycidae | *Anoplura glabripennis* | Hardwoods |
| Scolytidae | *Xylosandrus crassiusculus* | Hardwoods |
| | *X. mutilatus* | Hardwoods |
| | *Tomicus piniperda* | Conifers |

TABLE B

Examples of native woodborers of economic importance.

| Family | Species | Host or Crop Infested |
|---|---|---|
| Buprestidae | *Agrilus anxius* | Birch |
| | *Agrilus politus* | Willow, Maple |
| | *Agrilus sayi* | Bayberry, Sweetfern |
| | *Agrilus vittaticolllis* | Apple, Pear, Cranberry, Serviceberry, Hawthorn |
| | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |

TABLE B-continued

| Examples of native woodborers of economic importance. | | |
|---|---|---|
| Family | Species | Host or Crop Infested |
| | *Texania campestris* | Basswood, Beech, Maple, Oak, Sycamore, Willow, Yellow-poplar |
| Cerambycidae | *Goes pulverulentus* | Beech, Elm, Nuttall, Willow, Black oak, Cherrybark oak, Water oak, Sycamore |
| | *Goes tigrinus* | Oak |
| | *Neoclytus acuminatus* | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
| | *Neoptychodes trilineatus* | Fig, Alder, Mulberry, Willow, Netleaf hackberry |
| | *Oberea ocellata* | Sumac, Apple, Peach, Plum, Pear, Currant, Blackberry |
| | *Oberea tripunctata* | Dogwood, Viburnum, Elm, Sourwood, Blueberry, Rhododendron, Azalea, Laurel, Poplar, Willow, Mulberry |
| | *Oncideres cingulata* | Hickory, Pecan, Persimmon, Elm, Sourwood, Basswood, Honeylocust, Dogwood, Eucalyptus, Oak, Hackberry, Maple, Fruit trees |
| | *Saperda calcarata* | Poplar |
| | *Strophiona nitens* | Chestnut, Oak, Hickory, Walnut, Beech, Maple |
| | *Corthylus columbianus* | Maple, Oak, Yellow-poplar, Beech, Boxelder, Sycamore, Birch, Basswood, Chestnut, Elm |
| Scolytidae | *Dendroctonus frontalis* | Pine |
| | *Dryocoetes betulae* | Birch, Sweetgum, Wild cherry, Beech, Pear |
| | *Monarthrum fasciatum* | Oak, Maple, Birch, Chestnut, Sweetgum, Blackgum, Poplar, Hickory, Mimosa, Apple, Peach, Pine |
| | *Phloeotribus liminaris* | Peach, Cherry, Plum, Black cherry, Elm, Mulberry, Mountain-ash |
| | *Pseudopityophthorus pruinosus* | Oak, American beech, Black cherry, Chickasaw plum, Chestnut, Maple, Hickory, Hornbeam, Hophornbeam |
| Sesiidae | *Paranthrene simulans* | Oak, American chestnut |
| | *Sannina uroceriformis* | Persimmon |
| | *Synanthedon exitiosa* | Peach, Plum, Nectarine, Cherry, Apricot, Almond, Black cherry |
| | *Synanthedon pictipes* | Peach, Plum, Cherry, Beach, Black Cherry |
| | *Synanthedon rubrofascia* | Tupelo |
| | *Synanthedon scitula* | Dogwood, Pecan, Hickory, Oak, Chestnut, Beech, Birch, Black cherry, Elm, Mountain-ash, Viburnum, Willow, Apple, Loquat, Ninebark, Bayberry |
| | *Vitacea polistiformis* | Grape |

The present invention may be also used to control any insect pests that may be present in turfgrass, including for example beetles, caterpillars, fire ants, ground pearls, millipedes, sow bugs, mites, mole crickets, scales, mealybugs, ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as *Cyclocephala* spp. (e.g. masked chafer, *C. lurida*), *Rhizotrogus* spp. (e.g. European chafer, *R. majalis*), *Cotinus* spp. (e.g. Green June beetle, *C. nitida*), *Popillia* spp. (e.g. Japanese beetle, *P. japonica*), *Phyllophaga* spp. (e.g. May/June beetle), *Ataenius* spp. (e.g. Black turfgrass *Ataenius, A. spretulus*), *Maladera* spp. (e.g. Asiatic garden beetle, *M. castanea*) and *Tomarus* spp.), ground pearls (*Margarodes* spp.), mole crickets (tawny, southern, and short-winged; *Scapteriscus* spp., *Gryllotalpa africana*) and leatherjackets (European crane fly, *Tipula* spp.).

The present invention may also be used to control insect pests of turfgrass that are thatch dwelling, including armyworms (such as fall armyworm *Spodoptera frugiperda*, and common armyworm *Pseudaletia unipuncta*), cutworms, billbugs (*Sphenophorus* spp., such as *S. venatus verstitus* and *S. parvulus*), and sod webworms (such as *Crambus* spp. and the tropical sod webworm, *Herpetogramma phaeopteralis*).

The present invention may also be used to control insect pests of turfgrass that live above the ground and feed on the turfgrass leaves, including chinch bugs (such as southern chinch bugs, *Blissus insularis*), Bermudagrass mite (*Eriophyes cynodoniensis*), rhodesgrass mealybug (*Antonina graminis*), two-lined spittlebug (*Propsapia bicincta*), leafhoppers, cutworms (Noctuidae family), and greenbugs.

The present invention may also be used to control other pests of turfgrass such as red imported fire ants (*Solenopsis invicta*) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis*, *Periplaneta americana*, *Blattela germanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus*, and also hymenopterans such as *Sirexjuvencus, Urocerus gigas, Urocerus gigas taignus* and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina*. The compounds of formulae I, and I'a, or salts thereof, are especially suitable for controlling one or more pests selected from the family: Noctuidae, Plutellidae, Chrysomelidae, Thripidae, Pentatomidae, Tortricidae, Delphacidae, Aphididae, Noctuidae, Crambidae, Meloidogynidae, and Heteroderidae. In a preferred embodiment of each aspect, a compound TX (where the abbreviation "TX" means "one compound selected from the compounds defined in the Tables A-1 to A-21, B-1 to B-21, C-1 to C-21, D-1 to D-21 and E-1 to E-21, and Table P") controls one or more of pests selected from the family: Noctuidae, Plutellidae, Chrysomelidae, Thripidae, Pentatomidae, Tortricidae, Delphacidae, Aphididae, Noctuidae, Crambidae, Meloidogynidae, and Heteroderidae.

The compounds of formulae I, and I'a, or salts thereof, are especially suitable for controlling one or more of pests selected from the genus: *Spodoptera* spp, *Plutella* spp, *Frankliniella* spp, *Thrips* spp, *Euschistus* spp, *Cydia* spp, *Nilaparvata* spp, *Myzus* spp, *Aphis* spp, *Diabrotica* spp, *Rhopalosiphum* spp, *Pseudoplusia* spp and *Chilo* spp. In a preferred embodiment of each aspect, a compound TX (where the abbreviation "TX" means "one compound selected from the compounds defined in the Tables A-1 to A-21, B-1 to B-21, C-1 to C-21, D-1 to D-21 and E-1 to E-21, and Table P") controls one or more of pests selected from the genus: *Spodoptera* spp, *Plutella* spp, *Frankliniella* spp, *Thrips* spp, *Euschistus* spp, *Cydia* spp, *Nilaparvata* spp, *Myzus* spp, *Aphis* spp, *Diabrotica* spp, *Rhopalosiphum* spp, *Pseudoplusia* spp and *Chilo* spp.

The compounds of formulae I, and I'a, or salts thereof, are especially suitable for controlling one or more of *Spodoptera littoralis, Plutella xylostella, Frankliniella occidentalis, Thrips tabaci, Euschistus heros, Cydia pomonella, Nilaparvata lugens, Myzus persicae, Chrysodeixis includens, Aphis craccivora, Diabrotica balteata, Rhopalosiphum padi*, and *Chilo suppressalis*.

In a preferred embodiment of each aspect, a compound TX (where the abbreviation "TX" means "one compound selected from the compounds defined in the Tables A-1 to A-21, B-1 to B-21, C-1 to C-21, D-1 to D-21 and E-1 to E-21, and Table P") controls one or more of *Spodoptera littoralis, Plutella xylostella, Frankliniella occidentalis, Thrips tabaci, Euschistus heros, Cydia pomonella, Nilaparvata lugens, Myzus persicae, Chrysodeixis includens, Aphis craccivora, Diabrotica balteata, Rhopalosiphum padia*, and *Chilo suppressalis*, such as *Spodoptera littoralis*+TX, *Plutella xylostella*+TX; *Frankliniella occidentalis*+TX, *Thrips tabaci*+TX, *Euschistus heros*+TX, *Cydia pomonella*+TX, *Nilaparvata lugens*+TX, *Myzus persicae*+TX, *Chrysodeixis includens*+TX, *Aphis craccivora*+TX, *Diabrotica balteata*+TX, *Rhopalosiphum Padi*+TX, and *Chilo suppressalis*+TX.

In an embodiment, of each aspect, one compound selected from the compounds defined in the Tables A-1 to A-21, B-1 to B-21, C-1 to C-21, D-1 to D-21 and E-1 to E-21, and Table P, is suitable for controlling *Spodoptera littoralis, Plutella xylostella, Frankliniella occidentalis, Thrips tabaci, Euschistus heros, Cydia pomonella, Nilaparvata lugens,*

*Myzus persicae, Chrysodeixis includens, Aphis craccivora, Diabrotica balteata, Rhopalosiphum padia*, and *Chilo Suppressalis* in cotton, vegetable, maize, cereal, rice and soya crops.

In an embodiment, one compound from selected from the compounds defined in the Tables A-1 to A-21, B-1 to B-21, C-1 to C-21, D-1 to D-21 and E-1 to E-21, and Table P, is suitable for controlling *Mamestra* (preferably in vegetables), *Cydia pomonella* (preferably in apples), *Empoasca* (preferably in vegetables, vineyards), *Leptinotarsa* (preferably in potatoes) and *Chilo supressalis* (preferably in rice).

Compounds according to the invention may possess any number of benefits including, inter alia, advantageous levels of biological activity for protecting plants against insects or superior properties for use as agrochemical active ingredients (for example, greater biological activity, an advantageous spectrum of activity, an increased safety profile (against non-target organisms above and below ground (such as fish, birds and bees), improved physico-chemical properties, or increased biodegradability). In particular, it has been surprisingly found that certain compounds of formula I may show an advantageous safety profile with respect to non-target arthropods, in particular pollinators such as honey bees, solitary bees, and bumble bees. Most particularly, *Apis mellifera.*

The compounds according to the invention can be used as pesticidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspo-emulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood New Jersey (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, $10^{th}$ Edition, Southern Illinois University, 2010.

The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):

Emulsifiable Concentrates:

- active ingredient: 1 to 95%, preferably 60 to 90%
- surface-active agent: 1 to 30%, preferably 5 to 20%
- liquid carrier: 1 to 80%, preferably 1 to 35%

Dusts:

- active ingredient: 0.1 to 10%, preferably 0.1 to 5%
- solid carrier: 99.9 to 90%, preferably 99.9 to 99%

Suspension Concentrates:

- active ingredient: 5 to 75%, preferably 10 to 50%
- water: 94 to 24%, preferably 88 to 30%
- surface-active agent: 1 to 40%, preferably 2 to 30%

Wettable Powders:

- active ingredient: 0.5 to 90%, preferably 1 to 80%
- surface-active agent: 0.5 to 20%, preferably 1 to 15%
- solid carrier: 5 to 95%, preferably 15 to 90%

Granules:

- active ingredient: 0.1 to 30%, preferably 0.1 to 15%
- solid carrier: 99.5 to 70%, preferably 97 to 85%

The following Examples further illustrate, but do not limit, the invention.

| Wettable powders | a) | b) | c) |
|---|---|---|---|
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 % |

The combination is thoroughly mixed with the adjuvants and the mixture is thoroughly ground in a suitable mill, affording powders that can be used directly for seed treatment.

| Emulsifiable concentrate | |
|---|---|
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extrude dranules | |
|---|---|
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
|---|---|
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

Suspension Concentrate

| | |
|---|---|
| activeingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Flowable Concentrate for Seed Treatment

| | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

Formulation types include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

PREPARATORY EXAMPLES

LCMS Methods:

Method 1:

Spectra were recorded on a Mass Spectrometer from Waters (SQD, SQDII Single quadrupole mass spectrometer) equipped with an electrospray source (Polarity: positive and negative ions, Capillary: 3.00 kV, Cone range: 30 V, Extractor: 2.00 V, Source Temperature: 150° C., Desolvation Temperature: 350° C., Cone Gas Flow: 50 l/h, Desolvation Gas Flow: 650 l/h, Mass range: 100 to 900 Da) and an Acquity UPLC from Waters: Binary pump, heated column compartment, diode-array detector and ELSD detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH, gradient: 10-100% B in 1.2 min; Flow (ml/min) 0.85.

Method 2:

Spectra were recorded on a Mass Spectrometer from Waters (SQD, SQDII Single quadrupole mass spectrometer) equipped with an electrospray source (Polarity: positive and negative ions), Capillary: 3.00 kV, Cone range: 30V, Extractor: 2.00 V, Source Temperature: 150° C., Desolvation Temperature: 350° C., Cone Gas Flow: 50 l/h, Desolvation Gas Flow: 650 l/h, Mass range: 100 to 900 Da) and an Acquity UPLC from Waters: Binary pump, heated column compartment, diode-array detector and ELSD detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH, gradient: 10-100% B in 2.7 min; Flow (ml/min) 0.85

Method 3:

Spectra were recorded on a Mass Spectrometer from Agilent (Single quad mass spectrometer) equipped with an Multimode-Electron Spray and APCI (Polarity: positive and negative ions), Capillary: 4.00 KV, Corona Current 4.0 μA, Charging Voltage, 2.00 kV, Nitrogen Gas Flow: 9.0 L/min, Nebulizer Pressure: 40 psig, Mass range: 100 to 1000 m/z), dry gas temperature 250° C., Vaporizer temperature 200° C. and Spectra were recorded on LCMS from Agilent: quaternary pump, heated column compartment, Variable wave length detector. Column: Eclipse XDB C18, 5.0 μm, 150×

4.6 mm, column Temp: Ambient, Wavelength (nm): 220 nm, Solvents: A=0.05% TFA in water, B=0.05% TFA in Acetonitrile. Gradient: time/% B: 0/5, 0.5/5, 3.5/90, 5/90, 5.1/5, 7/5; Flow rate: 1.0 ml/min Method 4:

Spectra were recorded on a Mass Spectrometer from Waters (SQD, SQDII Single quadrupole mass spectrometer) equipped with an electrospray source (Polarity: positive and negative ions, Capillary: 3.00 kV, Cone range: 41 V, Extractor: 2.00 V, Source Temperature: 150° C., Desolvation Temperature: 5000° C., Cone Gas Flow: 50 l/h, Desolvation Gas Flow: 1000 l/h, Mass range: 110 to 800 Da) and an Acquity UPLC from Waters: Binary pump, heated column compartment, diode-array detector and ELSD detector. Column: Waters UPLC HSS T3, 1.8 μm, 30×2.1 mm, Temp: 40° C., PDA Wavelength range (nm): 200 to 400, Solvent Gradient: A=water+5% Acetonitrile+0.1% HCOOH, B=Acetonitrile+0.05% HCOOH, gradient: 10-100% B in 1.3 min; Flow (ml/min) 0.6

Chiral SFC method 1: Spectra were recorded on a SFC from Waters (Waters Acquity UPC$^2$/QDa) equipped with a PDA Detector Waters Acquity UPC$^2$. Column: Daicel SFC CHIRALPAK® IC, (3 μm, 0.3 cm×10 cm, 40° C.; Mobile phase: A: CO2 B: MeOH isocratic: 10% B in 2.0 min; ABPR: 1800 psi; Flow rate: 2.0 ml/min; Detection: 220 nm; Sample concentration: 1 mg/mL in ACN; Injection: 1 μL Chiral SFC method 2: Spectra were recorded on a SFC from Waters (Waters Acquity UPC$^2$/QDa) equipped with a PDA Detector Waters Acquity UPC$^2$. Column: Daicel SFC CHIRALPAK® IG, (3 μm, 0.3 cm×10 cm, 40° C.; Mobile phase: A: CO2 B: MeOH isocratic: 15% B in 4.8 min; ABPR: 1800 psi; Flow rate: 2.0 ml/min; Detection: 270 nm; Sample concentration: 1 mg/mL in ACN/MeOH (1:1); Injection: 1 μL

Preparation of methyl 2-chloro-6-(trifluoromethyl)pyridine-4-carboxylate (Intermediate I1)

(I1)

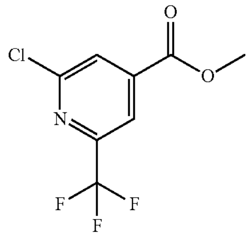

Sulfuric acid (2.46 mL, 44.3 mmol, 1.00 equiv.) was added dropwise at room temperature to a solution of 2-chloro-6-(trifluoromethyl)pyridine-4-carboxylic acid (CAS 796090-23-8, 10.0 g, 44.3 mmol) in methanol (266 mL). The reaction mixture was heated up to 65° C. and stirred overnight. After cooling down to room temperature, the reaction mixture was poured over a saturated sodium hydrogenocarbonate aqueous solution and the aqueous phase was extracted three times with dichloromethane. The combined organic layers were dried over sodium sulfate, filtered and evaporated to afford the desired product (10.2 g, 42.70 mmol) which was used without further purification.

$^1$H NMR (400 MHz, chloroform-d) δ ppm: 4.04 (s, 3H) 8.11 (s, 1H) 8.17 (d, J=1.10 Hz, 1H).

Preparation of methyl 2-cyclopropyl-6-(trifluoromethyl)pyridine-4-carboxylate (Intermediate I2) and 2-cyclopropyl-6-(trifluoromethyl)pyridine-4-carboxylic acid (Intermediate I3)

(I2)

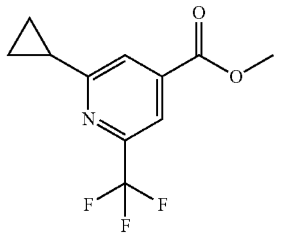

(I3)

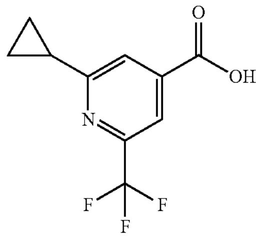

Cyclopropylboronic acid (1.43 g, 16.7 mmol, 2.00 equiv.) and sodium hydrogenocarbonate (2.10 g, 25.1 mmol, 3.00 equiv.) were added to a solution of methyl 2-chloro-6-(trifluoromethyl)pyridine-4-carboxylate (intermediate I1 prepared as described above) (2.00 g, 8.35 mmol) in 1,4-dioxane (20.9 mL) and water (8.35 mL), and the resulting suspension was flushed with argon for 10 min. [1,1'-bis (diphenylphosphino)ferrocene] dichloropalladium (II) (0.322 g, 0.417 mmol, 0.05 equiv.) was added and the resulting suspension was stirred at 100° C. for 1 hour under argon. After cooling down to room temperature, the reaction mixture was quenched with water and extracted twice with ethyl acetate. The combined organic phases were dried over sodium sulfate, filtered and evaporated to give of first crude material, which gave after purification by flash chromatography over silica gel (ethyl acetate in cyclohexane) the desired intermediate I2 (0.706 g, 2.88 mmol).

$^1$H NMR (400 MHz, chloroform-d) δ ppm: 1.04-1.23 (m, 4H) 2.14-2.28 (m, 1H) 4.00 (s, 3H) 7.88 (s, 1H) 7.95 (d, J=1.47 Hz, 1H).

LC-MS (method 1): retention time 1.12 min, m/z 246 $[M+H]^+$.

After acidification to pH 1, the aqueous layer was extracted again twice with ethyl acetate, the combined organic phases were dried over sodium sulfate, filtered and evaporated to give a second crude material, which upon purification by flash chromatography over silica gel (methanol in dichloromethane) afforded the intermediate I3 (0.166 g, 0.718 mmol).

$^1$H NMR (400 MHz, dimethylsulfoxide-d6) δ ppm: 0.94-1.03 (m, 2H) 1.06-1.15 (m, 2H) 2.37-2.46 (m, 1H) 7.88 (d, J=1.10 Hz, 1H) 8.05 (d, J=0.73 Hz, 1H) 13.89-14.33 (m, 1H).

LC-MS (method 1): retention time 0.94 min, m/z 232 $[M+H]^+$.

Preparation of 2-cyclopropyl-6-(trifluoromethyl) pyridine-4-carboxylic acid (Intermediate I3)

(I3)

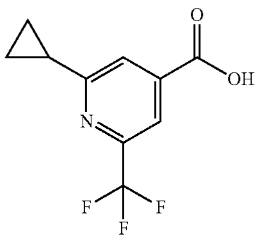

Lithium hydroxide monohydrate (0.147 g, 3.43 mmol, 1.20 equiv.) was added to a solution of methyl 2-cyclopropyl-6-(trifluoromethyl)pyridine-4-carboxylate (intermediate I2 prepared as described above) in a 3:1 tetrahydrofuran/water mixture (24.5 mL). After stirring for 2 hours at room temperature, the reaction mixture was concentrated, and the remaining aqueous phase was acidified to pH 1 by addition of a 1 M hydrochloric acid aqueous solution (3.43 mL). The aqueous layer was extracted three times with ethyl acetate, the combined organic phases were dried over sodium sulfate, filtered and concentrated to afford 2-cyclopropyl-6-(trifluoromethyl)pyridine-4-carboxylic acid.

$^1$H NMR (400 MHz, dimethylsulfoxide-d6) δ ppm: 0.96-1.02 (m, 2H) 1.07-1.15 (m, 2H) 2.40 (tt, $J_1$=8.12 Hz, $J_2$=4.72 Hz, 1H) 7.88 (d, J=1.10 Hz, 1H) 8.04 (s, 1H) 13.90-14.36 (m, 1H)

LC-MS (method 1): retention time 0.94 min, m/z 232 $[M+H]^+$.

Preparation of methyl 3-cyclopropyl-5-(trifluoromethyl)benzoate (Intermediate I4)

(I4)

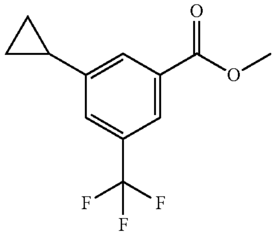

A solution of propargyl bromide in toluene (80% weight, 0.89 g, 0.67 mL) was added to a white suspension of 9-BBN dimer (3.0 g, 12 mmol) in 26 mL of dry tetrahydrofuran under argon to give a pale yellow solution. The mixture was refluxed for 2 hours and then cooled to room temperature. A previously degassed sodium hydroxide 4M aqueous solution (4.4 mL, 18 mmol) was added to give a cloudy colorless solution. The mixture obtained was stirred for 1 hour at room temperature under argon. The resulting very pale yellow solution was then added to a previously degassed light yellow solution of methyl 3-bromo-5-(trifluoromethyl)benzoate (187331-46-0, 1.5 g, 5.2 mmol) and tetrakis(triphenylphosphine) palladium(0) (0.30 g, 0.26 mmol) in 52 mL of dry tetrahydrofuran to give a light yellow solution. The resulting mixture was stirred for 19 hours at reflux. The mixture was cooled down at room temperature, diluted with ethyl acetate, quenched with water (+few drops of brine) and the aqueous layer was extracted twice with ethyl acetate. Organic layers were combined, washed once with brine, dried over sodium sulfate, filtered and evaporated under vacuum at 60° C. The crude was purified by chromatography over silica gel to afford methyl 3-cyclopropyl-5-(trifluoromethyl)benzoate as a colorless liquid.

$^1$H NMR (400 MHz, chloroform-d) δ ppm: 0.76-0.85 (m, 2H) 1.06-1.15 (m, 2H) 2.03 (tt, $J_1$=8.39 Hz, $J_2$=5.00 Hz, 1H) 3.96 (s, 3H) 7.52 (s, 1H) 7.91 (s, 1H) 8.08 (d, J=0.73 Hz, 1H).

$^{19}$F NMR (377 MHz, chloroform-d) δ ppm: −62.75 (s, 3 F).

Preparation of 3-cyclopropyl-5-(trifluoromethyl)benzoic acid (Intermediate I5)

(I5)

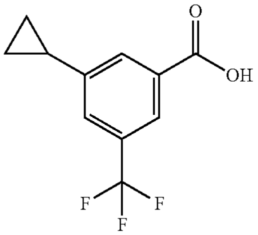

Methyl 3-cyclopropyl-5-(trifluoromethyl)benzoate (7.00 g, 28.7 mmol) was dissolved in tetrahydrofuran (57.3 mL) and water (28.7 mL). Then lithium hydroxide (1.21 g, 28.7 mmol) was added and the resulting pale yellow cloudy solution was stirred for 4 hours at room temperature. The reaction mixture was diluted in ethyl acetate and water. The organic phase was washed twice with water. The combined aqueous layers were acidified with 1N aqueous hydrochloric acid until pH 1-2 and extracted three times with ethyl acetate. The combined organic layers were washed once with brine, dried over sodium sulfate, filtered and concentrated under reduced pressure at 60° C. to afford 3-cyclopropyl-5-(trifluoromethyl)benzoic acid, which was used without further purification.

$^1$H NMR (400 MHz, dimethylsulfoxide-d6) δ ppm: 0.79-0.85 (m, 2H) 1.03-1.10 (m, 2H) 2.12-2.22 (m, 1H) 7.70 (s, 1H) 7.88 (s, 1H) 7.93 (s, 1H) 13.47 (br s, 1H).

LC-MS (method 1): retention time 0.99 min, m/z 229 $[M-H]^-$.

Preparation of methyl 3-(trifluoromethyl)-5-vinyl-benzoate (Intermediate I6)

(I6)

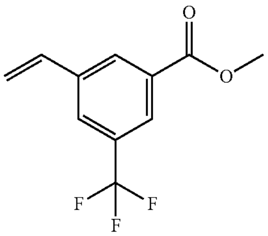

In a three neck flask under argon, methyl 3-bromo-5-(trifluoromethyl)benzoate (CAS: 187331-46-0, 20 g, 69.24 mmol) was dissolved in toluene (312 mL). Then Tributyl (vinyl) Tin (25.56 mL, 83.09 mmol) was added and the resulting solution was degassed with argon for 10 min. Tetrakis(triphenylphosphine) palladium(0) (0.816543 g, 0.69 mmol) was added, and the resulting mixture was stirred at 110° C. for 2 hours. After cooling at room temperature, the mixture was diluted with ethyl acetate (100 mL), filtered though a pad of Celite, washed with ethyl acetate and the filtrate was concentrated under vacuum. The crude was purified by chromatography over silica gel to afford methyl 3-(trifluoromethyl)-5-vinyl-benzoate.

$^1$H NMR (400 MHz, chloroform-d) δ ppm: 3.98 (s, 3H) 5.47 (d, J=11.00 Hz, 1H) 5.93 (d, J=17.61 Hz, 1H) 6.79 (dd, $J_1$=17.42 Hz, $J_2$=10.82 Hz, 1H) 7.82 (s, 1H) 8.19 (s, 1H) 8.24-8.29 (m, 1H).

Preparation of diphenyl(2,2,2-trifluoroethyl)sulfonium trifluoromethanesulfonate

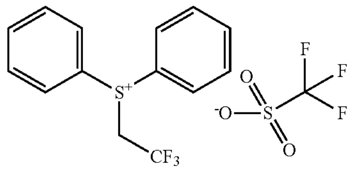

In an autoclave, diphenyl sulfide (36.43 mL, 211.1 mmol) and 2,2,2-trifluoroethyl trifluoromethanesulfonate (6.207 mL, 42.22 mmol) were mixed. The mixture was stirred for 2 min at room temperature then the autoclave was closed and heated at 150° C. for 20 hours. The reaction was cooled at room temperature and a white precipitate was formed. 75 ml of diethyl ether was added, then the white solid was filtered. It was washed four times with 30 mL of diethyl ether and then dried under reduced pressure to afford diphenyl(2,2,2-trifluoroethyl)sulfonium trifluoromethanesulfonate.

$^1$H NMR (400 MHz, chloroform-d) δ ppm: 5.78 (d, J=8.80 Hz, 2H) 7.89 (d, J=8.07 Hz, 4H) 7.93-8.00 (m, 2H) 8.37 (dd, $J_1$=8.62 Hz, $J_2$=1.28 Hz, 4H).

$^{19}$F NMR (377 MHz, chloroform-d) δ ppm: −78.91 (s, 3 F)-61.26 (s, 3 F).

Preparation of methyl 3-(trifluoromethyl)-5-[2-(trifluoromethyl)cyclopropyl]benzoate (Intermediate I7)

(I7)

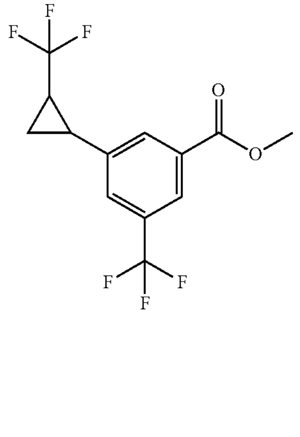

In a vial under argon, 3-(trifluoromethyl)-5-vinyl-benzoate (1.9 g, 8.3 mmol) and cesium fluoride (1.5 g, 9.9 mmol) were dissolved in dimethylacetamide (33 mL) to give a colorless solution which was degassed under argon for 20 min. 5,10,15,20-Tetraphenyl-21H,23H-porphine Iron(III) chloride (0.31 g, 0.41 mmol) was added. The reaction became a green suspension and diphenyl(2,2,2-trifluoroethyl)sulfonium trifluoromethanesulfonic acid (3.8 g, 9.1 mmol) was also added portionwise. The reaction was stirred at room temperature overnight. The resulting mixture was diluted with dichloromethane, then water was added. The organic layer was washed four times with water, dried over sodium sulfate, filtered and concentrated under reduced pressure at 40° C. under 160 mbar. The crude was purified by chromatography over silica gel to afford methyl 3-(trifluoromethyl)-5-[2-(trifluoromethyl)cyclopropyl]benzoate.

$^1$H NMR (400 MHz, chloroform-d) δ ppm: 1.25-1.34 (m, 1H) 1.48-1.55 (m, 1H) 1.88-2.00 (m, 1H) 2.46-2.53 (m, 1H) 3.98 (s, 3H) 7.60 (s, 1H) 7.98 (s, 1H) 8.19 (s, 1H).

Preparation of 3-(trifluoromethyl)-5-[2-(trifluoromethyl)cyclopropyl]benzoic acid (I8)

(I8)

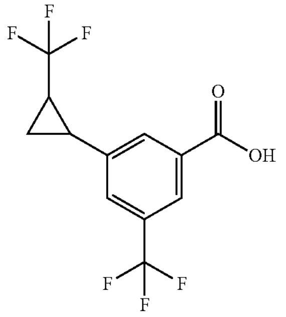

3-(trifluoromethyl)-5-[2-(trifluoromethyl)cyclopropyl] benzoate (1.43 g, 3.80 mmol) was dissolved in tetrahydrofuran (11.4 mL) and water (7.60 mL). Lithium hydroxide monohydrate (0.322 g, 7.60 mmol) was added and the resulting mixture was stirred 3 hours 30 min at room temperature. The reaction mixture was cooled to 0° C. then it was acidified with a 2M hydrochloric acid solution. The aqueous layer was extracted twice with ethyl acetate, the organic layer was washed with brine, dried over sodium sulfate, filtered and concentrated under reduced pressure to afford 3-(trifluoromethyl)-5-[2-(trifluoromethyl)cyclopropyl]benzoic acid.

$^1$H NMR (400 MHz, dimethylsulfoxide-d6) δ ppm 1.40-1.47 (m, 2H) 2.53-2.60 (m, 1H) 2.72 (td, $J_1$=7.70 Hz, $J_2$=4.77 Hz, 1H) 7.87 (s, 1H) 8.02 (s, 1H) 8.05-8.08 (m, 1H) 13.54 (br s, 1H).

LC-MS (method 1): retention time 1.04 min, m/z 297 $[M-H]^-$.

Preparation of methyl 3-(trifluoromethyl)-5-(trifluoromethylsulfanyl)benzoate (Intermediate I9)

(I9)

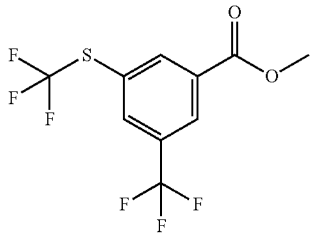

(2,2'-bipyridine)(trifluoromethanethiolato) copper (CAS 1413732-47-4) (3.9 g, 12 mmol, 2.0 equiv.) was added to a solution of methyl 3-iodo-5-(trifluoromethyl)benzoate (2.0 g, 6.1 mmol) in acetonitrile (18 mL) under argon. The reaction mixture was heated up to 90° C. and stirred overnight. After cooling down to room temperature, the reaction mixture was filtered over a pad of Celite and concentrated. The crude material was purified by two flash chromatographies over silica gel (ethyl acetate in cyclohexane) to afford the desired product as a yellow gum (1.5 g, 4.9 mmol).

$^{1}H$ NMR (400 MHz, chloroform-d) δ ppm: 4.02 (s, 3H), 8.11 (s, 1H), 8.44 (s. 1H), 8.53 (s, 1H).

LC-MS (method 1): retention time 1.21 min, m/z 279 $[M-MeO+H]^+$.

Preparation of methyl 3-(trifluoromethyl)-5-(trifluoromethylsulfonyl)benzoate (Intermediate I10)

(I10)

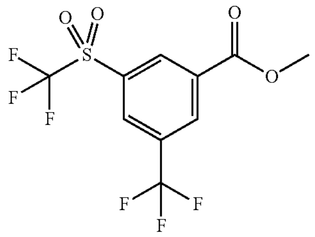

3-Chloroperbenzoic acid (2.3 g, 11 mmol, 2.1 equiv.) was added portionwise to a 0° C. cooled solution of methyl 3-(trifluoromethyl)-5-(trifluoromethylsulfanyl)benzoate (intermediate I13 prepared as described above) (1.8 g, 5.3 mmol) in dichloromethane (16 mL). After stirring for 1 hour at room temperature, more 3-chloroperbenzoic acid (2.3 g, 11 mmol, 2.1 equiv.) was added and the reaction mixture was stirred overnight. The precipitate formed was filtered. The filtrate was washed with 10% aqueous solution of sodium thiosulfate and with $NaHCO_3$ sat solution. The organic phase was dried over sodium sulfate, filtered and concentrated under reduced pressure. The crude was purified by chromatography over silica gel to afford methyl 3-(trifluoromethyl)-5-(trifluoromethylsulfonyl) benzoate.

$^{1}H$ NMR (400 MHz, Chloroform) δ ppm 4.07 (s, 3H) 8.43-8.51 (m, 1H) 8.70-8.80 (m, 1H) 8.84-8.91 (m, 1H).

$^{19}F$ NMR (377 MHz, chloroform-d) δ ppm: −77.49 (s, 3 F)-62.96 (s, 3 F)

Preparation of 3-(trifluoromethyl)-5-(trifluoromethylsulfonyl)benzoic acid (I11)

(I11)

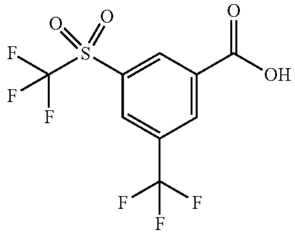

Methyl 3-(trifluoromethyl)-5-(trifluoromethylsulfonyl) benzoate (1.8 g, 5.4 mmol) was charged in a flask and dissolved in tetrahydrofuran (16 mL) and water (11 mL). To this mixture was added lithium hydroxide monohydrate (0.26 g, 11 mmol) and the reaction was stirred for 1 hour at room temperature. The reaction mixture was acidified with 1 M hydrochloric acid, and the aqueous phase was extracted with ethyl acetate twice. The combined organic phases were dried over sodium sulfate, filtered and then concentrated to afford 3-(trifluoromethyl)-5-(trifluoromethylsulfonyl)benzoic acid which was used without further purification.

$^{1}H$ NMR (400 MHz, dimethylsulfoxide-d6) δ ppm: 8.68 (s, 2H) 8.71-8.76 (m, 1H) 13.33-15.22 (m, 1H).

Preparation of methyl 3-(cyclopropanecarbonyl)-5-(trifluoromethyl)benzoate (Intermediate I12)

(I12)

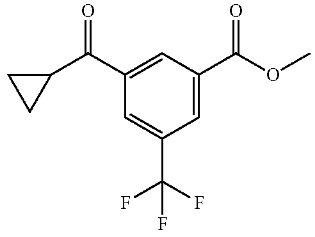

Methyl 3-iodo-5-(trifluoromethyl)benzoate (10 g, 28.78 mmol) was taken in tetrahydrofuran (115 mL) under argon. The resulting pale brown solution was cooled down to −78° C. with a dry ice/acetone bath. The Turbo-Grignard 1.3 M in tetrahydrofuran solution (31 mL, 40.29 mmol) was added dropwise with a syringe over 20 minutes to give directly a dark solution while maintaining the temperature below −65° C. The resulting mixture was stirred at −78° C. for 15 minutes. Cuprous cyanide (3.125 g, 34.5 mmol) and anhydrous lithium chloride (1.479 g, 34.5 mmol) were added simultaneously at once to give a dark suspension. The resulting mixture was stirred again at −78° C. for 15 minutes. Cyclopropanecarbonyl chloride (5.340 mL, 57.5 mmol) was finally added dropwise over 5 minutes (temperature reached −68° *C. maximum*). The resulting mixture was stirred at −78° C. for 1 hour, warmed up to room temperature and stirred for 30 minutes to give a brown suspension. The reaction mixture was cooled down to −78° C. and quenched slowly with 20 ml of methanol. The resulting mixture was allowed to reach room temperature and the suspension obtained was filtered over Celite. Saturated aqueous ammonium chloride and ethyl acetate were added to the filtrate. The aqueous layer was extracted twice with ethyl acetate. The combined organic layers were dried over sodium sulfate, filtered and concentrated under reduced pressure at 40° C. The crude material was purified by chromatography over silica gel to afford methyl 3-(cyclopropanecarbonyl)-5-(trifluoromethyl)benzoate.

$^1H$ NMR (400 MHz, chloroform-d) δ ppm: 1.16-1.22 (m, 2H) 1.35 (quin, J=3.76 Hz, 2H) 2.74 (tt, $J_1$=7.84 Hz, $J_2$=4.45 Hz, 1H) 4.02 (s, 3H) 8.45 (d, J=0.73 Hz, 1H) 8.51 (d, J=0.73 Hz, 1H) 8.86 (s, 1H).

Preparation of methyl 3-[cyclopropyl(difluoro) methyl]-5-(trifluoromethyl)benzoate (Intermediate I13)

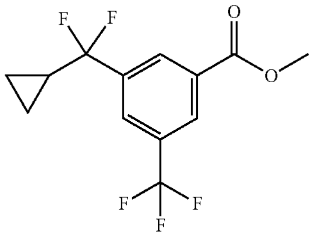

(I13)

Methyl 3-(cyclopropanecarbonyl)-5-(trifluoromethyl) benzoate (5.5 g, 20 mmol) was taken in 2,2-difluoro-1,3-dimethyl-imidazolidine (36 mL, 280 mmol) under argon to give a light yellow solution. The resulting mixture was stirred for 5 hours at 110° C. to give a light brown solution. The reaction mixture was cooled down to room temperature and added dropwise to 1.0 L of a vigorously stirred saturated aqueous sodium hydrogenocarbonate solution at 0° C. (temperature was maintained below 10° C.). The resulting mixture (pH 8-9) was then extracted 3 times with ethyl acetate. The combined organic layers were dried over sodium sulfate, filtered and concentrated under reduced pressure at 50° C. The crude material was purified by chromatography over silica gel to afford methyl 3-[cyclopropyl(difluoro)methyl]-5-(trifluoromethyl)benzoate.

$^1H$ NMR (400 MHz, chloroform-d) δ ppm: 0.73-0.79 (m, 2H) 0.82-0.89 (m, 2H) 1.47-1.60 (m, 1H) 8.00 (d, J=0.73 Hz, 1H) 8.39 (s, 1H) 8.42 (s, 1H). $^{19}F$ NMR (377 MHz, chloroform-d) δ ppm: −98.40 (s, 3 F)-62.81 (s, 2 F).

Preparation of 3-[cyclopropyl(difluoro)methyl]-5-(trifluoromethyl)benzoic acid (I14)

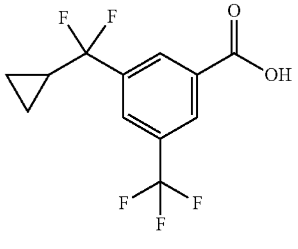

(I14)

Methyl 3-[cyclopropyl(difluoro)methyl]-5-(trifluoromethyl)benzoate (4.45 g, 15.1 mmol) was taken in tetrahydrofuran (30.3 mL) and water (15.1 mL). Lithium hydroxide monohydrate (0.833 g, 19.7 mmol) was added and the resulting colourless cloudy solution was stirred for 1 hour at room temperature. The reaction mixture was diluted with ethyl acetate and water. The organic phase was washed twice with water. The combined aqueous layers were acidified with 1N aqueous hydrochloric acid until pH 1-2 and extracted three times with ethyl acetate. The combined organic layers were washed once with brine, dried over sodium sulfate, filtered and concentrated under reduced pressure at 60° C. to afford 3-[cyclopropyl(difluoro)methyl]-5-(trifluoromethyl)benzoic, which was used without further purification.

$^1H$ NMR (400 MHz, dimethylsulfoxide-d6) δ ppm: 0.62-0.84 (m, 4H) 1.65-1.97 (m, 1H) 7.93-8.23 (m, 1H) 8.23-8.51 (m, 2H) 13.24-14.48 (m, 1H).

LC-MS (method 1): retention time 1.03 min, m/z 279 $[M-H]^-$.

Preparation of methyl 2-(1-cyano-2-ethoxy-2-oxo-ethyl)-6-(trifluoromethyl)pyridine-4-carboxylate (Intermediate I15)

(I15)

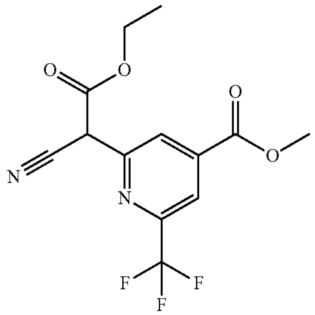

Methyl 2-chloro-6-(trifluoromethyl)pyridine-4-carboxylate (1.05 g, 4.40 mmol) was dissolved in dimethylsulfoxide (13.2 mL). Then ethyl 2-cyanoacetate (0.702 mL, 6.60 mmol), potassium carbonate (1.535 g, 11.00 mmol) and tetrabutylammonium bromide (0.145 g, 0.440 mmol) were added successively at room temperature. The resulting suspension was stirred 1 hour at 90° C. and then let stirred overnight at room temperature. The reaction mass was diluted with 50 mL of water and 100 mL of ethyl acetate, cooled to O-10° C. and slowly quenched with 1N hydrochloric acid via dropping funnel until pH 3. The aqueous phase was extracted with ethyl acetate. The combined organic layers were dried over sodium sulfate and concentrated under reduced pressure at 50° C. The crude material was purified by chromatography over silica gel with ethyl acetate in cyclohexane to afford methyl 2-(1-cyano-2-ethoxy-2-oxo-ethyl)-6-(trifluoromethyl)pyridine-4-carboxylate.

$^1H$ NMR (400 MHz, chloroform-d) δ ppm: 1.36-1.43 (m, 3H) 4.01 (s, 3H) 4.34 (q, J=7.58 Hz, 2H) 7.34 (s, 1H) 8.06 (s, 1H) 14.46-14.67 (m, 1H).

LC-MS (method 1): retention time 1.01 min, m/z 317 $[M+H]^+$.

Preparation of methyl 2-(cyanomethyl)-6-(trifluoromethyl)pyridine-4-carboxylate (I16)

(I16)

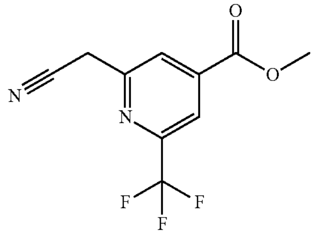

To a solution of methyl 2-(1-cyano-2-ethoxy-2-oxo-ethyl)-6-(trifluoromethyl)pyridine-4-carboxylate (0.800 g, 2.53 mmol) in dimethyl sulfoxide (20 mL) was added sodium chloride (0.299 g, 5.06 mmol) in water (10 mL). The resulting mixture was stirred for 4 hours at 95° C. After cooling down to room temperature, the reaction mixture was diluted with water (50 mL) and extracted with ethyl acetate (3*50 mL). The combined organic layers were dried over sodium sulfate, filtered and contracted under reduced pressure to afford methyl 2-(cyanomethyl)-6-(trifluoromethyl) pyridine-4-carboxylate which was used without further purification.

$^1$H NMR (400 MHz, chloroform-d) δ ppm: 4.05 (s, 3H) 4.13 (s, 2H) 8.24 (s, 1H) 8.26 (s, 1H).

LC-MS (method 1): retention time 0.89 min, m/z 243 $[M-H]^-$.

Preparation of 2-(1-cyanocyclopropyl)-6-(trifluoromethyl)pyridine-4-carboxylic acid (I17)

(I17)

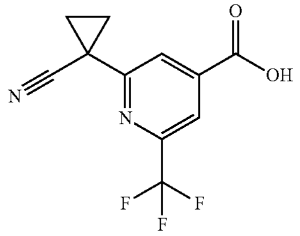

Methyl 2-(cyanomethyl)-6-(trifluoromethyl)pyridine-4-carboxylate (0.05 g, 0.20 mmol) was dissolved in dimethylformamide (2 mL). Sodium hydride (24 mg, 0.61 mmol) was added at room temperature and the colorless solution became a dark purple suspension. After 10 min, 1,2-dibromoethane (0.02 mL, 0.24 mmol) was added and the resulting suspension was stirred for 15 min at room temperature. The reaction mixture was quenched with a saturated ammonium chloride solution at 0-5° C. and diluted with ethyl acetate. The aqueous layer was acidified to pH 2-3 with 1N hydrochloric acid and extracted twice with ethyl acetate. The combined organic layers were dried over sodium sulfate, filtered and evaporated under reduced pressure. The crude was purified by reverse phase chromatography to afford 2-(1-cyanocyclopropyl)-6-(trifluoromethyl)pyridine-4-carboxylic acid.

$^1$H NMR (400 MHz, dimethylsulfoxide-d6) δ ppm: 1.76-1.83 (m, 2H) 1.96-2.03 (m, 2H) 8.07 (d, J=1.10 Hz, 1H) 8.17 (s, 1H) 13.35-15.45 (m, 1H).

LC-MS (method 1): retention time 0.89 min, m/z 255 $[M-H]^-$.

Preparation of methyl 3-(cyanomethyl)-5-(trifluoromethyl)benzoate (Intermediate I18)

(I18)

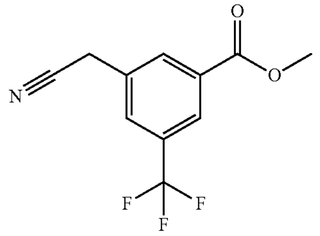

Methyl 3-bromo-5-(trifluoromethyl)benzoate (0.600 g, 2.08 mmol) was dissolved in N,N-dimethylformamide (4.2 mL). (Trimethylsilyl)acetonitrile (0.862 mL, 6.23 mmol) was added dropwise with a syringe. The solution was degassed under Ar for 5 min. Then $ZnF_2$ (0.130 g, 1.25 mmol), Xantphos (0.0481 g, 0.0831 mmol) and $Pd_2(dba)_3$ (0.0384 g, 0.0415 mmol) were added. The resulting black suspension was stirred at 100° C. for 22 hours then cooled down to room temperature. The mixture was concentrated under reduced pressure at 50° C. The crude material was purified by chromatography over silica gel with ethyl acetate in cyclohexane to afford methyl 3-(cyanomethyl)-5-(trifluoromethyl)benzoate.

$^1$H NMR (400 MHz, chloroform-d) δ ppm: 8.30 (1H, s), 8.23 (1H, s), 7.81 (1H, s), 3.99 (3H, s), 3.90 (2H, s); LC-MS (method 1): retention time 0.92 min, m/z 242 $[M-H]^-$.

Preparation of methyl 3-(1-cyanocyclopropyl)-5-(trifluoromethyl)benzoate (Intermediate I19)

(I19)

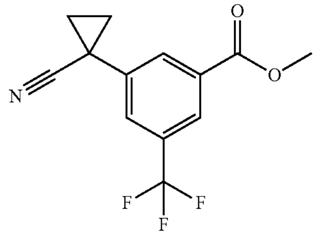

methyl 3-(cyanomethyl)-5-(trifluoromethyl)benzoate (2.15 g, 7.07 mmol) was dissolved in N,N-dimethylformamide (32.3 mL). Cesium carbonate (7.13 g, 21.2 mmol) was added to the stirred solution and the mixture was stirred at room temperature for 10 min. 1,2-dibromoethane (0.68 mL 7.78 mmol) was added and the mixture was stirred at 60° C. for 3 hours then cooled down to room temperature. Water (30 mL) was added, then the aqueous layer was extracted with ethyl acetate (60 mL). The combined organic layers were dried over sodium sulfate, filtered and concentrated in vacuo. The crude material was purified by flash chromatography (silica gel, ethyl acetate in hexanes) to afford methyl 3-(1-cyanocyclopropyl)-5-(trifluoromethyl)benzoate.

$^{1}$H NMR (400 MHz, chloroform-d) δ ppm: 8.23 (1H, s), 8.09 (1H, s), 7.79 (1H, s), 3.98 (3H, s), 1.84-1.92 (2H, m), 1.47-1.57 (m, 2H).

Preparation of 3-(1-cyanocyclopropyl)-5-(trifluoromethyl)benzoic acid (Intermediate I20)

(I20)

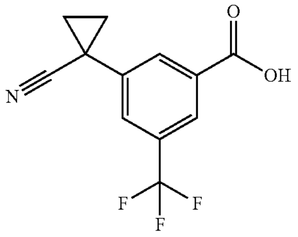

Methyl 3-(1-cyanocyclopropyl)-5-(trifluoromethyl)benzoate (59 mg, 0.22 mmol) was dissolved in tetrahydrofuran (0.66 mL) and water (0.33 ml). Lithium hydroxide monohydrate (9.3 mg, 0.22 mmol) was added and the mixture was stirred at room temperature for 42 hours. 1N hydrochloric acid was added until pH=2. The aqueous layer was extracted three times with ethyl acetate. The combined organic layers were dried over sodium sulfate, filtered and concentrated in vacuo to afford 3-(1-cyanocyclopropyl)-5-(trifluoromethyl) benzoic acid.

$^{1}$H NMR (400 MHz, chloroform-d) δ ppm: 8.60-9.90 (1H, br s), 8.29 (1H, s), 8.15 (1H, s), 7.84 (1H, s), 1.84-1.93 (2H, m), 1.50-1.60 (2H, m).

LC-MS (method 1): retention time 0.86 min. m/z 254 $[M-H]^-$.

Preparation of 1-[3-bromo-5-(trifluoromethyl)phenyl]ethanol

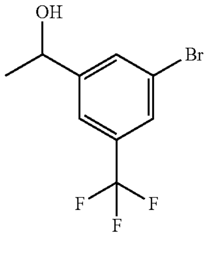

Methyl magnesium bromide (1.00 M in THF, 63.2 mL, 63.2 mmol) was added to a solution of 3-bromo-5-(trifluoromethyl)benzaldehyde (8.00 g, 31.6 mmol) in tetrahydrofuran (100 mL) at 0° C. under nitrogen. resulting brown reaction mixture was stirred at room temperature for 30 min. The reaction mixture was quenched with saturated ammonium chloride solution. The aqueous layer was extracted with ethyl acetate, dried over sodium sulfate and concentrated under reduced pressure to obtain 1-[3-bromo-5-(trifluoromethyl)phenyl]ethanol as a light yellow liquid. 1H NMR (400 MHz, DMSO-d) δ ppm: 7.78-7.88 (m, 2H), 7.71 (s, 1H), 5.52 (d, 1H), 4.81 (m, 1H), 1.35 (d, 3H).

Preparation of 1-[3-bromo-5-(trifluoromethyl)phenyl]ethanone

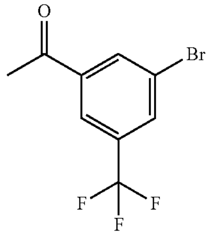

Pyridinium chlorochromate (5.05 g, 23.4 mmol) was added portionwise to a stirred solution of 1-[3-bromo-5-(trifluoromethyl)phenyl]ethanol (7.00 g, 15.6 mmol) in dichloromethane (150 mL) at 0° C. The resulting brown colour reaction mixture was stirred at room temperature for 2 hours. The reaction mixture was filtered through celite pad then the filtrate was evaporated under reduced pressure. The crude residue was purified by flash chromatography over silica gel (eluting with ethyl acetate in hexanes) to afford 1-[3-bromo-5-(trifluoromethyl)phenyl]ethanone as a colorless oil.

1H NMR (400 MHz, DMSO-d) δ ppm: 8.38 (1H, s), 8.26 (1H, s), 8.19 (1H, s), 2.69 (s, 1H).

Preparation of 1-[3-bromo-5-(trifluoromethyl)phenyl]cyclopropanol

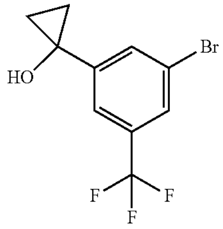 [SMILES: OC1(c2cc(Br)cc(C(F)(F)F)c2)CC1]

A solution of 1-[3-bromo-5-(trifluoromethyl)phenyl]ethanone (5.00 g, 18.3 mmol) in dichloromethane (30 mL) at 0° C. was treated with triethylamine (3.84 mL, 27.5 mmol) and trimethylsilyl trifluoromethanesulfonate (6.12 g, 27.5 mmol). The mixture was stirred for 2 hours at room temperature. The reaction mixture was quenched with saturated sodium bicarbonate solution (100 mL). The aqueous layer was extracted with dichloromethane. The organic layer was dried over sodium sulfate and concentrated under reduced pressure. The crude silyl enol ether was dissolved in dichloromethane and cooled down to 0° C. Di-iodomethane (7.37 g, 27.5 mmol) and diethylzinc (1.00 M in hexane, 27.5 mL, 27.5 mmol) were added dropwise and the mixture was stirred for 16 hours at room temperature. The reaction mixture was quenched with saturated ammonium chloride solution. The aqueous layer was extracted with dichloromethane. The organic layer was dried over sodium sulfate and concentrated under reduced pressure. The residue was dissolved in methanol at 0° C. and potassium carbonate (0.254 g, 1.83 mmol) was added. The resulting light yellow reaction mixture was stirred at 0° C. for 1 hour. The reaction mixture was concentrated under reduced pressure. The residue was purified by flash chromatography over silica gel (eluting with ethyl acetate in hexanes) to afford 1-[3-bromo-5-(trifluoromethyl)phenyl]cyclopropanol as an off-white solid.

1H NMR (400 MHz, chloroform-d) δ ppm: 7.75 (1H, s), 7.65 (1H, s), 7.58 (1H, s), 6.30 (s, 1H), 1.15-1.25 (m, 2H), 1.05-1.15 (m, 2H).

Preparation of 1-bromo-3-(1-methoxycyclopropyl)-5-(trifluoromethyl)benzene (I50)

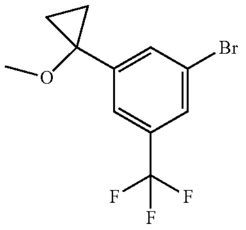 [SMILES: COC1(c2cc(Br)cc(C(F)(F)F)c2)CC1]

A solution of 1-[3-bromo-5-(trifluoromethyl)phenyl]cyclopropanol (500 mg, 1.74 mmol) in tetrahydrofuran (2.0 mL) was added dropwise to a suspension of sodium hydride (60% in oil, 139 mg, 3.49 mmol) in tetrahydrofuran (2.0 mL). The mixture was stirred at 0° C. for 10 minutes. Methyl iodide (371 mg, 2.62 mmol) was added dropwise and the resulting mixture was stirred at 0° C. for 1 hour. Saturated ammonium chloride solution was added. The aqueous layer was extracted with ethyl acetate. The combined organic layers were dried over sodium sulfate and concentrated under reduced pressure. The crude residue was purified by flash chromatography over silica gel (gradient of ethyl acetate in hexanes) to afford 1-bromo-3-(1-methoxycyclopropyl)-5-(trifluoromethyl)benzene as a colorless liquid.

1H NMR (400 MHz, DMSO-d) δ ppm: 7.82 (s, 1H), 7.69 (s, 1H), 7.55 (s, 1H), 3.27 (s, 3H), 1.20-1.28 (m, 2H), 1.09-1.18 (m, 2H).

Preparation of methyl 3-(1-methoxycyclopropyl)-5-(trifluoromethyl)benzoate (I51)

(I51)

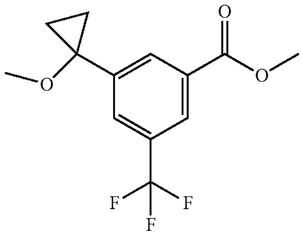

An autoclave was charged with 1-bromo-3-(1-methoxycyclopropyl)-5-(trifluoromethyl)benzene (1.50 g, 4.83 mmol), triethylamine (1.02 mL, 7.24 mmol) and methanol (30 mL). The reaction mixture was purged with argon. [1,1'-bis(diphenylphosphino)ferrocene]dichloropalladium (II) (353 mg, 0.483 mmol) was added. The autoclave was placed under carbon monoxide atmosphere (200 psi) and heated to 100° C. for 16 hours. The autoclave was cooled down to room temperature and filled with argon. The reaction mixture was filtered through celite. Water and ethyl acetate were added to the filtrate and the aqueous layer was extracted with ethyl acetate. The combined organic layers were dried over sodium sulfate and concentrated in vacuo. The crude residue was purified by flash chromatography over silica gel (gradient of ethyl acetate in hexanes) to afford methyl 3-(1-methoxycyclopropyl)-5-(trifluoromethyl)benzoate as a pale yellow liquid.

1H NMR (400 MHz, chloroform-d) δ ppm: 8.17 (s, 1H), 8.05 (s, 1H), 7.78 (s, 1H), 3.95 (s, 3H), 3.25 (s, 3H), 1.30 (t, 2H), 1.05 (t, 2H).

Preparation of 3-(1-methoxycyclopropyl)-5-(trifluoromethyl)benzoic acid (I52)

(I52)

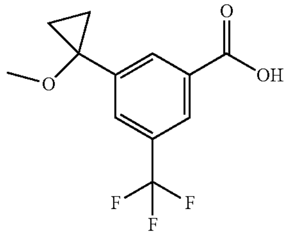

Methyl 3-(1-methoxycyclopropyl)-5-(trifluoromethyl)benzoate (1.00 g, 3.46 mmol) was dissolved in tetrahydrofuran (6.0 mL) and water (3.0 mL). Lithium hydroxide monohydrate (291 mg, 6.93 mmol) was added and the mixture was stirred at room temperature for 3 hours. The mixture was concentrated and 2N hydrochloric acid was added at 0° C. The precipitate that formed was filtered off, washed with water and dried to afford 3-(1-methoxycyclopropyl)-5-(trifluoromethyl)benzoic acid as a white solid.

1H NMR (400 MHz, chloroform-d) δ ppm: 13.4-13.7 (br. S, 1H), 8.00-8.10 (m, 2H), 7.72 (s, 1H), 3.19 (s, 3H), 1.25-1.35 (m, 2H), 1.08-1.15 (m, 2H).

Preparation of 1-(3-pyrimidin-2-ylpyrazin-2-yl)ethenone (I21)

(I21)

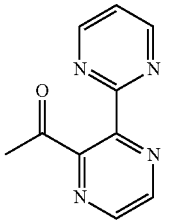

To a previously degassed solution of 1-(3-chloropyrazin-2-yl)ethanone (8.14 g, 52.0 mmol) in toluene (160 mL) were added tetrakis(triphenylphosphine)palladium(0) (4.72 g, 4.00 mmol), copper(I) iodide (0.777 g, 4.00 mmol) and tributyl(pyrimidin-2-yl)stannane (12.7 mL, 40.0 mmol). The reaction mixture was heated up to reflux and stirred overnight. After cooling down to room temperature, it was filtered though Celite and the filtrate was concentrated under reduced pressure. Two purifications of the crude material by flash chromatography over silica gel (eluting first with ethyl acetate:ethanol 3:1 in dichloromethane, and then with ethyl acetate in cyclohexane) afforded 1-(3-pyrimidin-2-ylpyrazin-2-yl)ethenone.

LCMS (method 1): retention time 0.37 min, m/z 201 [M+H$^+$]; $^1$H-NMR (400 MHz, $CDCl_3$): δ ppm: 8.89 (d, J=4.77 Hz, 2H) 8.82 (d, J=2.20 Hz, 1H) 8.68 (d, J=2.20 Hz, 1H) 7.37 (t, J=4.95 Hz, 1H) 2.76 (s, 3H).

Preparation of 1-(3-pyrimidin-2-ylpyrazin-2-yl)ethanamine (I31)

(I31)

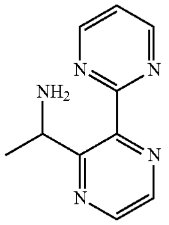

To a solution of 1-(3-pyrimidin-2-ylpyrazin-2-yl)ethanone (0.401 g, 2.01 mmol) in a saturated solution of ammonium acetate in ethanol (32 mL) were added ammonia (7 M in methanol, 14.3 mL) and sodium cyanoborohydride (0.398 g, 6.02 mmol). The reaction mixture was heated up to reflux and stirred for 16.5 hours. After cooling down to room temperature, it was concentrated under reduced pressure. The resulting residue was diluted in 2 M sodium hydroxide (10 mL) and it was extracted with dichloromethane. The combined organic layers were dried over magnesium sulfate, filtered and concentrated under reduced pressure. One purification of the crude material by reverse-phase chromatography (eluting acetonitrile in water), followed by a second purification by flash chromatography over silica gel (eluting methanol in dichloromethane) afforded 1-(3-pyrimidin-2-ylpyrazin-2-yl)ethanamine as a yellow solid.

LCMS (method 1): retention time 0.19 min, m/z 202 [M+H$^+$]; $^1$H-NMR (400 MHz, $CDCl_3$): δ ppm: 8.97 (d, J=4.77 Hz, 2H), 8.68 (d, J=2.20 Hz, 1H), 8.64 (d, J=2.57 Hz, 1H), 7.41 (t, J=4.95 Hz, 1H), 4.64 (q, J=6.60 Hz, 1H), 2.13 (br s, 2H), 1.48 (d, J=6.60 Hz, 3H).

Preparation of tributyl-(5-cyclopropylpyrimidin-2-yl)stannane

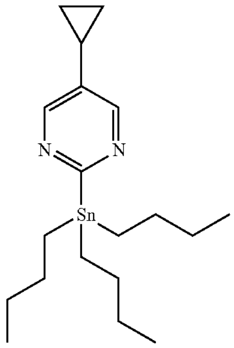 [SMILES: CCC[CH2][Sn]([CH2]CCC)([CH2]CCC)[c]1ncc(C2CC2)cn1]

To a solution of 2-chloro-5-cyclopropyl-pyrimidine (90%, 2.70 g, 15.7 mmol) in toluene (40 mL) were added hexa-n-butylditin (15.9 mL, 31.4 mmol) and tetrakis(triphenylphosphine)palladium(0) (1.82 g, 1.57 mmol). The reaction mixture was purged with argon for 10 minutes, heated up to 100° C. and stirred for 2 hours. After cooling down to room temperature, it was diluted with water and extracted three times with ethyl acetate. The combined organic layers were washed with brine, dried over sodium sulfate, filtered and concentrated under reduced pressure. Purification of the crude material by flash chromatography over silica gel (eluting with ethyl acetate in hexane) afforded tributyl-(5-cyclopropylpyrimidin-2-yl)stannane as a yellow oil. $^1$H-NMR (400 MHz, $CDCl_3$): δ ppm: 7.3 (m, 2H), 1.65 (m, 6H), 1.35 (m, 16H), 0.9 (m, 12H).

Preparation of 1-[3-(5-cyclopropylpyrimidin-2-yl) pyrazin-2-yl]ethanone (I23)

(I23)

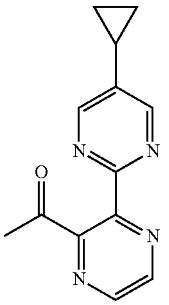

To a solution of 1-(3-chloropyrazin-2-yl)ethanone (90%, 2.00 g, 11.5 mmol) in toluene (20 mL) were added tributyl-(5-cyclopropylpyrimidin-2-yl)stannane (6.80 g, 14.9 mmol) and tetrakis(triphenylphosphine)palladium(0) (1.33 g, 1.15 mmol). The reaction mixture was purged with argon for 10 minutes. Then copper(I) iodide (0.438 g, 2.30 mmol.) was added and the resulting reaction mixture was heated up to 100° C. and stirred for 12 hours. After cooling down to room temperature, it was diluted with water and extracted twice with ethyl acetate. The combined organic layers were washed with brine, dried over sodium sulfate, filtered and concentrated under reduced pressure. Purification of the crude material by flash chromatography over silica gel (eluting with ethyl acetate in hexane) afforded 1-[3-(5-cyclopropylpyrimidin-2-yl)pyrazin-2-yl]ethanone as a brown solid.

$^1$H-NMR (400 MHz, $CDCl_3$): δ ppm: 8.7 (d, 1H), 8.55 (d, 1H), 8.50 (s, 2H), 2.7 (s, 3H), 1.85 (m, 1H), 1.1 (m, 2H), 0.8 (m, 2H).

Preparation of 1-[3-(5-cyclopropylpyrimidin-2-yl) pyrazin-2-yl]ethanamine (I32)

(I32)

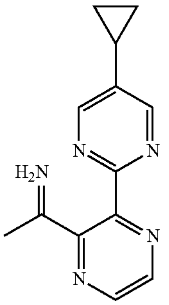

To a solution of 1-[3-(5-cyclopropylpyrimidin-2-yl) pyrazin-2-yl]ethanone (90%, 1.00 g, 3.75 mmol) in a saturated solution of ammonium acetate in ethanol (75 mL) was added ammonia (30% in water, 30 mL). The reaction mixture was stirred at room temperature for 10 minutes. Then sodium cyanoborohydride (0.706 g, 11.2 mmol) was added and the reaction mixture was heated up to 100° C. and stirred for 12 hours. After cooling down to room temperature, it was concentrated under reduced pressure. Purification of the crude material by reverse-phase chromatography (eluting acetonitrile in water) afforded 1-[3-(5-cyclopropylpyrimidin-2-yl)pyrazin-2-yl]ethanamine as a brown oil.

$^1$H-NMR (400 MHz, DMSO): δ ppm 8.85 (m, 2H), 8.80 (m, 2H), 5.0 (m, 1H), 3.2 (m, 3H) 2.1 (m, 1H), 1.15 (m, 2H), 1.0 (m, 2H).

Preparation of tert-butyl N-(6-tributylstannyl-3-pyridyl)carbamate

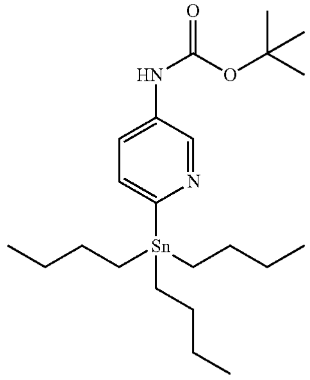 [SMILES: CCC[CH2][Sn]([CH2]CCC)([CH2]CCC)[c]1ccc(NC(=O)OC(C)(C)C)cn1]

A solution of tert-butyl N-(6-bromo-3-pyridyl)carbamate (2.50 g, 8.24 mmol) in dry tetrahydrofuran (50 mL) was cooled to −75° C. and n-Butyllithium (2.50 M, 5.77 mL, 14.4 mmol) was added dropwise over 5 min. The reaction mixture was stirred for 1 hour at the same temperature. Then tributyltin chloride (4.69 g, 14.4 mmol) was added to the reaction mixture which was then allowed to stir at room temperature for 3 hours. The reaction mixture was quenched with saturated ammonium chloride solution and it was extracted with ethyl acetate. Combined organic layers were washed with brine, dried over sodium sulfate, filtered and concentrated under reduced pressure. Purification of the crude material by chromatography over neutral alumina afforded the desired product.

$^1$H-NMR (400 MHz, $CDCl_3$): δ ppm: 8.5 (m, 1H), 7.85 (br s, 1H), 7.4 (dd, 1H), 6.5 (s, 1H), 1.55 (m, 15H), 1.35 (m, 6H), 1.15 (m, 6H), 0.9 (m, 9H).

Preparation of tert-butyl N-[6-(3-acetylpyrazine-2-yl)-3-pyridyl]carbamate (I28)

(I28)

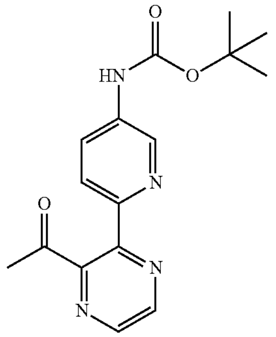

To a solution of tert-butyl N-(6-tributylstannyl-3-pyridyl) carbamate (36.0 g, 70.8 mmol) in toluene (720 mL) were added 1-(3-chloropyrazin-2-yl)ethanone (12.3 g, 70.8 mmol) and copper(I) iodide (2.70 g, 14.2 mmol). The reaction mixture was purged with argon for 20 min and tetrakis(triphenylphosphine)palladium(0) (4.09 g, 3.54 mmol) was added. The reaction was stirred at 100° C. for 5 h. After cooling down at room temperature, the reaction mixture was filtered through celite pad and the filtrate was evaporated under reduced pressure. The residue was diluted with ethyl acetate, washed with water, brine and saturated potassium fluoride solution, over sodium sulfate, filtered and concentrated under reduced pressure. Purification of the crude material by flash chromatography over silica gel (eluting with ethylacetate in n-hexane) afforded tert-butyl N-[6-(3-acetylpyrazin-2-yl)-3-pyridyl]carbamate.

$^1$H-NMR (400 MHz, DMSO): δ ppm: 9.9 (s, 1H), 8.6-8.9 (m, 3H), 8.1-8.25 (m, 2H), 2.55 (s, 1H), 1.5 (s, 9H).

Preparation of 1-[3-(5-amino-2-pyridyl)pyrazin-2-yl]ethanone (I29)

(I29)

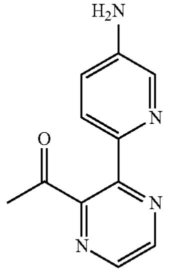

HCl in 1,4-dioxane (4.00 M, 73.0 mL, 0.292 mol) was added as dropwise to a solution of tert-butyl N-[6-(3-acetylpyrazin-2-yl)-3-pyridyl]carbamate (17.0 g, 0.0487 mol) in dichloromethane (510 mL) cooled to 0° C. The mixture was stirred for 10 min then allowed to stir at room temperature for 16 hours. The reaction mixture was concentrated in vacuo and poured into a mixture of ice-cold water and dichloromethane. The pH was adjusted to 12 with 2N sodium hydroxide solution. The aqueous layer was extracted with dichloromethane three times. The combined organic layers were washed with brine, dried over sodium sulfate and concentrated in vacuo. Purification of the crude material by flash chromatography over silica gel (eluting with methanol in dichloromethane) afforded 1-[3-(5-amino-2-pyridyl) pyrazin-2-yl]ethenone as a yellow solid.

LC-MS (method 3): retention time 1.41 min, m/z 215.1 $[M+H]^+$

Preparation of 1-[3-(5-chloro-2-pyridyl)pyrazin-2-yl]ethanone (I25)

(I25)

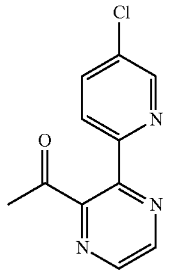

A solution of 1-[3-(5-amino-2-pyridyl)pyrazin-2-yl]ethanone (3.00 g, 12.6 mmol) in acetonitrile (200 mL) was cooled to 0° C. Copper (11) chloride (3.39 g, 25.2 mmol) was added, followed by tert-butyl nitrite (2.17 mL, 25.2 mmol) dropwise. The reaction mixture was stirred for 16 hours at room temperature. The reaction mixture was quenched with saturated ammonium chloride solution, stirred for 15 min and concentrated under reduced pressure. Purification of the crude material by reverse phase chromatography (C18; eluting with acetonitrile in water) afforded 1-[3-(5-chloro-2-pyridyl)pyrazin-2-yl]ethanone. $^1$H-NMR (400 MHz, DMSO): δ ppm: 8.9 (s, 1H), 8.8 (d, 1H), 8.7 (s, 1H), 8.2 (m, 2H), 2.6 (s, 3H).

Preparation of 1-[3-(5-chloro-2-pyridyl)pyrazin-2-yl]ethanamine (I35)

(I35)

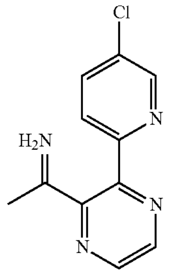

To a solution of 1-[3-(5-chloro-2-pyridyl)pyrazin-2-yl] ethanone (3.20 g, 11.0 mmol) in a saturated solution of ammonium acetate in ethanol (150 mL) were added at room temperature sodium cyanoborohydride (2.04 g, 32.9 mmol) and ammonia (30% in water, 100 mL). The reaction mixture was stirred at 90° C. for 12 hours. After cooling down to room temperature, it was concentrated under reduced pressure. Purification of the crude material by reverse-phase chromatography (eluting acetonitrile in water) afforded 1-[3-(5-chloro-2-pyridyl)pyrazin-2-yl]ethanamine.

LCMS (method 3): retention time 2.7 min, m/z=235 $[M+H^+]$

Preparation of tert-butyl N-[2-(3-acetylpyrazin-2-yl) pyrimidin-5-yl]carbamate (I53)

(I53)

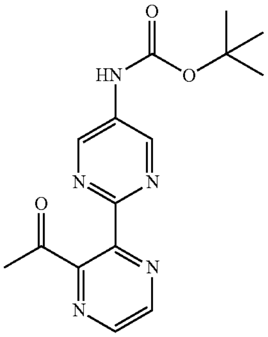

To a solution of tert-butyl N-(2-tributylstannylpyrimidin-5-yl)carbamate (600 mg, 0.867 mmol) in toluene (20 mL) were added 1-(3-chloropyrazin-2-yl)ethanone (151 mg, 0.867 mmol) and copper(I) iodide (33 mg, 0.173 mmol). The reaction mixture was purged with argon for 5 min and tetrakis(triphenylphosphine)palladium(0) (50.1 mg, 0.0434 mmol) was added. The reaction was stirred at 90° C. for 3 hours. After cooling down at room temperature, the reaction mixture was filtered through celite pad and the filtrate was evaporated under reduced pressure. The residue was purified by flash chromatography over silica gel (eluting with ethylacetate in n-hexane) afforded tert-butyl N-[2-(3-acetylpyrazin-2-yl)pyrimidin-5-yl]carbamate as a brown gum.

LCMS (method 3): retention time 1.04 min, m/z=216.1 $[M+H^+]$

Preparation of 1-[3-(5-bromopyrimidin-2-yl) pyrazin-2-yl]ethanone (I54)

(I54)

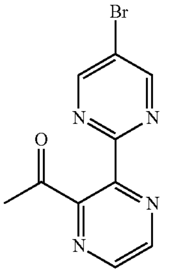

A solution of 1-[3-(5-aminopyrimidin-2-yl)pyrazin-2-yl] ethanone (2.80 g, 11.7 mmol) in acetonitrile (50 mL) was cooled to 0° C. Isoamyl nitrite (2.74 g, 23.4 mmol) was added followed by cupric bromide (5.23 g, 23.4 mmol). The reaction mixture was stirred for 6 hours at room temperature. The reaction mixture was quenched with saturated ammonium chloride solution, stirred for 15 min and concentrated under reduced pressure. Purification of the crude material by flash chromatography over silica gel (eluting with ethylacetate in n-hexane) afforded 1-[3-(5-bromopyrimidin-2-yl) pyrazin-2-yl]ethenone as a brown solid.

$^1$H-NMR (400 MHz, DMSO): δ ppm: 9.15 (s, 2H), 8.95 (m, 1H), 8.88 (m, 1H), 2.63 (s, 3H).

LCMS (method 3): retention time 3.54 min, m/z=279/281 [M+H]+(bromo pattern)

Preparation of 1-[3-(5-chloro-2-pyridyl)pyrazin-2-yl]ethanamine (I55)

(I55)

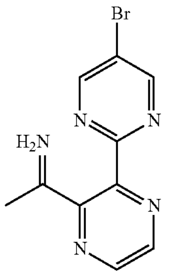

To a solution of 1-[3-(5-bromopyrimidin-2-yl)pyrazin-2-yl]ethanone (495 mg, 1.60 mmol) in aqueous ammonia (30% in water, 4.3 mL) was added a saturated solution of ammonium acetate in ethanol (10.8 mL) followed by sodium cyanoborohydride (301 mg, 4.79 mmol). The reaction mixture was stirred at 90° C. for 12 hours. After cooling down to room temperature, it was concentrated under reduced pressure to afford 1-[3-(5-chloro-2-pyridyl)pyrazin-2-yl] ethanamine.

$^1$H-NMR (400 MHz, DMSO): δ ppm: 9.22 (s, 2H), 8.70-9.00 (m, 2H), 4.50-4.80 (m, 1H), 1.42 (d, 3H).

Preparation of 3,5-dichloro-2-pyrimidin-2-yl-pyrazine

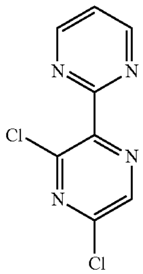 [SMILES: Clc1cnc(-c2ncccn2)c(Cl)n1]

To a solution of 3,5-dichloro-2-iodo-pyrazine (0.500 g, 1.81 mmol) in dioxane (5 mL) was added at room temperature tributyl(pyrimidin-2-yl)stannane (CAS 153435-63-3, 0.671 g, 1.81 mmol followed tetrakis(triphenylphosphine) palladium (0.211 g, 0.181 mmol). The reaction mixture was heated to 180° C. for 2 hours in microwave. After cooling down to room temperature, the reaction mixture was concentrated under reduced pressure to afford crude mass which was purified by flash column chromatography over silica gel (ethyl acetate in cyclohexane) to afford 3,5-dichloro-2-pyrimidin-2-yl-pyrazine as a brown solid.

LC-MS (method 4): retention time 1.23 min, m/z 228 $[M+H^+]$; $^1$H NMR (400 MHz, chloroform-d) δ ppm: 8.99 (d, 2H), 8.68 (s, 1H), 7.46 (t, 1H).

Preparation of 3-chloro-5-methoxy-2-pyrimidin-2-yl-pyrazine

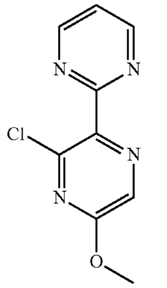

To a solution of 3,5-dichloro-2-pyrimidin-2-yl-pyrazine (0.100 g, 0.440 mmol) in methanol (1 mL), was added sodium methoxide (0.0099 mL, 0.044 mmol) at 0° C. and the reaction mass was stirred for 2 hours at room temperature. The reaction mixture was quenched in acetic acid and water (20 mL), extracted three times with ethyl acetate and the combined organic layers were washed with brine, dried over sodium sulfate, filtered and concentrated under reduced pressure to give 3-chloro-5-methoxy-2-pyrimidin-2-yl-pyrazine as a white solid.

LC-MS (method 4): retention time 0.37 min, m/z 223 $[M+H^+]$; $^1$H NMR (400 MHz, $CDCl_3$) δ ppm: 8.95 (d, 2H) 8.29 (s, 1H) 7.37 (t, 1H) 4.07 (s, 3H)

Preparation of 3-(1-ethoxyvinyl)-5-methoxy-2-pyrimidin-2-yl-pyrazine

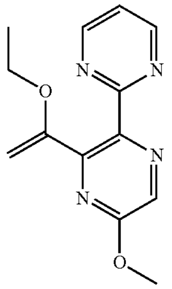 [SMILES: C=C(OCC)c1nc(OC)cnc1-c1ncccn1]

To a solution of 3-chloro-5-methoxy-2-pyrimidin-2-yl-pyrazine (0.060 g, 0.269 mmol) in dioxane (1 mL) was added at room temperature tributyl (1-ethoxyvinyl) stannane (0.140 mL, 0.404 mmol) and tetrakis(triphenylphosphine) palladium (0.013 g, 0.026 mmol). The reaction mixture was heated to 150° C. and stirred for 1 hour in the microwave. After cooling down to room temperature, the reaction mixture was concentrated under reduced pressure and purified by flash column chromatography over silica gel (ethyl acetate in cyclohexane) to afford 3-(1-ethoxyvinyl)-5-methoxy-2-pyrimidin-2-yl-pyrazine as a brown solid.

LC-MS (method 4): retention time 1.11 min, m/z 259 $[M+H^+]$.

Preparation of 1-(6-methoxy-3-pyrimidin-2-yl-pyrazin-2-yl)ethenone (I47)

(I47)

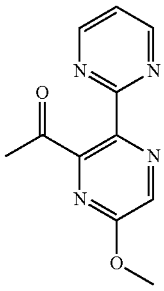

To a solution of 3-(1-ethoxyvinyl)-5-methoxy-2-pyrimidin-2-yl-pyrazine (0.10 g, 0.387 mmol) in acetonitrile (1 mL), acetic acid (1 mL) and water (1 mL) were added at room temperature and the reaction mixture was heated at 50° C. for 2 hours. The reaction mixture was quenched with water (20 mL), extracted three times with ethyl acetate and the combined organic layers were washed with brine, dried over sodium sulfate, filtered and concentrated under reduced pressure to give 1-(6-methoxy-3-pyrimidin-2-yl-pyrazin-2-yl)ethenone as a white solid.

LC-MS (method 4): retention time 1.07 min, m/z 231 $[M+H^+]$.

Preparation of 1-(6-methoxy-3-pyrimidin-2-yl-pyrazin-2-yl)ethanamine (I48)

(I48)

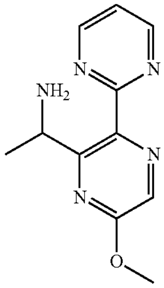

To a solution of 1-(6-methoxy-3-pyrimidin-2-yl-pyrazin-2-yl)ethanone (0.060 g, 0.260 mmol) in methanol (5 mL), ammonium acetate (0.209 g, 2.60 mmol) was added at room temperature and the reaction mixture was stirred for 1 hour at room temperature. To this reaction mixture, sodium cyanoborohydride (0.051 g, 0.781 mmol) was added and the reaction mixture was heated at 50° C. for 2 hours. The reaction mixture was diluted in water (40 mL) extracted three times with 20% in methanol in chloroform. The combined organic layers were washed with brine, dried over sodium sulfate, filtered and concentrated under reduced pressure to give 1-(6-methoxy-3-pyrimidin-2-yl-pyrazin-2-yl)ethanamine as a brown solid.

LC-MS (method 4): retention time 0.35 min, m/z 232 $[M+H^+]$.

Preparation of 1-(3-chloropyrazin-2-yl)ethanamine

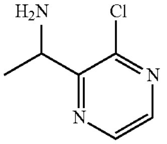

To a of 1-(3-chloropyrazin-2-yl)ethanone (0.200 g, 1.28 mmol) in methanol (4.5 mL) were added at room temperature ammonium acetate (0.995 g, 12.8 mmol) and sodium cyanoborohydride (0.0591 g, 0.894 mmol). The resulting suspension was stirred at room temperature for 18 hours, then concentrated in vacuo. The crude material was purified by reverse phase chromatography (C18 column, gradient of acetonitrile in water) to afford 1-(3-chloropyrazin-2-yl) ethanamine.

$^1H$ NMR (400 MHz, $CDCl_3$) δ ppm: 8.49 (d, 1H), 8.26 (d, 1H), 4.56 (q, 1H), 1.95 (br s, 2H), 1.44 (d, 3H)

Preparation of (1S)-1-(3-chloropyrazin-2-yl) ethanamine (I45)

(I45)

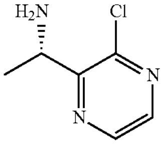

To a solution if 1-(3-chloropyrazin-2-yl)ethanamine (202.2 mg, 1.20 mmol) in tert-butyl methyl ether (11 mL) was added Novozym® 435 (240 mg), followed by ethyl methoxyacetate (1.44 mL, 12.0 mmol) at room temperature. The mixture was stirred at 40° C. for 5.5 hours. The reaction mixture was diluted with dichloromethane and filtered. The filtrate was concentrated in vacuo. The crude material was purified by flash chromatography over silica gel (eluting with a gradient of methanol in dichloromethane) to afford (1S)-1-(3-chloropyrazin-2-yl)ethanamine.

$^1H$ NMR (400 MHz, $CDCl_3$) δ ppm: 8.49 (d, 1H), 8.27 (d, 1H), 4.56 (q, 1H), 1.73 (br s, 2H), 1.44 (d, 3H); $[\alpha]_D^{20}$: −32.3° (c: 1.157, $CHCl_3$)

Preparation of (1R)-1-(3-chloropyrazin-2-yl)ethanol (I44)

(I44)

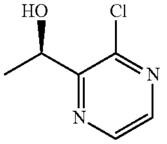

1-(3-chloropyrazin-2-yl)ethanone (157 mg, 1.00 mmol) was dissolved in dichloromethane (10.0 mL) and the flask was evacuated and backfilled with argon three times. Then $RuBF_4$[(R,R)-TsDPEN](p-cymene) (0.0362 g, 0.0526 mmol) was added. A cooled solution of triethylamine (0.348 mL, 2.50 mmol.) and formic acid (0.160 mL, 4.29 mmol) was added dropwise to the reaction mixture, which was stirred at room temperature for 4 hours. The reaction mixture was concentrated in vacuo. The crude material was purified by flash chromatography over silica gel (eluting with a gradient of ethyl acetate in cyclohexane) to afford (1R)-1-(3-chloropyrazin-2-yl)ethanol.

$^1$H-NMR (400 MHz, $CDCl_3$) δ ppm 8.49 (d, 1H), 8.34 (d, 1H), 5.18 (m, 1H), 3.81 (d, 1H), 1.52 (d, 3H) Chiral SFC (method 2): 1.98 min (minor enantiomer), 2.55 min (major enantiomer); ee=85%

Preparation of (1S)-1-(3-chloropyrazin-2-yl)ethanamine (I45)

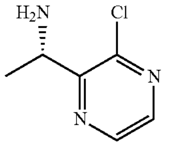

(I45)

(1R)-1-(3-chloropyrazin-2-yl)ethanol (87.8 mg, 0.554 mmol) was dissolved in tetrahydrofuran (1.9 mL). Then, 1,8-diazabicyclo[5.4.0]undec-7-ene (0.10 mL, 0.66 mmol) was added dropwise to the reaction mixture followed by diphenylphosphine azide (0.130 mL, 0.585 mmol). The reaction mixture was stirred at rt for 19 hours.

Tetrahydrofuran (1.4 mL) was added, followed by triphenylphosphine (179.4 mg, 0.677 mmol). The reaction mixture was stirred at room temperature for 2 hours. Water (0.15 mL) was added, and the reaction mixture was stirred at room temperature for 46 hours.

The reaction mixture was concentrated to a volume of 1 mL then diluted with dichloromethane. 1 M hydrochloric acid was added, then the aqueous layer was washed with dichloromethane. The aqueous layer was basified to pH=14 with 4 M sodium hydroxide solution and extracted with dichloromethane. The combined organic layers were dried over magnesium sulfate and concentrated in vacuo. The crude material was purified by flash chromatography over silica gel (eluting with a gradient of methanol in dichloromethane) to afford (1S)-1-(3-chloropyrazin-2-yl)ethanamine.

$^1$H NMR (400 MHz, $CDCl_3$) δ ppm: 8.49 (d, 1H), 8.27 (d, 1H), 4.56 (q, 1H), 1.84 (s, 2H), 1.44 (d, 3H) $[\alpha]_D^{20}$: −26.0° (c: 0.960, $CHCl_3$)

Preparation of (2R)—N-[(1S)-1-(3-chloropyrazin-2-yl)ethyl]-2-hydroxy-2-phenyl-acetamide

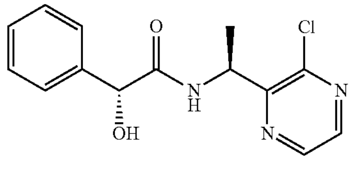 [SMILES: C[C@H](NC(=O)[C@H](O)c1ccccc1)c1nccnc1Cl]

To a solution of 1-(3-chloropyrazin-2-yl)ethanamine;hydrochloride (700 mg, 3.61 mmol) in dichloromethane (18 mL) were added (R)-(−)-mandelic acid (610 mg, 3.97 mmol), N-ethyldiisopropylamine (1.26 mL, 7.21 mmol), 1-hydroxybenzotriazole (50.8 mg, 0.361 mmol) and N,N'-dicyclohexylcarbodiimide (844 mg, 3.97 mmol). The reaction mixture was stirred at room temperature for 18 hours. The reaction mixture was diluted with saturated aqueous sodium carbonate solution and extracted with dichloromethane. The organic layers were dried over magnesium sulfate and concentrated in vacuo. Purification of the crude material by flash chromatography over silica gel (eluting with methanol in dichloromethane) afforded (2R)—N-[(1R)-1-(3-chloropyrazin-2-yl)ethyl]-2-hydroxy-2-phenyl-acetamide and (2R)—N-[(1R)-1-(3-chloropyrazin-2-yl)ethyl]-2-hydroxy-2-phenyl-acetamide. The relative stereochemistry of (2R)—N-[(1R)-1-(3-chloropyrazin-2-yl)ethyl]-2-hydroxy-2-phenyl-acetamide was determined by X-ray crystallography (crystallized from acetonitrile/water).

Analytical data for (2R)—N-[(1R)-1-(3-chloropyrazin-2-yl)ethyl]-2-hydroxy-2-phenyl-acetamide: LCMS (method 1): retention time 0.74 min, m/z=291 [M+H$^+$]

Preparation of (1S)-1-(3-chloropyrazin-2-yl)ethanamine;hydrochloride

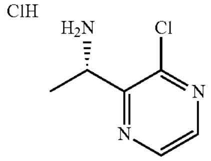

A solution of (2R)—N-[(1S)-1-(3-chloropyrazin-2-yl)ethyl]-2-hydroxy-2-phenyl-acetamide (0.93 g, 3.2 mmol) in hydrochloric acid (32% in water, 13 mL) was heated up to reflux and stirred for 2 hours. After cooling down to room temperature, the reaction mixture was basified with 3 N sodium hydroxide and diluted and extracted with ethyl acetate. The aqueous layer was freeze-dried overnight and the resulting solid was suspended in acetone. The suspension was filtered and the filtrate was concentrated under reduced pressure. The resulting oil was dissolved in ethyl acetate and 1 N hydrochloric acid was added. A precipitate appeared, it was filtered and dried under reduced pressure to afford the desired product. LCMS (method 1): retention time 0.19 min, m/z=158 [M+H+].

Preparation of (1S)-1-(3-chloropyrazin-2-yl)-N-(cyclopropylmethyl)ethanamine (I46)

(I46)

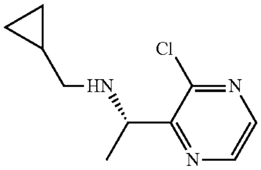

Sodium triacetoxyborohydride (59.4 mg, 0.267 mmol) was added to a stirred solution of (1S)-1-(3-chloropyrazin-2-yl)ethanamine (30.0 mg, 0.190 mmol), cyclopropanecarboxyladehyde (15.0 mg, 0.209 mmol) and acetic acid (0.0109 mL, 0.190 mmol) in 1,2-dichloroethane (0.95 mL). The mixture was stirred at room temperature for 4 hours. Saturated aqueous sodium carbonate solution was added, the aqueous layer was extracted with dichloromethane. The organic layer was dried over magnesium sulfate and concentrated in vacuo. The crude material was purified by flash chromatography over silica gel (eluting with ethyl acetate in cyclohexane) to afford (1S)-1-(3-chloropyrazin-2-yl)-N-(cyclopropylmethyl)ethanamine.

$^1$H NMR (400 MHz, $CDCl_3$) δ ppm −0.03-0.10 (m, 2H) 0.38-0.52 (m, 2H) 0.83-1.00 (m, 1H) 1.40 (d, 3H) 2.07 (dd, 1H) 2.15-2.29 (m, 1H) 2.53 (dd, 1H) 4.39 (q, 1H) 8.26 (d, 1H) 8.51 (d, 1H); $[\alpha]_D^{20}$=−540 (c 0.327, $CHCl_3$)

Preparation of tert-butyl N-[(1S)-3-(5-bromo-2-pyridyl)-2-hydroxy-1-methyl-3-oxo-propyl]carbamate

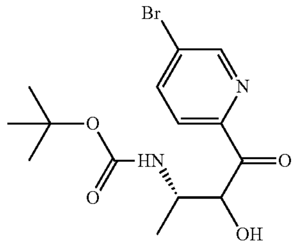 [SMILES: C[C@H](NC(=O)OC(C)(C)C)C(O)C(=O)c1ccc(Br)cn1]

In a round-bottomed flask was prepared a solution of tert-butyl N-[(1S)-1-methyl-2-oxo-ethyl]carbamate (CAS 79069-50-4, 1.07 g, 6.18 mmol) in dichloromethane (12 mL). The flask was evacuated and refilled with argon three times. Then, 2-(3-benzyl-4-methyl-thiazol-3-ium-5-yl)ethanol;bromide (0.388 g, 1.24 mmol), 5-bromopyridine-2-carbaldehyde (CAS 31181-90-5, 1.81 g, 9.27 mmol) and dichloromethane (6 mL) were added successively, followed by N,N-diisopropylethylamine (2.16 mL, 12.4 mmol). The reaction mixture was stirred for 1 hour at room temperature. It was quenched with ammonium chloride sat. aq. and extracted three times with dichloromethane. The combined organic layers were dried over magnesium sulfate, filtered and concentrated under reduced pressure. Purification of the crude material by flash chromatography over silica gel (eluting with ethyl acetate in cyclohexane) afforded tert-butyl N-[(1S)-3-(5-bromo-2-pyridyl)-2-hydroxy-1-methyl-3-oxo-propyl]carbamate as an orange gum.

LCMS (method 1): retention time 0.98 min, m/z=359-361[M+H+] (Bromo pattern); 1H-NMR (400 MHz, CDCl3) δ ppm: 1.37-1.40 (m, 3H) 1.43-1.44 (m, 9H) 4.34-4.69 (m, 2H) 5.22-5.36 (m, 1H) 7.86-8.08 (m, 2H) 8.73 (d, J=2.20 Hz, 1H).

Preparation of tert-butyl N-[(1 S)-3-(5-bromo-2-pyridyl)-1-methyl-2,3-dioxo-propyl]carbamate

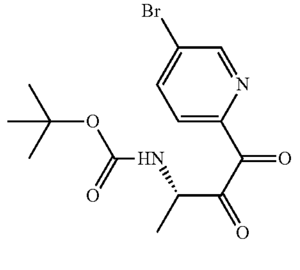 [SMILES: C[C@H](NC(=O)OC(C)(C)C)C(=O)C(=O)c1ccc(Br)cn1]

To a solution of tert-butyl N-[(1S)-3-(5-bromo-2-pyridyl)-2-hydroxy-1-methyl-3-oxo-propyl]carbamate (15.2 g, 42.3 mmol) in dichloromethane (100 mL) and dimethyl sulfoxide (20 mL) were added at 0° C. N,N-diisopropylethylamine (21.8 mL, 127 mmol, 3.00 equiv.) and in two portions sulfur trioxide pyridine complex (13.9 g, 84.6 mmol, 2.00 equiv.). The reaction mixture was stirred at 0° C. for 1 hour. It was quenched water and diluted with dichloromethane and 1 N hydrochloric acid. The aqueous layer was extracted twice with dichloromethane. The combined organic layers were dried over magnesium sulfate, filtered and concentrated under reduced pressure. Purification of the crude material by flash chromatography over silica gel (eluting with ethyl acetate in cyclohexane) afforded tert-butyl N-[(1S)-3-(5-bromo-2-pyridyl)-1-methyl-2,3-dioxo-propyl]carbamate as an orange oil.

1H-NMR (400 MHz, CDCl3) δ ppm: 1.36-1.41 (m, 9H) 1.45-1.48 (m, 3H) 4.82-4.96 (m, 1H) 5.10 (br s, 1H) 7.91-8.00 (m, 1H) 8.01-8.11 (m, 1H) 8.79 (d, J=1.83 Hz, 1H).

Preparation of tert-butyl N-[(1S)-1-[3-(5-bromo-2-pyridyl)pyrazin-2-yl]ethyl]carbamate (I42)

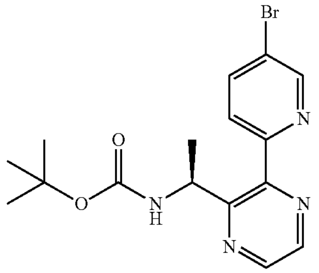 [SMILES: C[C@H](NC(=O)OC(C)(C)C)c1nccnc1-c1ccc(Br)cn1]

To a solution of tert-butyl N-[(1S)-3-(5-bromo-2-pyridyl)-1-methyl-2,3-dioxo-propyl]carbamate (2.00 g, 5.60 mmol) in ethanol (22 mL) was added ethylenediamine (1.91 mL, 28.0 mmol). The reaction mixture was stirred at room temperature for 60 h in the presence of air. It was concentrated under reduced pressure. Purification of the crude material by flash chromatography over silica gel (eluting with ethyl acetate in cyclohexane) afforded tert-butyl N-[(1S)-1-[3-(5-bromo-2-pyridyl)pyrazin-2-yl]ethyl]carbamate as a colorless gum.

LCMS (method 1): Retention time 1.09 min, m/z=379-381 [M+H+] (Bromo pattern);

1H-NMR (400 MHz, $CDCl_3$) δ ppm: 1.33-1.45 (m, 9H) 1.52-1.56 (m, 3H) 5.65-5.83 (m, 2H) 7.96-8.02 (m, 2H) 8.53-8.60 (m, 2H) 8.79 (dd, J=2.20, 1.10 Hz, 1H);

Chiral SFC (method 1): 1.80 min (major enantiomer), 1.11 min (minor enantiomer); ee=92%

Preparation of tert-butyl N-[(1S)-1-[6-amino-3-(5-bromo-2-pyridyl)pyrazin-2-yl]ethyl]carbamate (I49)

(I49)

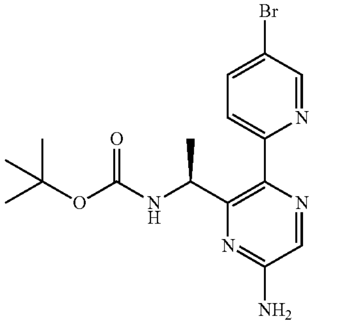

2-aminoacetamide dihydrobromide (1.21 g, 4.11 mmol) was added to a mixture of tert-butyl N-[(1S)-3-(5-bromo-2-pyridyl)-1-methyl-2,3-dioxo-propyl]carbamate (500 mg, 0.894 mmol) in 2-propanol (13.4 mL). Potassium acetate (266 mg, 2.68 mmol) was added, and the mixture was stirred at room temperature for 2.5 hours. Water was added, the aqueous layer was extracted with ethyl acetate, the organic layer was washed with brine, dried over magnesium sulfate and concentrated. The crude mixture was purified by reverse-phase chromatography (C18 column, gradient of acetonitrile in water) to give tert-butyl N-[(1S)-1-[6-amino-3-(5-bromo-2-pyridyl)pyrazin-2-yl]ethyl]carbamate.

LCMS (method 1): Retention time 1.04 min, m/z=394-396 [M+H$^+$] (Bromo pattern); $^1$H NMR (600 MHz, CDCl3) δ ppm: 1.45-1.47 (m, 12H) 4.84 (br s, 2H) 5.66-5.74 (m, 1H) 5.89 (br s, 1H) 7.86-7.88 (m, 1H) 7.89 (br d, 1H) 7.90 (s, 1H) 8.72 (s, 1H).

Preparation of tert-butyl N-[(1S)-1-[3-(5-bromo-2-pyridyl)-6-methyl-pyrazin-2-yl]ethyl]carbamate and tert-butyl N-[(1S)-1-[3-(5-bromo-2-pyridyl)-5-methyl-pyrazin-2-yl]ethyl]carbamate

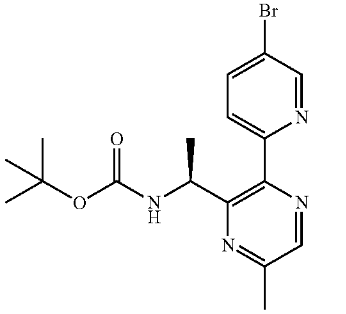

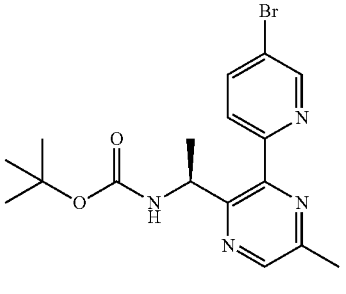

1,2-diaminopropane (16.4 mL, 190 mmol) was added in 4 portions over 36 hours to a mixture of tert-butyl N-[(1S)-3-(5-bromo-2-pyridyl)-1-methyl-2,3-dioxo-propyl]carbamate (1.130 g, 3.16 mmol) in ethanol (12.7 mL). Water was added, the aqueous layer was extracted with ethyl acetate, the organic layer was washed with brine, dried over magnesium sulfate and concentrated. The crude mixture was purified by chromatography over silica gel (gradient of ethyl acetate in cyclohexane) to give a mixture of tert-butyl N-[(1S)-1-[3-(5-bromo-2-pyridyl)-6-methyl-pyrazin-2-yl]ethyl]carbamate and tert-butyl N-[(1S)-1-[3-(5-bromo-2-pyridyl)-5-methyl-pyrazin-2-yl]ethyl]carbamate.

LCMS (method 1): Retention time 1.14 and 1.15 min, m/z=393-395 [M+H$^+$] (Bromo pattern); $^1$H NMR (600 MHz, CDCl3) δ ppm (mixture): 1.45-1.47 (m, 24H) 4.84 (br s, 4H) 5.66-5.74 (m, 2H) 5.89 (br s, 2H) 7.86-7.88 (m, 2H) 7.89 (br d, 2H) 7.90 (s, 1H) 8.72 (s, 2H).

Preparation of (1S)-1-[3-(5-bromo-2-pyridyl)-6-methyl-pyrazin-2-yl]ethanamine and (1S)-1-[3-(5-bromo-2-pyridyl)-5-methyl-pyrazin-2-yl]ethanamine

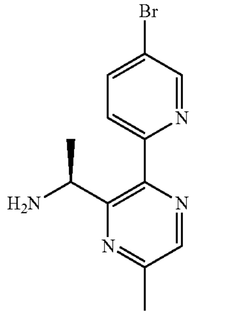

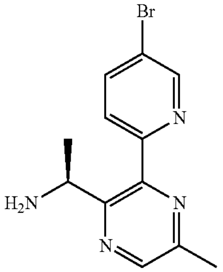

Trifluoroacetic acid (2.00 mL, 25.2 mmol) was added in two portions to a solution of tert-butyl N-[(1S)-1-[3-(5-bromo-2-pyridyl)-6-methyl-pyrazin-2-yl]ethyl]carbamate and tert-butyl N-[(1S)-1-[3-(5-bromo-2-pyridyl)-5-methyl-pyrazin-2-yl]ethyl]carbamate (550 mg, 1.40 mmol) in dichloromethane (9.0 mL) at 0° C. The reaction was stirred at room temperature for 28 hours. The reaction mixture was poured in sat. aq. Sodium bicarbonate. The aqueous layer was extracted with dichloromethane, the organic layer was dried with magnesium sulfate and concentrated to give a mixture of (1S)-1-[3-(5-bromo-2-pyridyl)-6-methyl-pyrazin-2-yl]ethanamine and (1S)-1-[3-(5-bromo-2-pyridyl)-5-methyl-pyrazin-2-yl]ethanamine as a brown oil.

LCMS (method 1): Retention time 0.54 min, m/z=293-295 [M+H$^+$] (Bromo pattern); $^1$H NMR (400 MHz, CDCl3) δ ppm: 1.40-1.46 (m, 6H) 2.55-2.62 (m, 6H) 4.56-4.73 (m, 2H) 7.86-8.02 (m, 4H) 7.93-7.93 (m, 1H) 8.34-8.48 (m, 2H) 8.72-8.78 (m, 2H)

Preparation of (1S)-1-[3-(5-bromo-2-pyridyl)pyrazin-2-yl]ethanamine (I43)

(I43)

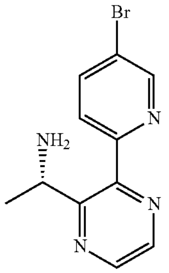

To a solution of tert-butyl N-[(1S)-1-[3-(5-bromo-2-pyridyl)pyrazin-2-yl]ethyl]carbamate (1.14 g, 3.00 mmol) in dichloromethane (27 mL) was added at 0° C. trifluoroacetic acid (5.40 mL, 68.0 mmol). The reaction mixture was stirred at room temperature overnight. It was added dropwise to a saturated solution of sodium carbonate. The layers were separated and the aqueous layer was extracted with dichloromethane. The combined organic layers were dried over magnesium sulfate, filtered and concentrated under reduced pressure to afford (1S)-1-[3-(5-bromo-2-pyridyl)pyrazin-2-yl]ethanamine as a yellow oil.

LCMS (method 1): Retention time 0.54, m/z=279-281 [M+H+] (Bromo pattern); 1H-NMR (400 MHz, CDCl3) δ ppm: 1.47 (d, J=6.60 Hz, 3H) 2.09 (s, 2H) 4.67-4.76 (m, 1H) 7.90-7.94 (m, 1H) 7.96-8.03 (m, 1H) 8.51 (d, J=2.20 Hz, 1H) 8.60 (d, J=2.57 Hz, 1H) 8.77 (dd, J=2.20, 0.73 Hz, 1H).

Preparation of 2-(1-cyanocyclopropyl)-N-[1-[3-(5-cyclopropylpyrimidin-2-yl)pyrazin-2-yl]ethyl]-6-(trifluoromethyl)pyridine-4-carboxamide (P32)

(P32)

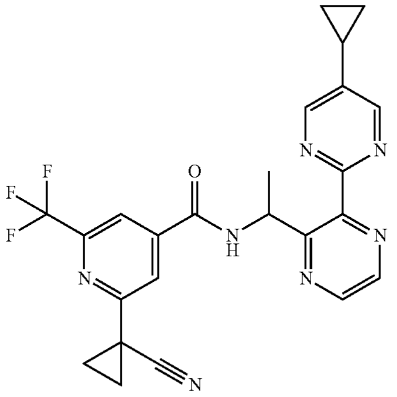

To a solution of 1-[3-(5-cyclopropylpyrimidin-2-yl)pyrazin-2-yl]ethanamine (20.7 mg, 85.9 μmol) in N,N-dimethylformamide (1 mL) were added at 0° C. 2-(1-cyanocyclopropyl)-6-(trifluoromethyl)pyridine-4-carboxylic acid (22 mg, 85.9 μmol), N,N-diisopropylethylamine (44.9 μL, 0.258 mmol) and propanephosphonic acid anhydride (78.1 μL, 0.172 mmol). The reaction mixture was stirred at room temperature for 6 hours. It was then poured on ice water and extracted twice with ethyl acetate. The combined organic layers were dried over sodium sulfate, filtered and concentrated under reduced pressure. Purification of the crude material by flash chromatography over silica gel (eluting with ethyl acetate in hexane) afforded 2-(1-cyanocyclopropyl)-N-[1-[3-(5-cyclopropylpyrimidin-2-yl)pyrazin-2-yl]ethyl]-6-(trifluoromethyl)pyridine-4-carboxamide as a light brown solid.

$^{1}$H-NMR (400 MHz, DMSO): δ ppm: 9.4 (d, 1H), 8.75 (m, 1H), 8.7 (m, 3H), 8.1 (s, 1H), 7.95 (s, 1H), 5.65 (m, 1H), 2.0 (m, 1H), 1.95 (m, 2H), 1.75 (m, 2H), 1.6 (m, 3H), 1.1 (m, 2H), 0.85 (m, 2H).

Preparation of N-[1-[3-(5-chloro-2-pyridyl)pyrazin-2-yl]ethyl]-3-(1-cyanocyclopropyl)-5-(trifluoromethyl)benzamide (P17)

(P17)

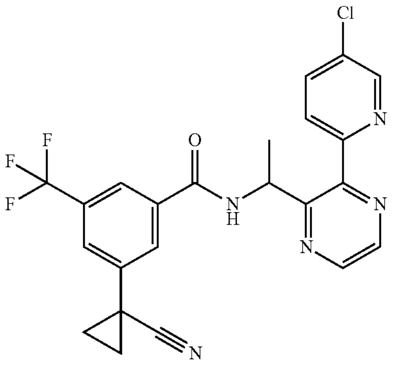

To a solution of 3-[cyano(cyclopropyl)methyl]-5-(trifluoromethyl)benzoic acid (130 mg, 0.484 mmol) in toluene (20 mL) was added dropwise at 0° C. thionyl chloride (0.141 mL, 1.94 mmol). The reaction mixture was stirred at 90° C. for 20 hours. After cooling down to room temperature, it was concentrated under reduced pressure. The resulting residue was dissolved in dichloromethane (10 mL) and added at 0° C. to a solution of 1-[3-(5-chloro-2-pyridyl)pyrazin-2-yl]ethanamine (139 mg, 0.532 mmol) and triethylamine (0.272 mL, 1.94 mmol) in dichloromethane (10 mL). The reaction mixture was stirred at room temperature for 2 hours. It was then diluted with dichloromethane and washed with water. The organic layer was dried over sodium sulfate, filtered and concentrated under reduced pressure. Purification of the crude material by reverse-phase chromatography (eluting acetonitrile in water) afforded N-[1-[3-(5-chloro-2-pyridyl)pyrazin-2-yl]ethyl]-3-(1-cyanocyclopropyl)-5-(trifluoromethyl)benzamide.

1H-NMR (400 MHz, DMSO): δ ppm: 9.25 (d, 1H), 8.8 (m, 1H), 8.75 (m, 1H), 8.65 (m, 1H), 8.15 (m, 1H), 8.05 (s, 1H), 8 (d, 1H), 7.95 (m, 1H), 7.75 (s, 1H), 5.8 (m, 1H), 1.8 (m, 2H), 1.65 (m, 5H).

Preparation of N-[1-[3-(5-chloro-2-pyridyl)pyrazin-2-yl]ethyl]-2-(1-cyanocyclopropyl)-6-(trifluoromethyl)pyridine-4-carboxamide (P16)

(P16)

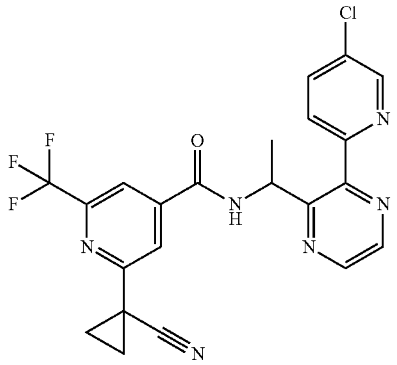

To a solution of 2-(1-cyanocyclopropyl)-6-(trifluoromethyl)pyridine-4-carboxylic acid (130 mg, 0.482 mmol) in toluene (20 mL) was added dropwise at 0° C. thionyl chloride (0.141 mL, 1.94 mmol). The reaction mixture was stirred at 90° C. for 2 hours. After cooling down to room temperature, it was concentrated under reduced pressure. The resulting residue was dissolved in dichloromethane (10 mL) and added at 0° C. to a solution of 1-[3-(5-chloro-2-pyridyl)pyrazin-2-yl]ethanamine (138 mg, 0.530 mmol) and triethylamine (0.271 mL, 1.93 mmol) in dichloromethane (10 mL). The reaction mixture was stirred at room temperature for 2 hours. It was then diluted with dichloromethane and washed with water. The organic layer was dried over sodium sulfate, filtered and concentrated under reduced pressure. Purification of the crude material by reverse-phase chromatography (eluting acetonitrile in water) afforded N-[1-[3-(5-chloro-2-pyridyl)pyrazin-2-yl]ethyl]-2-(1-cyanocyclopropyl)-6-(trifluoromethyl)pyridine-4-carboxamide as an off-white solid.

$^1$H-NMR (400 MHz, DMSO): δ ppm: 9.55 (d, 1H), 8.60-8.80 (m, 3H), 8.12 (m, 1H), 8.01 (m, 2H), 7.95 (s, 1H), 5.83 (m, 1H), 1.92 (m, 2H), 1.75 (m, 2H), 1.67 (d, 3H).

Preparation of N-[1-[3-(5-bromo-2-pyridyl)pyrazin-2-yl]ethyl]-2-(1-cyanocyclopropyl)-6-(trifluoromethyl)pyridine-4-carboxamide (P28)

(P28)

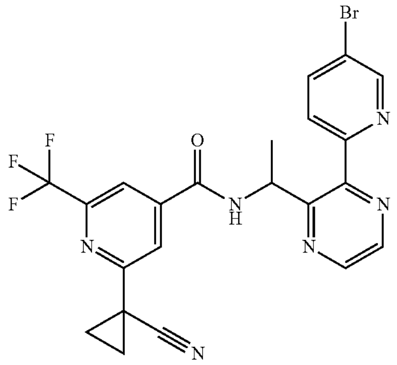

To a solution of 2-(1-cyanocyclopropyl)-6-(trifluoromethyl)pyridine-4-carboxylic acid (100 mg, 0.371 mmol) in toluene (15 mL) was added dropwise at 0° C. thionyl chloride (0.108 mL, 1.48 mmol). The reaction mixture was stirred at 90° C. for 2.5 hours. After cooling down to room temperature, it was concentrated under reduced pressure. The resulting residue was dissolved in dichloromethane (10 mL) and added at 0° C. to a solution of 1-[3-(5-bromo-2-pyridyl)pyrazin-2-yl]ethanamine (108 mg, 0.371 mmol) and triethylamine (0.208 mL, 1.48 mmol) in dichloromethane (10 mL). The reaction mixture was stirred at room temperature for 3 hours. It was then diluted with dichloromethane and washed with water. The organic layer was dried over sodium sulfate, filtered and concentrated under reduced pressure. Purification of the crude material by reverse-phase chromatography (eluting acetonitrile in water) afforded N-[1-[3-(5-bromo-2-pyridyl)pyrazin-2-yl]ethyl]-2-(1-cyanocyclopropyl)-6-(trifluoromethyl)pyridine-4-carboxamide as an off-white solid.

$^1$H-NMR (400 MHz, DMSO): δ ppm: 9.53 (d, 1H), 8.80-8.90 (m, 1H), 8.60-8.80 (m, 2H), 8.20-8.30 (m, 1H), 8.12 (m, 1H), 7.97 (m, 2H), 5.79-5.90 (m, 1H), 1.93 (m, 2H), 1.70-1.80 (m, 2H), 1.65 (d, 3H); $^{19}$F-NMR (377 MHz, DMSO): δ ppm: −66.69.

Preparation of 3-cyclopropyl-N-[1-(3-pyrimidin-2-ylpyrazin-2-yl)ethyl]-5-(trifluoromethyl)-benzamide (P41)

(P41)

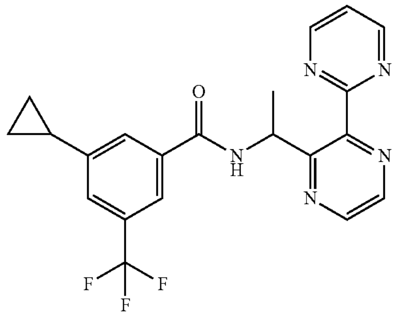

A mixture of 2-cyclopropyl-6-(trifluoromethyl)pyridine-4-carboxylic (0.10 g, 0.43 mmol, 1.0 equiv.), 1-(3-pyrimidin-2-ylpyrazin-2-yl)ethanamine trifluoroacetate salt (1.6 g, 0.52 mmol, 1.2 equiv.), and HATU (0.17 g, 1.3 mmol, 3.0 equiv.) in N,N-dimethylformamide (2.9 mL) was stirred at room temperature 1 hour. The reaction mixture was then diluted with ethyl acetate and the organic phase was washed with water (5 times), brine, dried over magnesium sulfate, filtered and concentrated. The crude material was purified by chromatography over silica gel to afford the title compound as an off-white solid.

$^1$H NMR (400 MHz, chloroform-d) δ ppm: 0.79 (q, J=5.14 Hz, 2H), 1.03-1.11 (m, 2H), 1.64 (d, J=6.6 Hz, 3H), 1.97-2.05 (m, 1H), 6.22-6.29 (m, 1H), 7.42 (s, 1H), 7.46 (t, J=4.9 Hz, 1H), 7.64-7.72 (m, 2H), 7.77 (s, 1H), 8.72 (s, 1H), 8.76 (s, 1H), 9.04 (d, J=5.1 Hz, 2H)

$^{19}$F NMR (376 MHz, chloroform-d) δ/ppm −62.58 (s, 3 F)

LC-MS (method 1): retention time 0.97 min, m/z 414 $[M+H]^+$

Preparation of 3-[cyclopropyl(difluoro)methyl]-N-[1-(3-pyrimidin-2-ylpyrazin-2-yl)ethyl]-5-(trifluoromethyl)benzamide (P30)

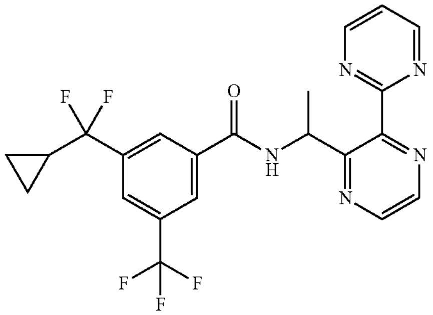

(P30)

To a solution of 1-(3-pyrimidin-2-ylpyrazin-2-yl) ethanamine (50 mg, 0.22 mmol) in N,N-dimethylformamide (2 mL) were added at 0° C. 3-[cyclopropyl(difluoro) methyl]-5-(trifluoromethyl)benzoic acid (84 mg, 0.27 mmol), 1-propanephosphonic acid cyclic anhydride (0.21 g, 0.67 mmol) and N,N-diisopropylethylamine (87 mg, 0.67 mmol). The reaction mixture was stirred at room temperature for 5 hours. It was then diluted with water and extracted twice with dichloromethane. The combined organic layers were washed with brine, dried over sodium sulfate, filtered and concentrated under reduced pressure. Purification of the crude material by reverse-phase chromatography (eluting acetonitrile in water) afforded 3-[cyclopropyl(difluoro) methyl]-N-[1-(3-pyrimidin-2-ylpyrazin-2-yl)ethyl]-5-(trifluoromethyl)benzamide as an off-white solid.

$^1$H-NMR (400 MHz, DMSO-d6): δ ppm: 9.3 (m, 1H) 8.95 (m, 2H) 8.75 (m, 2H) 8.2 (m, 2H), 8.0 (m, 1H) 7.55 (m, 1H) 5.6 (m, 1H) 1.8 (m, 1H) 1.6 (m, 3H) 0.7 (m, 4H).

Preparation of 3-(1-methoxycyclopropyl)-N-[1-(3-pyrimidin-2-ylpyrazin-2-yl)ethyl]-5-(trifluoromethyl)benzamide (P47)

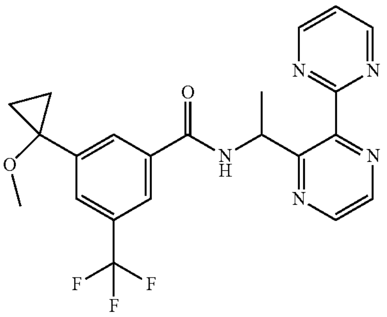

(P47)

To a solution of 3-(1-methoxycyclopropyl)-5-(trifluoromethyl)benzoic acid (130 mg, 0.490 mmol) in toluene (3 mL) was added dropwise at 0° C. thionyl chloride (0.107 mL, 1.47 mmol). The reaction mixture was stirred at 90° C. for 2 hours. After cooling down to room temperature, it was concentrated under reduced pressure. The resulting residue was dissolved in dichloromethane (2 mL) and added at 0° C. to a solution of 1-(3-pyrimidin-2-ylpyrazin-2-yl)ethanamine (201 mg, 0.979 mmol) and triethylamine (0.206 mL, 1.47 mmol) in dichloromethane (2 mL). The reaction mixture was stirred at room temperature for 2 hours. It was then diluted with dichloromethane and washed with water. The organic layer was dried over sodium sulfate, filtered and concentrated under reduced pressure. Purification of the crude material by reverse-phase chromatography (eluting acetonitrile in water) afforded 3-(1-methoxycyclopropyl)-N-[1-(3-pyrimidin-2-ylpyrazin-2-yl)ethyl]-5-(trifluoromethyl)benzamide as an off-white solid.

$^1$H-NMR (400 MHz, DMSO-d6): δ ppm: 9.1 (m, 1H) 8.95 (m, 2H) 8.77 (m, 1H) 8.66 (m, 1H), 7.92 (m, 1H), 7.78 (m, 1H), 7.64 (m, 1H), 7.50-7.60 (m, 1H), 5.55-5.65 (m, 1H), 3.12 (s, 3H), 1.61 (d, 3H), 1.20-1.30 (m, 2H), 1.00-1.13 (m, 2H)

Preparation of N-[1-[3-(5-bromopyrimidin-2-yl) pyrazin-2-yl]ethyl]-3-cyclopropyl-5-(trifluoromethyl)benzamide (P58)

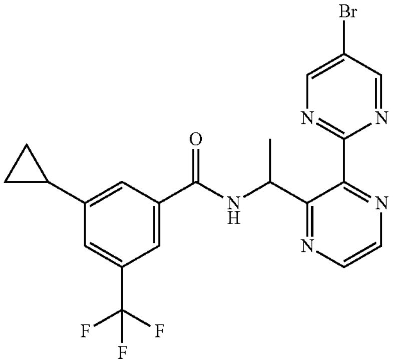

(P58)

To a solution of 3-cyclopropyl-5-(trifluoromethyl)benzoic acid (60 mg, 0.248 mmol) in toluene (8 mL) was added dropwise at 0° C. thionyl chloride (0.723 mL, 9.91 mmol). The reaction mixture was stirred at 90° C. for 2.5 hours. After cooling down to room temperature, it was concentrated under reduced pressure. The resulting residue was dissolved in dichloromethane (10 mL) and added at 0° C. to a solution of 1-[3-(5-bromopyrimidin-2-yl)pyrazin-2-yl] ethanamine (217 mg, 0.310 mmol) and triethylamine (0.139 mL, 0.991 mmol) in dichloromethane (10 mL). The reaction mixture was stirred at room temperature for 3 hours. It was then diluted with dichloromethane and washed with water. The organic layer was dried over sodium sulfate, filtered and concentrated under reduced pressure. Purification of the crude material by reverse-phase chromatography (eluting acetonitrile in water) afforded N-[1-[3-(5-bromopyrimidin-2-yl)pyrazin-2-yl]ethyl]-3-cyclopropyl-5-(trifluoromethyl) benzamide as an off-white solid.

$^1$H-NMR (400 MHz, DMSO-d6): δ ppm: 9.12 (m, 2H) 9.00 (m, 1H) 8.76 (m, 1H) 8.68 (m, 1H), 7.77 (m, 1H), 7.58 (m, 2H), 5.52-5.61 (m, 1H), 2.05-2.12 (m, 1H), 1.60 (d, 3H), 0.98-1.08 (m, 2H), 0.75-0.82 (m, 2H)

Preparation of N-[1-[3-(5-bromopyrimidin-2-yl) pyrazin-2-yl]ethyl]-2-(1-cyanocyclopropyl)-6-(trifluoromethyl)pyridine-4-carboxamide (P55)

(P55)

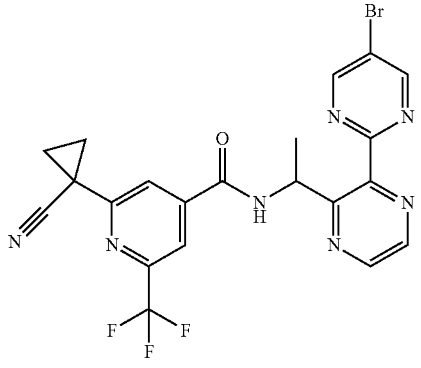

To a solution of 2-(1-cyanocyclopropyl)-6-(trifluoromethyl)pyridine-4-carboxylic acid (60 mg, 0.222 mmol) in toluene (10 mL) was added dropwise at 0° C. thionyl chloride (0.162 mL, 2.22 mmol). The reaction mixture was stirred at 90° C. for 2 hours. After cooling down to room temperature, it was concentrated under reduced pressure. The resulting residue was dissolved in dichloromethane (10 mL) and added at 0° C. to a solution of 1-[3-(5-bromopyrimidin-2-yl)pyrazin-2-yl]ethanamine (78 mg, 0.222 mmol) and triethylamine (0.125 mL, 0.890 mmol) in dichloromethane (10 mL). The reaction mixture was stirred at room temperature for 2 hours. It was then diluted with dichloromethane and washed with water. The organic layer was dried over sodium sulfate, filtered and concentrated under reduced pressure. Purification of the crude material by reverse-phase chromatography (eluting acetonitrile in water) afforded N-[1-[3-(5-bromopyrimidin-2-yl)pyrazin-2-yl] ethyl]-2-(1-cyanocyclopropyl)-6-(trifluoromethyl)pyridine-4-carboxamide as an off-white solid.

$^1$H-NMR (400 MHz, DMSO-d6): δ ppm: 9.44 (m, 1H) 9.16 (s, 2H) 8.80 (m, 1H) 8.71 (m, 1H), 8.05 (m, 1H), 7.95 (m, 1H), 5.55-5.65 (m, 1H), 1.90-2.00 (m, 2H), 1.70-1.80 (m, 2H) 1.61 (d, 3H)

Preparation of N-[1-[3-(5-bromopyrimidin-2-yl) pyrazin-2-yl]ethyl]-3-[cyclopropyl(difluoro)methyl]-5-(trifluoromethyl)benzamide (P53)

(P53)

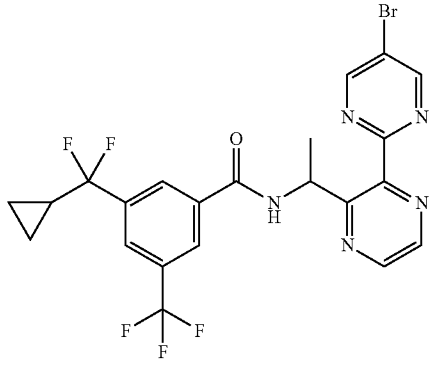

To a solution of 3-[cyclopropyl(difluoro)methyl]-5-(trifluoromethyl)benzoic acid (90 mg, 0.305 mmol) in toluene (10 mL) was added dropwise at 0° C. thionyl chloride (0.089 mL, 1.22 mmol). The reaction mixture was stirred at 90° C. for 2.5 hours. After cooling down to room temperature, it was concentrated under reduced pressure. The resulting residue was dissolved in dichloromethane (10 mL) and added at 0° C. to a solution of 1-[3-(5-bromopyrimidin-2-yl)pyrazin-2-yl]ethanamine (321 mg, 0.458 mmol) and triethylamine (0.172 mL, 1.22 mmol) in dichloromethane (10 mL). The reaction mixture was stirred at room temperature for 3 hours. It was then diluted with dichloromethane and washed with water. The organic layer was dried over sodium sulfate, filtered and concentrated under reduced pressure. Purification of the crude material by reverse-phase chromatography (eluting acetonitrile in water) afforded N-[1-[3-(5-bromopyrimidin-2-yl)pyrazin-2-yl]ethyl]-3-[cyclopropyl (difluoro)methyl]-5-(trifluoromethyl)benzamide as a brown solid.

$^1$H-NMR (400 MHz, DMSO-d6): δ ppm: 9.29 (d, 1H) 9.14 (s, 2H) 8.81 (m, 1H) 8.70 (m, 1H), 8.15-8.25 (m, 2H), 8.00 (m, 1H), 5.58-5.68 (m, 1H), 1.70-1.90 (m, 1H), 1.61 (d, 3H), 0.65-0.75 (m, 4H)

Preparation of N-[(1S)-1-[3-(5-bromo-2-pyridyl) pyrazin-2-yl]ethyl]-3-[cyclopropyl(difluoro)methyl]-5-(trifluoromethyl)benzamide (P42)

(P42)

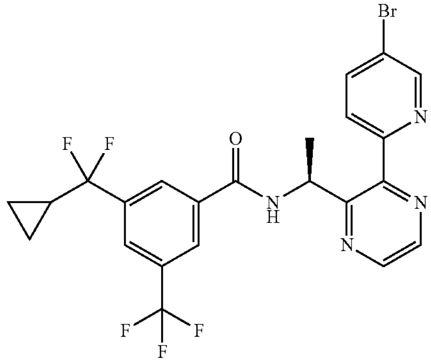

Oxalyl chloride (0.0281 mL, 0.321 mmol) was added to a solution of 3-[cyclopropyl(difluoro)methyl]-5-(trifluoromethyl)benzoic acid (0.0600 g, 0.214 mmol) in dichloromethane (0.65 mL) containing one drop of N,N-dimethylformamide. After 30 minutes, the reaction mixture was concentrated in vacuo. The crude acyl chloride was dissolved in ethyl acetate (0.86 mL), and (1S)-1-[3-(5-bromo-2-pyridyl)pyrazin-2-yl]ethanamine (0.0598 g, 0.214 mmol) and aqueous sodium bicarbonate (1N, 0.86 mL) were added. The mixture was stirred at room temperature for 45 minutes. The layers were separated, the aqueous layer was extracted with ethyl acetate. The combined organic layers were dried over magnesium sulfate and concentrated in vacuo. Purification of the crude material by flash chromatography over silica gel (eluting with ethyl acetate in cyclohexane) afforded N-[(1S)-1-[3-(5-bromo-2-pyridyl)pyrazin-2-yl] ethyl]-3-[cyclopropyl(difluoro)methyl]-5-(trifluoromethyl) benzamide.

$^1$H-NMR (400 MHz, chloroform-d): δ ppm: 0.71-0.80 (m, 2H) 0.81-0.88 (m, 2H) 1.47-1.61 (m, 1H) 1.68 (d, J=6.97 Hz, 3H) 6.25-6.35 (m, 1H) 7.83 (br d, J=8.07 Hz, 1H) 7.93 (s, 1H) 8.02-8.07 (m, 1H) 8.07-8.11 (m, 1H) 8.12 (s, 1H) 8.18

(s, 1H) 8.61-8.67 (m, 2H) 8.87 (dd, J=2.20, 0.73 Hz, 1H); $[\alpha]_D^{20}$+1150 (c: 0.580, $CHCl_3$)

Compounds described in table P were prepared by methods similar to those described for the examples above:

TABLE P

Examples of prepared compounds of formula I

| Entry | IUPAC name | STRUCTURE | RT (min) | [M + H] (measured) | Method | MP° C. |
|---|---|---|---|---|---|---|
| P1 | 2-chloro-N-[1-(3-pyrimidin-2-ylpyrazin-2-yl)ethyl]-6-(trifluoromethyl)pyridine-4-carboxamide | 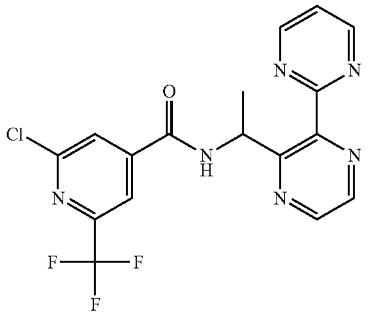 [SMILES: CC(NC(=O)c1cc(Cl)nc(C(F)(F)F)c1)c1nccnc1-c1ncccn1] | 0.88 | 409 | 1 | |
| P2 | 2-(1-cyanocyclopropyl)-N-[1-[3-(5-methylpyrimidin-2-yl)pyrazin-2-yl]ethyl]-6-(trifluoromethyl)pyridine-4-carboxamide | 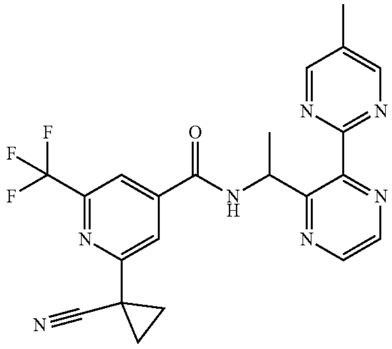 [SMILES: Cc1cnc(-c2nccnc2C(C)NC(=O)c2cc(C(F)(F)F)nc(C3(C#N)CC3)c2)nc1] | | | | 200-205 |
| P3 | 3-(1-cyanocyclopropyl)-N-[1-[3-(5-cyclopropylpyrimidin-2-yl)pyrazin-2-yl]ethyl]-5-(trifluoromethyl)benzamide | 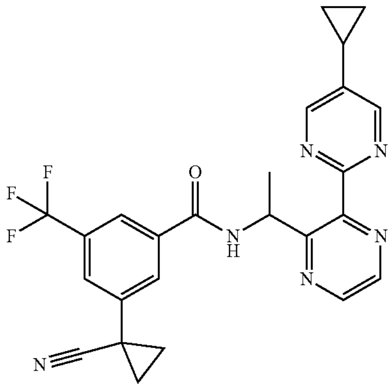 [SMILES: CC(NC(=O)c1cc(C(F)(F)F)cc(C2(C#N)CC2)c1)c1nccnc1-c1ncc(C2CC2)cn1] | | | | 170-180 |
| P4 | N-[1-[3-(5-chloro-2-pyridyl)pyrazin-2-yl]ethyl]-3-[cyclopropyl(difluoro)methyl]-5-(trifluoromethyl)benzamide | 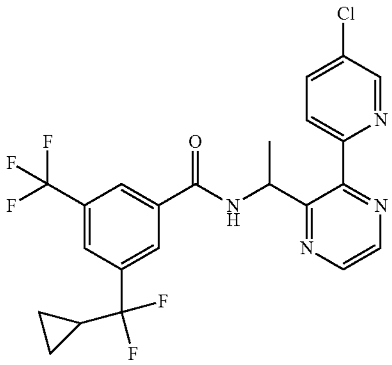 | | | | 105-110 |

TABLE P-continued

| Examples of prepared compounds of formula I | | | | | | |
|---|---|---|---|---|---|---|
| Entry | IUPAC name | STRUCTURE | RT (min) | [M + H] (mea- sured) | Meth- od | MP° C. |
| P5 | 3-(1-cyano-1-methyl-ethyl)-N-[1-[3-(5-fluoro-2-pyridyl)pyrazin-2-yl]ethyl]-5-(trifluoromethyl) benzamide | 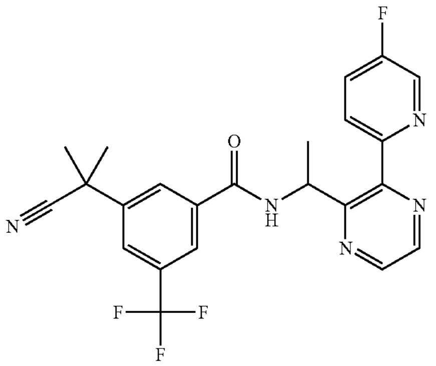 [SMILES: CC(NC(=O)c1cc(C(F)(F)F)cc(C(C)(C)C#N)c1)c1nccnc1-c1ccc(F)cn1] | | | | 210-220 |
| P6 | 3-(1-cyano-1-methyl-ethyl)-N-[1-[3-(5-cyclopropylpyrimidin-2-yl)pyrazin-2-yl]ethyl]-5-(trifluoromethyl) benzamide | 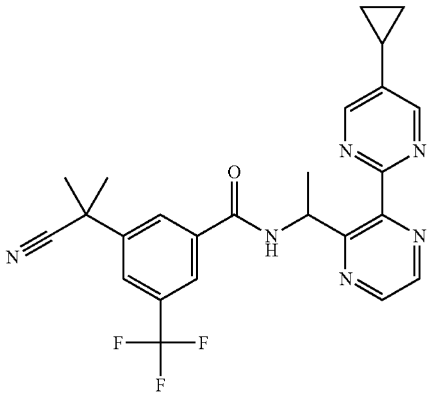 [SMILES: CC(NC(=O)c1cc(C(F)(F)F)cc(C(C)(C)C#N)c1)c1nccnc1-c1ncc(C2CC2)cn1] | | | | 130-140 |
| P7 | 3-(1-cyano-1-methyl-ethyl)-N-[1-[3-(2-pyridyl)pyrazin-2-yl]ethyl]-5-(trifluoromethyl) benzamide | 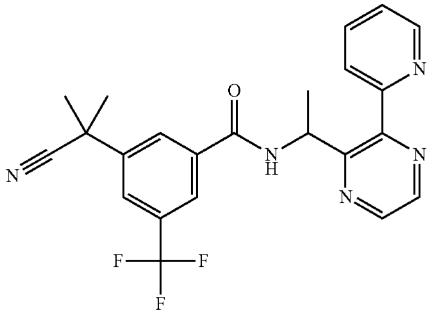 [SMILES: CC(NC(=O)c1cc(C(F)(F)F)cc(C(C)(C)C#N)c1)c1nccnc1-c1ccccn1] | | | | 150-160 |
| P8 | N-[1-[3-(5-chloro-2-pyridyl)pyrazin-2-yl]ethyl]-3-(1-cyano-1-methyl-ethyl)-5-(trifluoromethyl) benzamide | 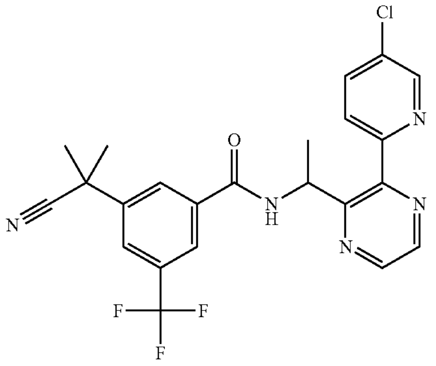 [SMILES: CC(NC(=O)c1cc(C(F)(F)F)cc(C(C)(C)C#N)c1)c1nccnc1-c1ccc(Cl)cn1] | | | | 120-125 |

TABLE P-continued

| Entry | IUPAC name | STRUCTURE | RT (min) | [M + H] (measured) | Method | MP° C. |
|---|---|---|---|---|---|---|
| Examples of prepared compounds of formula I | | | | | | |
| P9 | N-[1-[3-(5-bromo-2-pyridyl)pyrazin-2-yl]ethyl]-3-(1-cyano-1-methyl-ethyl)-5-(trifluoromethyl) benzamide | 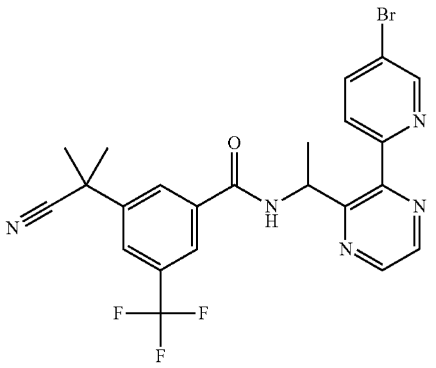 [SMILES: CC(NC(=O)c1cc(C(F)(F)F)cc(C(C)(C)C#N)c1)c1nccnc1-c1ccc(Br)cn1] | | | | 130-135 |
| P10 | 3-cyclopropylsulfonyl-N-[1-(3-pyrimidin-2-ylpyrazin-2-yl)ethyl]-5-(trifluoromethyl) benzamide | 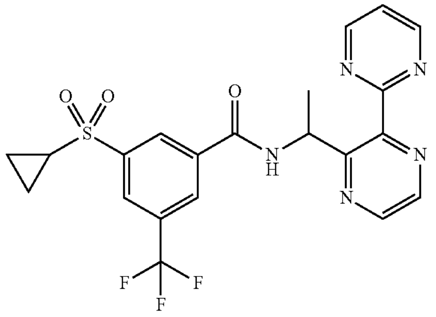 [SMILES: CC(NC(=O)c1cc(C(F)(F)F)cc(S(=O)(=O)C2CC2)c1)c1nccnc1-c1ncccn1] | 0.85 | 478 | 1 | |
| P11 | N-[1-[3-(5-cyclopropylpyrimidin-2-yl)pyrazin-2-yl]ethyl]-3-(trifluoromethyl)-5-(trifluoromethylsulfonyl) benzamide | 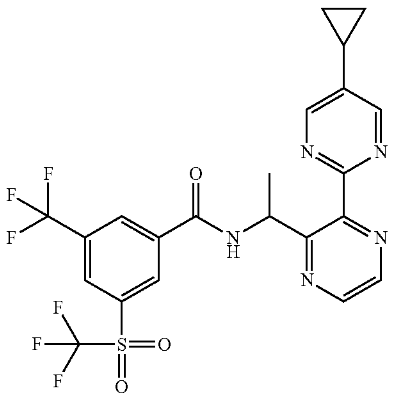 [SMILES: CC(NC(=O)c1cc(C(F)(F)F)cc(S(=O)(=O)C(F)(F)F)c1)c1nccnc1-c1ncc(C2CC2)cn1] | | | | 195-200 |
| P12 | N-[1-[3-(5-fluoro-2-pyridyl)pyrazin-2-yl] ethyl]-3-(trifluoromethyl)-5-(trifluoromethylsulfonyl) benzamide | 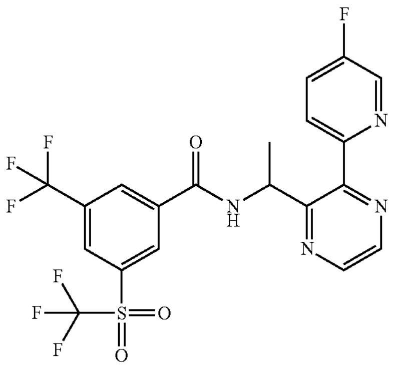 [SMILES: CC(NC(=O)c1cc(C(F)(F)F)cc(S(=O)(=O)C(F)(F)F)c1)c1nccnc1-c1ccc(F)cn1] | | | | 145-150 |

TABLE P-continued

| Examples of prepared compounds of formula I | | | | | | |
|---|---|---|---|---|---|---|
| Entry | IUPAC name | STRUCTURE | RT (min) | [M + H] (measured) | Method | MP° C. |
| P13 | N-[1-[3-(2-pyridyl) pyrazin-2-yl]ethyl]-3-(trifluoromethyl)-5-(trifluoromethylsulfonyl) benzamide | 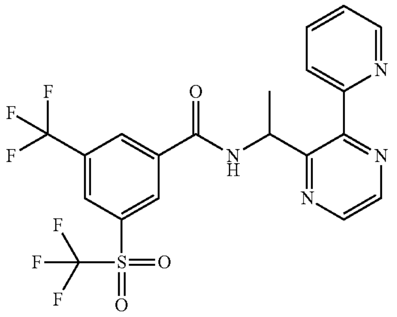 [SMILES: CC(NC(=O)c1cc(C(F)(F)F)cc(S(=O)(=O)C(F)(F)F)c1)c1nccnc1-c1ccccn1] | | | | 170-180 |
| P14 | N-[1-[3-(5-bromo-2-pyridyl)pyrazin-2-yl] ethyl]-3-(trifluoromethyl)-5-(trifluoromethylsulfonyl) benzamide | 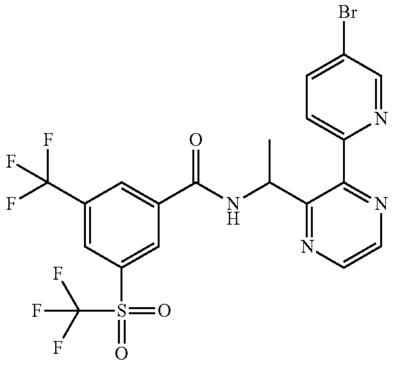 [SMILES: CC(NC(=O)c1cc(C(F)(F)F)cc(S(=O)(=O)C(F)(F)F)c1)c1nccnc1-c1ccc(Br)cn1] | | | | 190-195 |
| P15 | N-[1-[3-(5-chloro-2-pyridyl)pyrazin-2-yl]ethyl]-3-(trifluoromethyl)-5-(trifluoromethylsulfonyl) benzamide | 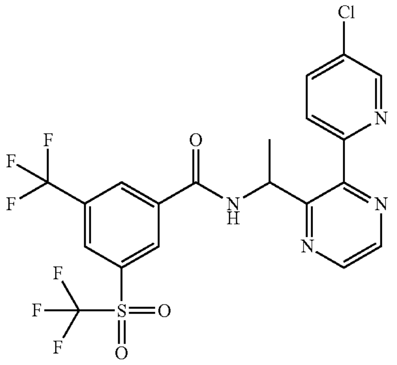 [SMILES: CC(NC(=O)c1cc(C(F)(F)F)cc(S(=O)(=O)C(F)(F)F)c1)c1nccnc1-c1ccc(Cl)cn1] | | | | 190-195 |
| P16 | N-[1-[3-(5-chloro-2-pyridyl)pyrazin-2-yl]ethyl]-2-(1-cyanocyclopropyl)-6-(trifluoromethyl)pyridine-4-carboxamide | 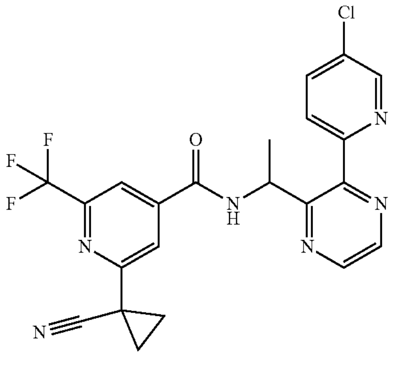 [SMILES: CC(NC(=O)c1cc(C(F)(F)F)nc(C2(C#N)CC2)c1)c1nccnc1-c1ccc(Cl)cn1] | | | | 165-170 |

TABLE P-continued

| Examples of prepared compounds of formula I | | | | | | |
|---|---|---|---|---|---|---|
| Entry | IUPAC name | STRUCTURE | RT (min) | [M + H] (mea-sured) | Meth-od | MP° C. |
| P17 | N-[1-[3-(5-chloro-2-pyridyl)pyrazin-2-yl]ethyl]-3-(1-cyanocyclopropyl)-5-(trifluoromethyl)benzamide | 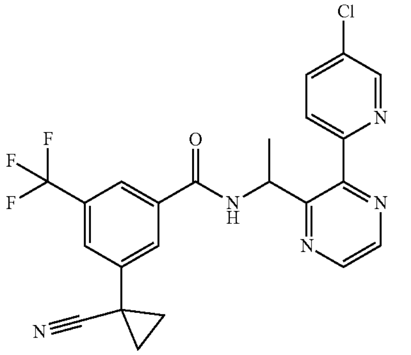 [SMILES: CC(NC(=O)c1cc(C(F)(F)F)cc(C2(C#N)CC2)c1)c1nccnc1-c1ccc(Cl)cn1] | | | | 170-175 |
| P18 | N-[1-[3-(5-chloro-2-pyridyl)pyrazin-2-yl]ethyl]-3-cyclopropyl-5-(trifluoromethyl)benzamide | 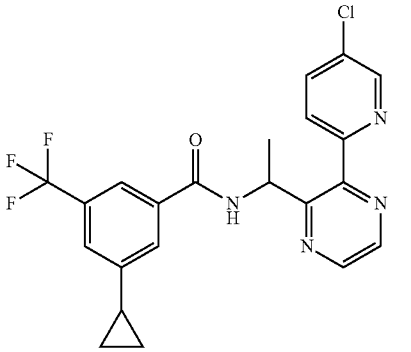 [SMILES: CC(NC(=O)c1cc(C2CC2)cc(C(F)(F)F)c1)c1nccnc1-c1ccc(Cl)cn1] | | | | 155-160 |
| P19 | N-[1-(3-pyrimidin-2-ylpyrazin-2-yl)ethyl]-3-(trifluoromethyl)-5-(trifluoromethylsulfonyl) benzamide | 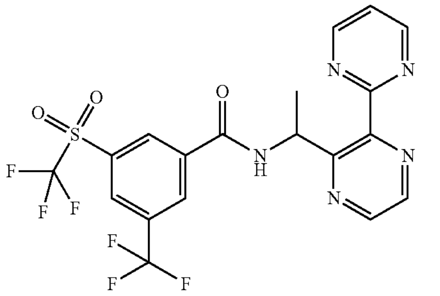 [SMILES: CC(NC(=O)c1cc(C(F)(F)F)cc(S(=O)(=O)C(F)(F)F)c1)c1nccnc1-c1ncccn1] | | | | 215-220 |
| P20 | 3-[cyclopropyl (difluoro)methyl]-N-[1-[3-(2-pyridyl)pyrazin-2-yl]ethyl]-5-(trifluoromethyl) benzamide | 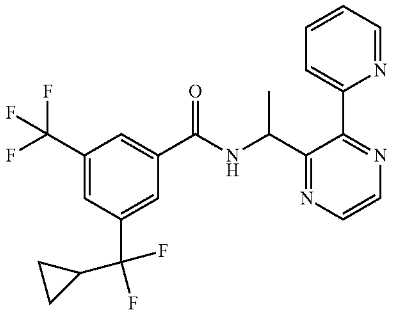 [SMILES: CC(NC(=O)c1cc(C(F)(F)F)cc(C(F)(F)C2CC2)c1)c1nccnc1-c1ccccn1] | | | | 130-140 |

TABLE P-continued

| Examples of prepared compounds of formula I | | | | | | |
|---|---|---|---|---|---|---|
| Entry | IUPAC name | STRUCTURE | RT (min) | [M + H] (mea-sured) | Meth-od | MP° C. |
| P21 | N-[1-[3-(5-bromo-2-pyridyl)pyrazin-2-yl]ethyl]-3-[cyclopropyl(difluoro)methyl]-5-(trifluoromethyl)benzamide | 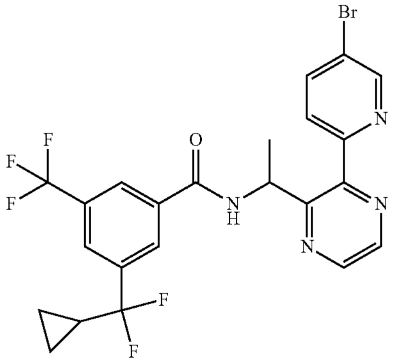 [SMILES: CC(NC(=O)c1cc(C(F)(F)F)cc(C(F)(F)C2CC2)c1)c1nccnc1-c1ccc(Br)cn1] | | | | 130-135 |
| P22 | 3-(1-cyanocyclopropyl)-N-[1-[3-(2-pyridyl)pyrazin-2-yl]ethyl]-5-(trifluoromethyl)benzamide | 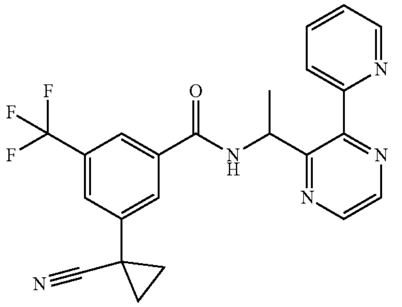 [SMILES: CC(NC(=O)c1cc(C(F)(F)F)cc(C2(C#N)CC2)c1)c1nccnc1-c1ccccn1] | | | | 130-140 |
| P23 | 3-(1-cyanocyclopropyl)-N-[1-[3-(5-fluoro-2-pyridyl)pyrazin-2-yl]ethyl]-5-(trifluoromethyl)benzamide | 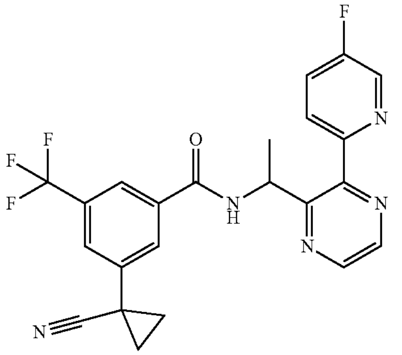 [SMILES: CC(NC(=O)c1cc(C(F)(F)F)cc(C2(C#N)CC2)c1)c1nccnc1-c1ccc(F)cn1] | | | | 175-180 |
| P24 | N-[1-[3-(5-bromo-2-pyridyl)pyrazin-2-yl]ethyl]-3-(1-cyanocyclopropyl)-5-(trifluoromethyl)benzamide | 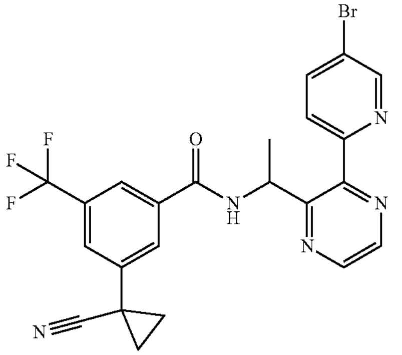 | | | | 125-130 |

TABLE P-continued

| Examples of prepared compounds of formula I | | | | | | |
|---|---|---|---|---|---|---|
| Entry | IUPAC name | STRUCTURE | RT (min) | [M + H] (measured) | Method | MP° C. |
| P25 | 3-(1-cyanocyclopropyl)-N-[1-(3-pyrimidin-2-ylpyrazin-2-yl)ethyl]-5-(trifluoromethyl)benzamide | 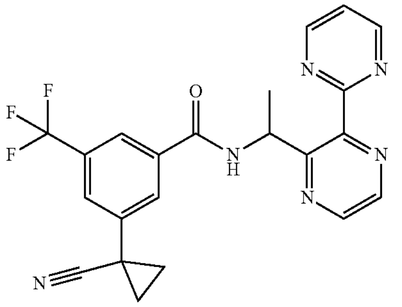 [SMILES: CC(NC(=O)c1cc(C(F)(F)F)cc(C2(C#N)CC2)c1)c1nccnc1-c1ncccn1] | | | | 178-182 |
| P26 | 2-(1-cyanocyclopropyl)-N-[1-[3-(2-pyridyl)pyrazin-2-yl]ethyl]-6-(trifluoromethyl)pyridine-4-carboxamide | 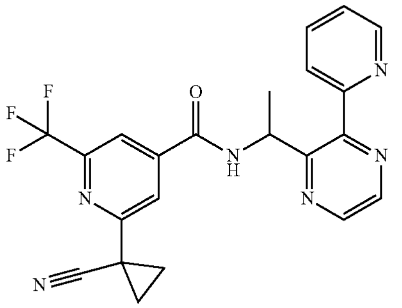 [SMILES: CC(NC(=O)c1cc(C(F)(F)F)nc(C2(C#N)CC2)c1)c1nccnc1-c1ccccn1] | | | | 120-130 |
| P27 | 2-(1-cyanocyclopropyl)-N-[1-[3-(5-fluoro-2-pyridyl)pyrazin-2-yl]ethyl]-6-(trifluoromethyl)pyridine-4-carboxamide | 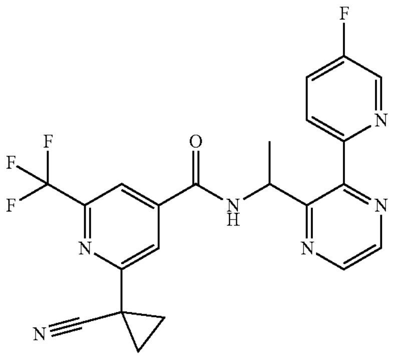 [SMILES: CC(NC(=O)c1cc(C(F)(F)F)nc(C2(C#N)CC2)c1)c1nccnc1-c1ccc(F)cn1] | | | | 185-190 |
| P28 | N-[1-[3-(5-bromo-2-pyridyl)pyrazin-2-yl]ethyl]-2-(1-cyanocyclopropyl)-6-(trifluoromethyl)pyridine-4-carboxamide | 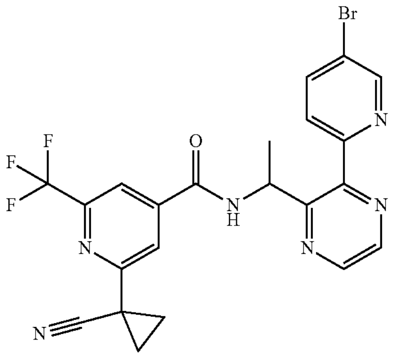 | | | | 120-125 |

TABLE P-continued

Examples of prepared compounds of formula I

| Entry | IUPAC name | STRUCTURE | RT (min) | [M + H] (measured) | Method | MP° C. |
|---|---|---|---|---|---|---|
| P29 | N-[1-[3-(5-bromo-2-pyridyl)pyrazin-2-yl]ethyl]-3-cyclopropyl-5-(trifluoromethyl)benzamide | 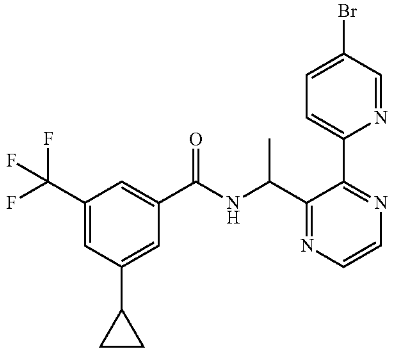 | | | | 120-125 |
| P30 | 3-[cyclopropyl(difluoro)methyl]-N-[1-(3-pyrimidin-2-ylpyrazin-2-yl)ethyl]-5-(trifluoromethyl)benzamide | 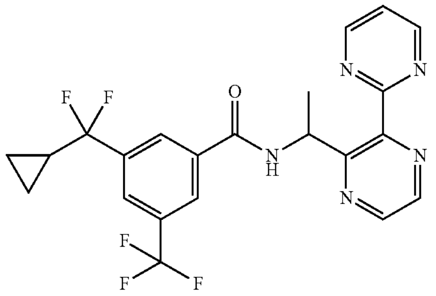 [SMILES: CC(NC(=O)c1cc(C(F)(F)F)cc(C(F)(F)C2CC2)c1)c1nccnc1-c1ncccn1] | | | | 152-155 |
| P31 | 2-cyclopropyl-N-[1-(3-pyrimidin-2-ylpyrazin-2-yl)ethyl]-6-(trifluoromethyl)pyridine-4-carboxamide | 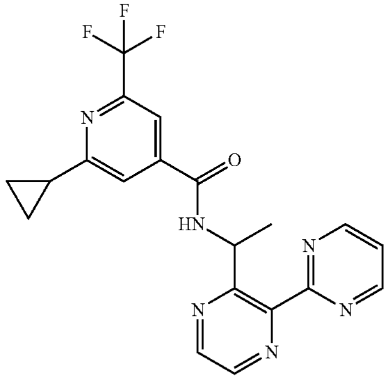 [SMILES: CC(NC(=O)c1cc(C2CC2)nc(C(F)(F)F)c1)c1nccnc1-c1ncccn1] | | | | 165-168 |
| P32 | 2-(1-cyanocyclopropyl)-N-[1-(3-pyrimidin-2-ylpyrazin-2-yl)ethyl]-6-(trifluoromethyl)pyridine-4-carboxamide | 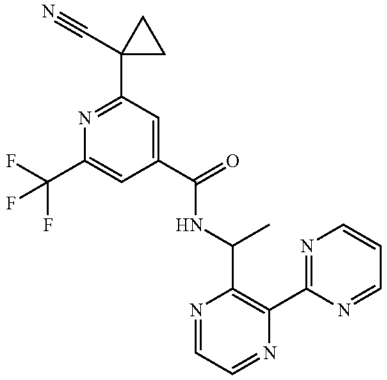 [SMILES: CC(NC(=O)c1cc(C(F)(F)F)nc(C2(C#N)CC2)c1)c1nccnc1-c1ncccn1] | | | | 160-165 |

TABLE P-continued

| Examples of prepared compounds of formula I | | | | | | |
|---|---|---|---|---|---|---|
| Entry | IUPAC name | STRUCTURE | RT (min) | [M + H] (measured) | Method | MP° C. |
| P33 | 3-cyclopropyl-N-[1-[3-(2-pyridyl)pyrazin-2-yl] ethyl]-5-(trifluoromethyl)benzamide | 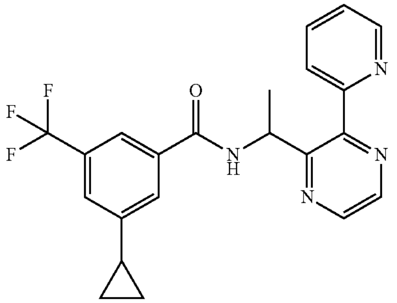 [SMILES: CC(NC(=O)c1cc(C2CC2)cc(C(F)(F)F)c1)c1nccnc1-c1ccccn1] | | | | 130-140 |
| P34 | 3-cyclopropyl-N-[1-[3-[5-(difluoromethoxy)pyrimidin-2-yl]pyrazin-2-yl]ethyl]-5-(trifluoromethyl)benzamide | 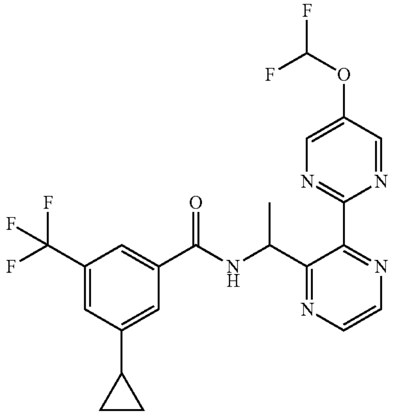 [SMILES: CC(NC(=O)c1cc(C2CC2)cc(C(F)(F)F)c1)c1nccnc1-c1ncc(OC(F)F)cn1] | | | | 90-95 |
| P35 | 3-cyclopropyl-N-[1-[3-(5-cyclopropylpyrimidin-2-yl)pyrazin-2-yl]ethyl]-5-(trifluoromethyl)benzamide | 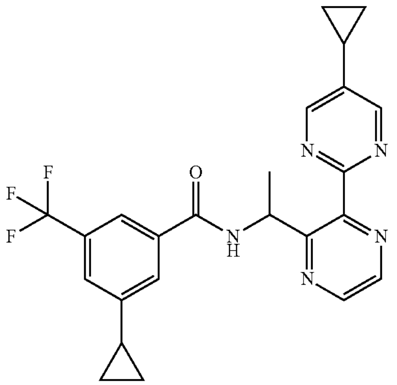 [SMILES: CC(NC(=O)c1cc(C2CC2)cc(C(F)(F)F)c1)c1nccnc1-c1ncc(C2CC2)cn1] | | | | 75-80 |
| P36 | 2-(1-cyanocyclopropyl)-N-[1-[3-(5-cyclopropylpyrimidin-2-yl)pyrazin-2-yl]ethyl]-6-(trifluoromethyl)pyridine-4-carboxamide | 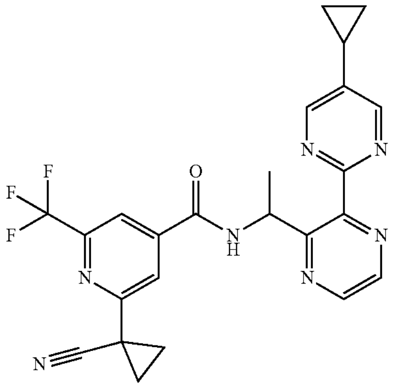 | | | | 230-232 |

TABLE P-continued

| Examples of prepared compounds of formula I | | | | | | |
|---|---|---|---|---|---|---|
| Entry | IUPAC name | STRUCTURE | RT (min) | [M + H] (measured) | Method | MP° C. |
| P37 | N-[1-(3-pyrimidin-2-ylpyrazin-2-yl)ethyl]-3-(trifluoromethyl)-5-[2-(trifluoromethyl) cyclopropyl] benzamide | 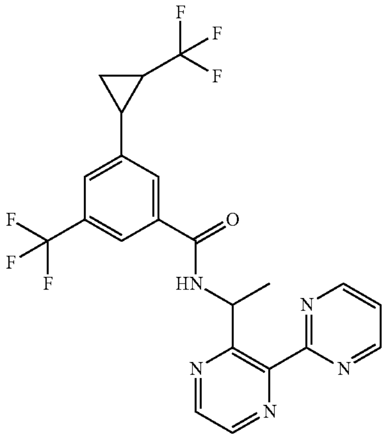 [SMILES: CC(NC(=O)c1cc(C2CC2C(F)(F)F)cc(C(F)(F)F)c1)c1nccnc1-c1ncccn1] | | | | 115-120 |
| P38 | 3-[cyclopropyl (difluoro)methyl]-N-[1-[3-(5-fluoro-2-pyridyl)pyrazin-2-yl]ethyl]-5-(trifluoromethyl)benzamide | 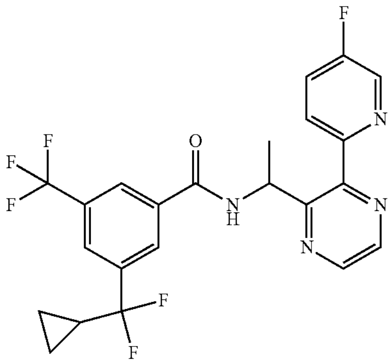 [SMILES: CC(NC(=O)c1cc(C(F)(F)F)cc(C(F)(F)C2CC2)c1)c1nccnc1-c1ccc(F)cn1] | | | | 63-66 |
| P39 | 3-[cyclopropyl(difluoro) methyl]-N-[1-[3-(5-cyclopropylpyrimidin-2-yl)pyrazin-2-yl]ethyl]-5-(trifluoromethyl)benzamide | 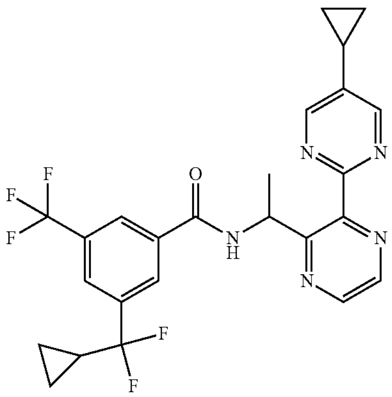 [SMILES: CC(NC(=O)c1cc(C(F)(F)F)cc(C(F)(F)C2CC2)c1)c1nccnc1-c1ncc(C2CC2)cn1] | | | | 85-90 |

TABLE P-continued

| Examples of prepared compounds of formula I | | | | | | |
|---|---|---|---|---|---|---|
| Entry | IUPAC name | STRUCTURE | RT (min) | [M + H] (measured) | Method | MP° C. |
| P40 | 3-cyclopropyl-N-[1-[3-(5-fluoro-2-pyridyl)pyrazin-2-yl]ethyl]-5-(trifluoromethyl)benzamide | 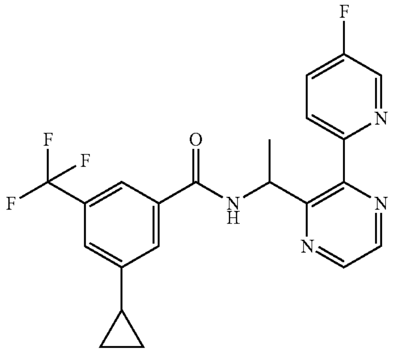 [SMILES: CC(NC(=O)c1cc(C2CC2)cc(C(F)(F)F)c1)c1nccnc1-c1ccc(F)cn1] | | | | 152-160 |
| P41 | 3-cyclopropyl-N-[1-(3-pyrimidin-2-ylpyrazin-2-yl)ethyl]-5-(trifluoromethyl)benzamide | 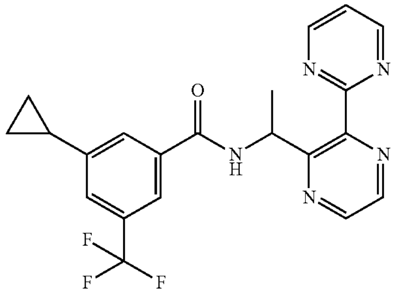 [SMILES: CC(NC(=O)c1cc(C2CC2)cc(C(F)(F)F)c1)c1nccnc1-c1ncccn1] | 0.97 | 414 | 1 | |
| P42 | N-[(1S)-1-[3-(5-bromo-2-pyridyl)pyrazin-2-yl]ethyl]-3-[cyclopropyl(difluoro)methyl]-5-(trifluoromethyl)benzamide | 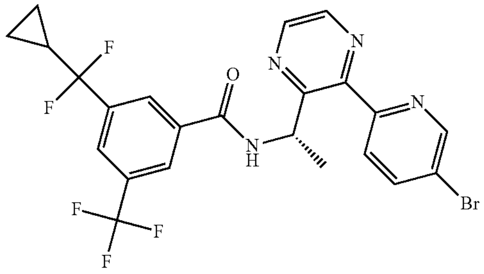 [SMILES: C[C@H](NC(=O)c1cc(C(F)(F)F)cc(C(F)(F)C2CC2)c1)c1nccnc1-c1ccc(Br)cn1] | 1.23 | 541-543 | 1 | |
| P43 | 2-(cyclopropylmethoxy)-N-[1-(3-pyrimidin-2-ylpyrazin-2-yl)ethyl]-6-(trifluoromethyl)pyridine-4-carboxamide | 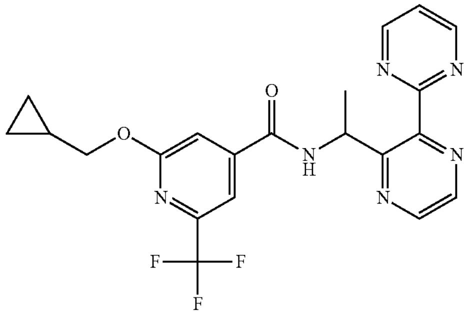 [SMILES: CC(NC(=O)c1cc(OCC2CC2)nc(C(F)(F)F)c1)c1nccnc1-c1ncccn1] | | | | 123-134 |

TABLE P-continued

| Examples of prepared compounds of formula I | | | | | | |
|---|---|---|---|---|---|---|
| Entry | IUPAC name | STRUCTURE | RT (min) | [M + H] (measured) | Method | MP° C. |
| P44 | 3-(1-cyanocyclopropyl)-5-(difluoromethoxy)-N-[1-(3-pyrimidin-2-ylpyrazin-2-yl)ethyl]benzamide | 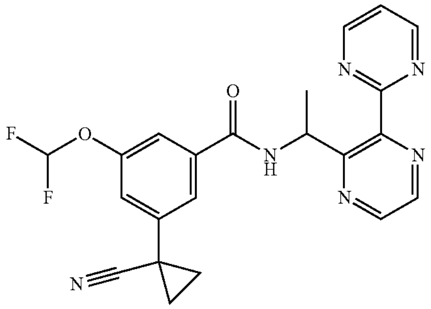 [SMILES: CC(NC(=O)c1cc(OC(F)F)cc(C2(C#N)CC2)c1)c1nccnc1-c1ncccn1] | | | | 120-130 |
| P45 | 3-(difluoromethoxy)-N-[1-(3-pyrimidin-2-ylpyrazin-2-yl)ethyl]-5-(trifluoromethylsulfonyl) benzamide | 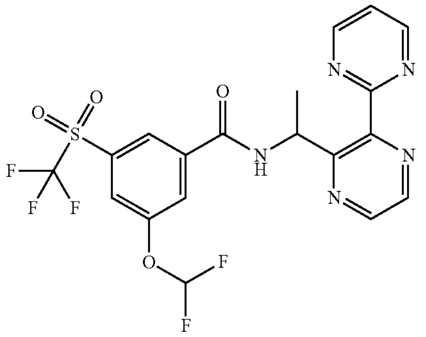 [SMILES: CC(NC(=O)c1cc(OC(F)F)cc(S(=O)(=O)C(F)(F)F)c1)c1nccnc1-c1ncccn1] | | | | 225-230 |
| P46 | 3-(1-cyanocyclopropyl)-N-[1-(3-pyrimidin-2-ylpyrazin-2-yl)ethyl]-5-(trifluoromethoxy) benzamide | 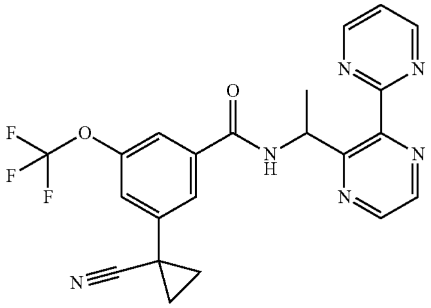 [SMILES: CC(NC(=O)c1cc(OC(F)(F)F)cc(C2(C#N)CC2)c1)c1nccnc1-c1ncccn1] | | | | 150-160 |
| P47 | 3-(1-methoxycyclopropyl)-N-[1-(3-pyrimidin-2-ylpyrazin-2-yl)ethyl]-5-(trifluoromethyl)benzamide | 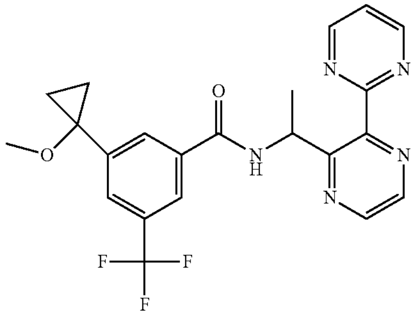 [SMILES: COC1(c2cc(C(=O)NC(C)c3nccnc3-c3ncccn3)cc(C(F)(F)F)c2)CC1] | | | | 140-150 |

TABLE P-continued

| Examples of prepared compounds of formula I | | | | | | |
|---|---|---|---|---|---|---|
| Entry | IUPAC name | STRUCTURE | RT (min) | [M + H] (measured) | Method | MP° C. |
| P48 | 3-(1-cyano-1-methyl-ethyl)-N-[1-[3-(5-methylpyrimidin-2-yl)pyrazin-2-yl]ethyl]-5-(trifluoromethyl)benzamide | 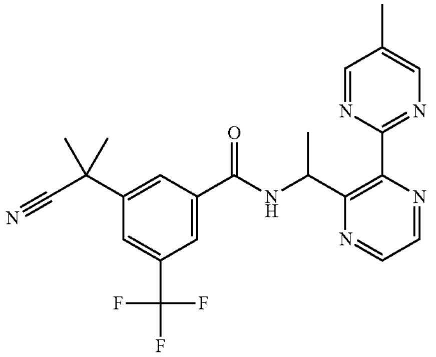 [SMILES: Cc1cnc(-c2nccnc2C(C)NC(=O)c2cc(C(F)(F)F)cc(C(C)(C)C#N)c2)nc1] | | | | 175-180 |
| P49 | N-[1-[3-(5-bromopyrimidin-2-yl)pyrazin-2-yl]ethyl]-3-(1-cyano-1-methyl-ethyl)-5-(trifluoromethyl)benzamide | 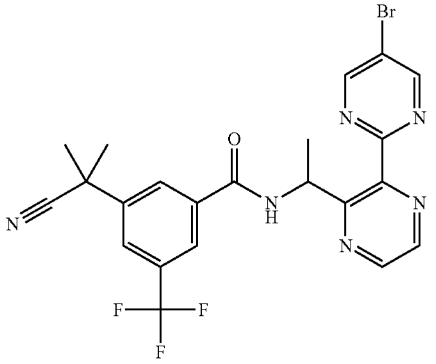 | | | | 170-175 |
| P50 | 3-(1-cyano-1-methyl-ethyl)-N-[1-(3-pyrimidin-2-ylpyrazin-2-yl) ethyl]-5-(trifluoromethyl)benzamide | 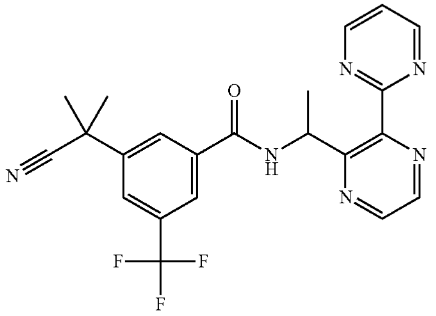 | | | | 160-165 |
| P51 | 3-cyclopropyl-N-[1-[3-(5-methylpyrimidin-2-yl) pyrazin-2-yl]ethyl]-5-(trifluoromethyl)benzamide | 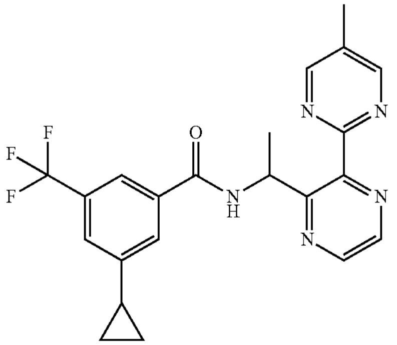 [SMILES: Cc1cnc(-c2nccnc2C(C)NC(=O)c2cc(C3CC3)cc(C(F)(F)F)c2)nc1] | | | | 135-140 |

TABLE P-continued

| Examples of prepared compounds of formula I | | | | | | |
|---|---|---|---|---|---|---|
| Entry | IUPAC name | STRUCTURE | RT (min) | [M + H] (measured) | Method | MP° C. |
| P52 | 3-[cyclopropyl (difluoro)methyl]-N-[1-[3-(5-methylpyrimidin-2-yl)pyrazin-2-yl]ethyl]-5-(trifluoromethyl)benzamide | 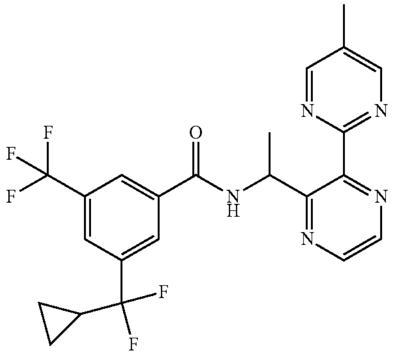 [SMILES: Cc1cnc(-c2nccnc2C(C)NC(=O)c2cc(C(F)(F)F)cc(C(F)(F)C3CC3)c2)nc1] | | | | 140-145 |
| P53 | N-[1-[3-(5-bromopyrimidin-2-yl)pyrazin-2-yl]ethyl]-3-[cyclopropyl(difluoro) methyl]-5-(trifluoromethyl)benzamide | 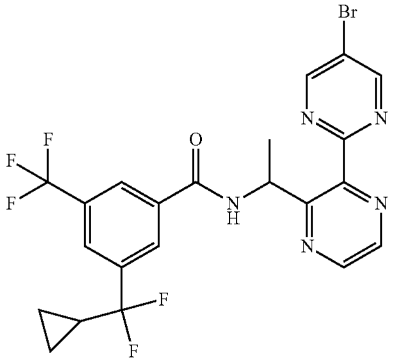 | | | | 130-135 |
| P54 | 3-(1-cyanocyclopropyl)-N-[1-[3-(5-methylpyrimidin-2-yl)pyrazin-2-yl]ethyl]-5-(trifluoromethyl)benzamide | 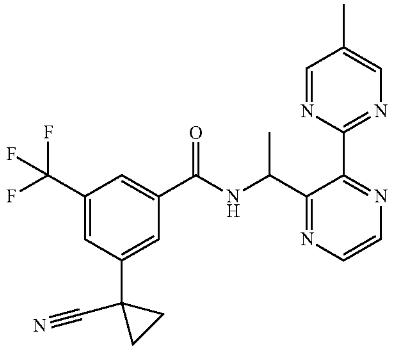 [SMILES: Cc1cnc(-c2nccnc2C(C)NC(=O)c2cc(C(F)(F)F)cc(C3(C#N)CC3)c2)nc1] | | | | 150-155 |
| P55 | N-[1-[3-(5-bromopyrimidin-2-yl)pyrazin-2-yl]ethyl]-2-(1-cyanocyclopropyl)-6-(trifluoromethyl)pyridine-4-carboxamide | 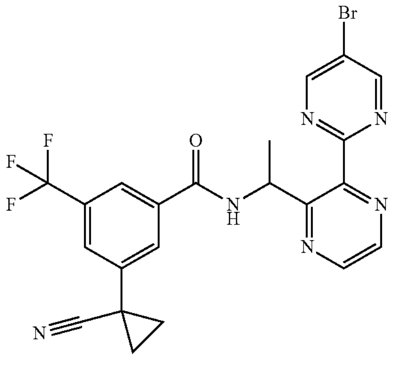 [SMILES: CC(NC(=O)c1cc(C(F)(F)F)cc(C2(C#N)CC2)c1)c1nccnc1-c1ncc(Br)cn1] | | | | 175-185 |

TABLE P-continued

| Examples of prepared compounds of formula I | | | | | | |
|---|---|---|---|---|---|---|
| Entry | IUPAC name | STRUCTURE | RT (min) | [M + H] (measured) | Method | MP° C. |
| P56 | N-[1-[3-(5-methylpyrimidin-2-yl)pyrazin-2-yl]ethyl]-3-(trifluoromethyl)-5-(trifluoromethylsulfonyl) benzamide | 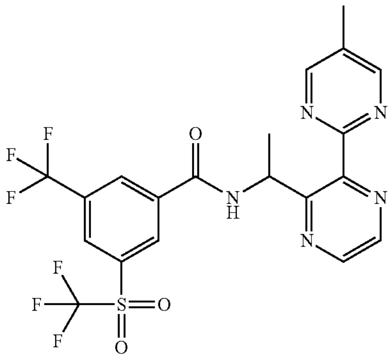 [SMILES: Cc1cnc(-c2nccnc2C(C)NC(=O)c2cc(C(F)(F)F)cc(S(=O)(=O)C(F)(F)F)c2)nc1] | | | | 200-205 |
| P57 | N-[1-[3-(5-bromopyrimidin-2-yl)pyrazin-2-yl]ethyl]-3-(trifluoromethyl)-5-(trifluoromethylsulfonyl) benzamide | 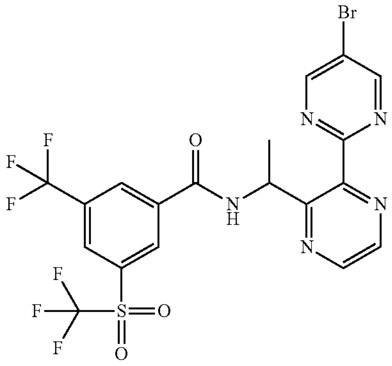 [SMILES: CC(NC(=O)c1cc(C(F)(F)F)cc(S(=O)(=O)C(F)(F)F)c1)c1nccnc1-c1ncc(Br)cn1] | | | | 185-190 |
| P58 | N-[1-[3-(5-bromopyrimidin-2-yl)pyrazin-2-yl]ethyl]-3-cyclopropyl-5-(trifluoromethyl) benzamide | 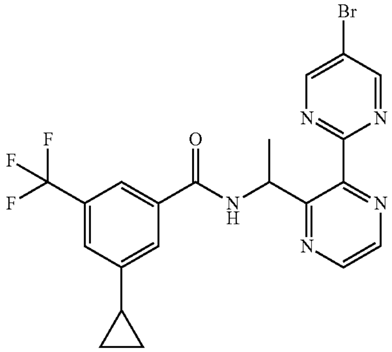 [SMILES: CC(NC(=O)c1cc(C2CC2)cc(C(F)(F)F)c1)c1nccnc1-c1ncc(Br)cn1] | | | | 130-140 |

TABLE I

| Table of Intermediates | | | | | | |
|---|---|---|---|---|---|---|
| Index | IUPAC name | STRUCTURE | RT (min) | m/z (measured) | Method | NMR |
| I1 | methyl 2-chloro-6-(trifluoromethyl)pyridine-4-carboxylate | 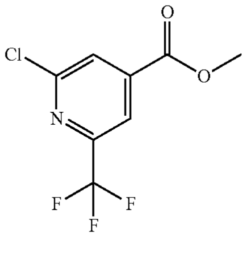 | | | | 1) |

TABLE I-continued

Table of Intermediates

| Index | IUPAC name | STRUCTURE | RT (min) | m/z (measured) | Method | NMR |
|---|---|---|---|---|---|---|
| I2 | methyl 2-cyclopropyl-6-(trifluoromethyl)pyridine-4-carboxylate | 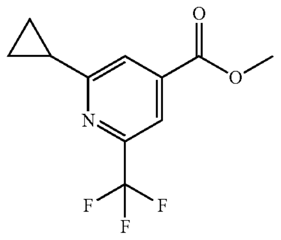 [SMILES: COC(=O)c1cc(C2CC2)nc(C(F)(F)F)c1] | 1.12 | 246 [M + H]+ | 1 | |
| I3 | 2-cyclopropyl-6-(trifluoromethyl)pyridine-4-carboxylic acid | 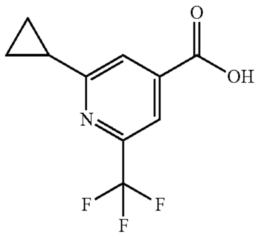 [SMILES: O=C(O)c1cc(C2CC2)nc(C(F)(F)F)c1] | 0.94 | 232 [M + H]+ | 1 | |
| I4 | methyl 3-cyclopropyl-5-(trifluoromethyl)benzoate | 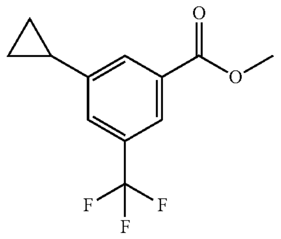 [SMILES: COC(=O)c1cc(C2CC2)cc(C(F)(F)F)c1] | | | | 2) |
| I5 | 3-cyclopropyl-5-(trifluoromethyl)benzoic acid | 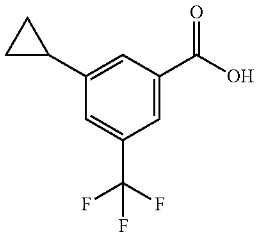 [SMILES: O=C(O)c1cc(C2CC2)cc(C(F)(F)F)c1] | 0.99 | 229 [M − H]− | 1 | |
| I6 | methyl 3-(trifluoromethyl)-5-vinyl-benzoate | 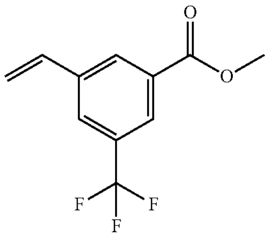 [SMILES: C=Cc1cc(C(=O)OC)cc(C(F)(F)F)c1] | | | | 3) |

TABLE I-continued

| Table of Intermediates | | | | | | |
|---|---|---|---|---|---|---|
| Index | IUPAC name | STRUCTURE | RT (min) | m/z (measured) | Method | NMR |
| I7 | methyl 3-(trifluoromethyl)-5-[2-(trifluoromethyl)cyclo-propyl]benzoate | 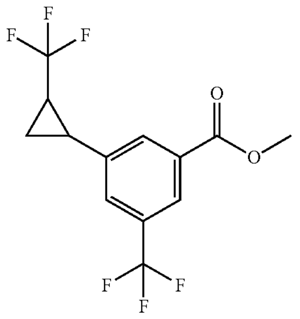 [SMILES: COC(=O)c1cc(C2CC2C(F)(F)F)cc(C(F)(F)F)c1] | | | | 4) |
| I8 | 3-(trifluoromethyl)-5-[2-(trifluoromethyl)cyclo-propyl]benzoic acid | 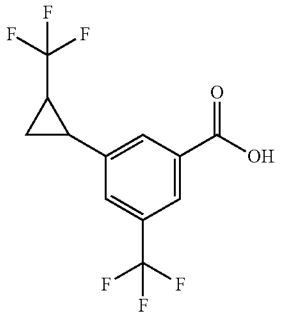 [SMILES: O=C(O)c1cc(C2CC2C(F)(F)F)cc(C(F)(F)F)c1] | 1.04 | 297 [M − H]$^-$ | 1 | |
| I9 | methyl 3-(trifluoromethyl)-5-(trifluoromethyl-sulfanyl)benzoate | 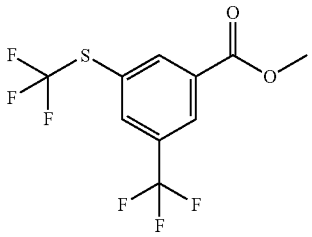 [SMILES: COC(=O)c1cc(SC(F)(F)F)cc(C(F)(F)F)c1] | | | | 5) |
| I10 | methyl 3-(trifluoromethyl)-5-(trifluoromethyl-sulfonyl)benzoate | 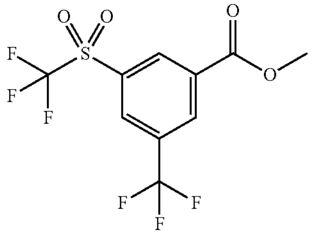 [SMILES: COC(=O)c1cc(C(F)(F)F)cc(S(=O)(=O)C(F)(F)F)c1] | | | | 6) |
| I11 | 3-(trifluoromethyl)-5-(trifluoromethyl-sulfonyl)benzoic acid | 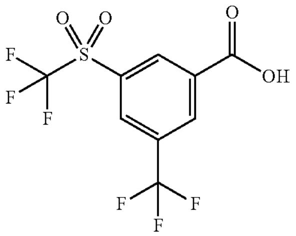 [SMILES: O=C(O)c1cc(C(F)(F)F)cc(S(=O)(=O)C(F)(F)F)c1] | | | | 7) |

TABLE I-continued

| Table of Intermediates | | | | | | |
|---|---|---|---|---|---|---|
| Index | IUPAC name | STRUCTURE | RT (min) | m/z (measured) | Method | NMR |
| I12 | methyl 3-(cyclopropanecarbonyl)-5-(trifluoromethyl)benzoate | 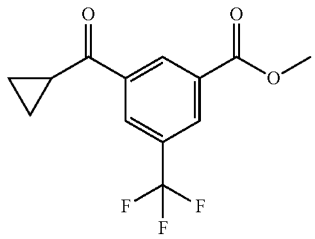 [SMILES: COC(=O)c1cc(C(=O)C2CC2)cc(C(F)(F)F)c1] | | | | 8) |
| I13 | methyl 3-[cyclo-propyl(difluoro)methyl]-5-(trifluoromethyl)benzoate | 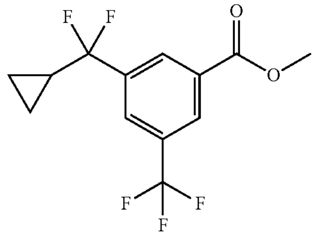 [SMILES: COC(=O)c1cc(C(F)(F)F)cc(C(F)(F)C2CC2)c1] | | | | 9) |
| I14 | 3-[cyclo-propyl(difluoro)methyl]-5-(trifluoromethyl)benzoic acid | 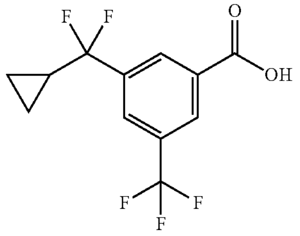 [SMILES: O=C(O)c1cc(C(F)(F)F)cc(C(F)(F)C2CC2)c1] | 1.03 | 279 [M − H]$^-$ | 1 | |
| I15 | methyl 2-(1-cyano-2-ethoxy-2-oxo-ethyl)-6-(trifluoromethyl)pyridine-4-carboxylate | 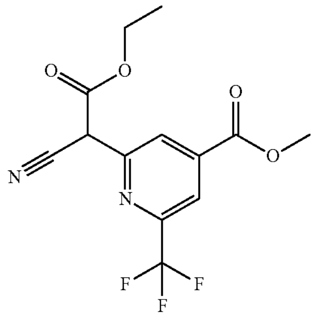 [SMILES: CCOC(=O)C(C#N)c1cc(C(=O)OC)cc(C(F)(F)F)n1] | 1.01 | 317 [M + H]$^+$ | 1 | |
| I16 | methyl 2-(cyanomethyl)-6-(trifluoromethyl)pyridine-4-carboxylate | 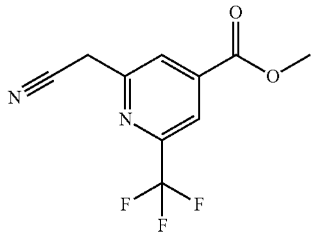 [SMILES: COC(=O)c1cc(CC#N)nc(C(F)(F)F)c1] | | | | 10) |
| I17 | 2-(1-cyanocyclopropyl)-6-(trifluoromethyl)pyridine-4-carboxylic acid | 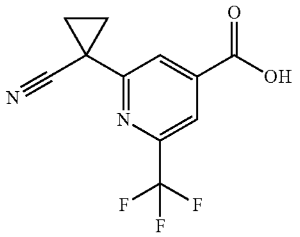 [SMILES: N#CC1(c2cc(C(=O)O)cc(C(F)(F)F)n2)CC1] | 0.89 | 255 [M − H]$^-$ | 1 | |

TABLE I-continued

| Table of Intermediates | | | | | | |
|---|---|---|---|---|---|---|
| Index | IUPAC name | STRUCTURE | RT (min) | m/z (measured) | Method | NMR |
| I18 | methyl 3-(cyanomethyl)-5-(trifluoromethyl)benzoate | 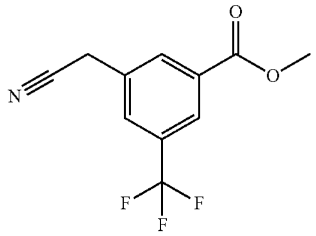 [SMILES: COC(=O)c1cc(CC#N)cc(C(F)(F)F)c1] | | | | 11) |
| I19 | methyl 3-(1-cyanocyclopropyl)-5-(trifluoromethyl)benzoate | 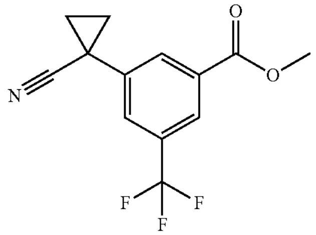 [SMILES: COC(=O)c1cc(C(F)(F)F)cc(C2(C#N)CC2)c1] | | | | 12) |
| I20 | 3-(1-cyanocyclopropyl)-5-(trifluoromethyl)benzoic acid | 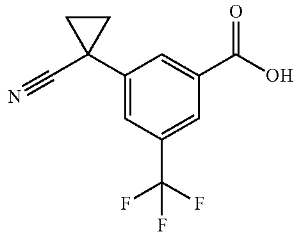 [SMILES: N#CC1(c2cc(C(=O)O)cc(C(F)(F)F)c2)CC1] | | | | 13) |
| I21 | 1-(3-pyrimidin-2-ylpyrazin-2-yl)ethanone | 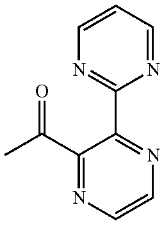 | 0.39 | 201.0 [M + H]$^+$ | 1 | |
| I22 | 1-[3-(5-methylpyrimidin-2-yl)pyrazin-2-yl]ethanone | 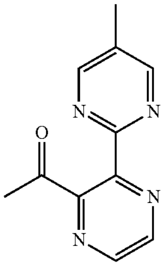 [SMILES: CC(=O)c1nccnc1-c1ncc(C)cn1] | | | | 14) |
| I23 | 1-[3-(5-cyclopropylpyrimidin-2-yl)pyrazin-2-yl]ethanone | 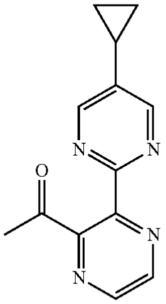 [SMILES: CC(=O)c1nccnc1-c1ncc(C2CC2)cn1] | | | | 15) |

TABLE I-continued
Table of Intermediates
| Index | IUPAC name | STRUCTURE | RT (min) | m/z (measured) | Method | NMR |
|---|---|---|---|---|---|---|
| I24 | 1-[3-(2-pyridyl)pyrazin-2-yl]ethanone | 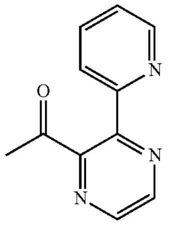 | 0.35 | 200.3 $[M + H]^+$ | 1 | |
| I25 | 1-[3-(5-chloro-2-pyridyl)pyrazin-2-yl]ethanone | 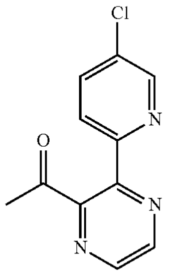 [SMILES: CC(=O)c1nccnc1-c1ccc(Cl)cn1] | | | | 16) |
| I26 | 1-[3-(5-bromo-2-pyridyl)pyrazin-2-yl]ethanone | 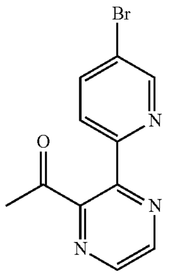 [SMILES: CC(=O)c1nccnc1-c1ccc(Br)cn1] | 3.64 | 278.0/280.0 $[M + H]^+$ (bromo pattern) | 3 | |
| I27 | 1-[3-(5-fluoro-2-pyridyl)pyrazin-2-yl]ethanone | 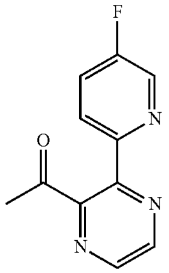 [SMILES: CC(=O)c1nccnc1-c1ccc(F)cn1] | 0.69 | 218.3 $[M + H]^+$ | 1 | |
| I28 | tert-butyl N-[6-(3-acetylpyrazin-2-yl)-3-pyridyl]carbamate | 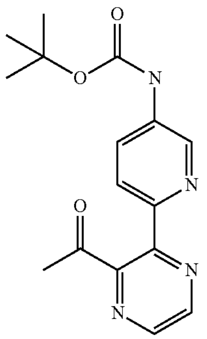 [SMILES: CC(=O)c1nccnc1-c1ccc(NC(=O)OC(C)(C)C)cn1] | | | | 17) |

TABLE I-continued
Table of Intermediates
| Index | IUPAC name | STRUCTURE | RT (min) | m/z (measured) | Method | NMR |
|---|---|---|---|---|---|---|
| I29 | 1-[3-(5-amino-2-pyridyl)pyrazin-2-yl]ethanone | 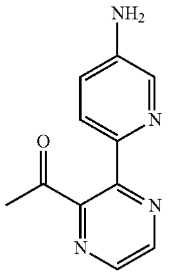 [SMILES: CC(=O)c1nccnc1-c1ccc(N)cn1] | 1.41 | 215.1 [M + H]$^+$ | 3 | |
| I30 | 1-(6-methyl-3-pyrimidin-2-yl-pyrazin-2-yl)ethanone | 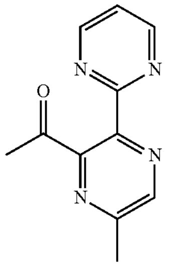 [SMILES: CC(=O)c1nc(C)cnc1-c1ncccn1] | 0.56 | 215.0 | 1 | |
| I31 | 1-(3-pyrimidin-2-ylpyrazin-2-yl)ethanamine | 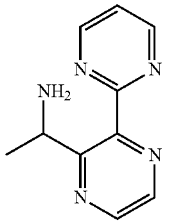 | 0.17 | 202 [M + H]$^+$ | 1 | |
| I32 | 1-[3-(5-cyclopropylpyrimidin-2-yl)pyrazin-2-yl]ethanamine | 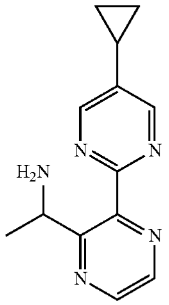 [SMILES: CC(N)c1nccnc1-c1ncc(C2CC2)cn1] | | | | 18) |
| I34 | 1-[3-(2-pyridyl)pyrazin-2-yl]ethanamine | 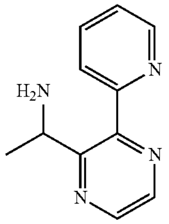 | 0.53 | 201.1 [M + H]$^+$ | | |

TABLE I-continued

| Table of Intermediates | | | | | | |
|---|---|---|---|---|---|---|
| Index | IUPAC name | STRUCTURE | RT (min) | m/z (measured) | Method | NMR |
| I35 | 1-[3-(5-chloro-2-pyridyl)pyrazin-2-yl]ethanamine | 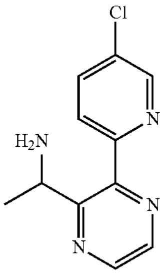 [SMILES: CC(N)c1nccnc1-c1ccc(Cl)cn1] | 2.7 | 235 $[M + H]^+$ | 3 | |
| I36 | 1-[3-(5-bromo-2-pyridyl)pyrazin-2-yl]ethanamine | 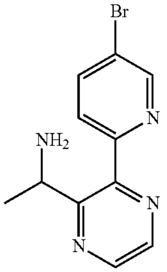 [SMILES: CC(N)c1nccnc1-c1ccc(Br)cn1] | 0.53 | 279/281 $[M + H]^+$ (bromo pattern) | 1 | |
| I37 | 1-[3-(5-fluoro-2-pyridyl)pyrazin-2-yl]ethanamine | 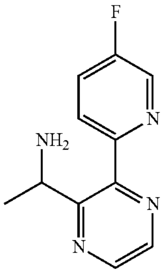 [SMILES: CC(N)c1nccnc1-c1ccc(F)cn1] | 0.18 | 219.3 $[M + H]^+$ | 1 | |
| I38 | tert-butyl N-[6-[3-(1-aminoethyl)pyrazin-2-yl]-3-pyridyl]carbamate | 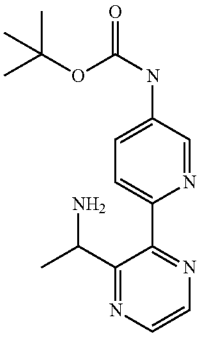 [SMILES: CC(N)c1nccnc1-c1ccc(NC(=O)OC(C)(C)C)cn1] | | | | 19) |
| I39 | 1-(6-methyl-3-pyrimidin-2-yl-pyrazin-2-yl)ethanamine | 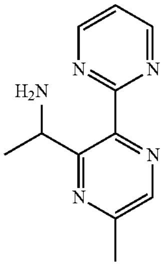 [SMILES: Cc1cnc(-c2ncccn2)c(C(C)N)n1] | 0.19 | 216 $[M + H]^+$ | 1 | |

TABLE I-continued

Table of Intermediates

| Index | IUPAC name | STRUCTURE | RT (min) | m/z (measured) | Method | NMR |
|---|---|---|---|---|---|---|
| I40 | (1R)-1-(3-pyrimidin-2-ylpyrazin-2-yl)ethanol | 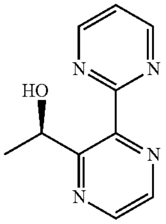 | 0.25 | 203.1 [M + H]$^+$ | 1 | |
| I41 | (1S)-1-(3-pyrimidin-2-ylpyrazin-2-yl)ethanamine | 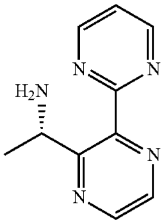 | 0.17 | 202 [M + H]$^+$ | 1 | |
| I42 | tert-butyl N-[(1S)-1-[3-(5-bromo-2-pyridyl)pyrazin-2-yl]ethyl]carbamate | 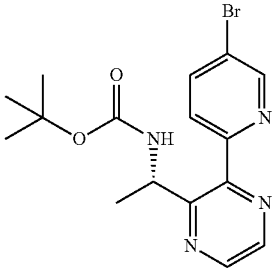 [SMILES: C[C@H](NC(=O)OC(C)(C)C)c1nccnc1-c1ccc(Br)cn1] | 1.09 | 379/381 [M + H]$^+$ (bromo pattern) | 1 | |
| I43 | (1S)-1-[3-(5-bromo-2-pyridyl)pyrazin-2-yl]ethanamine | 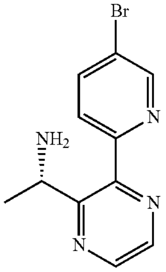 [SMILES: C[C@H](N)c1nccnc1-c1ccc(Br)cn1] | 0.53 | 279/281 [M + H]$^+$ (bromo pattern) | 1 | |
| I44 | (1R)-1-(3-chloropyrazin-2-yl)ethanol | 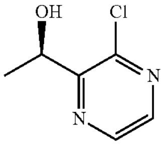 | 0.40 | 159/160 [M + H]$^+$ | | |

TABLE I-continued

| Table of Intermediates | | | | | | |
|---|---|---|---|---|---|---|
| Index | IUPAC name | STRUCTURE | RT (min) | m/z (measured) | Method | NMR |
| I45 | (1S)-1-(3-chloropyrazin-2-yl)ethanamine | 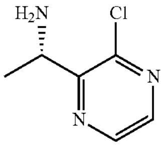 | 0.17 | 158 [M + H]+ | 1 | |
| I46 | (1S)-1-(3-chloropyrazin-2-yl)-N-(cyclopropyl-methyl)ethanamine | 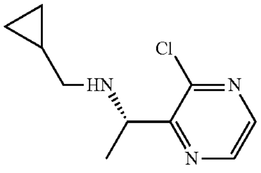 | 0.26 | 212 [M + H]+ | 2 | |
| I47 | 1-(6-methoxy-3-pyrimidin-2-yl-pyrazin-2-yl)ethanone | 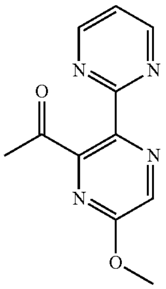 [SMILES: COc1cnc(-c2ncccn2)c(C(C)=O)n1] | 1.07 | 231 [M + H]+ | 4 | |
| I48 | 1-(6-methoxy-3-pyrimidin-2-yl-pyrazin-2-yl)ethanamine | 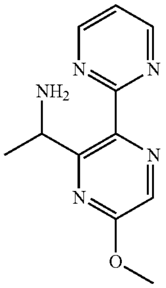 [SMILES: COc1cnc(-c2ncccn2)c(C(C)N)n1] | 0.35 | 232 [M + H]+ | 4 | |
| I49 | tert-butyl N-[(1S)-1-[6-amino-3-(5-bromo-2-pyridyl)pyrazin-2-yl]ethyl]carbamate | 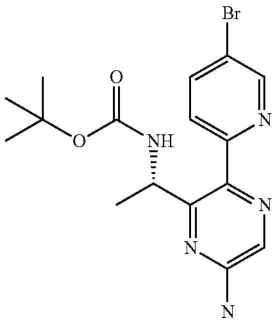 [SMILES: C[C@H](NC(=O)OC(C)(C)C)c1nc(N)cnc1-c1ccc(Br)cn1] | 1.04 | 394/396 [M + H]+ (bromo pattern) | 1 | |

TABLE I-continued

| Table of Intermediates | | | | | | |
|---|---|---|---|---|---|---|
| Index | IUPAC name | STRUCTURE | RT (min) | m/z (measured) | Method | NMR |
| I50 | 1-bromo-3-(1-methoxycyclopropyl)-5-(trifluoromethyl)benzene | 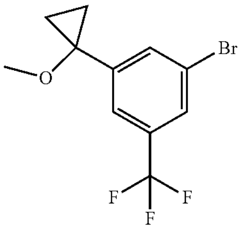 [SMILES: COC1(c2cc(Br)cc(C(F)(F)F)c2)CC1] | | | | 21) |
| I51 | methyl 3-(1-methoxycyclopropyl)-5-(trifluoromethyl)benzoate | 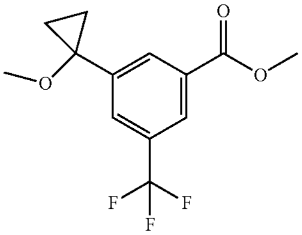 | | | | 22) |
| I52 | 3-(1 methoxycyclopropyl)-5-(trifluoromethyl)benzoic acid | 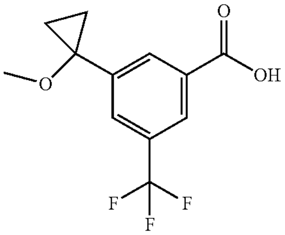 [SMILES: COC1(c2cc(C(=O)O)cc(C(F)(F)F)c2)CC1] | | | | 23) |
| I53 | tert-butyl N-[2-(3-acetylpyrazin-2-yl)pyrimidin-5-yl]carbamate | 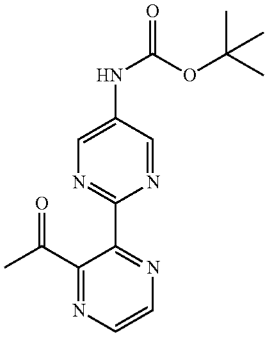 [SMILES: CC(=O)c1nccnc1-c1ncc(NC(=O)OC(C)(C)C)cn1] | 1.04 | 216.1 | 3 | |
| I54 | 1-[3-(5-bromopyrimidin-2-yl)pyrazin-2-yl]ethanone | 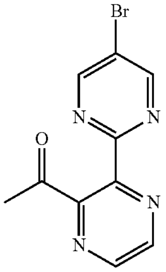 [SMILES: CC(=O)c1nccnc1-c1ncc(Br)cn1] | 3.54 | 279/281 [M + H]$^+$ (bromo pattern) | 3 | |

TABLE I-continued

Table of Intermediates

| Index | IUPAC name | STRUCTURE | RT (min) | m/z (measured) | Method | NMR |
|---|---|---|---|---|---|---|
| I55 | 1-[3-(5-bromopyrimidin-2-yl)pyrazin-2-yl]ethanamine | 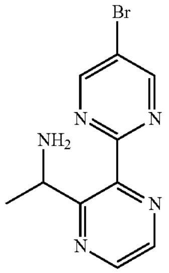 [SMILES: CC(N)c1nccnc1-c1ncc(Br)cn1] | | | | 24) |

1) $^{1}$H NMR (400 MHz, chloroform-d) δ ppm: 4.04 (s, 3 H) 8.11 (s, 1 H) 8.17 (d, J = 1.10 Hz, 1 H).

2) $^{1}$H NMR (400 MHz, chloroform-d) δ ppm: 0.76-0.85 (m, 2 H) 1.06-1.15 (m, 2 H) 2.03 (tt, $J_1$ = 8.39 Hz, $J_2$ = 5.00 Hz, 1 H 3.96 (s, 3 H) 7.52 (s, 1 H) 7.91 (s, 1 H) 8.08 (d, J = 0.73 Hz, 1 H); $^{19}$F NMR (377 MHz, chloroform-d) δ ppm: −62.75 (s, 3 F).

3) $^{1}$H NMR (400 MHz, chloroform-d) δ ppm: 3.98 (s, 3 H) 5.47 (d, J = 11.00 Hz, 1 H) 5.93 (d, J = 17.61 Hz, 1 H) 6.79 (dd, $J_1$ = 17.42 Hz, $J_2$ = 10.82 Hz, 1 H) 7.82 (s, 1 H) 8.19 (s, 1 H) 8.24-8.29 (m, 1 H).

4) $^{1}$H NMR (400 MHz, chloroform-d) δ ppm: 1.25-1.34 (m, 1 H) 1.48-1.55 (m, 1 H) 1.88-2.00 (m, 1 H) 2.46-2.53 (m, 1 H) 3.98 (s, 3 H) 7.60 (s, 1 H) 7.98 (s, 1 H) 8.19 (s, 1 H).

5) $^{1}$H NMR (400 MHz, chloroform-d) δ ppm: 4.02 (s, 3 H), 8.11 (s, 1 H), 8.44 (s, 1H), 8.53 (s, 1 H).

6) $^{1}$H NMR (400 MHz, Chloroform) δ ppm 4.07 (s, 3 H) 8.43-8.51 (m, 1 H) 8.70-8.80 (m, 1 H) 8.84-8.91 (m, 1 H); $^{19}$F NMR (377 MHz, chloroform-d) δ ppm: −77.49 (s, 3 F) −62.96 (s, 3 F)

7) $^{1}$H NMR (400 MHz, dimethylsulfoxide-d6) δ ppm: 8.68 (s, 2 H) 8.71-8.76 (m, 1 H) 13.33-15.22 (m, 1 H).

8) $^{1}$H NMR (400 MHz, chloroform-d) δ ppm: 1.16-1.22 (m, 2 H) 1.35 (quin, J = 3.76 Hz, 2 H) 2.74 (tt, $J_1$ = 7.84 Hz, $J_2$ = 4.45 Hz, 1 H) 4.02 (s, 3 H) 8.45 (d, J = 0.73 Hz, 1 H) 8.51 (d, J = 0.73 Hz, 1 H) 8.86 (s, 1 H).

9) $^{1}$H NMR (400 MHz, chloroform-d) δ ppm: 0.73-0.79 (m, 2 H) 0.82-0.89 (m, 2 H) 1.47-1.60 (m, 1 H) 8.00 (d, J = 0.73 Hz, 1 H) 8.39 (s, 1 H) 8.42 (s, 1 H); $^{19}$F NMR (377 MHz, chloroform-d) δ ppm: −98.40 (s, 3 F) −62.81 (s, 2 F).

10) $^{1}$H NMR (400 MHz, chloroform-d) δ ppm: 4.05 (s, 3 H) 4.13 (s, 2 H) 8.24 (s, 1 H) 8.26 (s, 1 H).

11) $^{1}$H NMR (400 MHz, chloroform-d) δ ppm: 8.30 (1 H, s), 8.23 (1 H, s), 7.81 (1 H, s), 3.99 (3 H, s), 3.90 (2 H, s).

12) $^{1}$H NMR (400 MHz, chloroform-d) δ ppm: 8.23 (1 H, s), 8.09 (1 H, s), 7.79 (1 H, s), 3.98 (3 H, s), 1.84-1.92 (2 H, m), 1.47-1.57 (m, 2H).

13) $^{1}$H NMR (400 MHz, chloroform-d) δ ppm: 8.60-9.90 (1 H, br s), 8.29 (1H, s), 8.15 (1H, s), 7.84 (1H, s), 1.84-1.93 (2 H, m), 1.50-1.60 (2 H, m)

14) $^{1}$H NMR (400 MHz, DMSO-d6) δ ppm: 8.93 (d, 1H), 8.84 (d, 1H), 8.78 (m, 2H), 2.64 (s, 3H), 2.36 (s, 3H)

15) $^{1}$H-NMR (400 MHz, CDCl3): δ ppm 8.7 (d, 1H), 8.55 (d, 1H), 8.50 (s, 2H), 2.7 (s, 3H), 1.85 (m, 1H), 1.1 (m, 2H), 0.8 (m, 2H).

16) 1H-NMR (400 MHz, DMSO): δ ppm 8.9 (s, 1H), 8.8 (d, 1H), 8.7 (s, 1H), 8.2 (m, 2H), 2.6 (s, 3H)

17) 1H-NMR (400 MHz, DMSO): δ ppm 9.9 (s, 1H), 8.6-8.9 (m, 3H), 8.1-8.25 (m, 2H), 2.55 (s, 1H), 1.5 (s, 9H)

18) $^{1}$H-NMR (400 MHz, DMSO): δ ppm 8.85 (m, 2H), 8.80 (m, 2H), 5.0 (m, 1H), 3.2 (m, 3H) 2.1 (m, 1H), 1.15 (m, 2H), 1.0 (m, 2H)

19) $^{1}$H-NMR (400 MHz, DMSO): δ ppm 9.9 (s, 1H), 8.6-8.9 (m, 3H), 8.1-8.25 (m, 2H), 2.55 (s, 1H), 1.5 (s, 9H)

20) $^{1}$H-NMR (400 MHz, chloroform-d) δ ppm 8.49 (d, 1H), 8.34 (d, 1H), 5.18 (m, 1H), 3.81 (d, 1H), 1.52 (d, 3H)

21) 1H NMR (400 MHz, DMSO-d) δ ppm: 7.82 (s, 1H), 7.69 (s, 1H), 7.55 (s, 1H), 3.27 (s, 3H), 1.20-1.28 (m, 2H), 1.09-1.18 (m, 2H).

22) 1H NMR (400 MHz, chloroform-d) δ ppm: 8.17 (s, 1H), 8.05 (s, 1H), 7.78 (s, 1H), 3.95 (s, 3H), 3.25 (s, 3H), 1.30 (t, 2H), 1.05 (t, 2H).

23) 1H NMR (400 MHz, chloroform-d) δ ppm: 13.4-13.7 (br. s, 1H), 8.00-8.10 (m, 2H), 7.72 (s, 1H), 3.19 (s, 3H), 1.25-1.35 (m, 2H), 1.08-1.15 (m, 2H).

24) 1H-NMR (400 MHz, DMSO): δ ppm: 9.22 (s, 2H), 8.70-9.00 (m, 2H), 4.50-4.80 (m, 1H), 1.42 (d, 3H).

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (where the abbreviation "TX" means "one compound selected from the compounds defined in the Tables A-1 to A-21, B-1 to B-21, C-1 to C-21, D-1 to D-21 and E-1 to E-21, and Table P"): an adjuvant selected from the group of substances consisting of petroleum oils (alternative name) (628)+TX, an insect control active substance selected from Abamectin+TX, Acequinocyl+TX, Acetamiprid+TX, Acetoprole+TX, Acrinathrin+TX, Acynonapyr+TX, Afidopyropen+TX, Afoxalaner+TX, Alanycarb+TX, Allethrin+TX, Alpha-Cypermethrin+TX, Alphamethrin+TX, Amidoflumet+TX, Aminocarb+TX, Azocyclotin+TX, Bensultap+TX, Benzoximate+TX, Benzpyrimoxan+TX, Betacyfluthrin+TX, Beta-cypermethrin+TX, Bifenazate+TX, Bifenthrin+TX, Binapacryl+TX, Bioallethrin+TX, Bioallethrin S)-cyclopentylisomer+TX, Bioresmethrin+TX, Bistrifluron+TX, Broflanilide+TX, Brofluthrinate+TX, Bromophos-ethyl+TX, Buprofezine+TX, Butocarboxim+TX, Cadusafos+TX, Carbaryl+TX, Carbosulfan+TX, Cartap+TX, CAS number: 1472050-04-6+TX, CAS number: 1632218-00-8+TX, CAS number: 1808115-49-2+TX, CAS number: 2032403-97-5+TX, CAS number: 2044701-44-0+TX, CAS number: 2128706-05-6+TX, CAS number: 2249718-27-0+TX, Chlorantraniliprole+TX, Chlordane+TX, Chlorfenapyr+TX, Chloroprallethrin+TX, Chromafenozide+TX, Clenpirin+TX, Cloethocarb+TX, Clothianidin+TX, 2-chlorophenyl N-methylcarbamate (CPMC)+TX, Cyanofenphos+TX, Cyantraniliprole+TX, Cyclaniliprole+TX, Cyclobutrifluram+TX, Cycloprothrin+TX, Cycloxaprid+TX, Cycloxaprid+TX, Cyenopyrafen+TX, Cyetpyrafen (or Etpyrafen)+TX, Cyflumetofen+TX, Cyfluthrin+TX, Cyhalodiamide+TX, Cyhalothrin+TX, Cypermethrin+TX, Cyphenothrin+TX, Cyromazine+TX, Deltamethrin+TX, Diafenthiuron+TX, Dialifos+TX, Dibrom+TX, Dicloromezotiaz+TX, Diflovidazine+TX, Diflubenzuron+TX, dimpropyridaz+TX, Dinactin+TX, Dinocap+TX, Dinotefuran+TX, Dioxabenzofos+TX, Emamectin+TX, Empenthrin+TX, Epsilon-momfluorothrin+TX, Epsilon-metofluthrin+TX, Esfenvalerate+TX, Ethion+TX, Ethiprole+TX, Etofenprox+TX, Etoxazole+TX, Famphur+TX, Fenazaquin+TX, Fenfluthrin+TX, Fenitrothion+TX, Fenobucarb+TX, Fenothiocarb+TX, Fenoxycarb+TX, Fenpropathrin+TX, Fenpyroxymate+TX, Fensulfothion+TX, Fenthion+TX, Fentinacetate+TX, Fenvalerate+TX, Fipronil+TX, Flometoquin+TX, Flonicamid+TX, Fluacrypyrim+TX, Fluazaindolizine+TX, Fluazuron+TX, Flubendiamide+TX, Flubenzimine+TX, Flucitrinate+TX, Flucycloxuron+TX, Flucythrinate+TX, Fluensulfone+TX, Flufenerim+TX, Flufenprox+TX, Flufiprole+TX, Fluhexafon+TX, Flumethrin+TX, Fluopyram+TX, Flupentiofenox+TX, Flupyradifurone+TX, Flupyrimin+TX, Fluralaner+TX, Fluvalinate+TX, Fluxametamide+TX, Fosthiazate+TX, Gamma-Cyhalothrin+TX, Gossyplure™+TX, Guadipyr+TX, Halofenozide+TX, Halofenozide+TX, Halofenprox+TX, Heptafluthrin+TX, Hexythiazox+TX, Hydramethylnon+TX, Imicyafos+TX, Imidacloprid+TX, Imiprothrin+TX, Indoxacarb+TX, Iodomethane+TX, Iprodione+TX, Isocycloseram+TX, Isothioate+TX, Ivermectin+TX, Kappa-bifenthrin+TX, Kappa-tefluthrin+TX, Lambda-Cyhalothrin+TX, Lepimectin+TX, Lufenuron+TX, Metaflumizone+TX, Metaldehyde+TX, Metam+TX, Methomyl+TX, Methoxyfenozide+TX, Metofluthrin+TX, Metolcarb+TX, Mexacarbate+TX, Milbemectin+TX, Momfluorothrin+TX, Niclosamide+TX, Nitenpyram+TX, Nithiazine+TX, Omethoate+TX, Oxamyl+TX, Oxazosufyl+TX, Parathion-ethyl+TX, Permethrin+TX, Phenothrin+TX, Phosphocarb+TX, Piperonylbutoxide+TX, Pirimicarb+TX, Pirimiphos-ethyl+TX, Polyhedrosis virus+TX, Prallethrin+TX, Profenofos+TX, Profenofos+TX, Profluthrin+TX, Propargite+TX, Propetamphos+TX, Propoxur+TX, Prothiophos+TX, Protrifenbute+TX, Pyflubumide+TX, Pymetrozine+TX, Pyraclofos+TX, Pyrafluprole+TX, Pyridaben+TX, Pyridalyl+TX, Pyrifluquinazon+TX, Pyrimidifen+TX, Pyrimostrobin+TX, Pyriprole+TX, Pyriproxyfen+TX, Resmethrin+TX, Sarolaner+TX, Selamectin+TX, Silafluofen+TX, Spinetoram+TX, Spinosad+TX, Spirodiclofen+TX, Spiromesifen+TX, Spiropidion+TX, Spirotetramat+TX, Sulfoxaflor+TX, Tebufenozide+TX, Tebufenpyrad+TX, Tebupirimiphos+TX, Tefluthrin+TX, Temephos+TX, Tetrachloraniliprole+TX, Tetradiphon+TX, Tetramethrin+TX, Tetramethylfluthrin+TX, Tetranactin+TX, Tetraniliprole+TX, Theta-cypermethrin+TX, Thiacloprid+TX, Thiamethoxam+TX, Thiocyclam+TX, Thiodicarb+TX, Thiofanox+TX, Thiometon+TX, Thiosultap+TX, Tioxazafen+TX, Tolfenpyrad+TX, Toxaphene+TX, Tralomethrin+TX, Transfluthrin+TX, Triazamate+TX, Triazophos+TX, Trichlorfon+TX, Trichloronate+TX, Trichlorphon+TX, Triflumezopyrim+TX, Tyclopyrazoflor+TX, Zeta-Cypermethrin+TX, Extract of seaweed and fermentation product derived from melasse+TX, Extract of seaweed and fermentation product derived from melasse comprising urea+TX, amino acids+TX, potassium and molybdenum and EDTA-chelated manganese+TX, Extract of seaweed and fermented plant products+TX, Extract of seaweed and fermented plant products comprising phytohormones+TX, vitamins+TX, EDTA-chelated copper+TX, zinc+TX, and iron+TX, Azadirachtin+TX, *Bacillus aizawai*+TX, *Bacillus* chitinosporus AQ746 (NRRL Accession No B-21 618)+TX, *Bacillus firmus*+TX, *Bacillus* kurstaki+TX, *Bacillus mycoides* AQ726 (NRRL Accession No. B-21664)+TX, *Bacillus pumilus* (NRRL Accession No B-30087)+TX, *Bacillus pumilus* AQ717 (NRRL Accession No. B-21662)+TX, *Bacillus* sp. AQ178 (ATCC Accession No. 53522)+TX, *Bacillus* sp. AQ175 (ATCC Accession No. 55608)+TX, *Bacillus* sp. AQ177 (ATCC Accession No. 55609)+TX, *Bacillus subtilis* unspecified+TX, *Bacillus subtilis* AQ153 (ATCC Accession No. 55614)+TX, *Bacillus subtilis* AQ30002 (NRRL Accession No. B-50421)+TX, *Bacillus subtilis* AQ30004 (NRRL Accession No. B-50455)+TX, *Bacillus subtilis* AQ713 (NRRL Accession No. B-21661)+TX, *Bacillus subtilis* AQ743 (NRRL Accession No. B-21665)+TX, *Bacillus thuringiensis* AQ52 (NRRL Accession No. B-21619)+TX, *Bacillus thuringiensis* BD #32 (NRRL Accession No B-21530)+TX, *Bacillus thuringiensis* subspec. kurstaki BMP 123+TX, *Beauveria bassiana*+TX, D-limonene+TX, Granulovirus+TX, Harpin+TX, *Helicoverpa armigera* Nucleopolyhedrovirus+TX, *Helicoverpa zea* Nucleopolyhedrovirus+TX, *Heliothis virescens* Nucleopolyhedrovirus+TX, *Heliothis punctigera* Nucleopolyhedrovirus+TX, *Metarhizium* spp.+TX, *Muscodor albus* 620 (NRRL Accession No. 30547)+TX, *Muscodor roseus* A3-5 (NRRL Accession No. 30548)+TX, Neem tree based products+TX, *Paecilomyces* fumosoroseus+TX, *Paecilomyces lilacinus*+TX, *Pasteuria nishizawae*+TX, *Pasteuria penetrans*+TX, *Pasteuria ramosa*+TX, *Pasteuria thornei*+TX, *Pasteuria* usgae+TX, P-cymene+TX, *Plutella xylostella* Granulosis virus+TX, *Plutella xylostella* Nucleopolyhedrovirus+TX, Polyhedrosis virus+TX, pyrethrum+TX, QRD 420 (a terpenoid blend)+TX, QRD 452 (a terpenoid blend)+TX, QRD 460 (a terpenoid blend)+TX, *Quillaja saponaria*+TX, *Rhodococcus globerulus* AQ719 (NRRL Accession No B-21663)+TX, *Spodoptera frugiperda* Nucleopolyhedrovirus+TX, *Streptomyces galbus* (NRRL Accession No. 30232)+TX, *Streptomyces* sp. (NRRL Accession No. B-30145)+TX, Terpenoid blend+TX, and *Verticillium* spp., an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, Cyclobutrifluram+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine

[CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. japonensis (scientific name) (51)+TX, *Bacillus thuringiensis* subsp. kurstaki (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces* fumosoroseus (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, Cyclobutrifluram+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, fluopyram+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, a biologically active substance selected from 1,1-bis(4-chloro-phenyl)-2-ethoxyethanol+TX, 2,4-dichlorophenyl benzenesulfonate+TX, 2-fluoro-N-methyl-N-1-naphthylacetamide+TX, 4-chlorophenyl phenyl sulfone+TX, acetoprole+TX, aldoxycarb+TX, amidithion+TX, amidothioate+TX, amiton+TX, amiton hydrogen oxalate+TX, amitraz+TX, aramite+TX, arsenous oxide+TX, azobenzene+TX, azothoate+TX, benomyl+TX, benoxa-fos+TX, benzyl benzoate+TX, bixafen+TX, brofenvalerate+TX, bromo-cyclen+TX, bromophos+TX, bromopropylate+TX, buprofezin+TX, butocarboxim+TX, butoxycarboxim+TX, butylpyridaben+TX, calcium polysulfide+TX, camphechlor+TX, carbanolate+TX, carbophenothion+TX, cymiazole+TX, chinomethionat+TX, chlorbenside+TX, chlordimeform+TX, chlordimeform hydrochloride+TX, chlorfenethol+TX, chlorfenson+TX, chlorfensulfide+TX, chlorobenzilate+TX, chloromebuform+TX, chloromethiuron+TX, chloropropylate+TX, chlorthiophos+TX, cinerin I+TX, cinerin II+TX, cinerins+TX, closantel+TX, coumaphos+TX, crotamiton+TX, crotoxyphos+TX, cufraneb+TX, cyanthoate+TX, DCPM+TX, DDT+TX, demephion+TX, demephion-O+TX, demephion-S+TX, demeton-methyl+TX, demeton-O+TX, demeton-O-methyl+TX, demeton-S+TX, demeton-S-methyl+TX, demeton-S-methylsulfon+TX, dichlofluanid+TX, dichlorvos+TX, dicliphos+TX, dienochlor+TX, dimefox+TX, dinex+TX, dinex-diclexine+TX, dinocap-4+TX, dinocap-6+TX, dinocton+TX, dino-penton+TX, dinosulfon+TX, dinoterbon+TX, dioxathion+TX, diphenyl sulfone+TX, disulfiram+TX, DNOC+TX, dofenapyn+TX, doramectin+TX, endothion+TX, eprinomectin+TX, ethoate-methyl+TX, etrimfos+TX, fenazaflor+TX, fenbutatin oxide+TX, fenothiocarb+TX, fenpyrad+TX, fen-pyroximate+TX, fenpyrazamine+TX, fenson+TX, fentrifanil+TX, flubenzimine+TX, flucycloxuron+TX, fluenetil+TX, fluorbenside+TX, FMC 1137+TX, formetanate+TX, formetanate hydrochloride+TX, formparanate+TX, gamma-HCH+TX, glyodin+TX, halfenprox+TX, hexadecyl cyclopropanecarboxylate+TX, isocarbophos+TX, jasmolin I+TX, jasmolin II+TX, jodfenphos+TX, lindane+TX, malonoben+TX, mecarbam+TX, mephosfolan+TX, mesulfen+TX, methacrifos+TX, methyl bromide+TX, metolcarb+TX, mexacarbate+TX, milbemycin oxime+TX, mipafox+TX, monocrotophos+TX, morphothion+TX, moxidectin+TX, naled+TX, 4-chloro-2-(2-chloro-2-methyl-propyl)-5-[(6-iodo-3-pyridyl)methoxy]pyridazin-3-one+TX, nifluridide+TX, nikkomycins+TX, nitrilacarb+TX, nitrilacarb 1:1 zinc chloride complex+TX, omethoate+TX, oxydeprofos+TX, oxydisulfoton+TX, pp'-DDT+TX, parathion+TX, permethrin+TX, phenkapton+TX, phosalone+TX, phosfolan+TX, phosphamidon+TX, polychloroterpenes+TX, polynactins+TX, proclonol+TX, promacyl+TX, propoxur+TX, prothidathion+TX, prothoate+TX, pyrethrin I+TX, pyrethrin II+TX, pyrethrins+TX, pyridaphenthion+TX, pyrimitate+TX, quinalphos+TX, quintiofos+TX, R-1492+TX, phosglycin+TX, rotenone+TX, schradan+TX, sebufos+TX, selamectin+TX, sophamide+TX, SSI-121+TX, sulfiram+TX, sulfluramid+TX, sulfotep+TX, sulfur+TX, diflovidazin+TX, tau-fluvalinate+TX, TEPP+TX, terbam+TX, tetradifon+TX, tetrasul+TX, thiafenox+TX, thiocarboxime+TX, thiofanox+TX, thiometon+TX, thioquinox+TX, thuringiensin+TX, triamiphos+TX, triarathene+TX, triazophos+TX, triazuron+TX, trifenofos+TX, trinactin+TX, vamidothion+TX, vaniliprole+TX, bethoxazin+TX, copper dioctanoate+TX, copper sulfate+TX, cybutryne+TX, dichlone+TX, dichlorophen+TX, endothal+TX, fentin+TX, hydrated lime+TX, nabam+TX, quinoclamine+TX, quinonamid+TX, simazine+TX, triphenyltin acetate+TX, triphenyltin hydroxide+TX, crufomate+TX, piperazine+TX, thiophanate+TX, chloralose+TX, fenthion+TX, pyridin-4-amine+TX, strychnine+TX, 1-hydroxy-1H-pyridine-2-thione+TX, 4-(quinoxalin-2-ylamino) benzenesulfonamide+TX, 8-hydroxyquinoline sulfate+TX, bronopol+TX, copper hydroxide+TX, cresol+TX, dipyrithione+TX, dodicin+TX, fenaminosulf+TX, formaldehyde+TX, hydrargaphen+TX, kasugamycin+TX, kasugamycin hydrochloride hydrate+TX, nickel bis(dimethyldithiocarbamate)+TX, nitrapyrin+TX, octhilinone+TX, oxolinic acid+TX, oxytetracycline+TX, potassium hydroxyquinoline sulfate+TX, probenazole+TX, streptomycin+TX, streptomycin sesquisulfate+TX, tecloftalam+TX, thiomersal+TX, *Adoxophyes orana* GV+TX, *Agrobacterium radiobacter*+TX, *Amblyseius* spp.+TX, *Anagrapha falcifera* NPV+TX, *Anagrus atomus*+TX, *Aphelinus abdominalis*+TX, *Aphidius colemani*+TX, *Aphidoletes aphidimyza*+TX, *Autographa californica* NPV+TX, *Bacillus sphaericus* Neide+TX, *Beauveria brongniartii*+TX, *Chrysoperla carnea*+TX, *Cryptolaemus montrouzieri*+TX, *Cydia pomonella* GV+TX, *Dacnusa sibirica*+TX, *Diglyphus isaea*+TX, *Encarsia formosa*+TX, *Eretmocerus eremicus*+TX, *Heterorhabditis bacteriophora* and *H. megidis*+TX, *Hippodamia convergens*+TX, *Leptomastix dactylopii*+TX, *Macrolophus caliginosus*+TX, *Mamestra brassicae* NPV+TX, *Metaphycus helvolus*+TX, *Metarhizium anisopliae* var. *acridum*+TX, *Metarhizium anisopliae* var. *anisopliae*+TX, *Neodiprion sertifer* NPV and *N. lecontei* NPV+TX, *Orius* spp.+TX, *Paecilomyces* fumosoroseus+TX, *Phytoseiulus persimilis*+TX, *Steinernema bibionis*+TX, *Steinernema carpocapsae*+TX, *Steinernema feltiae*+TX, *Steinernema glaseri*+TX, *Steinernema* riobrave+TX, *Steinernema* riobravis+TX, *Steinernema* scapterisci+TX, *Steinernema* spp.+TX, *Trichogramma* spp.+TX,

*Typhlodromus occidentalis*+TX, *Verticillium lecanii*+TX, apholate+TX, bisazir+TX, busulfan+TX, dimatif+TX, hemel+TX, hempa+TX, metepa+TX, methiotepa+TX, methyl apholate+TX, morzid+TX, penfluron+TX, tepa+TX, thiohempa+TX, thiotepa+TX, tretamine+TX, uredepa+TX, (E)-dec-5-en-1-yl acetate with (E)-dec-5-en-1-ol+TX, (E)-tridec-4-en-1-yl acetate+TX, (E)-6-methylhept-2-en-4-ol+TX, (E,Z)-tetradeca-4,10-dien-1-yl acetate+TX, (Z)-dodec-7-en-1-yl acetate+TX, (Z)-hexadec-11-enal+TX, (Z)-hexadec-11-en-1-yl acetate+TX, (Z)-hexadec-13-en-11-yn-1-yl acetate+TX, (Z)-icos-13-en-10-one+TX, (Z)-tetradec-7-en-1-al+TX, (Z)-tetradec-9-en-1-ol+TX, (Z)-tetradec-9-en-1-yl acetate+TX, (7E,9Z)-dodeca-7,9-dien-1-yl acetate+TX, (9Z,11E)-tetradeca-9,11-dien-1-yl acetate+TX, (9Z,12E)-tetradeca-9,12-dien-1-yl acetate+TX, 14-methyloctadec-1-ene+TX, 4-methylnonan-5-ol with 4-methylnonan-5-one+TX, alpha-multistriatin+TX, brevicomin+TX, codlelure+TX, codlemone+TX, cuelure+TX, disparlure+TX, dodec-8-en-1-yl acetate+TX, dodec-9-en-1-yl acetate+TX, dodeca-8+TX, 10-dien-1-yl acetate+TX, dominicalure+TX, ethyl 4-methyloctanoate+TX, eugenol+TX, frontalin+TX, grandlure+TX, grandlure I+TX, grandlure II+TX, grandlure III+TX, grandlure IV+TX, hexalure+TX, ipsdienol+TX, ipsenol+TX, japonilure+TX, lineatin+TX, litlure+TX, looplure+TX, medlure+TX, megatomoic acid+TX, methyl eugenol+TX, muscalure+TX, octadeca-2,13-dien-1-yl acetate+TX, octadeca-3,13-dien-1-yl acetate+TX, orfralure+TX, oryctalure+TX, ostramone+TX, siglure+TX, sordidin+TX, sulcatol+TX, tetradec-11-en-1-yl acetate+TX, trimedlure+TX, trimedlure A+TX, trimedlure $B_1$+TX, trimedlure $B_2$+TX, trimedlure C+TX, trunc-call+TX, 2-(octylthio)-ethanol+TX, butopyronoxyl+TX, butoxy(polypropylene glycol)+TX, dibutyl adipate+TX, dibutyl phthalate+TX, dibutyl succinate+TX, diethyltoluamide+TX, dimethyl carbate+TX, dimethyl phthalate+TX, ethyl hexanediol+TX, hexamide+TX, methoquin-butyl+TX, methylneodecanamide+TX, oxamate+TX, picaridin+TX, 1-dichloro-1-nitroethane+TX, 1,1-dichloro-2,2-bis(4-ethylphenyl)-ethane+TX, 1,2-dichloropropane with 1,3-dichloropropene+TX, 1-bromo-2-chloroethane+TX, 2,2,2-trichloro-1-(3,4-dichlorophenyl)ethyl acetate+TX, 2,2-dichlorovinyl 2-ethylsulfinylethyl methyl phosphate+TX, 2-(1,3-dithiolan-2-yl)phenyl dimethylcarbamate+TX, 2-(2-butoxyethoxy)ethyl thiocyanate+TX, 2-(4,5-dimethyl-1,3-dioxolan-2-yl)phenyl methylcarbamate+TX, 2-(4-chloro-3,5-xylyloxy)ethanol+TX, 2-chlorovinyl diethyl phosphate+TX, 2-imidazolidone+TX, 2-isovalerylindan-1,3-dione+TX, 2-methyl(prop-2-ynyl)aminophenyl methylcarbamate+TX, 2-thiocyanatoethyl laurate+TX, 3-bromo-1-chloroprop-1-ene+TX, 3-methyl-1-phenylpyrazol-5-yl dimethyl-carbamate+TX, 4-methyl(prop-2-ynyl)amino-3,5-xylyl methylcarbamate+TX, 5,5-dimethyl-3-oxocyclohex-1-enyl dimethylcarbamate+TX, acethion+TX, acrylonitrile+TX, aldrin+TX, allosamidin+TX, allyxycarb+TX, alpha-ecdysone+TX, aluminium phosphide+TX, aminocarb+TX, anabasine+TX, athidathion+TX, azamethiphos+TX, *Bacillus thuringiensis* delta endotoxins+TX, barium hexafluorosilicate+TX, barium polysulfide+TX, barthrin+TX, Bayer 22/190+TX, Bayer 22408+TX, beta-cyfluthrin+TX, beta-cypermethrin+TX, bioethanomethrin+TX, biopermethrin+TX, bis(2-chloroethyl) ether+TX, borax+TX, bromfenvinfos+TX, bromo-DDT+TX, bufencarb+TX, butacarb+TX, butathiofos+TX, butonate+TX, calcium arsenate+TX, calcium cyanide+TX, carbon disulfide+TX, carbon tetrachloride+TX, cartap hydrochloride+TX, cevadine+TX, chlorbicyclen+TX, chlordane+TX, chlordecone+TX, chloroform+TX, chloropicrin+TX, chlorphoxim+TX, chlorprazophos+TX, cis-resmethrin+TX, cismethrin+TX, clocythrin+TX, copper acetoarsenite+TX, copper arsenate+TX, copper oleate+TX, coumithoate+TX, cryolite+TX, CS 708+TX, cyanofenphos+TX, cyanophos+TX, cyclethrin+TX, cythioate+TX, d-tetramethrin+TX, DAEP+TX, dazomet+TX, decarbofuran+TX, diamidafos+TX, dicapthon+TX, dichlofenthion+TX, dicresyl+TX, dicyclanil+TX, dieldrin+TX, diethyl 5-methylpyrazol-3-yl phosphate+TX, dilor+TX, dimefluthrin+TX, dimetan+TX, dimethrin+TX, dimethylvinphos+TX, dimetilan+TX, dinoprop+TX, dinosam+TX, dinoseb+TX, diofenolan+TX, dioxabenzofos+TX, dithicrofos+TX, DSP+TX, ecdysterone+TX, EI 1642+TX, EMPC+TX, EPBP+TX, etaphos+TX, ethiofencarb+TX, ethyl formate+TX, ethylene dibromide+TX, ethylene dichloride+TX, ethylene oxide+TX, EXD+TX, fenchlorphos+TX, fenethacarb+TX, fenitrothion+TX, fenoxacrim+TX, fenpirithrin+TX, fensulfothion+TX, fenthion-ethyl+TX, flucofuron+TX, fosmethilan+TX, fospirate+TX, fosthietan+TX, furathiocarb+TX, furethrin+TX, guazatine+TX, guazatine acetates+TX, sodium tetrathiocarbonate+TX, halfenprox+TX, HCH+TX, HEOD+TX, heptachlor+TX, heterophos+TX, HHDN+TX, hydrogen cyanide+TX, hyquincarb+TX, IPSP+TX, isazofos+TX, isobenzan+TX, isodrin+TX, isofenphos+TX, isolane+TX, isoprothiolane+TX, isoxathion+TX, juvenile hormone I+TX, juvenile hormone II+TX, juvenile hormone III+TX, kelevan+TX, kinoprene+TX, lead arsenate+TX, leptophos+TX, lirimfos+TX, lythidathion+TX, m-cumenyl methylcarbamate+TX, magnesium phosphide+TX, mazidox+TX, mecarphon+TX, menazon+TX, mercurous chloride+TX, mesulfenfos+TX, metam+TX, metam-potassium+TX, metam-sodium+TX, methanesulfonyl fluoride+TX, methocrotophos+TX, methoprene+TX, methothrin+TX, methoxychlor+TX, methyl isothiocyanate+TX, methylchloroform+TX, methylene chloride+TX, metoxadiazone+TX, mirex+TX, naftalofos+TX, naphthalene+TX, NC-170+TX, nicotine+TX, nicotine sulfate+TX, nithiazine+TX, nornicotine+TX, O-5-dichloro-4-iodophenyl O-ethyl ethylphosphonothioate+TX, O,O-diethyl O-4-methyl-2-oxo-2H-chromen-7-yl phosphorothioate+TX, O,O-diethyl O-6-methyl-2-propylpyrimidin-4-yl phosphorothioate+TX, O,O,O',O'-tetrapropyl dithiopyrophosphate+TX, oleic acid+TX, para-dichlorobenzene+TX, parathion-methyl+TX, pentachlorophenol+TX, pentachlorophenyl laurate+TX, PH 60-38+TX, phenkapton+TX, phosnichlor+TX, phosphine+TX, phoxim-methyl+TX, pirimetaphos+TX, polychlorodicyclopentadiene isomers+TX, potassium arsenite+TX, potassium thiocyanate+TX, precocene I+TX, precocene II+TX, precocene III+TX, primidophos+TX, profluthrin+TX, promecarb+TX, prothiofos+TX, pyrazophos+TX, pyresmethrin+TX, quassia+TX, quinalphos-methyl+TX, quinothion+TX, rafoxanide+TX, resmethrin+TX, rotenone+TX, kadethrin+TX, ryania+TX, ryanodine+TX, sabadilla)+TX, schradan+TX, sebufos+TX, SI-0009+TX, thiapronil+TX, sodium arsenite+TX, sodium cyanide+TX, sodium fluoride+TX, sodium hexafluorosilicate+TX, sodium pentachlorophenoxide+TX, sodium selenate+TX, sodium thiocyanate+TX, sulcofuron+TX, sulcofuron-sodium+TX, sulfuryl fluoride+TX, sulprofos+TX, tar oils+TX, tazimcarb+TX, TDE+TX, tebupirimfos+TX, temephos+TX, terallethrin+TX, tetrachloroethane+TX, thicrofos+TX, thiocyclam+TX, thiocyclam hydrogen oxalate+TX, thionazin+TX, thiosultap+TX, thiosultap-sodium+TX, tralomethrin+TX, transpermethrin+TX, triazamate+TX, trichlormetaphos-3+TX, trichloronat+TX, trimethacarb+TX, tolprocarb+TX, triclopyricarb+TX, triprene+TX, veratridine+TX, veratrine+TX, XMC+TX, zetamethrin+TX, zinc phosphide+TX, zolaprofos+TX, and meperfluthrin+TX, tetramethylfluthrin+TX, bis(tributyltin) oxide+TX, bromoacetamide+TX, ferric phosphate+TX, niclosamide-olamine+TX, tributyltin oxide+TX, pyrimorph+TX, trifenmorph+TX, 1,2-dibromo-3-chloropropane+TX, 1,3-dichloropropene+TX, 3,4-dichlorotetrahydrothiophene 1,1-dioxide+TX, 3-(4-chlorophenyl)-5-methylrhodanine+TX, 5-methyl-6-thioxo-1,3,5-thiadiazinan-3-ylacetic acid+TX, 6-isopentenylaminopurine+TX, 2-fluoro-N-(3-methoxyphenyl)-9H-purin-6-amine+TX, benclothiaz+TX, cytokinins+TX, DCIP+TX, furfural+TX, isamidofos+TX, kinetin+TX, *Myrothecium verrucaria* composition+TX, tetrachlorothiophene+TX, xylenols+TX, zeatin+TX, potassium ethylxanthate+TX, acibenzolar+TX, acibenzolar-S-methyl+TX, *Reynoutria sachalinensis* extract+TX, alpha-chlorohydrin+TX, antu+TX, barium carbonate+TX, bisthiosemi+TX, brodifacoum+TX, bromadiolone+TX, bromethalin+TX, chlorophacinone+TX, cholecalciferol+TX, coumachlor+TX, coumafuryl+TX, coumatetralyl+TX, crimidine+TX, difenacoum+TX, difethialone+TX, diphacinone+TX, ergocalciferol+TX, flocoumafen+TX, fluoroacetamide+TX, flupropadine+TX, flupropadine hydrochloride+TX, norbormide+TX, phosacetim+TX, phosphorus+TX, pindone+TX, pyrinuron+TX, scilliroside+TX, -sodium fluoroacetate+TX, thallium sulfate+TX, warfarin+TX, -2-(2-butoxyethoxy)ethyl piperonylate+TX, 5-(1,3-benzodioxol-5-yl)-3-hexylcyclohex-2-enone+TX, farnesol with nerolidol+TX, verbutin+TX, MGK 264+TX, piperonyl butoxide+TX, piprotal+TX, propyl isomer+TX, S421+TX, sesamex+TX, sesasmolin+TX, sulfoxide+TX, anthraquinone+TX, copper naphthenate+TX, copper oxychloride+TX, dicyclopentadiene+TX, thiram+TX, zinc naphthenate+TX, ziram+TX, imanin+TX, ribavirin+TX, mercuric oxide+TX, thiophanate-methyl+TX, azaconazole+TX, bitertanol+TX, bromuconazole+TX, cyproconazole+TX, difenoconazole+TX, diniconazole-+TX, epoxiconazole+TX, fenbuconazole+TX, fluquinconazole+TX, flusilazole+TX, flutriafol+TX, furametpyr+TX, hexaconazole+TX, imazalil-+TX, imiben-conazole+TX, ipconazole+TX, metconazole+TX, myclobutanil+TX, paclobutrazole+TX, pefurazoate+TX, penconazole+TX, prothioconazole+TX, pyrifenox+TX, prochloraz+TX, propiconazole+TX, pyrisoxazole+TX, -simeconazole+TX, tebucon-azole+TX, tetraconazole+TX, triadimefon+TX, triadimenol+TX, triflumizole+TX, triticonazole+TX, ancymidol+TX, fenarimol+TX, nuarimol+TX, bupirimate+TX, dimethirimol+TX, ethirimol+TX, dodemorph+TX, fenpropidine+TX, fenpropimorph+TX, spiroxamine+TX, tridemorph+TX, cyprodinil+TX, mepanipyrim+TX, pyrimethanil+TX, fenpiclonil+TX, fludioxonil+TX, benalaxyl+TX, furalaxyl+TX, -metalaxyl-+TX, Rmetalaxyl+TX, ofurace+TX, oxadixyl+TX, carbendazim+TX, debacarb+TX, fuberidazole-+TX, thiabendazole+TX, chlozolinate+TX, dichlozoline+TX, myclozoline-+TX, procymidone+TX, vinclozoline+TX, boscalid+TX, carboxin+TX, fenfuram+TX, flutolanil+TX, mepronil+TX, oxycarboxin+TX, penthiopyrad+TX, thifluzamide+TX, dodine+TX, iminoctadine+TX, azoxystrobin+TX, dimoxystrobin+TX, enestroburin+TX, fenaminstrobin+TX, flufenoxystrobin+TX, fluoxastrobin+TX, kresoxim-methyl+TX, metominostrobin+TX, trifloxystrobin+TX, orysastrobin+TX, picoxystrobin+TX, pyraclostrobin+TX, pyrametostrobin+TX, pyraoxystrobin+TX, ferbam+TX, mancozeb+TX, maneb+TX, metiram+TX, propineb+TX, zineb+TX, captafol+TX, captan+TX, fluoroimide+TX, folpet+TX, tolylfluanid+TX, bordeaux mixture+TX, copper oxide+TX, mancopper+TX, oxine-copper+TX, nitrothal-isopropyl+TX, edifenphos+TX, iprobenphos+TX, phosdiphen+TX, tolclofos-methyl+TX, anilazine+TX, benthiavalicarb+TX, blasticidin-S+TX, chloroneb-+TX, chloro-thalonil+TX, cyflufenamid+TX, cymoxanil+TX, cyclobutrifluram+TX, diclocymet+TX, diclomezine-+TX, dicloran+TX, diethofencarb+TX, dimethomorph-+TX, flumorph+TX, dithianon+TX, ethaboxam+TX, etridiazole+TX, famoxadone+TX, fenamidone+TX, fenoxanil+TX, ferimzone+TX, fluazinam+TX, fluopicolide+TX, flusulfamide+TX, fluxapyroxad+TX, -fenhexamid+TX, fosetyl-aluminium-+TX, hymexazol+TX, iprovalicarb+TX, cyazofamid+TX, methasulfocarb+TX, metrafenone+TX, pencycuron+TX, phthalide+TX, polyoxins+TX, propamocarb+TX, pyribencarb+TX, proquinazid+TX, pyroquilon+TX, pyriofenone+TX, quinoxyfen+TX, quintozene+TX, tiadinil+TX, triazoxide+TX, tricyclazole+TX, triforine+TX, validamycin+TX, valifenalate+TX, zoxamide+TX, mandipropamid+TX, flubeneteram+TX, isopyrazam+TX, sedaxane+TX, benzovindiflupyr+TX, pydiflumetofen+TX, 3-difluoromethyl-1-methyl-1H-pyrazole-4-carboxylic acid (3',4',5'-trifluoro-biphenyl-2-yl)-amide+TX, isoflucypram+TX, isotianil+TX, dipymetitrone+TX, 6-ethyl-5,7-dioxo-pyrrolo[4,5][1,4]dithiino[1,2-c]isothiazole-3-carbonitrile+TX, 2-(difluoromethyl)-N-[3-ethyl-1,1-dimethyl-indan-4-yl]pyridine-3-carboxamide+TX, 4-(2,6-difluorophenyl)-6-methyl-5-phenyl-pyridazine-3-carbonitrile+TX, (R)-3-(difluoromethyl)-1-methyl-N-[1,1,3-trimethylindan-4-yl]pyrazole-4-carboxamide+TX, 4-(2-bromo-4-fluoro-phenyl)-N-(2-chloro-6-fluoro-phenyl)-2,5-dimethyl-pyrazol-3-amine+TX, 4-(2-bromo-4-fluorophenyl)-N-(2-chloro-6-fluorophenyl)-1,3-dimethyl-1H-pyrazol-5-amine+TX, fluindapyr+TX, coumethoxystrobin (jiaxiangjunzhi)+TX, Ivbenmixianan+TX, dichlobentiazox+TX, mandestrobin+TX, 3-(4,4-difluoro-3,4-dihydro-3,3-dimethylisoquinolin-1-yl)quinolone+TX, 2-[2-fluoro-6-[(8-fluoro-2-methyl-3-quinolyl)oxy]phenyl]propan-2-ol+TX, oxathiapiprolin+TX, tert-butyl N-[6-[[[(1-methyltetrazol-5-yl)-phenyl-methylene]amino]oxymethyl]-2-pyridyl]carbamate+TX, pyraziflumid+TX, inpyrfluxam+TX, trolprocarb+TX, mefentrifluconazole+TX, ipfentrifluconazole+TX, 2-(difluoromethyl)-N-[(3R)-3-ethyl-1,1-dimethyl-indan-4-yl]pyridine-3-carboxamide+TX, N'-(2,5-dimethyl-4-phenoxy-phenyl)-N-ethyl-N-methyl-formamidine+TX, N'-[4-(4,5-dichlorothiazol-2-yl)oxy-2,5-dimethyl-phenyl]-N-ethyl-N-methyl-formamidine+TX, [2-[3-[2-[1-[2-[3,5-bis(difluoromethyl)pyrazol-1-yl]acetyl]-4-piperidyl]thiazol-4-yl]-4,5-dihydroisoxazol-5-yl]-3-chloro-phenyl] methanesulfonate+TX, but-3-ynyl N-[6-[[(Z)-[(1-methyltetrazol-5-yl)-phenyl-methylene]amino]oxymethyl]-2-pyridyl]carbamate+TX, methyl N-[[5-[4-(2,4-dimethylphenyl)triazol-2-yl]-2-methyl-phenyl]methyl]carbamate+TX, 3-chloro-6-methyl-5-phenyl-4-(2,4,6-trifluorophenyl)pyridazine+TX, pyridachlometyl+TX, 3-(difluoromethyl)-1-methyl-N-[1,1,3-trimethylindan-4-yl]pyrazole-4-carboxamide+TX, 1-[2-[[1-(4-chlorophenyl)pyrazol-3-yl]oxymethyl]-3-methyl-phenyl]-4-methyl-tetrazol-5-one+TX, 1-methyl-4-[3-methyl-2-[[2-methyl-4-(3,4,5-trimethylpyrazol-1-yl)phenoxy]methyl]phenyl]tetrazol-5-one+TX, aminopyrifen+TX, ametoctradin+TX, amisulbrom+TX, penflufen+TX, (Z,2E)-5-[1-(4-chlorophenyl)pyrazol-3-yl]oxy-2-methoxyimino-N,3-dimethyl-pent-3-enamide+TX, florylpicoxamid+TX, fenpicoxamid+TX, tebufloquin+TX, ipflufenoquin+TX, quinofumelin+TX, isofetamid+TX, N-[2-[2,4-dichloro-phenoxy]phenyl]-3-(difluoromethyl)-1-methyl-pyrazole-4-carboxamide+TX, N-[2-[2-chloro-4-(trifluoromethyl)phenoxy]phenyl]-3-(difluoromethyl)-1-methyl-pyrazole-4-carboxamide+TX, benzothiostrobin+TX, phenamacril+TX, 5-amino-1,3,4-thiadiazole-2-thiol zinc salt (2:1)+TX, fluopyram+TX, flutianil+TX, fluopimomide+TX, pyrapropoyne+TX, picarbutrazox+TX, 2-(difluoromethyl)-N-(3-ethyl-1,1-dimethyl-indan-4-yl)pyridine-3-carboxamide+TX, 2-(difluoromethyl)-N-((3R)-1, 1, 3-trimethylindan-4-yl) pyridine-3-carboxamide+TX, 4-[[6-[2-(2,4-difluorophenyl)-1,1-difluoro-2-hydroxy-3-(1,2,4-triazol-1-yl)propyl]-3-pyridyl]oxy]benzonitrile+TX, metyltetraprole+TX, 2-(difluoromethyl)-N-((3R)-1, 1, 3-trimethylindan-4-yl) pyridine-3-carboxamide+TX, α-(1, 1-dinethylethyl)-α-[4'-(trifluoromethoxy) [1, 1'-biphenyl]-4-yl]-5-pyrimidinemethanol+TX, fluoxapiprolin+TX, enoxastrobin+TX, 4-[[6-[2-(2,4-difluorophenyl)-1,1-difluoro-2-hydroxy-3-(1,2,4-triazol-1-yl)propyl]-3-pyridyl]oxy] benzonitrile+TX, 4-[[6-[2-(2,4-difluorophenyl)-1,1-difluoro-2-hydroxy-3-(5-sulfanyl-1,2,4-triazol-1-yl)propyl]-3-pyridyl]oxy] benzonitrile+TX, 4-[[6-[2-(2,4-difluorophenyl)-1,1-difluoro-2-hydroxy-3-(5-thioxo-4H-1,2,4-triazol-1-yl) propyl]-3-pyridyl]oxy]benzonitrile+TX, trinexapac+TX, coumoxystrobin+TX, zhongshengmycin+TX, thiodiazole copper+TX, zinc thiazole+TX, amectotractin+TX, iprodione+TX; N'-[5-bromo-2-methyl-6-[(1S)-1-methyl-2-propoxy-ethoxy]-3-pyridyl]-N-ethyl-N-methyl-formamidine+TX, N'-[5-bromo-2-methyl-6-[(1R)-1-methyl-2-propoxy-ethoxy]-3-pyridyl]-N-ethyl-N-methyl-formamidine+TX, N'-[5-bromo-2-methyl-6-(1-methyl-2-propoxy-ethoxy)-3-pyridyl]-N-ethyl-N-methyl-formamidine+TX, N'-[5-chloro-2-methyl-6-(1-methyl-2-propoxy-ethoxy)-3-pyridyl]-N-ethyl-N-methyl-formamidine+TX, N'-[5-bromo-2-methyl-6-(1-methyl-2-propoxy-ethoxy)-3-pyridyl]-N-isopropyl-N-methyl-formamidine+TX (these compounds may be prepared from the methods described in WO2015/155075); N'-[5-bromo-2-methyl-6-(2-propoxypropoxy)-3-pyridyl]-N-ethyl-N-methyl-formamidine+TX (this compound may be prepared from the methods described in IPCOM000249876D); N-isopropyl-N'-[5-methoxy-2-methyl-4-(2,2,2-trifluoro-1-hydroxy-1-phenyl-ethyl)phenyl]-N-methyl-formamidine+TX, N'-[4-(1-cyclopropyl-2,2,2-trifluoro-1-hydroxy-ethyl)-5-methoxy-2-methyl-phenyl]-N-isopropyl-N-methyl-formamidine+TX (these compounds may be prepared from the methods described in WO2018/228896); N-ethyl-N'-[5-methoxy-2-methyl-4-[2-trifluoromethyl)oxetan-2-yl]phenyl]-N-methyl-formamidine+TX, N-ethyl-N'-[5-methoxy-2-methyl-4-[2-trifuoromethyl)tetrahydrofuran-2-yl]phenyl]-N-methyl-formamidine+TX (these compounds may be prepared from the methods described in WO2019/110427); N-[(1R)-1-benzyl-3-chloro-1-methyl-but-3-enyl]-8-fluoro-quinoline-3-carboxamide+TX, N-[(1S)-1-benzyl-3,3,3-trifluoro-1-methyl-propyl]-8-fluoro-quinoline-3-carboxamide+TX, N-[(1S)-1-benzyl-1,3-dimethyl-butyl]-7,8-difluoro-quinoline-3-carboxamide+TX, 8-fluoro-N-[1-[(3-fluorophenyl)methyl]-1,3-dimethyl-butyl]quinoline-3-carboxamide+TX, N-(1-benzyl-1,3-dimethyl-butyl)-8-fluoro-quinoline-3-carboxamide+TX, N-[(1R)-1-benzyl-1,3-dimethyl-butyl]-8-fluoro-quinoline-3-carboxamide+TX, N-[(1S)-1-benzyl-1,3-dimethyl-butyl]-8-fluoro-quinoline-3-carboxamide+TX, N-(1-benzyl-3-chloro-1-methyl-but-3-enyl)-8-fluoro-quinoline-3-carboxamide+TX (these compounds may be prepared from the methods described in WO2017/153380); 1-(6,7-dimethylpyrazolo[1,5-a]pyridin-3-yl)-4,4,5-trifluoro-3,3-dimethyl-isoquinoline+TX, 1-(6,7-dimethylpyrazolo[1,5-a]pyridin-3-yl)-4,4,6-trifluoro-3,3-dimethyl-isoquinoline+TX, 4,4-difluoro-3,3-dimethyl-1-(6-methylpyrazolo[1,5-a]pyridin-3-yl)isoquinoline+TX, 4,4-difluoro-3,3-dimethyl-1-(7-methylpyrazolo[1,5-a]pyridin-3-yl)isoquinoline+TX, 1-(6-chloro-7-methyl-pyrazolo[1,5-a]pyridin-3-yl)-4,4-difluoro-3,3-dimethyl-isoquinoline+TX (these compounds may be prepared from the methods described in WO2017/025510); 1-(4,5-dimethylbenzimidazol-1-yl)-4,4,5-trifluoro-3,3-dimethyl-isoquinoline+TX, 1-(4,5-dimethylbenzimidazol-1-yl)-4,4-difluoro-3,3-dimethyl-isoquinoline+TX, 6-chloro-4,4-difluoro-3,3-dimethyl-1-(4-methylbenzimidazol-1-yl)isoquinoline+TX, 4,4-difluoro-1-(5-fluoro-4-methyl-benzimidazol-1-yl)-3,3-dimethyl-isoquinoline+TX, 3-(4,4-difluoro-3,3-dimethyl-1-isoquinolyl)-7,8-dihydro-6H-cyclopenta[e]benzimidazole+TX (these compounds may be prepared from the methods described in WO2016/156085); N-methoxy-N-[[4-[5-(trifluoromethyl)-1,2,4-oxadiazol-3-yl]phenyl]methyl]cyclopropanecarboxamide+TX, N,2-dimethoxy-N-[[4-[5-(trifluoromethyl)-1,2,4-oxadiazol-3-yl]phenyl]methyl]propanamide+TX, N-ethyl-2-methyl-N-[[4-[5-(trifluoromethyl)-1,2,4-oxadiazol-3-yl]phenyl]methyl]propanamide+TX, 1-methoxy-3-methyl-1-[[4-[5-(trifluoromethyl)-1,2,4-oxadiazol-3-yl]phenyl]methyl]urea+TX, 1,3-dimethoxy-1-[[4-[5-(trifluoromethyl)-1,2,4-oxadiazol-3-yl]phenyl]methyl]urea+TX, 3-ethyl-1-methoxy-1-[[4-[5-(trifluoromethyl)-1,2,4-oxadiazol-3-yl]phenyl]methyl]urea+TX, N-[[4-[5-(trifluoromethyl)-1,2,4-oxadiazol-3-yl]phenyl]methyl]propanamide+TX, 4,4-dimethyl-2-[[4-[5-(trifluoromethyl)-1,2,4-oxadiazol-3-yl]phenyl]methyl]isoxazolidin-3-one+TX, 5,5-dimethyl-2-[[4-[5-(trifluoromethyl)-1,2,4-oxadiazol-3-yl]phenyl]methyl]isoxazolidin-3-one+TX, ethyl 1-[[4-[5-(trifluoromethyl)-1,2,4-oxadiazol-3-yl]phenyl]methyl]pyrazole-4-carboxylate+TX, N,N-dimethyl-1-[[4-[5-(trifluoromethyl)-1,2,4-oxadiazol-3-yl]phenyl]methyl]-1,2,4-triazol-3-amine+TX. The compounds in this paragraph may be prepared from the methods described in WO 2017/055473, WO 2017/055469, WO 2017/093348 and WO 2017/118689; 2-[6-(4-chlorophenoxy)-2-(trifluoromethyl)-3-pyridyl]-1-(1,2,4-triazol-1-yl)propan-2-ol+TX (this compound may be prepared from the methods described in WO 2017/029179); 2-[6-(4-bromophenoxy)-2-(trifluoromethyl)-3-pyridyl]-1-(1,2,4-triazol-1-yl)propan-2-ol+TX (this compound may be prepared from the methods described in WO 2017/029179); 3-[2-(1-chlorocyclopropyl)-3-(2-fluorophenyl)-2-hydroxy-propyl]imidazole-4-carbonitrile+TX (this compound may be prepared from the methods described in WO 2016/156290); 3-[2-(1-chlorocyclopropyl)-3-(3-chloro-2-fluoro-phenyl)-2-hydroxy-propyl]imidazole-4-carbonitrile+TX (this compound may be prepared from the methods described in WO 2016/156290); (4-phenoxyphenyl)methyl 2-amino-6-methyl-pyridine-3-carboxylate+TX (this compound may be prepared from the methods described in WO 2014/006945); 2,6-Dimethyl-1H,5H-[1,4]dithiino[2,3-c:5,6-c']dipyrrole-1,3,5,7(2H,6H)-tetrone+TX (this compound may be prepared from the methods described in WO 2011/138281); N-methyl-4-[5-(trifluoromethyl)-1,2,4-oxadiazol-3-yl]benzenecarbothioamide+TX; N-methyl-4-[5-(trifluoromethyl)-1,2,4-oxadiazol-3-yl]benzamide+TX; (Z,2E)-5-[1-(2,4-dichlorophenyl)pyrazol-3-yl]oxy-2-methoxyimino-N,3-dimethyl-pent-3-enamide+TX (this compound may be prepared from the methods described in WO 2018/153707); N'-(2-chloro-5-methyl-4-phenoxy-phenyl)-N-ethyl-N-methyl-formamidine+TX; N'-[2-chloro-4-(2-fluorophenoxy)-5-methyl-phenyl]-N-ethyl-N-methyl-formamidine+TX (this compound may be prepared from the methods described in WO 2016/202742); 2-(difluoromethyl)-N-[(3S)-3-ethyl-1,1-dimethyl-indan-4-yl]pyridine-3-carboxamide+TX (this compound may be prepared from the methods described in WO 2014/095675); (5-methyl-2-pyridyl)-[4-[5-(trifluoromethyl)-1,2,4-oxadiazol-3-yl]phenyl]methanone+TX, (3-methylisoxazol-5-yl)-[4-[5-(trifluoromethyl)-1,2,4-oxadiazol-3-yl]phenyl]methanone+TX (these compounds may be prepared from the methods described in WO 2017/220485); 2-oxo-N-propyl-2-[4-[5-(trifluoromethyl)-1,2,4-oxadiazol-3-yl]phenyl]acetamide+TX (this compound may be prepared from the methods described in WO 2018/065414); ethyl 1-[[5-[5-(trifluoromethyl)-1,2,4-oxadiazol-3-yl]-2-thienyl]methyl]pyrazole-4-carboxylate+TX (this compound may be prepared from the methods described in WO 2018/158365); 2,2-difluoro-N-methyl-2-[4-[5-(trifluoromethyl)-1,2,4-oxadiazol-3-yl]phenyl]acetamide+TX, N-[(E)-methoxyiminomethyl]-4-[5-(trifluoromethyl)-1,2,4-oxadiazol-3-yl]benzamide+TX, N—[(Z)-methoxyiminomethyl]-4-[5-(trifluoromethyl)-1,2,4-oxadiazol-3-yl]benzamide+TX, N—[N-methoxy-C-methyl-carbonimidoyl]-4-[5-(trifluoromethyl)-1,2,4-oxadiazol-3-yl]benzamide+TX (these compounds may be prepared from the methods described in WO 2018/202428);

microbials including: *Acinetobacter lwoffii*+TX, *Acremonium alternatum*+TX+TX, *Acremonium cephalosporium*+TX+TX, *Acremonium diospyri*+TX, *Acremonium obclavatum*+TX, *Adoxophyes orana* granulovirus (AdoxGV) (Capex®)+TX, *Agrobacterium radiobacter* strain K84 (Galltrol-A®)+TX, *Alternaria* alternate+TX, *Alternaria cassia*+TX, *Alternaria destruens* (Smolder®)+TX, *Ampelomyces quisqualis* (AQ10®)+TX, *Aspergillus flavus* AF36 (AF36®)+TX, *Aspergillus flavus* NRRL 21882 (Aflaguard®)+TX, *Aspergillus* spp.+TX, *Aureobasidium pullulans*+TX, *Azospirillum*+TX, (MicroAZ®+TX, TAZO B®)+TX, *Azotobacter*+TX, *Azotobacter chroocuccum* (Azotomeal®)+TX, *Azotobacter* cysts (Bionatural Blooming Blossoms®)+TX, *Bacillus amyloliquefaciens*+TX, *Bacillus cereus*+TX, *Bacillus* chitinosporus strain CM-1+TX, *Bacillus chitinosporus* strain AQ746+TX, *Bacillus licheniformis* strain HB-2 (Biostart™ Rhizoboost®)+TX, *Bacillus licheniformis* strain 3086 (EcoGuard®+TX, Green Releaf®)+TX, *Bacillus circulans*+TX, *Bacillus firmus* (BioSafe®+TX, BioNem-WP®+TX, VOTiVO®)+TX, *Bacillus firmus* strain 1-1582+TX, *Bacillus macerans*+TX, *Bacillus marismortui*+TX, *Bacillus megaterium*+TX, *Bacillus mycoides* strain AQ726+TX, *Bacillus* papillae (Milky Spore Powder®)+TX, *Bacillus pumilus* spp.+TX, *Bacillus pumilus* strain GB34 (Yield Shield®)+TX, *Bacillus pumilus* strain AQ717+TX, *Bacillus pumilus* strain QST 2808 (Sonata®+TX, Ballad Plus®)+TX, *Bacillus spahericus* (VectoLex®)+TX, *Bacillus* spp.+TX, *Bacillus* spp. strain AQ175+TX, *Bacillus* spp. strain AQ177+TX, *Bacillus* spp. strain AQ178+TX, *Bacillus subtilis* strain QST 713 (CEASE®+TX, Serenade®+TX, Rhapsody®)+TX, *Bacillus subtilis* strain QST 714 (JAZZ®)+TX, *Bacillus subtilis* strain AQ153+TX, *Bacillus subtilis* strain AQ743+TX, *Bacillus subtilis* strain QST3002+TX, *Bacillus subtilis* strain QST3004+TX, *Bacillus subtilis* var. *amyloliquefaciens* strain FZB24 (Taegro®+TX, Rhizopro®)+TX, *Bacillus thuringiensis* Cry 2Ae+TX, *Bacillus thuringiensis* Cry1Ab+TX, *Bacillus thuringiensis aizawai* GC 91 (Agree®)+TX, *Bacillus thuringiensis israelensis* (BMP123®+TX, Aquabac®+TX, VectoBac®)+TX, *Bacillus thuringiensis* kurstaki (Javelin®+TX, Deliver®+TX, CryMax®+TX, Bonide®+TX, Scutella WP®+TX, Turilav WP®+TX, Astuto®+TX, Dipel WP®+TX, Biobit®+TX, Foray®)+TX, *Bacillus thuringiensis* kurstaki BMP 123 (Baritone®)+TX, *Bacillus thuringiensis* kurstaki HD-1 (Bioprotec-CAF/3P®)+TX, *Bacillus thuringiensis* strain BD #32+TX, *Bacillus thuringiensis* strain AQ52+TX, *Bacillus thuringiensis* var. *aizawai* (XenTari®+TX, DiPel®)+TX, bacteria spp. (GROWMEND®+TX, GROWSWEET®+TX, Shootup®)+TX, bacteriophage of *Clavipacter michiganensis* (AgriPhage®)+TX, Bakflor®+TX, *Beauveria bassiana* (Beaugenic®+TX, Brocaril WP®)+TX, *Beauveria bassiana* GHA (Mycotrol ES®+TX, Mycotrol O®+TX, BotaniGuard®)+TX, *Beauveria brongniartii* (Engerlingspilz®+TX, Schweizer Beauveria®+TX, Melocont®)+TX, *Beauveria* spp.+TX, *Botrytis cineria*+TX, *Bradyrhizobium japonicum* (TerraMax®)+TX, *Brevibacillus brevis*+TX, *Bacillus thuringiensis tenebrionis* (Novodor®)+TX, BtBooster+TX, *Burkholderia cepacia* (Deny®+TX, Intercept®+TX, Blue Circle®)+TX, *Burkholderia gladii*+TX, *Burkholderia gladioli*+TX, *Burkholderia* spp.+TX, Canadian thistle fungus (CBH Canadian Bioherbicide®)+TX, *Candida butyri*+TX, *Candida famata*+TX, *Candida* fructus+TX, *Candida glabrata*+TX, *Candida guilliermondii*+TX, *Candida melibiosica*+TX, *Candida oleophila* strain O+TX, *Candida parapsilosis*+TX, *Candida pelliculosa*+TX, *Candida pulcherrima*+TX, *Candida reukaufii*+TX, *Candida saitoana* (Bio-Coat®+TX, Biocure®)+TX, *Candida sake*+TX, *Candida* spp.+TX, *Candida tenius*+TX, *Cedecea dravisae*+TX, *Cellulomonas flavigena*+TX, *Chaetomium cochliodes* (Nova-Cide®)+TX, *Chaetomium globosum* (Nova-Cide®)+TX, *Chromobacterium subtsugae* strain PRAA4-1T (Grandevo®)+TX, *Cla-*

*dosporium cladosporioides*+TX, *Cladosporium oxysporum*+TX, *Cladosporium chlorocephalum*+TX, *Cladosporium* spp.+TX, *Cladosporium tenuissimum*+TX, *Clonostachys rosea* (EndoFine®)+TX, *Colletotrichum acutatum*+TX, *Coniothyrium minitans* (Cotans WG®)+TX, *Coniothyrium* spp.+TX, *Cryptococcus albidus* (YIELDPLUS®)+TX, *Cryptococcus humicola*+TX, *Cryptococcus infirmo-miniatus*+TX, *Cryptococcus laurentii*+TX, *Cryptophlebia leucotreta* granulovirus (Cryptex®)+TX, *Cupriavidus campinensis*+TX, *Cydia pomonella* granulovirus (CYD-X®)+TX, *Cydia pomonella* granulovirus (Madex®+TX, Madex Plus®+TX, Madex Max/Carpovirusine®)+TX, Cylindrobasidium laeve (Stumpout®)+TX, *Cylindrocladium*+TX, *Debaryomyces hansenii*+TX, *Drechslera hawaiinensis*+TX, *Enterobacter cloacae*+TX, Enterobacteriaceae+TX, *Entomophtora virulenta* (Vektor®)+TX, *Epicoccum nigrum*+TX, *Epicoccum purpurascens*+TX, *Epicoccum* spp.+TX, *Filobasidium floriforme*+TX, *Fusarium acuminatum*+TX, *Fusarium chlamydosporum*+TX, *Fusarium oxysporum* (Fusaclean®/Biofox C®)+TX, *Fusarium proliferatum*+TX, *Fusarium* spp.+TX, *Galactomyces geotrichum*+TX, *Gliocladium catenulatum* (Primastop®+TX, Prestop®)+TX, *Gliocladium roseum*+TX, *Gliocladium* spp. (SoilGard®)+TX, *Gliocladium virens* (Soilgard®)+TX, Granulovirus (Granupom®)+TX, *Halobacillus halophilus*+TX, *Halobacillus litoralis*+TX, *Halobacillus trueperi*+TX, *Halomonas* spp.+TX, *Halomonas subglaciescola*+TX, *Halovibrio variabilis*+TX, *Hanseniaspora uvarum*+TX, *Helicoverpa armigera* nucleopolyhedrovirus (Helicovex®)+TX, *Helicoverpa zea* nuclear polyhedrosis virus (Gemstar®)+TX, Isoflavone-formononetin (Myconate®)+TX, *Kloeckera apiculata*+TX, *Kloeckera* spp.+TX, *Lagenidium giganteum* (Laginex®)+TX, *Lecanicillium longisporum* (Vertiblast®)+TX, *Lecanicillium muscarium* (Vertikil®)+TX, *Lymantria Dispar* nucleopolyhedrosis virus (Disparvirus®)+TX, *Marinococcus halophilus*+TX, *Meira geulakonigii*+TX, *Metarhizium anisopliae* (Met52®)+TX, *Metarhizium anisopliae* (Destruxin WP®)+TX, *Metschnikowia fruticola* (Shemer®)+TX, *Metschnikowia pulcherrima*+TX, Microdochium *dimerum* (Antibot®)+TX, *Micromonospora coerulea*+TX, *Microsphaeropsis ochracea*+TX, *Muscodor albus* 620 (Muscudor®)+TX, *Muscodor roseus* strain A3-5+TX, *Mycorrhizae* spp. (AMykor®+TX, Root Maximizer®)+TX, *Myrothecium verrucaria* strain AARC-0255 (DiTera®)+TX, BROS PLUS®+TX, *Ophiostoma piliferum* strain D97 (Sylvanex®)+TX, *Paecilomyces farinosus*+TX, *Paecilomyces fumosoroseus* (PFR-97®+TX, PreFeRal®)+TX, *Paecilomyces linacinus* (Biostat WP®)+TX, *Paecilomyces lilacinus* strain 251 (MeloCon WG®)+TX, *Paenibacillus polymyxa*+TX, *Pantoea agglomerans* (BlightBan C9-1®)+TX, *Pantoea* spp.+TX, *Pasteuria* spp. (Econem®)+TX, *Pasteuria nishizawae*+TX, *Penicillium aurantiogriseum*+TX, *Penicillium billai* (Jumpstart®+TX, TagTeam®)+TX, *Penicillium brevicompactum*+TX, *Penicillium frequentans*+TX, *Penicillium griseofulvum*+TX, *Penicillium purpurogenum*+TX, *Penicillium* spp.+TX, *Penicillium viridicatum*+TX, *Phlebiopsis gigantean* (Rotstop®)+TX, phosphate solubilizing bacteria (Phosphomeal®)+TX, *Phytophthora cryptogea*+TX, *Phytophthora palmivora* (Devine®)+TX, *Pichia anomala*+TX, *Pichia guilermondii*+TX, *Pichia membranaefaciens*+TX, *Pichia onychis*+TX, *Pichia stipites*+TX, *Pseudomonas aeruginosa*+TX, *Pseudomonas aureofasciens* (Spot-Less Biofungicide®)+TX, *Pseudomonas cepacia*+TX, *Pseudomonas chlororaphis* (AtEze®)+TX, *Pseudomonas* corrugate+TX, *Pseudomonas fluorescens* strain A506 (BlightBan A506®)+TX, *Pseudomonas putida*+TX, *Pseudomonas* reactans+TX, *Pseudomonas* spp.+TX, *Pseudomonas syringae* (Bio-Save®)+TX, *Pseudomonas viridiflava*+TX, *Pseudomonas fluorescens* (Zequanox®)+TX, *Pseudozyma flocculosa* strain PF-A22 UL (Sporodex L®)+TX, *Puccinia canaliculata*+TX, *Puccinia thlaspeos* (Wood Warrior®)+TX, *Pythium paroecandrum*+TX, *Pythium oligandrum* (Polygandron®+TX, Polyversum®)+TX, *Pythium periplocum*+TX, *Rahnella aquatilis*+TX, *Rahnella* spp.+TX, *Rhizobia* (Dormal®+TX, Vault®)+TX, *Rhizoctonia*+TX, *Rhodococcus globerulus* strain AQ719+TX, *Rhodosporidium diobovatum*+TX, *Rhodosporidium toruloides*+TX, *Rhodotorula* spp.+TX, *Rhodotorula glutinis*+TX, *Rhodotorula graminis*+TX, *Rhodotorula mucilagnosa*+TX, *Rhodotorula rubra*+TX, *Saccharomyces cerevisiae*+TX, *Salinococcus roseus*+TX, *Sclerotinia minor*+TX, *Sclerotinia minor* (SARRITOR®)+TX, *Scytalidium* spp.+TX, *Scytalidium uredinicola*+TX, *Spodoptera exigua* nuclear polyhedrosis virus (Spod-X®+TX, Spexit®)+TX, *Serratia marcescens*+TX, *Serratia plymuthica*+TX, *Serratia* spp.+TX, *Sordaria fimicola*+TX, *Spodoptera littoralis* nucleopolyhedrovirus (Littovir®)+TX, *Sporobolomyces roseus*+TX, *Stenotrophomonas maltophilia*+TX, *Streptomyces ahygroscopicus*+TX, *Streptomyces albaduncus*+TX, *Streptomyces exfoliates*+TX, *Streptomyces galbus*+TX, *Streptomyces griseoplanus*+TX, *Streptomyces griseoviridis* (Mycostop®)+TX, *Streptomyces lydicus* (Actinovate®)+TX, *Streptomyces lydicus* WYEC-108 (ActinoGrow®)+TX, *Streptomyces violaceus*+TX, *Tilletiopsis minor*+TX, *Tilletiopsis* spp.+TX, *Trichoderma asperellum* (T34 Biocontrol®)+TX, *Trichoderma gamsii* (Tenet®)+TX, *Trichoderma atroviride* (Plantmate®)+TX, *Trichoderma hamatum* TH 382+TX, *Trichoderma harzianum* rifai (Mycostar®)+TX, *Trichoderma harzianum* T-22 (Trianum-P®+TX, PlantShield HCO+TX, RootShield®+TX, Trianum-G®)+TX, *Trichoderma harzianum* T-39 (Trichodex®)+TX, *Trichoderma inhamatum*+TX, *Trichoderma koningii*+TX, *Trichoderma* spp. LC 52 (Sentinel®)+TX, *Trichoderma lignorum*+TX, *Trichoderma longibrachiatum*+TX, *Trichoderma polysporum* (Binab T®)+TX, *Trichoderma taxi*+TX, *Trichoderma virens*+TX, *Trichoderma virens* (formerly *Gliocladium virens* GL-21) (SoilGuard®)+TX, *Trichoderma viride*+TX, *Trichoderma viride* strain ICC 080 (Remedier®)+TX, *Trichosporon pullulans*+TX, *Trichosporon* spp.+TX, *Trichothecium* spp.+TX, *Trichothecium roseum*+TX, *Typhula phacorrhiza* strain 94670+TX, *Typhula phacorrhiza* strain 94671+TX, *Ulocladium atrum*+TX, *Ulocladium oudemansii* (Botry-Zen®)+TX, *Ustilago maydis*+TX, various bacteria and supplementary micronutrients (Natural II®)+TX, various fungi (Millennium Microbes®)+TX, *Verticillium chlamydosporium*+TX, *Verticillium lecanii* (Mycotal®+TX, Vertalec®)+TX, Vip3Aa20 (VIPtera®)+TX, Virgibaclillus *marismortui*+TX, *Xanthomonas campestris* pv. *Poae* (Camperico®)+TX, *Xenorhabdus bovienii*+TX, *Xenorhabdus nematophilus;*

Plant extracts including: pine oil (Retenol®)+TX, azadirachtin (Plasma Neem Oil®+TX, AzaGuard®+

TX, MeemAzal®+TX, Molt-X®+TX, Botanical IGR (Neemazad®+TX, Neemix®)+TX, canola oil (Lilly Miller Vegol®)+TX, *Chenopodium ambrosioides* near *ambrosioides* (Requiem®)+TX, *Chrysanthemum* extract (Crisant®)+TX, extract of neem oil (Trilogy®)+TX, essentials oils of *Labiatae* (Botania®)+TX, extracts of clove rosemary peppermint and thyme oil (Garden insect Killer®)+TX, Glycinebetaine (Greenstim®)+TX, garlic+TX, lemongrass oil (GreenMatch®)+TX, neem oil+TX, *Nepeta cataria* (Catnip oil)+TX, *Nepeta catarina*+TX, nicotine+TX, oregano oil (MossBuster®)+TX, Pedaliaceae oil (Nematon®)+TX, pyrethrum+TX, *Quillaja saponaria* (NemaQ®)+TX, *Reynoutria sachalinensis* (Regalia®+TX, Sakalia®)+TX, rotenone (Eco Roten®)+TX, *Rutaceae* plant extract (Soleo®)+TX, soybean oil (Ortho Ecosense®)+TX, tea tree oil (Timorex Gold®)+TX, thymus oil+TX, AGNIQUE® MMF+TX, BugOil®+TX, mixture of rosemary sesame pepermint thyme and cinnamon extracts (EF 300®)+TX, mixture of clove rosemary and peppermint extract (EF 400®)+TX, mixture of clove pepermint garlic oil and mint (Soil Shot®)+TX, kaolin (Screen®)+TX, storage glucam of brown algae (Laminarin®);

pheromones including: blackheaded fireworm pheromone (3M Sprayable Blackheaded Fireworm Pheromone®)+TX, Codling Moth Pheromone (Paramount dispenser-(CM)/Isomate C-Plus®)+TX, Grape Berry Moth Pheromone (3M MEC-GBM Sprayable Pheromone®)+TX, Leafroller pheromone (3M MEC-LR Sprayable Pheromone®)+TX, Muscamone (Snip7 Fly Bait®+TX, Starbar Premium Fly Bait®)+TX, Oriental Fruit Moth Pheromone (3M oriental fruit moth sprayable Pheromone®)+TX, Peachtree Borer Pheromone (Isomate-P®)+TX, Tomato Pinworm Pheromone (3M Sprayable Pheromone®)+TX, Entostat powder (extract from palm tree) (Exosex CM®)+TX, (E+TX,Z+TX,Z)-3+TX,8+TX,11 Tetradecatrienyl acetate+TX, (Z+TX,Z+TX,E)-7+TX,11+TX,13-Hexadecatrienal+TX, (E+TX,Z)-7+TX,9-Dodecadien-1-yl acetate+TX, 2-Methyl-1-butanol+TX, Calcium acetate+TX, Scenturion®+TX, Biolure®+TX, Check-Mate®+TX, Lavandulyl senecioate;

Macrobials including: *Aphelinus abdominalis*+TX, *Aphidius ervi* (Aphelinus-System®)+TX, *Acerophagus papaya*+TX, *Adalia bipunctata* (Adalia-System®)+TX, *Adalia bipunctata* (Adaline®)+TX, *Adalia bipunctata* (Aphidalia®)+TX, *Ageniaspis citricola*+TX, *Ageniaspis fuscicollis*+TX, *Amblyseius andersoni* (Anderline®+TX, Andersoni-System®)+TX, *Amblyseius californicus* (Amblyline®+TX, Spical®)+TX, *Amblyseius cucumeris* (Thripex®+TX, Bugline Cucumeris®)+TX, *Amblyseius fallacis* (Fallacis®)+TX, *Amblyseius swirskii* (Bugline Swirskii®+TX, Swirskii-Mite®)+TX, *Amblyseius womersleyi* (WomerMite®)+TX, *Amitus hesperidum*+TX, *Anagrus atomus*+TX, *Anagyrus fusciventris*+TX, *Anagyrus kamali*+TX, *Anagyrus loecki*+TX, *Anagyrus pseudococci* (Citripar®)+TX, *Anicetus benefices*+TX, *Anisopteromalus calandrae*+TX, *Anthocoris nemoralis* (Anthocoris-System®)+TX, *Aphelinus abdominalis* (Apheline®+TX, Aphiline®)+TX, *Aphelinus asychis*+TX, *Aphidius colemani* (Aphipar®)+TX, *Aphidius ervi* (Ervipar®)+TX, *Aphidius gifuensis*+TX, *Aphidius matricariae* (Aphipar-M®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria* (Staphyline®)+TX, *Bombus* spp.+TX, *Bombus terrestris* (Natupol Beehive®)+TX, *Bombus terrestris* (Beeline®+TX, Tripol®)+TX, *Cephalonomia stephanoderis*+TX, *Chilocorus nigritus*+TX, *Chrysoperla carnea* (Chrysoline®)+TX, *Chrysoperla carnea* (Chrysopa®)+TX, *Chrysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, Cryptoline®)+TX, *Cybocephalus nipponicus*+TX, *Dacnusa sibirica*+TX, *Dacnusa sibirica* (Minusa®)+TX, *Diglyphus isaea* (Diminex®)+TX, *Delphastus catalinae* (Delphastus®)+TX, *Delphastus pusillus*+TX, *Diachasmimorpha krausii*+TX, *Diachasmimorpha longicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+TX, *Dacnusa sibirica* (DacDigline®+TX, Minex®)+TX, *Diversinervus* spp.+TX, *Encarsia citrina*+TX, *Encarsia formosa* (Encarsia Max®+TX, Encarline®+TX, En-Strip®)+TX, *Eretmocerus eremicus* (Enermix®)+TX, *Encarsia guadeloupae*+TX, *Encarsia haitiensis*+TX, *Episyrphus balteatus* (Syrphidend®)+TX, *Eretmoceris siphonini*+TX, *Eretmocerus californicus*+TX, *Eretmocerus eremicus* (Ercal®+TX, Eretline E®)+TX, *Eretmocerus eremicus* (Bemimix®)+TX, *Eretmocerus hayati*+TX, *Eretmocerus mundus* (Bemipar®+TX, Eretline M®)+TX, *Eretmocerus siphonini*+TX, *Exochomus quadripustulatus*+TX, *Feltiella acarisuga* (Spidend®)+TX, *Feltiella acarisuga* (Feltiline®)+TX, *Fopius arisanus*+TX, *Fopius ceratitivorus*+TX, Formononetin (Wirless Beehome®)+TX, *Franklinothrips vespiformis* (Vespop®)+TX, *Galendromus occidentalis*+TX, *Goniozus legneri*+TX, *Habrobracon hebetor*+TX, *Harmonia axyridis* (HarmoBeetle®)+TX, *Heterorhabditis* spp. (Lawn Patrol®)+TX, *Heterorhabditis bacteriophora* (NemaShield HB®+TX, Nemaseek®+TX, TerranemNam®+TX, Terranem®+TX, Larvanem®+TX, B-Green®+TX, NemAttack®+TX, Nematop®)+TX, *Heterorhabditis megidis* (Nemasys H®+TX, BioNem H®+TX, Exhibitline Hm®+TX, Larvanem-M®)+TX, *Hippodamia convergens*+TX, *Hypoaspis aculeifer* (Aculeifer-System®+TX, Entomite-A®)+TX, *Hypoaspis miles* (Hypoline M®+TX, Entomite-M®)+TX, *Lobalia leucospoides*+TX, *Lecanoideus floccissimus*+TX, *Lemophagus errabundus*+TX, *Leptomastidea abnormis*+TX, *Leptomastix dactylopii* (Leptopar®)+TX, *Leptomastix epona*+TX, *Lindorus lophanthae*+TX, *Lipolexis oregmae*+TX, *Lucilia caesar* (Natufly®)+TX, *Lysiphlebus testaceipes*+TX, *Macrolophus caliginosus* (Mirical-N®+TX, Macroline C®+TX, Mirical®)+TX, *Mesoseiulus longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spalangia cameroni* (Biopar®)+TX, *Neodryinus typhlocybae*+TX, *Neoseiulus californicus*+TX, *Neoseiulus cucumeris* (THRYPEX®)+TX, *Neoseiulus fallacis*+TX, *Nesideocoris tenuis* (NesidioBug®+TX, Nesibug®)+TX, *Ophyra aenescens* (Biofly®)+TX, *Orius insidiosus* (Thripor-I®+TX, Oriline I®)+TX, *Orius laevigatus* (Thripor-L®+TX, Oriline I®)+TX, *Orius majusculus*

(Oriline M®)+TX, *Orius strigicollis* (Thripor-S®)+TX, *Pauesia juniperorum*+TX, *Pediobius foveolatus*+TX, *Phasmarhabditis hermaphrodita* (Nemaslug®)+TX, *Phymastichus coffea*+TX, *Phytoseiulus macropilus*+TX, *Phytoseiulus persimilis* (Spidex®+TX, Phytoline P®)+TX, *Podisus maculiventris* (Podisus®)+TX, *Pseudacteon curvatus*+TX, *Pseudacteon obtusus*+TX, *Pseudacteon tricuspis*+TX, *Pseudaphycus maculipennis*+TX, *Pseudleptomastix mexicana*+TX, *Psyllaephagus pilosus*+TX, *Psyttalia concolor* (complex)+TX, *Quadrastichus* spp.+TX, *Rhyzobius lophanthae*+TX, *Rodolia cardinalis*+TX, *Rumina decollate*+TX, *Semielacher petiolatus*+TX, *Sitobion avenae* (Ervibank®)+TX, *Steinernema carpocapsae* (Nematac C®+TX, Millenium®+TX, BioNem C®+TX, NemAttack®+TX, Nemastar®+TX, Capsanem®)+TX, *Steinernema feltiae* (NemaShield®+TX, Nemasys F®+TX, BioNem F®+TX, Steinernema-System®+TX, NemAttack®+TX, Nemaplus®+TX, Exhibitline Sf®+TX, Scia-Rid®+TX, Entonem®)+TX, *Steinernema kraussei* (Nemasys L®+TX, BioNem L®+TX, Exhibitline Srb®)+TX, *Steinernema riobrave* (BioVector®+TX, BioVektor®)+TX, *Steinernema scapterisci* (Nematac S®)+TX, *Steinernema* spp.+TX, *Steinernematid* spp. (Guardian Nematodes®)+TX, *Stethorus punctillum* (Stethorus®)+TX, *Tamarixia radiate*+TX, *Tetrastichus setifer*+TX, *Thripobius semiluteus*+TX, *Torymus sinensis*+TX, *Trichogramma brassicae* (Tricholine B®)+TX, *Trichogramma brassicae* (Tricho-Strip®)+TX, *Trichogramma evanescens*+TX, *Trichogramma minutum*+TX, *Trichogramma ostriniae*+TX, *Trichogramma platneri*+TX, *Trichogramma pretiosum*+TX, *Xanthopimpla stemmator*; and other biologicals including: abscisic acid+TX, bioSea®+TX, *Chondrostereum purpureum* (Chontrol Paste®)+TX, *Colletotrichum gloeosporioides* (Collego®)+TX, Copper Octanoate (Cueva®)+TX, Delta traps (Trapline D®)+TX, *Erwinia amylovora* (Harpin) (ProAct®+TX, Ni-HIBIT Gold CST®)+TX, Ferri-phosphate (Ferramol®)+TX, Funnel traps (Trapline Y®)+TX, Gallex®+TX, Grower's Secret®+TX, Homo-brassonolide+TX, Iron Phosphate (Lilly Miller Worry Free Ferramol Slug & Snail Bait®)+TX, MCP hail trap (Trapline F®)+TX, Microctonus hyperodae+TX, *Mycoleptodiscus terrestris* (Des-X®)+TX, BioGain®+TX, Aminomite®+TX, Zenox®+TX, Pheromone trap (Thripline Ams®)+TX, potassium bicarbonate (MilStop®)+TX, potassium salts of fatty acids (Sanova®)+TX, potassium silicate solution (Sil-Matrix®)+TX, potassium iodide+potassiumthiocyanate (Enzicur®)+TX, SuffOil-X®+TX, Spider venom+TX, *Nosema locustae* (Semaspore Organic Grasshopper Control®)+TX, Sticky traps (Trapline YF®+TX, Rebell Amarillo®)+TX and Traps (Takitrapline y+B®)+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright © 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula I selected from the compounds defined in the Tables A-1 to A-21, B-1 to B-21, C-1 to C-21, D-1 to D-21 and E-1 to E-21 and with active ingredients described above comprises a compound selected from one compound defined in the Tables A-1 to A-21, B-1 to B-21, C-1 to C-21, D-1 to D-21 and E-1 to E-21 and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from the compounds defined in the Tables A-1 to A-21, B-1 to B-21, C-1 to C-21, D-1 to D-21 and E-1 to E-21 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of formula I of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term “coated or treated with and/or containing” generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula I. Further, it is hereby made available, a composition comprising a plant propagation material treated with a compound of formula I.

Seed treatment comprises all suitable seed treatment techniques known in the art, such as seed dressing, seed coating, seed dusting, seed soaking and seed pelleting. The seed treatment application of the compound formula I can be carried out by any known methods, such as spraying or by dusting the seeds before sowing or during the sowing/planting of the seeds.

In each aspect and embodiment of the invention, “consisting essentially” and inflections thereof are a preferred embodiment of “comprising” and its inflections, and “consisting of” and inflections thereof are a preferred embodiment of “consisting essentially of” and its inflections.

The disclosure in the present application makes available each and every combination of embodiments disclosed herein.

It should be noted that the disclosure herein in respect of a compound of formula I applies equally in respect of a compound of each of formulae I*, I'a, I-A, I'-A, and Tables A-1 to A-21, B-1 to B-21, C-1 to C-21, D-1 to D-21 and E-1 to E-21. Further the preferred enantiomer of formula I'a or I'-A applies also to compounds of Tables A-1 to A-21, B-1 to B-21, C-1 to C-21, D-1 to D-21 and E-1 to E-21 and Table P. Also, made available herein is an agrochemically acceptable salt, stereoisomer, enantiomer, tautomer and/or N-oxide of the compound of formula formulae I*, I'a, I-A, I'-A, and Tables A-1 to A-21, B-1 to B-21, C-1 to C-21, D-1 to D-21 and E-1 to E-21 and Table P.

The compounds of the invention can be distinguished from other similar compounds by virtue of greater efficacy at low application rates and/or different pest control, which can be verified by the person skilled in the art using the experimental procedures, using lower concentrations if necessary, for example 10 ppm, 5 ppm, 2 ppm, 1 ppm or 0.2 ppm; or lower application rates, such as 300, 200 or 100, mg of A1 per $m^2$. The greater efficacy can be observed by an increased safety profile (against non-target organisms above and below ground (such as fish, birds and bees), improved physico-chemical properties, or increased biodegradability).

BIOLOGICAL EXAMPLES

The Examples which follow serve to illustrate the invention. Certain compounds of the invention can be distinguished from known compounds by virtue of greater efficacy at low application rates, which can be verified by the person skilled in the art using the experimental procedures outlined in the Examples, using lower application rates if necessary, for example 50 ppm, 24 ppm, 12.5 ppm, δ ppm, 3 ppm, 1.5 ppm, 0.8 ppm or 0.2 ppm.

Example B1: *Diabrotica balteata* (Corn Root Worm)

Maize sprouts placed onto an agar layer in 24-well microtiter plates were treated with aqueous test solutions prepared from 10'000 ppm DMSO stock solutions by spraying. After drying, the plates were infested with L2 larvae (6 to 10 per well). The samples were assessed for mortality and growth inhibition in comparison to untreated samples 4 days after infestation.

The following compounds gave an effect of at least 80% control in at least one of the two categories (mortality or growth inhibition) at an application rate of 200 ppm:

P1, P6, P7, P8, P9, P13, P16, P17, P19, P20, P22, P24, P25, P26, P28, P30, P31, P32, P33, P34, P35, P36, P37, P39, P40, P41, P42, P44, P46, P49, P50, P53, P55, P57, P58.

Example B2: *Euschistus heros* (Neotropical Brown Stink Bug)

Soybean leaves on agar in 24-well microtiter plates were sprayed with aqueous test solutions prepared from 10'000 ppm DMSO stock solutions. After drying the leaves were infested with N2 nymphs. The samples were assessed for mortality and growth inhibition in comparison to untreated samples 5 days after infestation.

The following compounds gave an effect of at least 80% control in at least one of the two categories (mortality or growth inhibition) at an application rate of 200 ppm:

P1, P2, P3, P10, P21, P25, P30, P31, P32, P44, P46, P48, P50, P55

Example B3: *Frankliniella occidentalis* (Western Flower Thrips): Feeding/Contact Activity Sunflower leaf discs were placed on agar in 24-well microtiter plates and sprayed with aqueous test solutions prepared from 10'000 DMSO stock solutions. After drying the leaf discs were infested with a *Frankliniella* population of mixed ages. The samples were assessed for mortality 7 days after infestation.

The following compounds resulted in at least 80% mortality at an application rate of 200 ppm:

P10, P31, P32, P44

Example B4: *Chilo suppressalis* (Striped Rice Stemborer)

24-well microtiter plates with artificial diet were treated with aqueous test solutions prepared from 10'000 ppm DMSO stock solutions by pipetting. After drying, the plates were infested with L2 larvae (6-8 per well). The samples were assessed for mortality, anti-feeding effect, and growth inhibition in comparison to untreated samples 6 days after infestation. Control of *Chilo suppressalis* by a test sample is given when at least one of the categories mortality, anti-feedant effect, and growth inhibition is higher than the untreated sample.

The following compounds resulted in at least 80% control in at least one of the three categories (mortality, anti-feedant or growth inhibition) at an application rate of 200 ppm:

P1, P2, P3, P4, P6, P7, P8, P9, P10, P11, P12, P13, P16, P17, P18, P19, P20, P22, P24, P25, P26, P27, P28, P30, P31, P32, P33, P34, P35, P36, P37, P39, P40, P41, P42, P43, P44, P45, P46, P47, P48, P49, P50, P53, P54, P55, P56, P57, P58

Example B5: *Plutella xylostella* (Diamond Back Moth)

24-well microtiter plates with artificial diet were treated with aqueous test solutions prepared from 10'000 ppm DMSO stock solutions by pipetting. After drying, *Plutella* eggs were pipetted through a plastic stencil onto a gel blotting paper and the plate was closed with it. The samples were assessed for mortality and growth inhibition in comparison to untreated samples 8 days after infestation.

The following compounds gave an effect of at least 80% control in at least one of the two categories (mortality or growth inhibition) at an application rate of 200 ppm:

P1, P2, P3, P4, P5, P6, P7, P8, P9, P10, P11, P13, P16, P17, P18, P19, P20, P21, P22, P23, P24, P25, P26, P27, P28, P29, P30, P31, P32, P33, P34, P35, P36, P37, P38, P39, P40, P41, P42, P43, P44, P45, P46, P47, P48, P49, P50, P51, P52, P53, P54, P55, P56, P57, P58.

Example B6: *Myzus persicae* (Green Peach Aphid): Feeding/Contact Activity

Sunflower leaf discs were placed onto agar in a 24-well microtiter plate and sprayed with aqueous test solutions prepared from 10'000 ppm DMSO stock solutions. After drying, the leaf discs were infested with an aphid population of mixed ages. The samples were assessed for mortality 6 days after infestation.

The following compounds resulted in at least 80% mortality at an application rate of 200 ppm:

P44, P45, P46

Example B7: *Myzus persicae* (Green Peach Aphid): Systemic Activity

Roots of pea seedlings infested with an aphid population of mixed ages were placed directly into aqueous test solutions prepared from 10'000 DMSO stock solutions. The samples were assessed for mortality 6 days after placing seedlings into test solutions.

The following compounds resulted in at least 80% mortality at a test rate of 24 ppm:

P10, P25, P44, P46, P50

Example B8: *Myzus persicae* (Green Peach Aphid): Intrinsic Activity

Test compounds prepared from 10'000 ppm DMSO stock solutions were applied by pipette into 24-well microtiter plates and mixed with sucrose solution. The plates were closed with a stretched Parafilm. A plastic stencil with 24 holes was placed onto the plate and infested pea seedlings were placed directly on the Parafilm. The infested plate was closed with a gel blotting paper and another plastic stencil and then turned upside down. The samples were assessed for mortality 5 days after infestation.

The following compounds resulted in at least 80% mortality at a test rate of 12 ppm:

P10, P19, P25, P30, P31, P32, P37, P41, P44, P46, P50, P55.

Example B9: *Spodoptera littoralis* (Egyptian Cotton Leaf Worm)

Cotton leaf discs were placed onto agar in 24-well microtiter plates and sprayed with aqueous test solutions prepared from 10'000 ppm DMSO stock solutions. After drying the leaf discs were infested with five L1 larvae. The samples were assessed for mortality, anti-feeding effect, and growth inhibition in comparison to untreated samples 3 days after infestation. Control of *Spodoptera littoralis* by a test sample is given when at least one of the categories mortality, anti-feedant effect, and growth inhibition is higher than the untreated sample.

The following compounds resulted in at least 80% control in at least one of the three categories (mortality, anti-feedant or growth inhibition) at an application rate of 200 ppm:

P2, P3, P4, P6, P7, P8, P9, P11, P13, P16, P17, P19, P20, P22, P24, P25, P26, P28, P30, P31, P32, P34, P35, P36, P37, P39, P40, P41, P42, P44, P45, P46, P48, P49, P50, P51, P52, P53, P54, P55, P56, P57, P58.

Example B10: *Spodoptera littoralis* (Egyptian Cotton Leaf Worm)

Test compounds were applied by pipette from 10'000 ppm DMSO stock solutions into 24-well plates and mixed with agar. Lettuce seeds were placed onto the agar and the multi well plate was closed by another plate which contained also agar. After 7 days the compound was absorbed by the roots and the lettuce grew into the lid plate. The lettuce leaves were then cut off into the lid plate. *Spodoptera* eggs were pipetted through a plastic stencil onto a humid gel blotting paper and the lid plate was closed with it. The samples were assessed for mortality, anti-feedant effect and growth inhibition in comparison to untreated samples 6 days after infestation.

The following compounds gave an effect of at least 80% control in at least one of the three categories (mortality, anti-feedant, or growth inhibition) at a test rate of 12.5 ppm:

P39

Example B11: *Myzus persicae* (Green Peach Aphid)

Test compounds prepared from 10'000 ppm DMSO stock solutions were applied by a liquid handling robot into 96-well microtiter plates and mixed with a sucrose solution. Parafilm was stretched over the 96-well microtiter plate and a plastic stencil with 96 holes was placed onto the plate. Aphids were sieved into the wells directly onto the Parafilm. The infested plates were closed with a gel blotting card and a second plastic stencil and then turned upside down. The samples were assessed for mortality 5 days after infestation.

The following compounds resulted in at least 80% mortality at an application rate of 50 ppm:

P19, P22, P23, P25, P26

Example B12: *Plutella xylostella* (Diamondback Moth)

96-well microtiter plates containing artificial diet were treated with aqueous test solutions, prepared from 10'000 ppm DMSO stock solutions, by a liquid handling robot. After drying, eggs (~30 per well) were infested onto a netted lid which was suspended above the diet. The eggs hatch and L1 larvae move down to the diet. The samples were assessed for mortality 9 days after infestation.

The following compounds gave an effect of at least 80% mortality at an application rate of 500 ppm:

P11, P12, P13, P14, P15, P16, P17, P18, P19, P20, P21, P22, P23, P24, P25, P26, P27, P28, P29, P33, P34, P35, P36, P37, P38, P39, P40, P42

The invention claimed is:

1. A compound of the formula I

I

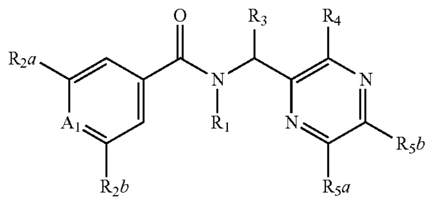

wherein

R1 is H, C1-C6alkyl, C1-C6cyanoalkyl, aminocarbonylC1-C6alkyl, hydroxycarbonylC1-C6alkyl, C1-C6nitroalkyl, trimethylsilaneC1-C6alkyl, C1-C6haloalkyl, C2-C6alkenyl, C2-C6haloalkeny, C2-C6alkynyl, C2-C6haloalkynyl, C3-C4cycloalkylC1-C2alkyl-, C3-C4cycloalkylC1-C2alkyl- wherein the C3-C4cycloalkyl group is substituted with 1 or 2 halogen atoms, oxetan-3-yl-CH2-, benzyl or benzyl substituted with halogen or C1-C6haloalkyl;

A1 is N or C—R2c;

R2c is H, halogen, C1-C3alkyl, C1-C3haloalkyl, C1-C3alkoxy, or C1-C3haloalkoxy;

R2a is C3-C6cycloalkyl, C3-C6cycloalkoxy, C3-C6cycloalkyl substituted with one to three substituents independently selected from C1-C3alkyl, C1-C3haloalkyl, C1-C3alkoxy, cyano, and halogen, C3-C6cycloalkoxy substituted with one to three substituents independently selected from C1-C3alkyl, C1-C3haloalkyl, cyano, and halogen, C3-C6cycloalkylC1-C4alkyl, C3-C6cycloalkylC1-C4alkoxy, C3-C6cycloalkylC1-C4alkyl substituted with one to five substituents independently selected from C1-C3alkyl, C1-C3haloalkyl, C1-C3alkoxy, cyano, and halogen, C3-C6cycloalkylC1-C4alkoxy substituted with one to five substituents independently selected from C1-C3alkyl, C1-C3haloalkyl, cyano, and halogen, C1-C5cyanoalkyl, C1-C4alkylsulfonyl, C1-C4haloalkylsulfonyl, C1-C4alkylsulfinyl, or C1-C4haloalkylsulfinyl;

R2b is H, halogen, C1-C3alkyl, C1-C3haloalkyl, C1-C3haloalkylthio, C1-C3alkoxy, C1-C3haloalkoxy, SF5, or CN;

R3 is C1-C3alkyl or C1-C3haloalkyl;

R4 is pyridine, pyrimidine, pyrazine, pyridazine, substituted pyridine, substituted pyrimidine, substituted pyrazine, or substituted pyridazine, wherein each of the substituted pyridine, the substituted pyrimidine, the substituted pyrazine, or the substituted pyridazine is independently substituted with one substituent selected from C1-C3alkyl, C1-C3haloalkyl, C1-C3alkoxy, C3-C4cycloalkyl, halogen and hydroxy;

R5a and R5b are, independently of each other, selected from hydrogen, halogen, CN, C1-C3alkyl, C1-C3haloalkyl, C3-C4cycloalkyl, C1-C3alkoxy, and C1-C3haloalkoxy; or agrochemically acceptable salts, stereoisomers, enantiomers, tautomers and N-oxides of the compounds of formula I.

2. The compound according to claim 1 wherein R3 is methyl.

3. The compound according to claim 1, wherein A1 is N.

4. The compound according to claim 1, wherein A1 is C—R2c, where R2c is hydrogen or halogen.

5. The compound according to claim 1, wherein R1 is hydrogen, methyl, ethyl, n-propyl, isobutyl, cyclopropylmethyl or HC≡CCH2-.

6. The compound according to claim 1, wherein R2a is C3-C6cycloalkyl, C3-C6cycloalkoxy, C3-C6cycloalkyl substituted with one to three substituents independently selected from C1-C3alkyl, C1-C3haloalkyl, C1-C3alkoxy, cyano, and halogen, C3-C6cycloalkylC1-C4alkyl substituted with one to five substituents independently selected from halogen and C1-C3haloalkyl, C1-C5cyanoalkyl, C3-C6cycloalkoxy, C1-C4haloalkylsulfonyl or C1-C4haloalkylsulfinyl.

7. The compound according to claim 1, wherein R2b is halogen, C1-C3haloalkyl, C1-C3haloalkylthio, C1-C3alkoxy, C1-C3haloalkoxy, or CN.

8. The compound according to claim 1, wherein R4 is 2-pyridine, 2-pyrimidine, 2-pyridine substituted with one substituent selected from cyclopropyl or halogen, or 2-pyrimidine substituted with one substituent selected from cyclopropyl or halogen.

9. The compound according to claim 1, wherein R5a and R5b, independent of each other, are selected from hydrogen, bromo, chloro, methyl, and methoxy.

10. A composition comprising the compound according to claim 1, one or more auxiliaries, one or more diluents, and optionally one more other active ingredient.

11. A method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of the compound according to claim 1, or an effective amount of a composition comprising said compound, one or more auxiliaries, one or more diluents, and optionally one more other active ingredient.

12. A plant propagation material, comprising, or treated with or adhered thereto, the compound according to claim 1, or a composition comprising said compound, one or more auxiliaries, one or more diluents, and optionally one more other active ingredient.

13. A compound of formulae IIaa to IIae

IIaa

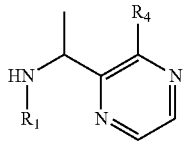

IIab

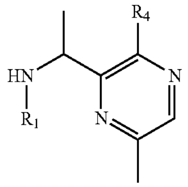

IIac

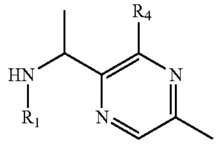

IIad

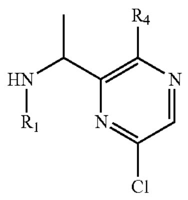

IIae

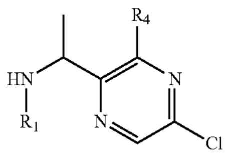

wherein

R1 is H, C1-C6alkyl, C1-C6cyanoalkyl, aminocarbonylC1-C6alkyl, hydroxycarbonylC1-C6alkyl, C1-C6nitroalkyl, trimethylsilaneC1-C6alkyl, C1-C6haloalkyl, C2-C6alkenyl, C2-C6haloalkeny, C2-C6alkynyl, C2-C6haloalkynyl, C3-C4cycloalkylC1-C2alkyl-, C3-C4cycloalkylC1-C2alkyl- wherein the C3-C4cycloalkyl group is substituted with 1 or 2 halogen atoms, oxetan-3-yl-CH2-, benzyl or benzyl substituted with halogen or $C_1$-$C_6$ haloalkyl; and R4 is 2-pyridine, 2-pyrimidine, 2-pyridine substituted with one substituent selected from cyclopropyl or halogen, or 2-pyrimidine substituted with one substituent selected from cyclopropyl or halogen.

14. A method for the protection of plant propagation material from the attack by insects, acarines, nematodes or molluscs, which comprises treating the propagation material or the site, where the propagation material is planted, with an effective amount of the compound according to claim 1, or an effective amount of a composition comprising said compound, one or more auxiliaries, one or more diluents, and optionally one more other active ingredient.

15. A method of controlling parasites in or on an animal in need thereof comprising administering an effective amount of the compound according to claim 1, or an effective amount of a composition comprising said compound, one or more auxiliaries, one or more diluents, and optionally one more other active ingredient.

16. The plant propagation material according to claim 12, wherein the plant propagation material is a seed.

17. The compound according to claim 13, wherein R1 is hydrogen, methyl, ethyl, n-propyl, isobutyl, cyclopropylmethyl or HC≡CCH2-.

18. The compound according to claim 1, selected from:

2-(1-cyanocyclopropyl)-N-[1-[3-(5-cyclopropylpyrimidin-2-yl)pyrazin-2-yllethyl]-6-(trifluoromethyl)pyridine-4-carboxamide (P32);

N-[1-[3-(5-chloro-2-pyridyl)pyrazin-2-yl]ethyl]-3-(1-cyanocyclopropyl)-5-(trifluoromethyl)benzamide (P17);

N-[1-[3-(5-chloro-2-pyridyl)pyrazin-2-yl]ethyl]-2-(1-cyanocyclopropyl)-6-(trifluoromethyl)pyridine-4-carboxamide (P16);

N-[1-[3-(5-bromo-2-pyridyl)pyrazin-2-yl]ethyl]-2-(1-cyanocyclopropyl)-6-(trifluoromethyl)pyridine-4-carboxamide (P28);

3-cyclopropyl-N-[1-(3-pyrimidin-2-ylpyrazin-2-yl)ethyl]-5-(trifluoromethyl)-benzamide (P41);

3-[cyclopropyl(difluoro)methyl]-N-[1-(3-pyrimidin-2-ylpyrazin-2-yl)ethyl]-5-(trifluoromethyl)benzamide (P30);

3-(1-methoxycyclopropyl)-N-[1-(3-pyrimidin-2-ylpyrazin-2-yl)ethyl]-5-(trifluoromethyl)benzamide (P47);

N-[1-[3-(5-bromopyrimidin-2-yl)pyrazin-2-yl]ethyl]-3-cyclopropyl-5-(trifluoromethyl)benzamide (P58);

N-[1-[3-(5-bromopyrimidin-2-yl)pyrazin-2-yl]ethyl]-2-(1-cyanocyclopropyl)-6-(trifluoromethyl)pyridine-4-carboxamide (P55);

N-[1-[3-(5-bromopyrimidin-2-yl)pyrazin-2-yl]ethyl]-3-[cyclopropyl(difluoro)methyl]-5-(trifluoromethyl)benzamide (P53); and N-[(1S)-1-[3-(5-bromo-2-pyridyl)pyrazin-2-yl]ethyl]-3-[cyclopropyl(difluoro)methyl]-5-(trifluoromethyl)benzamide (P42).

19. The compound according to claim 1, selected from:

2-chloro-N-[1-(3-pyrimidin-2-ylpyrazin-2-yl)ethyl]-6-(trifluoromethyl)pyridine-4-carboxamide;

2-(1-cyanocyclopropyl)-N-[1-[3-(5-methylpyrimidin-2-yl)pyrazin-2-yl]ethyl]-6-(trifluoromethyl)pyridine-4-carboxamide;

3-(1-cyanocyclopropyl)-N-[1-[3-(5-cyclopropylpyrimidin-2-yl)pyrazin-2-yl]ethyl]-5-(trifluoromethyl)benzamide;

N-[1-[3-(5-chloro-2-pyridyl)pyrazin-2-yl]ethyl]-3-[cyclopropyl(difluoro)methyl]-5-(trifluoromethyl)benzamide;

3-(1-cyano-1-methyl-ethyl)-N-[1-[3-(5-fluoro-2-pyridyl)pyrazin-2-yl]ethyl]-5-(trifluoromethyl)benzamide;

3-(1-cyano-1-methyl-ethyl)-N-[1-[3-(5-cyclopropylpyrimidin-2-yl)pyrazin-2-yl]ethyl]-5-(trifluoromethyl)benzamide;

3-(1-cyano-1-methyl-ethyl)-N-[143-(2-pyridyl)pyrazin-2-yl]ethyl]-5-(trifluoromethyl)benzamide;

N-[1-[3-(5-chloro-2-pyridyl)pyrazin-2-yl]ethyl]-3-(1-cyano-1-methyl-ethyl)-5-(trifluoromethyl)benzamide;

N-[1-[3-(5-bromo-2-pyridyl)pyrazin-2-yl]ethyl]-3-(1-cyano-1-methyl-ethyl)-5-(trifluoromethyl)benzamide;

3-cyclopropylsulfonyl-N-[1-(3-pyrimidin-2-ylpyrazin-2-yl)ethyl]-5-(trifluoromethyl)benzamide;

N-[1-[3-(5-cyclopropylpyrimidin-2-yl)pyrazin-2-yl]ethyl]-3-(trifluoromethyl)-5-(trifluoromethylsulfonyl)benzamide;

N-[1-[3-(5-fluoro-2-pyridyl)pyrazin-2-yl]ethyl]-3-(trifluoromethyl)-5-(trifluoromethylsulfonyl)benzamide;

N-[1-[3-(2-pyridyl)pyrazin-2-yl]ethyl]-3-(trifluoromethyl)-5-(trifluoromethylsulfonyl)benzamide;

N-[1-[3-(5-bromo-2-pyridyl)pyrazin-2-yl]ethyl]-3-(trifluoromethyl)-5-(trifluoromethylsulfonyl)benzamide;

N-[1-[3-(5-chloro-2-pyridyl)pyrazin-2-yl]ethyl]-3-(trifluoromethyl)-5-(trifluoromethylsulfonyl)benzamide;

N-[1-[3-(5-chloro-2-pyridyl)pyrazin-2-yl]ethyl]-2-(1-cyanocyclopropyl)-6-(trifluoromethyl)pyridine-4-carboxamide;

N-[1-[3-(5-chloro-2-pyridyl)pyrazin-2-yl]ethyl]-3-(1-cyanocyclopropyl)-5-(trifluoromethyl)benzamide;

N-[1-[3-(5-chloro-2-pyridyl)pyrazin-2-yl]ethyl]-3-cyclopropyl-5-(trifluoromethyl)benzamide;

N-[1-(3-pyrimidin-2-ylpyrazin-2-yl)ethyl]-3-(trifluoromethyl)-5-(trifluoromethylsulfonyl)benzamide;

3-[cyclopropyl(difluoro)methyl]-N-[143-(2-pyridyl)pyrazin-2-yl]ethyl]-5-(trifluoromethyl)benzamide;

N-[1-[3-(5-bromo-2-pyridyl)pyrazin-2-yl]ethyl]-3-[cyclopropyl(difluoro)methyl]-5-(trifluoromethyl)benzamide;

3-(1-cyanocyclopropyl)-N-[1-[3-(2-pyridyl)pyrazin-2-yl]ethyl]-5-(trifluoromethyl)benzamide;

3-(1-cyanocyclopropyl)-N-[1-[3-(5-fluoro-2-pyridyl)pyrazin-2-yl]ethyl]-5-(trifluoromethyl)benzamide;

N-[1-[3-(5-bromo-2-pyridyl)pyrazin-2-yl]ethyl]-3-(1-cyanocyclopropyl)-5-(trifluoromethyl)benzamide;

3-(1-cyanocyclopropyl)-N-[1-(3-pyrimidin-2-ylpyrazin-2-yl)ethyl]-5-(trifluoromethyl)benzamide;

2-(1-cyanocyclopropyl)-N-[1-[3-(2-pyridyl)pyrazin-2-yl]ethyl]-6-(trifluoromethyl)pyridine-4-carboxamide;

2-(1-cyanocyclopropyl)-N-[1-[3-(5-fluoro-2-pyridyl)pyrazin-2-yl]ethyl]-6-(trifluoromethyl)pyridine-4-carboxamide;

N-[1-[3-(5-bromo-2-pyridyl)pyrazin-2-yl]ethyl]-2-(1-cyanocyclopropyl)-6-(trifluoromethyl)pyridine-4-carboxamide;

N-[1-[3-(5-bromo-2-pyridyl)pyrazin-2-yl]ethyl]-3-cyclopropyl-5-(trifluoromethyl)benzamide;

3-[cyclopropyl(difluoro)methyl]-N-[1-(3-pyrimidin-2-ylpyrazin-2-yl)ethyl]-5-(trifluoromethyl)benzamide;

2-cyclopropyl-N-[1-(3-pyrimidin-2-ylpyrazin-2-yl)ethyl]-6-(trifluoromethyl)pyridine-4-carboxamide;

2-(1-cyanocyclopropyl)-N-[1-(3-pyrimidin-2-ylpyrazin-2-yl)ethyl]-6-(trifluoromethyl)pyridine-4-carboxamide;

3-cyclopropyl-N-[1-[3-(2-pyridyl)pyrazin-2-yl]ethyl]-5-(trifluoromethyl)benzamide;

3-cyclopropyl-N-[1-[3-[5-(difluoromethoxy)pyrimidin-2-yl]pyrazin-2-yl]ethyl]-5-(trifluoromethyl)benzamide;

3-cyclopropyl-N-[1-[3-(5-cyclopropylpyrimidin-2-yl)pyrazin-2-yl]ethyl]-5-(trifluoromethyl)benzamide;

2-(1-cyanocyclopropyl)-N-[1-[3-(5-cyclopropylpyrimidin-2-yl)pyrazin-2-yl]ethyl]-6-(trifluoromethyl)pyridine-4-carboxamide;

N-[1-(3-pyrimidin-2-ylpyrazin-2-yl)ethyl]-3-(trifluoromethyl)-5-[2-(trifluoromethyl)cyclopropyl]benzamide;

3-[cyclopropyl(difluoro)methyl]-N-[1-[3-(5-fluoro-2-pyridyl)pyrazin-2-yl]ethyl]-5-(trifluoromethyl)benzamide;

3-[cyclopropyl(difluoro)methyl]-N-[1-[3-(5-cyclopropylpyrimidin-2-yl)pyrazin-2-yl]ethyl]-5-(trifluoromethyl)benzamide;

3-cyclopropyl-N-[1-[3-(5-fluoro-2-pyridyl)pyrazin-2-yl]ethyl]-5-(trifluoromethyl)benzamide;

3-cyclopropyl-N-[1-(3-pyrimidin-2-ylpyrazin-2-yl)ethyl]-5-(trifluoromethyl)benzamide N-[(1S)-1-[3-(5-bromo-2-pyridyl)pyrazin-2-yl]ethyl]-3-[cyclopropyl(difluoro)methyl]-5-(trifluoromethyl)benzamide;

2-(cyclopropylmethoxy)-N-[1-(3-pyrimidin-2-ylpyrazin-2-yl)ethyl]-6-(trifluoromethyl)pyridine-4-carboxamide;

3-(1-cyanocyclopropyl)-5-(difluoromethoxy)-N-[1-(3-pyrimidin-2-ylpyrazin-2-yl)ethyl]benzamide;

3-(difluoromethoxy)-N-[1-(3-pyrimidin-2-ylpyrazin-2-yl)ethyl]-5-(trifluoromethylsulfonyl)benzamide;

3-(1-cyanocyclopropyl)-N-[1-(3-pyrimidin-2-ylpyrazin-2-yl)ethyl]-5-(trifluoromethoxy)benzamide;

3-(1-methoxycyclopropyl)-N-[1-(3-pyrimidin-2-ylpyrazin-2-yl)ethyl]-5-(trifluoromethyl)benzamide;

3-(1-cyano-1-methyl-ethyl)-N-[1-[3-(5-methylpyrimidin-2-yl)pyrazin-2-yl]ethyl]-5-(trifluoromethyl)benzamide;

N-[1-[3-(5-bromopyrimidin-2: yl)pyrazin-2-yl]ethyl]-3-(1-cyano-1-methyl-ethyl)-5-(trifluoromethyl)benzamide;

3-(1-cyano-1-methyl-ethyl)-N-[1-(3-pyrimidin-2-ylpyrazin-2-yl)ethyl]-5-(trifluoromethyl)benzamide;

3-cyclopropyl-N-[1-[3-(5-methylpyrimidin-2-yl)pyrazin-2-yl]ethyl]-5-(trifluoromethyl)benzamide;

3-[cyclopropyl(difluoro)methyl]-N-[1-[3-(5-methylpyrimidin-2-yl)pyrazin-2-yl]ethyl]-5-(trifluoromethyl)benzamide;

N-[1-[3-(5-bromopyrimidin-2-yl)pyrazin-2-yl]ethyl]-3-[cyclopropyl(difluoro)methyl]-5-(trifluoromethyl)benzamide;

3-(1-cyanocyclopropyl)-N-[1-[3-(5-methylpyrimidin-2-yl)pyrazin-2-yl]ethyl]-5-(trifluoromethyl)benzamide;

N-[1-[3-(5-bromopyrimidin-2-yl)pyrazin-2-yl]ethyl]-2-(1-cyanocyclopropyl)-6-(trifluoromethyl)pyridine-4-carboxamide;

N-[1-[3-(5-methylpyrimidin-2-yl)pyrazin-2-yl]ethyl]-3-(trifluoromethyl)-5-(trifluoromethylsulfonyl)benzamide;

N-[1-[3-(5-bromopyrimidin-2-yl)pyrazin-2-yl]ethyl]-3-(trifluoromethyl)-5-(trifluoromethylsulfonyl)benzamide; and N-[1-[3-(5-bromopyrimidin-2-yl)pyrazin-2-yl]ethyl]-3-cyclopropyl-5-(trifluoromethyl)benzamide.

20. A method for the protection of plant propagation material from the attack by insects, acarines, nematodes or molluscs, which comprises treating the propagation material or the site, where the propagation material is planted, with an effective amount of the compound according to claim 19, or an effective amount of a composition comprising the compound, one or more auxiliaries, one or more diluents, and optionally one more other active ingredient.

* * * * *